United States Patent
Zagrijtschuk et al.

(10) Patent No.: US 12,410,185 B2
(45) Date of Patent: Sep. 9, 2025

(54) COMPOUNDS TARGETING MUTANT CALRETICULIN

(71) Applicant: MYELOPRO DIAGNOSTICS AND RESEARCH GmbH, Vienna (AT)

(72) Inventors: Oleh Zagrijtschuk, Vienna (AT); Ruochen Jia, Vienna (AT)

(73) Assignee: MYELOPRO DIAGNOSTICS AND RESEARCH GmbH, Vienna (AT)

( * ) Notice: Subject to any disclaimer, the term of this patent is extended or adjusted under 35 U.S.C. 154(b) by 1140 days.

(21) Appl. No.: 17/296,730

(22) PCT Filed: Oct. 23, 2019

(86) PCT No.: PCT/EP2019/078918
§ 371 (c)(1),
(2) Date: May 25, 2021

(87) PCT Pub. No.: WO2020/084005
PCT Pub. Date: Apr. 30, 2020

(65) Prior Publication Data
US 2022/0024944 A1    Jan. 27, 2022

(30) Foreign Application Priority Data
Oct. 23, 2018 (EP) .................... 18202112

(51) Int. Cl.
| C07D 498/04 | (2006.01) |
|---|---|
| C07D 311/94 | (2006.01) |
| C07D 417/14 | (2006.01) |
| C07D 471/04 | (2006.01) |
| C07D 491/052 | (2006.01) |
| C07D 491/147 | (2006.01) |
| C07D 491/22 | (2006.01) |
| C07D 493/04 | (2006.01) |

(52) U.S. Cl.
CPC .......... *C07D 498/04* (2013.01); *C07D 311/94* (2013.01); *C07D 417/14* (2013.01); *C07D 471/04* (2013.01); *C07D 491/052* (2013.01); *C07D 491/147* (2013.01); *C07D 491/22* (2013.01); *C07D 493/04* (2013.01)

(58) Field of Classification Search
CPC .. C07D 498/04; C07D 311/94; C07D 417/14; C07D 471/04; C07D 491/052; C07D 491/147; C07D 491/22; C07D 493/04; C07D 313/20; C07D 417/12; A61P 35/00
See application file for complete search history.

(56) References Cited

U.S. PATENT DOCUMENTS

| 4,918,099 A * | 4/1990 | Moon | C07D 311/94 |
|---|---|---|---|
| | | | 514/833 |
| 7,652,058 B2 * | 1/2010 | DeVita | A61P 25/22 |
| | | | 548/453 |
| 2004/0229895 A1 | 11/2004 | Jagtap et al. | |
| 2005/0013820 A1 | 1/2005 | Holoshitz | |
| 2005/0261288 A1 | 11/2005 | Jagtap et al. | |
| 2007/0049555 A1 | 3/2007 | Jagtap et al. | |
| 2010/0137194 A1 * | 6/2010 | Lawrence | C07C 271/22 |
| | | | 549/417 |
| 2011/0111014 A1 * | 5/2011 | Langston | A61P 25/00 |
| | | | 514/567 |
| 2016/0067296 A1 | 3/2016 | Brownell | |

FOREIGN PATENT DOCUMENTS

| WO | 99-05172 A2 | 2/1999 |
|---|---|---|
| WO | 2006/093667 A1 | 9/2006 |
| WO | 2016-187013 A1 | 11/2016 |

OTHER PUBLICATIONS

Raj, H. G. et al. Mechanism of biochemical action of substituted 4-methylbenzopyran-2-ones. Part 10: identification of inhibitors for the liver microsomal acetoxycoumarin: protein transacetylase. Bioorganic & medicinal chemistry, 2003. vol. 11, 6: 1015-9. (Year: 2003).*

Oniciu, D. C. 14.01.6.1 Azocanes [Internet]. Comprehensive Heterocyclic Chemistry IV, 2022. Retrieved from ScienceDirect <https://www.sciencedirect.com/topics/chemistry/azocane> (Year: 2022).*

Suyavaran, A. et al. Synthesis and biological evaluation of isoindoloisoquinolinone, pyroloisoquinolinone and benzoquinazolinone derivatives as poly(ADP-ribose) polymerase-1 inhibitors. Bioorg Med Chem., 2015. vol. 23, 3: 488-498. (Year: 2015).*

International Search Report in PCT/EP2019/078918, mailed Jan. 23, 2020, 7 pages.

Craig et al. Nuclear Magnetic Resonance Spectra and Stereochemistry of the Antibacterial Principle from Haematoxylon braziletto1. The Journal of organic chemistry. May 1965;30(5):1573-6.

Hellwinkel et al. 12-Organyldibenz [b, g] azocin-5, 7-dione. Chemische Berichte. Oct. 1986;119(10):3165-97.

Huang et al. Multi-site cyclization via initial C—H activation using a rhodium (iii) catalyst: rapid assembly of frameworks containing indoles and indolines. Chemical Communications. 2015;51(14):2844-7.

Javed et al. Enantioselective syntheses of (+)-and (−)-brazilin. Tetrahedron: Asymmetry. Oct. 15, 2014;25(18-19):1270-4.

(Continued)

*Primary Examiner* — Amy L Clark
*Assistant Examiner* — Chihyi Lee
(74) *Attorney, Agent, or Firm* — Kilpatrick Townsend & Stockton LLP

(57) ABSTRACT

The present invention relates to compounds binding to calreticulin which selectively inhibit growth of CALR mutant cells and/or exhibit selective cytotoxicity towards CALR mutant cells, to pharmaceutical compositions comprising such compounds as well as to their use in treating diseases or conditions caused by or associated with a mutation of CALR, in particular myeloid malignancies, such as myeloproliferative neoplasms or myelodysplasia syndrome. The present invention also relates to screening assays allowing the identification of such compounds.

1 Claim, 25 Drawing Sheets
Specification includes a Sequence Listing.

(56) References Cited

OTHER PUBLICATIONS

Passamonti et al. JAK inhibitor in CALR-mutant myelofibrosis. The New England journal of medicine. Mar. 1, 2014;370(12):1168-9.
Wang et al. Bioactive benzofuran derivatives from cortex mori radicis, and their neuroprotective and analgesic activities mediated by mGluR1. Molecules. Feb. 2017;22(2):236.
Yen et al. Antitumor agents. 271: Total synthesis and evaluation of brazilein and analogs as anti-inflammatory and cytotoxic agents. Bioorganic & medicinal chemistry letters. Feb. 1, 2010:20(3):1037-9.

\* cited by examiner

Figure 15
- CALR WT
- CALR heterozygous mutant
- CALR homozygous mutant
Hematoxylin
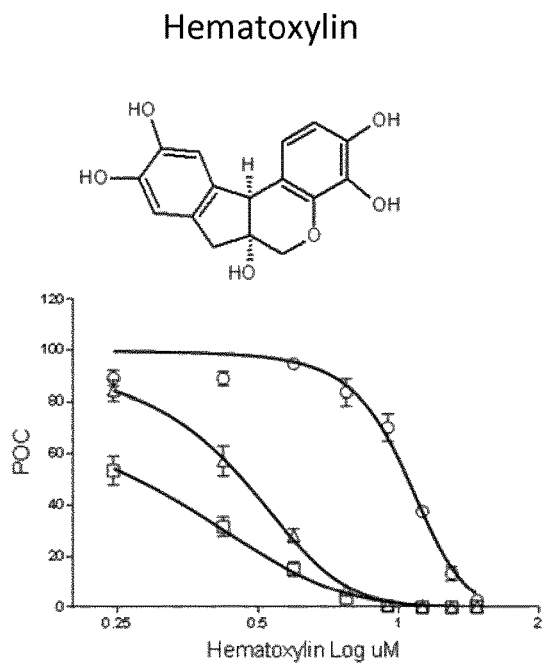
Brazilin
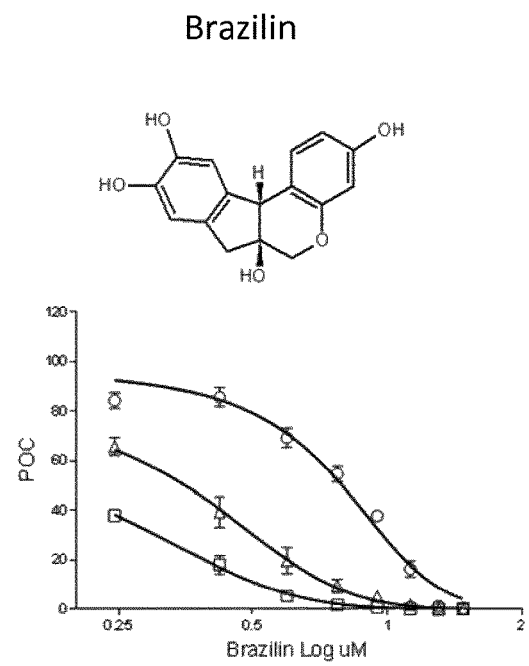
Hematein
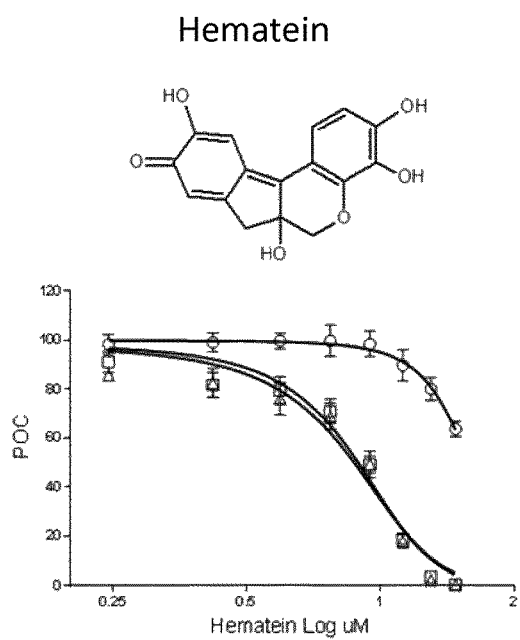
NSC7241
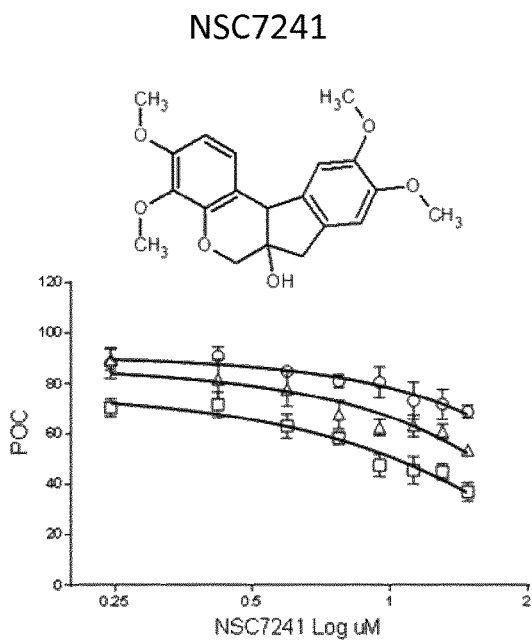

Figure 16
- CALR WT
- CALR heterozygous mutant
- CALR homozygous mutant
Protosappanin B
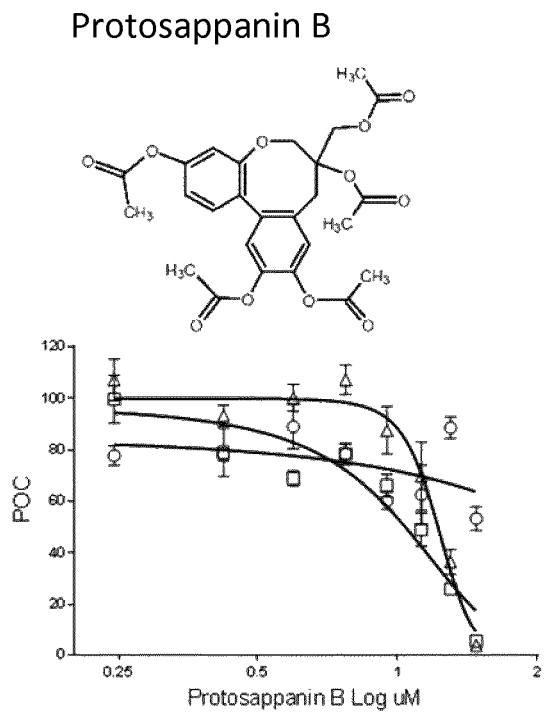
L-HEM3
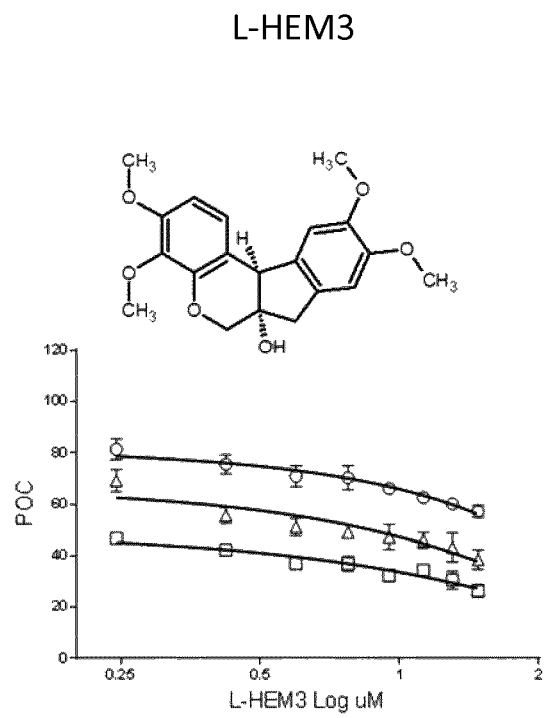
L-HEM1
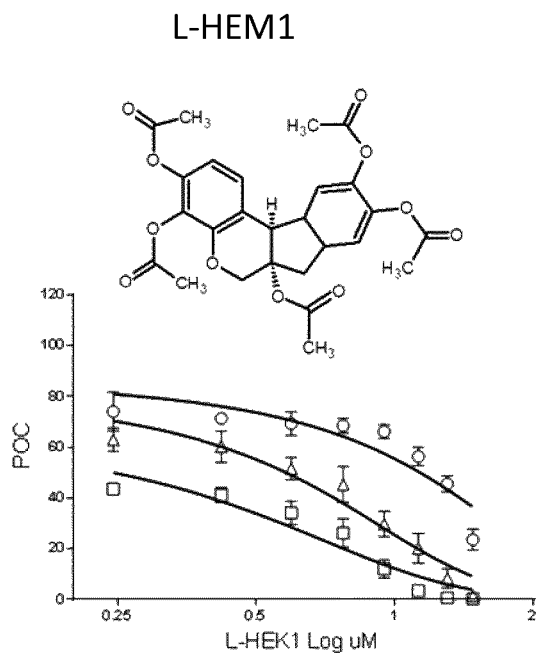

Figure 17
- CALR WT
- CALR heterozygous mutant
- CALR homozygous mutant
RJ002
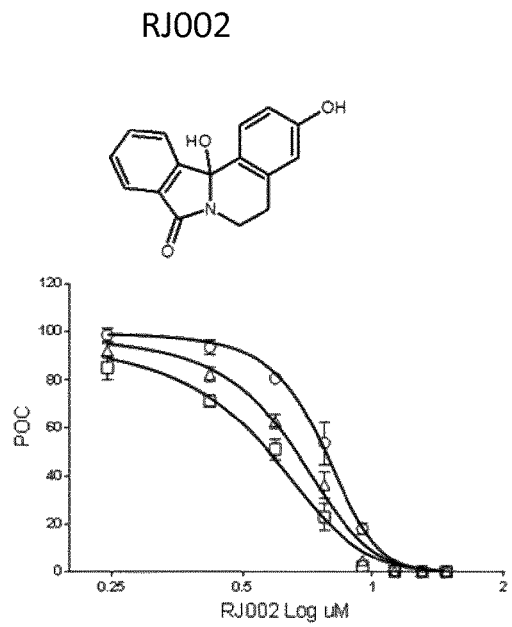
Hydroxyurea
Ruxolitinib
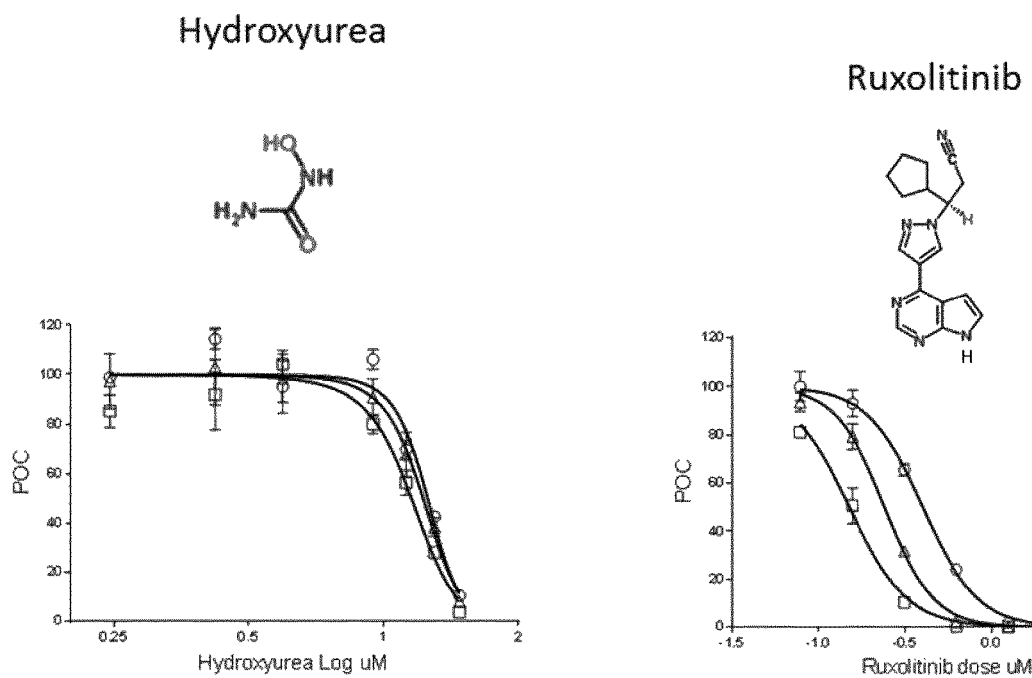

SEQUENCE LISTING

<160> NUMBER OF SEQ ID NOS: 17

<210> SEQ ID NO 1
<211> LENGTH: 417
<212> TYPE: PRT
<213> ORGANISM: Homo sapiens

<400> SEQUENCE: 1

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Tyr Val Lys Leu
                100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365
```

```
Glu Glu Glu Glu Asp Lys Lys Arg Lys Glu Glu Glu Ala Glu Asp
        370             375                 380
Lys Glu Asp Asp Glu Asp Lys Asp Glu Asp Glu Asp Glu Glu Asp
385                 390                 395                 400
Lys Glu Glu Asp Glu Glu Glu Asp Val Pro Gly Gln Ala Lys Asp Glu
                405                 410                 415
Leu

<210> SEQ ID NO 2
<211> LENGTH: 43
<212> TYPE: PRT
<213> ORGANISM: Homo sapiens

<400> SEQUENCE: 2

Arg Met Met Arg Thr Lys Met Arg Met Arg Arg Met Arg Arg Thr Arg
1               5                   10                  15
Arg Lys Met Arg Arg Lys Met Ser Pro Ala Arg Pro Arg Thr Ser Cys
                20                  25                  30
Arg Glu Ala Cys Leu Gln Gly Trp Thr Glu Ala
            35                  40

<210> SEQ ID NO 3
<211> LENGTH: 45
<212> TYPE: PRT
<213> ORGANISM: Homo sapiens

<400> SEQUENCE: 3

Thr Arg Arg Met Met Arg Thr Lys Met Arg Met Arg Arg Met Arg Arg
1               5                   10                  15
Thr Arg Arg Lys Met Arg Arg Lys Met Ser Pro Ala Arg Pro Arg Thr
                20                  25                  30
Ser Cys Arg Glu Ala Cys Leu Gln Gly Trp Thr Glu Ala
            35                  40                  45

<210> SEQ ID NO 4
<211> LENGTH: 411
<212> TYPE: PRT
<213> ORGANISM: Homo sapiens

<400> SEQUENCE: 4

Met Leu Leu Ser Val Pro Leu Leu Leu Gly Leu Leu Gly Leu Ala Val
1               5                   10                  15
Ala Glu Pro Ala Val Tyr Phe Lys Glu Gln Phe Leu Asp Gly Asp Gly
                20                  25                  30
Trp Thr Ser Arg Trp Ile Glu Ser Lys His Lys Ser Asp Phe Gly Lys
            35                  40                  45
Phe Val Leu Ser Ser Gly Lys Phe Tyr Gly Asp Glu Glu Lys Asp Lys
50                  55                  60
Gly Leu Gln Thr Ser Gln Asp Ala Arg Phe Tyr Ala Leu Ser Ala Ser
65                  70                  75                  80
Phe Glu Pro Phe Ser Asn Lys Gly Gln Thr Leu Val Val Gln Phe Thr
                85                  90                  95
Val Lys His Glu Gln Asn Ile Asp Cys Gly Gly Gly Tyr Val Lys Leu
                100                 105                 110
Phe Pro Asn Ser Leu Asp Gln Thr Asp Met His Gly Asp Ser Glu Tyr
            115                 120                 125
Asn Ile Met Phe Gly Pro Asp Ile Cys Gly Pro Gly Thr Lys Lys Val
            130                 135                 140
```

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Thr Arg
        355                 360                 365

Arg Met Met Arg Thr Lys Met Arg Met Arg Met Arg Thr Arg
370                 375                 380

Arg Lys Met Arg Arg Lys Met Ser Pro Ala Arg Pro Arg Thr Ser Cys
385                 390                 395                 400

Arg Glu Ala Cys Leu Gln Gly Trp Thr Glu Ala
                405                 410

<210> SEQ ID NO 5
<211> LENGTH: 46
<212> TYPE: PRT
<213> ORGANISM: Homo sapiens

<400> SEQUENCE: 5

Asn Cys Arg Arg Met Met Arg Thr Lys Met Arg Met Arg Met Arg
1               5                   10                  15

Arg Thr Arg Arg Lys Met Arg Arg Lys Met Ser Pro Ala Arg Pro Arg
                20                  25                  30

Thr Ser Cys Arg Glu Ala Cys Leu Gln Gly Trp Thr Glu Ala
            35                  40                  45

<210> SEQ ID NO 6
<211> LENGTH: 430
<212> TYPE: PRT
<213> ORGANISM: Homo sapiens

<400> SEQUENCE: 6

Met Leu Leu Ser Val Pro Leu Leu Leu Gly Leu Leu Gly Leu Ala Val
1               5                   10                  15

```
Ala Glu Pro Ala Val Tyr Phe Lys Glu Gln Phe Leu Asp Gly Asp Gly
             20                  25                  30

Trp Thr Ser Arg Trp Ile Glu Ser Lys His Lys Ser Asp Phe Gly Lys
         35                  40                  45

Phe Val Leu Ser Ser Gly Lys Phe Tyr Gly Asp Glu Glu Lys Asp Lys
 50                  55                  60

Gly Leu Gln Thr Ser Gln Asp Ala Arg Phe Tyr Ala Leu Ser Ala Ser
 65                  70                  75                  80

Phe Glu Pro Phe Ser Asn Lys Gly Gln Thr Leu Val Val Gln Phe Thr
                 85                  90                  95

Val Lys His Glu Gln Asn Ile Asp Cys Gly Gly Gly Tyr Val Lys Leu
             100                 105                 110

Phe Pro Asn Ser Leu Asp Gln Thr Asp Met His Gly Asp Ser Glu Tyr
         115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                 165                 170                 175

Arg Pro Asp Asn Thr Tyr Glu Val Lys Ile Asp Asn Ser Gln Val Glu
             180                 185                 190

Ser Gly Ser Leu Glu Asp Asp Trp Asp Phe Leu Pro Pro Lys Lys Ile
         195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                 245                 250                 255

Met Asp Gly Glu Trp Glu Pro Pro Val Ile Gln Asn Pro Glu Tyr Lys
             260                 265                 270

Gly Glu Trp Lys Pro Arg Gln Ile Asp Asn Pro Asp Tyr Lys Gly Thr
         275                 280                 285

Trp Ile His Pro Glu Ile Asp Asn Pro Glu Tyr Ser Pro Asp Pro Ser
290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                 325                 330                 335

Ala Tyr Ala Glu Glu Phe Gly Asn Glu Thr Trp Gly Val Thr Lys Ala
             340                 345                 350

Ala Glu Lys Gln Met Lys Asp Lys Gln Asp Glu Glu Gln Arg Leu Lys
         355                 360                 365

Glu Glu Glu Glu Asp Lys Lys Arg Lys Glu Glu Glu Glu Ala Glu Asp
 370                 375                 380

Asn Cys Arg Arg Met Met Arg Thr Lys Met Arg Met Arg Arg Met Arg
385                 390                 395                 400

Arg Thr Arg Arg Lys Met Arg Arg Lys Met Ser Pro Ala Arg Pro Arg
                 405                 410                 415

Thr Ser Cys Arg Glu Ala Cys Leu Gln Gly Trp Thr Glu Ala
             420                 425                 430
```

<210> SEQ ID NO 7
<211> LENGTH: 66
<212> TYPE: PRT
<213> ORGANISM: Homo sapiens

<400> SEQUENCE: 7

```
Ala Ala Glu Lys Gln Met Lys Asp Lys Gln Asp Glu Glu Gln Arg Lys
1               5                   10                  15

Lys Lys Leu Arg Ile Lys Arg Met Met Met Thr Glu Met Lys Met Arg
            20                  25                  30

Thr Lys Lys Met Arg Arg Arg Lys Met Arg Lys Asn Pro Leu Ala Lys
        35                  40                  45

Pro Arg Met Ser Cys Arg Gly His Thr Thr Cys Leu Gln Gly Trp Thr
    50                  55                  60

Glu Ala
65
```

<210> SEQ ID NO 8
<211> LENGTH: 52
<212> TYPE: PRT
<213> ORGANISM: Homo sapiens

<400> SEQUENCE: 8

```
Ala Ala Glu Lys Leu Arg Ile Lys Arg Met Met Met Thr Glu Met Lys
1               5                   10                  15

Met Arg Thr Lys Lys Met Arg Arg Arg Lys Met Arg Lys Asn Pro Leu
            20                  25                  30

Ala Lys Pro Arg Met Ser Cys Arg Gly His Thr Thr Cys Leu Gln Gly
        35                  40                  45

Trp Thr Glu Ala
    50
```

<210> SEQ ID NO 9
<211> LENGTH: 18
<212> TYPE: DNA
<213> ORGANISM: Artificial Sequence
<220> FEATURE:
<223> OTHER INFORMATION: Forward Primer
<220> FEATURE:
<221> NAME/KEY: misc_feature
<222> LOCATION: (1)..(1)
<223> OTHER INFORMATION: FAM

<400> SEQUENCE: 9
ggcaaggccc tgaggtgt                                                     18

<210> SEQ ID NO 10
<211> LENGTH: 18
<212> TYPE: DNA
<213> ORGANISM: Artificial Sequence
<220> FEATURE:
<223> OTHER INFORMATION: Reverse Primer

<400> SEQUENCE: 10
ggcctcagtc cagccctg                                                     18

<210> SEQ ID NO 11
<211> LENGTH: 400
<212> TYPE: PRT
<213> ORGANISM: Homo sapiens

<400> SEQUENCE: 11

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
            210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
            290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
                340                 345                 350

Glu Glu Glu Asp Lys Lys Arg Lys Glu Glu Glu Glu Ala Glu Asp Lys
            355                 360                 365

Glu Asp Asp Glu Asp Lys Asp Glu Asp Glu Asp Glu Glu Asp Lys
            370                 375                 380

Glu Glu Asp Glu Glu Asp Val Pro Gly Gln Ala Lys Asp Glu Leu
385                 390                 395                 400

<210> SEQ ID NO 12
<211> LENGTH: 256
<212> TYPE: PRT
```

-continued

<213> ORGANISM: Homo sapiens

<400> SEQUENCE: 12

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Gly Ser Gly Asp Pro
            180                 185                 190

Ser Ile Tyr Ala Tyr Asp Asn Phe Gly Val Leu Gly Leu Asp Leu Trp
        195                 200                 205

Gln Val Lys Ser Gly Thr Ile Phe Asp Asn Phe Leu Ile Thr Asn Asp
    210                 215                 220

Glu Ala Tyr Ala Glu Glu Phe Gly Asn Glu Thr Trp Gly Val Thr Lys
225                 230                 235                 240

Ala Ala Glu Lys Gln Met Lys Asp Lys Gln Asp Glu Glu Gln Arg Leu
                245                 250                 255

<210> SEQ ID NO 13
<211> LENGTH: 320
<212> TYPE: PRT
<213> ORGANISM: Mus musculus

<400> SEQUENCE: 13

Asp Pro Ala Ile Tyr Phe Lys Glu Gln Phe Leu Asp Gly Asp Ala Trp
1               5                   10                  15

Thr Asn Arg Trp Val Glu Ser Lys His Lys Ser Asp Phe Gly Lys Phe
            20                  25                  30

Val Leu Ser Ser Gly Lys Phe Tyr Gly Asp Leu Glu Lys Asp Lys Gly
        35                  40                  45

Leu Gln Thr Ser Gln Asp Ala Arg Phe Tyr Ala Leu Ser Ala Lys Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Ser Gly Leu Asp Gln Lys Asp Met His Gly Asp Ser Glu Tyr Asn

```
              100                 105                 110
Ile Met Phe Gly Pro Asp Ile Cys Gly Pro Gly Thr Lys Lys Val His
            115                 120                 125
Val Ile Phe Asn Tyr Lys Gly Lys Asn Val Leu Ile Asn Lys Asp Ile
            130                 135                 140
Arg Ser Lys Asp Asp Glu Phe Thr His Leu Tyr Thr Leu Ile Val Arg
145                 150                 155                 160
Pro Asp Asn Thr Tyr Glu Val Lys Ile Asp Asn Ser Gln Val Glu Ser
                165                 170                 175
Gly Ser Leu Glu Asp Asp Trp Asp Phe Leu Pro Pro Lys Lys Ile Lys
                180                 185                 190
Asp Pro Asp Ala Ala Lys Pro Glu Asp Trp Asp Glu Arg Ala Lys Ile
            195                 200                 205
Asp Asp Pro Thr Asp Ser Lys Pro Glu Asp Trp Asp Lys Gly Gly Ser
            210                 215                 220
Gly Gly Glu Trp Lys Pro Arg Gln Ile Asp Asn Pro Asp Tyr Lys Gly
225                 230                 235                 240
Thr Trp Ile His Pro Glu Ile Asp Asn Pro Glu Tyr Ser Pro Asp Ala
                245                 250                 255
Asn Ile Tyr Ala Tyr Asp Ser Phe Ala Val Leu Gly Leu Asp Leu Trp
                260                 265                 270
Gln Val Lys Ser Gly Thr Ile Phe Asp Asn Phe Leu Ile Thr Asn Asp
            275                 280                 285
Glu Ala Tyr Ala Glu Glu Phe Gly Asn Glu Thr Trp Gly Val Thr Lys
            290                 295                 300
Ala Ala Glu Lys Gln Met Lys Asp Lys Gln Asp Glu Glu Gln Arg Leu
305                 310                 315                 320

<210> SEQ ID NO 14
<211> LENGTH: 256
<212> TYPE: PRT
<213> ORGANISM: Mus musculus

<400> SEQUENCE: 14

Asp Pro Ala Ile Tyr Phe Lys Glu Gln Phe Leu Asp Gly Asp Ala Trp
1               5                   10                  15
Thr Asn Arg Trp Val Glu Ser Lys His Lys Ser Asp Phe Gly Lys Phe
                20                  25                  30
Val Leu Ser Ser Gly Lys Phe Tyr Gly Asp Leu Glu Lys Asp Lys Gly
            35                  40                  45
Leu Gln Thr Ser Gln Asp Ala Arg Phe Tyr Ala Leu Ser Ala Lys Phe
50                  55                  60
Glu Pro Phe Ser Asn Lys Gly Gln Thr Leu Val Val Gln Phe Thr Val
65                  70                  75                  80
Lys His Glu Gln Asn Ile Asp Cys Gly Gly Gly Tyr Val Lys Leu Phe
                85                  90                  95
Pro Ser Gly Leu Asp Gln Lys Asp Met His Gly Asp Ser Glu Tyr Asn
            100                 105                 110
Ile Met Phe Gly Pro Asp Ile Cys Gly Pro Gly Thr Lys Lys Val His
            115                 120                 125
Val Ile Phe Asn Tyr Lys Gly Lys Asn Val Leu Ile Asn Lys Asp Ile
            130                 135                 140
Arg Ser Lys Asp Asp Glu Phe Thr His Leu Tyr Thr Leu Ile Val Arg
145                 150                 155                 160
```

```
Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Gly Ser Gly
            180                 185                 190

Ser Gly Pro Asp Ala Asn Ile Tyr Ala Tyr Asp Ser Phe Ala Val Leu
        195                 200                 205

Gly Leu Asp Leu Trp Gln Val Lys Ser Gly Thr Ile Phe Asp Asn Phe
    210                 215                 220

Leu Ile Thr Asn Asp Glu Ala Tyr Ala Glu Glu Phe Gly Asn Glu Thr
225                 230                 235                 240

Trp Gly Val Thr Lys Ala Ala Glu Lys Gln Met Lys Asp Lys Gln Asp
                245                 250                 255

<210> SEQ ID NO 15
<211> LENGTH: 65
<212> TYPE: PRT
<213> ORGANISM: Mus musculus

<400> SEQUENCE: 15

Ala Ala Glu Lys Gln Met Lys Asp Lys Gln Asp Glu Glu Gln Arg Leu
1               5                   10                  15

Lys Glu Glu Glu Glu Asp Lys Lys Arg Lys Glu Glu Glu Glu Ala Glu
                20                  25                  30

Asp Lys Glu Asp Asp Asp Asp Arg Asp Glu Asp Glu Asp Gly Glu Asp
            35                  40                  45

Glu Lys Glu Glu Asp Glu Glu Ser Pro Gly Gln Ala Lys Asp Glu
        50                  55                  60

Leu
65

<210> SEQ ID NO 16
<211> LENGTH: 24
<212> TYPE: PRT
<213> ORGANISM: Homo sapiens

<400> SEQUENCE: 16

Ala Ala Glu Lys Gln Met Lys Asp Lys Gln Asp Glu Glu Gln Arg Leu
1               5                   10                  15

Lys Glu Glu Arg Gly Gln Glu Ala
                20

<210> SEQ ID NO 17
<211> LENGTH: 25
<212> TYPE: PRT
<213> ORGANISM: Homo sapiens

<400> SEQUENCE: 17

Ala Ala Glu Lys Gln Met Lys Asp Lys Gln Asp Glu Glu Gln Arg Leu
1               5                   10                  15

Lys Glu Glu Gly Arg Gly Gln Glu Ala
                20                  25
```

COMPOUNDS TARGETING MUTANT CALRETICULIN

REFERENCE TO SUBMISSION OF A SEQUENCE LISTING AS A TEXT FILE

The Sequence Listing written in file 1253526_SL.txt created on May 24, 2021, 26,113 bytes, machine format IBM-PC, MS-Windows operating system, is hereby incorporated by reference in its entirety for all purposes.

TECHNICAL FIELD OF THE INVENTION

The present invention relates to compounds binding to calreticulin which selectively inhibit growth of CALR mutant cells and/or exhibit selective cytotoxicity towards CALR mutant cells, to pharmaceutical compositions comprising such compounds as well as to their use in treating diseases or conditions caused by or associated with a mutation of CALR, in particular myeloid malignancies, such as myeloproliferative neoplasms or myelodysplasia syndrome. The present invention also relates to screening assays allowing the identification of such compounds.

TECHNICAL BACKGROUND OF THE INVENTION

The classical myeloproliferative neoplasms (MPN) are clonal hematopoietic diseases which are driven by somatic mutations acquired by hematopoietic stem/progenitor cells. Three phenotypic driver mutations have been identified in MPN which include mutations in the JAK2, c-MPL and CALR genes, which all result in constitutive activation of the Janus kinase (JAK)/signal transducers and activators of transcription (STAT) pathway (Baxter E J et al., Lancet, 2005, 365(9464):1054-61; James C et al., Nature, 2005, 434(7037):1144-8; Kralovics R et al., N Engl J Med., 2005, 352(17):1779-90; Levine R L et al., Cancer Cell, 2005, 7(4):387-97; Scott L M et al., N Engl J Med., 2007, 356(5):459-68; Pikman Y et al., PLoS Med, 2006, 3(7): e270; Klampfl T et al., N Engl J Med., 2013, 369(25):2379-90; Nangalia J et al., N Engl J Med., 2013, 369(25):2391-405).

Calreticulin mutations occur at exon 9 of the CALR gene, leading to an alternative reading frame protein product at the C-terminus which eliminates most of the original negatively charged amino acids as well as the KDEL ER retention sequence and replaces them with positively charged sequences enriched with lysine and arginine residues. Deletion 52 bp (CALR del52) is the most frequent mutation which contributes to more than 50% of mutant CALR cases, followed by insertion 5 bp (CALR ins5) which accounts for over 30% of the cases (Klampfl T et al., N Engl J Med., 2013, 369(25):2379-90; Nangalia J et al., N Engl J Med., 2013, 369(25):2391-405).

Pathogenesis of mutant calreticulin has been investigated extensively since its discovery, and major progress has been made by a few research groups. The requirement of thrombopoietin receptor (MPL) in the oncogenic function of mutant calreticulin has been revealed in CALR mutant cell line models. For instance, cytokine independent growth of Ba/F3, UT-7 and 32D cells can be induced by CALR mutations only if MPL is expressed either endogenously or ectopically in these cell lines and the outgrowth is accompanied by the constitutive activation of downstream JAK-STAT pathways (Araki M et al., Blood, 2016, 127(10):1307-16; Chachoua I et al., Blood, 2016, 127(10):1325-35; Elf S et al., Cancer Discov., 2016, 6(4):368-81; Han L et al., J Hematol Oncol., 2016, 9(1):45; Marty C et al., Blood, 2016, 127(10):1317-24; Nivarthi H et al., Leukemia, 2016, 30(8): 1759-63). Transgenic mice models carrying CALR disease frameshift mutations develop essential thrombocythemia phenotype characterized by elevation of platelets count and increased number of megakaryocytes in the bone marrow (Marty C et al., Blood, 2016, 127(10):1317-24; Li J et al., Blood, 2018, 131(6):649-61; Shide K et al., Leukemia, 2017, 31(5):1136-44). Physical interactions between mutant calreticulin and MPL have also been detected by co-immunoprecipitation, and the novel C-terminal peptide generated by the mutation is essential to this interaction (Araki M et al., Blood, 2016, 127(10):1307-16; Elf S et al., Blood, 2018, 131(7):782-6). Further studies suggest that mutant calreticulins tend to form oligomers and might interact with MPL as a homomultimeric complex (Araki M et al., Leukemia, 2018, published online on June 26). On the other hand, the calreticulin-MPL interaction seems crucial but not sufficient for the activation of downstream oncogenic pathways, as the truncation of the last 36 amino acids at the mutant protein C-terminus abolishes its oncogenic activity but retains the interaction with MPL (Elf S et al., Blood, 2018, 131(7):782-6).

An important domain for mutant calreticulin to activate the downstream oncogenic pathway is the N-glycan binding domain/site located in the globular lectin part of the protein. This domain mediates the binding of N-glycosylated protein substrates with calreticulin in the endoplasmic reticulum lumen, as part of calreticulin's chaperone function facilitating proper protein folding (Peterson J R et al., Mol Biol Cell., 1995, 6(9):1173-84). Mutagenesis at the two amino acid residues which has been shown to abrogate glycan binding capacity of calreticulin also abolishes JAK-STAT pathway activation by mutant calreticulin (Chachoua I et al., Blood, 2016, 127(10):1325-35; Kapoor M et al., Biochemistry, 2004, 43(1):97-106). Also, as MPL is a glycosylated protein, it has been shown that MPL activates mutant calreticulin through its glycosylation sites at the extracellular domain (Chachoua I et al., Blood, 2016, 127(10):1325-35). High-resolution crystal structures of the globular domain of both human and mouse calreticulin have been published (Chouquet A et al., PLoS One, 2011, 6(3):e17886; Kozlov G et al., J Biol Chem., 2010, 285(49):38612-20).

It was an object of the present invention to identify small molecule compounds specifically binding to this region of calreticulin, which show selective cytotoxicity towards CALR mutant cell lines and significantly reduce the protein abundance of mutant calreticulin. It was a further object of the present invention to provide a screening assay allowing the identification of such compounds.

These and other objects are solved by the present invention which will be described in the following.

SUMMARY OF THE INVENTION

In a first aspect, the present invention provides a compound selected from the group consisting of a polyheterocyclic derivative having the general formula (I)

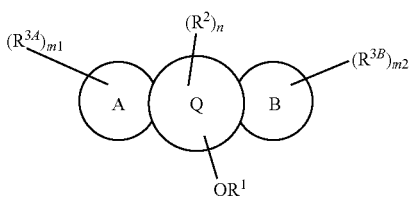

(I)

and solvates, salts, complexes, polymorphs, crystalline forms, racemic mixtures, diastereomers, enantiomers, tautomers, isotopically labeled forms, prodrugs, and combinations thereof, for use in therapy, wherein ring Q is a 9- or 8-membered bi- or monocyclic heterocyclyl which contains (i) one or two heteroatoms selected from N and O and (ii) a quaternary C atom to which the moiety —$OR^1$ is bound;

each of rings A and B is fused to ring Q and is independently selected from benzo, pyridino, pyrimidino, pyridazino, pyrazino, and hydrated forms thereof;

$R^1$ is selected from the group consisting of H, alkyl, alkenyl, alkynyl, cycloalkyl, aryl, heterocyclyl, heteroaryl, —$S(O)_{1-2}OR^{11}$, —$S(O)_{1-2}N(R^{12})(R^{13})$, —$P(O)(OR^{11})_2$, —$C(=X)R^{11}$, and —$C(=X)XR^{11}$, wherein each of the alkyl, alkenyl, alkynyl, cycloalkyl, aryl, heterocyclyl, and heteroaryl groups is optionally substituted with one or more independently selected $R^{30}$;

each $R^2$ is independently selected from the group consisting of alkyl, alkenyl, alkynyl, cycloalkyl, aryl, heterocyclyl, heteroaryl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$P(O)(OR^{11})_2$, —$OP(O)(OR^{11})_2$, —$C(=X)R^{11}$, —$C(=X)XR^{11}$, —$XC(=X)R^{11}$, and —$XC(=X)XR^{11}$, and/or any two $R^2$ which are bound to the same carbon atom of ring Q may join together to form =$X^Q$, wherein each of the alkyl, alkenyl, alkynyl, cycloalkyl, aryl, heterocyclyl, and heteroaryl groups is optionally substituted with one or more independently selected $R^{30}$;

each of $R^{3A}$ and $R^{3B}$ is independently selected from the group consisting of alkyl, alkenyl, alkynyl, cycloalkyl, aryl, heterocyclyl, heteroaryl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$P(O)(OR^{11})_2$, —$OP(O)(OR^{11})_2$, —$C(=X)R^{11}$, —$C(=X)XR^{11}$, —$XC(=X)R^{11}$, and —$XC(=X)XR^{11}$, and/or any two $R^{3A}$ which are bound to the same carbon atom of ring A may join together to form =$X^A$ and/or any two $R^{3B}$ which are bound to the same carbon atom of ring B may join together to form =$X^B$ and/or any two $R^{3A}$ on adjacent ring atoms of ring A may join together with the adjacent ring atoms of ring A to form a ring which is optionally substituted with one or more independently selected $R^{30}$ and/or any two $R^{3B}$ on adjacent ring atoms of ring B may join together with the adjacent ring atoms of ring B to form a ring which is optionally substituted with one or more independently selected $R^{30}$, wherein each of the alkyl, alkenyl, alkynyl, cycloalkyl, aryl, heterocyclyl, and heteroaryl groups is optionally substituted with one or more independently selected $R^{30}$;

n is 0, 1, 2, 3, or 4;

each of m1 and m2 is independently 0, 1, 2, 3, or 4;

X is independently selected from O, S, and $N(R^{14})$;

each of $X^Q$, $X^A$ and $X^B$ is independently selected from O, S, and NH;

$R^{11}$ is independently selected from the group consisting of H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$;

each of $R^{12}$ and $R^{13}$ is independently selected from the group consisting of H, alkyl, alkenyl, alkynyl, cycloalkyl, aryl, heteroaryl, and heterocyclyl, or $R^{12}$ and $R^{13}$ may join together with the nitrogen atom to which they are attached to form the group —$N=CR^{15}R^{16}$, wherein each of the alkyl, alkenyl, alkynyl, cycloalkyl, aryl, heteroaryl, and heterocyclyl groups is optionally substituted with one or more independently selected $R^{30}$;

$R^{14}$ is independently selected from the group consisting of H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more independently selected $R^{30}$;

each of $R^{15}$ and $R^{16}$ is independently selected from the group consisting of H, alkyl, alkenyl, alkynyl, cycloalkyl, aryl, heteroaryl, heterocyclyl, and —$NH_yR^{20}_{2-y}$, or $R^{15}$ and $R^{16}$ may join together with the atom to which they are attached to form a ring which is optionally substituted with one or more independently selected $R^{30}$, wherein each of the alkyl, alkenyl, alkynyl, cycloalkyl, aryl, heteroaryl, and heterocyclyl groups is optionally substituted with one or more independently selected $R^{30}$;

y is an integer from 0 to 2;

$R^{20}$ is independently selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, —$C(R^{71})$=(heterocyclylidene), halogen, —CN, azido, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-2}OR^{71}$, —$NR^{71}S(O)_{1-2}N(R^{72})(R^{73})$, —$OP(O)(OR^{71})_2$, —$C(=X^1)R^{71}$, —$C(=X^1)X^1R^{71}$, —$X^1C(=X^1)R^{71}$, and —$X^1C(=X^1)X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, heterocyclyl, and heterocyclylidene groups being a $1^{st}$ level substituent is optionally substituted by one or more $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, azido, —$NO_2$, —$OR^{81}$, —$N(R^{82})(R^{83})$, —$S(O)_{0-2}R^{81}$, —S(O)$_{1-2}$OR$^{81}$, —S(O)$_{1-2}$R$^{81}$, —OS(O)$_{1-2}$OR$^{81}$, —S(O)$_{1-2}$N(R$^{82}$)(R$^{83}$), —OS(O)$_{1-2}$N(R$^{82}$)(R$^{83}$), —NR$^{81}$S(O)$_{1-2}$R$^{81}$, —NR$^{81}$S(O)$_{1-2}$OR$^{81}$, —NR$^{81}$S(O)$_{1-2}$N(R$^{82}$)(R$^{83}$), —OP(O)(OR$^{81}$)$_2$, —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, and/or any two 2$^{nd}$ level substituents which are bound to the same carbon atom of a cycloalkyl or heterocyclyl group being a 1$^{st}$ level substituent may join together to form =X$^2$ and/or any two 2$^{nd}$ level substituents which are bound to the same carbon atom of a cycloalkyl or heterocyclyl group being a 1$^{st}$ level substituent may join together to form =C(R$^{81}$)(3- to 14-membered aryl) or =C(R$^{81}$)(3- to 14-membered heteroaryl), wherein each of the C$_{1-6}$ alkyl, C$_{2-6}$ alkenyl, C$_{2-6}$ alkynyl, 3- to 14-membered aryl (including the 3- to 14-membered aryl of the =C(R$^{81}$)(3- to 14-membered aryl) group), 3- to 14-membered heteroaryl (including the 3- to 14-membered heteroaryl of =C(R$^{81}$)(3- to 14-membered heteroaryl) group), 3- to 14-membered cycloalkyl, 3- to 14-membered heterocyclyl groups being a 2$^{nd}$ level substituent is optionally substituted with one or more 3$^{rd}$ level substituents, wherein said 3$^{rd}$ level substituent is, in each case, independently selected from the group consisting of C$_{1-3}$ alkyl, halogen, —CF$_3$, —CN, azido, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, and/or any two 3$^{rd}$ level substituents which are bound to the same carbon atom of a 3- to 14-membered cycloalkyl or heterocyclyl group being a 2$^{nd}$ level substituent may join together to form =O, =S, =NH, or =N(C$_{1-3}$ alkyl);

wherein

R$^{71}$, R$^{72}$, and R$^{73}$ are independently selected from the group consisting of H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl, wherein each of the C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —OCF$_3$, =O, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;

R$^{81}$, R$^{82}$, and R$^{83}$ are independently selected from the group consisting of H, C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl, wherein each of the C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —OCF$_3$, =O, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl; and X$^1$ and X$^2$ are independently selected from O, S, and N(R$^{84}$), wherein R$^{84}$ is —H or C$_{1-3}$ alkyl.

In one embodiment of the first aspect, ring Q is a 9-membered bicyclic heterocyclyl or an 8-membered monocyclic heterocyclyl, each of which is optionally substituted with one, two, three or four independently selected R$^2$. For example, ring Q may be a 9-membered bicyclic heterocyclyl having a formula selected from the group consisting of:

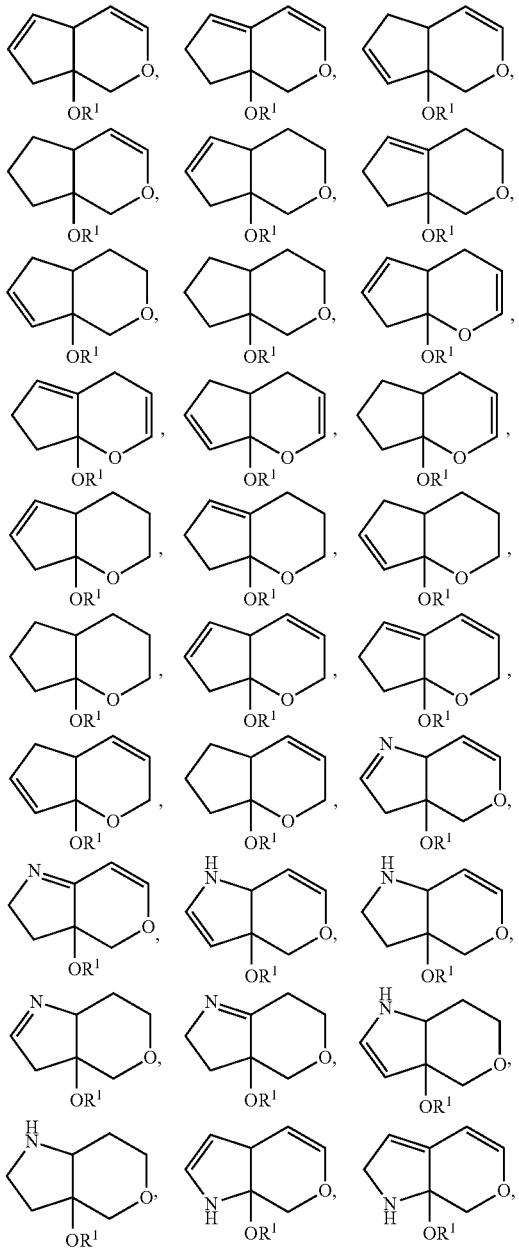

-continued

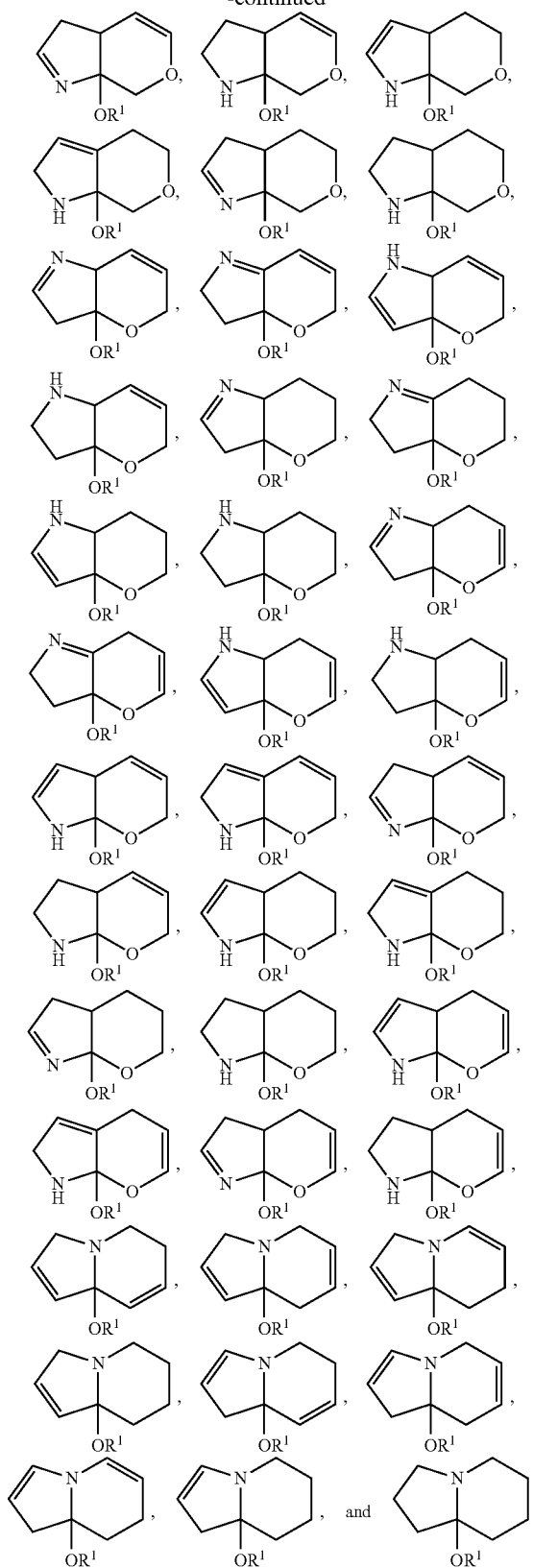

each of which is optionally substituted with one, two, three, or four independently selected $R^2$. In one embodiment, ring Q has a formula selected from the group consisting of:

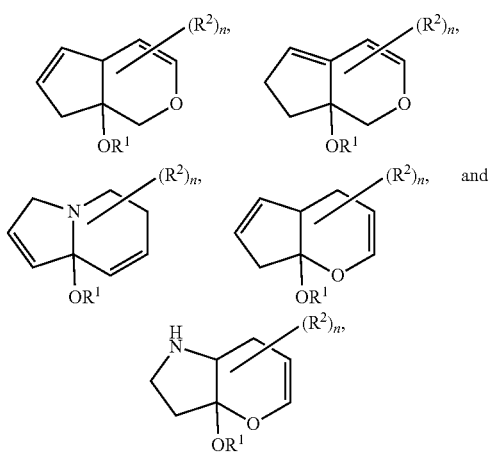

wherein n is 0, 1, or 2 (such as 0 or 2); and each R is independently selected from the group consisting of $C_{1-3}$ alkyl, halogen, —CN, —OH, —O($C_{1-3}$ alkyl), —NH$_2$, —NH($C_{1-3}$ alkyl), and —N($C_{1-3}$ alkyl)$_2$, or any two $R^2$ which are bound to the same carbon atom of ring Q may join together to form =O. In one preferred embodiment, ring Q has a formula selected from the group consisting of:

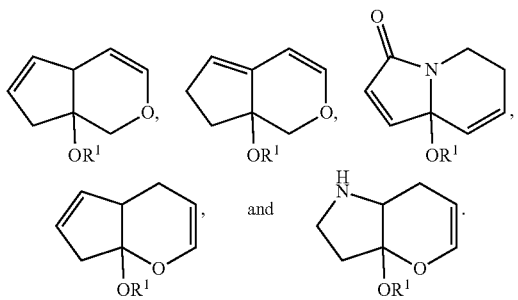

In one embodiment of the first aspect, each of rings A and B is independently selected from benzo, pyridino, pyrimidino, and hydrated forms thereof, wherein the sum of m1 and m2 is 1 to 7, such as 1, 2, 3, 4, 5, or 6.

In one embodiment of the first aspect, the compound has one of the following formulas:

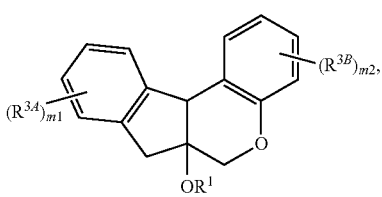

(VIa)

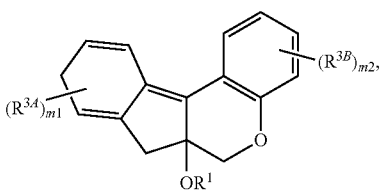

(VIb)

-continued

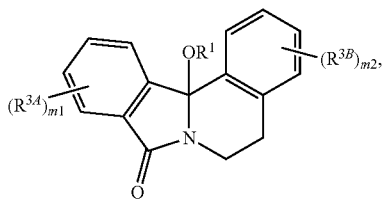
(VIc)

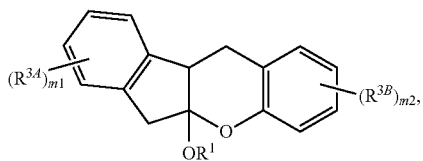
(VId)

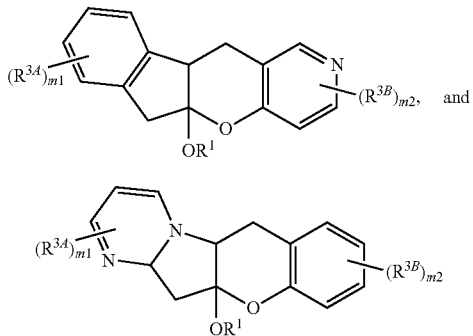
(VIe)

(VIf)

In an alternative embodiment of the first aspect, ring Q is a 8-membered monocyclic heterocyclyl having a formula selected from the group consisting of:

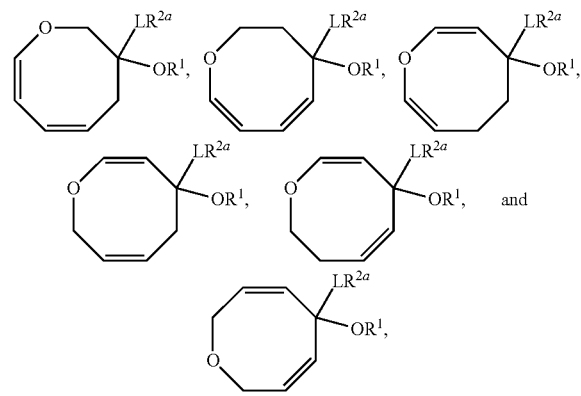

wherein L is selected from the group consisting of $C_{1-6}$ alkylene, $C_{2-6}$ alkenylene, $C_{2-6}$ alkynylene, and $—(CH_2)_m—[Y—(CH_2)_n]_o—$, wherein m is an integer between 1 and 6, n is an integer between 0 and 3, o is an integer between 1 and 3, wherein if n is 0 then o is 1; Y is independently selected from O, S, and $—N(R^{13})—$; and each of the $C_{1-6}$ alkylene, $C_{2-6}$ alkenylene, $C_{2-6}$ alkynylene, $—(CH_2)_m—$, and $—(CH_2)_n—$ groups is optionally substituted with one or two independently selected $R^{30}$; $R^{2a}$ is selected from the group consisting of alkenyl, alkynyl, cycloalkyl, aryl, heterocyclyl, heteroaryl, halogen, —CN, azido, $—NO_2$, $—OR^{11}$, $—N(R^{12})(R^{13})$, $—N(R^{11})(OR^{11})$, $—S(O)_{0-2}R^{11}$, $—S(O)_{1-2}OR^{11}$, $—OS(O)_{1-2}R^{11}$, $—OS(O)_{1-2}OR^{11}$, $—S(O)_{1-2}N(R^{12})(R^{13})$, $—OS(O)_{1-2}N(R^{12})(R^{13})$, $—N(R^{11})S(O)_{1-2}R^{11}$, $—NR^{11}S(O)_{1-2}OR^{11}$, $—NR^{11}S(O)_{1-2}N(R^{12})(R^{13})$, $—P(O)(OR^{11})_2$, $—OP(O)(OR^{11})_2$, $—C(=X)R^{11}$, $—C(=X)XR^{11}$, $—XC(=X)R^{11}$, and $—XC(=X)XR^{11}$, wherein each of the alkyl, alkenyl, alkynyl, cycloalkyl, aryl, heterocyclyl, and heteroaryl groups is optionally substituted with one or more independently selected $R^{30}$; and each of the above 8-membered monocyclic heterocyclyl structures is optionally substituted with one, two, or three independently selected $R^2$. For example, in this alternative embodiment of the first aspect ring Q may have the following formula:

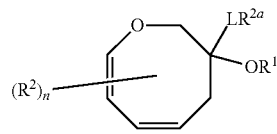

wherein L is $C_{1-3}$ alkylene (such as methylene); each $R^2$ is independently selected from the group consisting of $C_{1-3}$ alkyl, halogen, —CN, —OH, $—O(C_{1-3}$ alkyl), $—NH_2$, $—NH(C_{1-3}$ alkyl), and $—N(C_{1-3}$ alkyl)$_2$, or any two $R^2$ which are bound to the same carbon atom of ring Q may join together to form =O; and n is 0, 1, or 2. In one embodiment, n is 0 or 2, preferably 0. In one embodiment, $R^{2a}$ is selected from the group consisting of halogen, —CN, azido, $—NO_2$, —OH, $—O(C_{1-3}$ alkyl), $—NH_2$, $—NH(C_{1-3}$ alkyl), $—N(C_{1-3}$ alkyl)$_2$, $—OP(O)(OR^{11})_2$, and $—OC(=O)R^{11}$.

In the alternative embodiment of the first aspect, each of rings A and B may be independently selected from benzo, pyridino, pyrimidino, and hydrated forms thereof, wherein the sum of m1 and m2 is 1 to 7, such as 1, 2, 3, 4, 5, or 6. Preferably, each of rings A and B is benzo, wherein each of m1 and m2 is 1, 2, 3, or 4, such as 1, 2, or 3.

In the alternative embodiment of the first aspect, the compound may have the following formula:

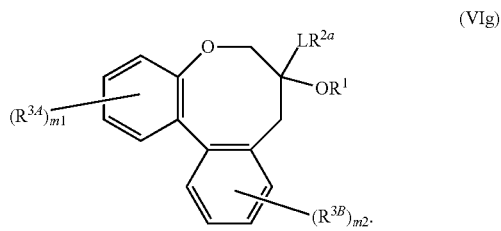
(VIg)

In one embodiment of the first aspect (irrespective of whether ring Q is a 9-membered bicyclic heterocyclyl or an 8-membered monocyclic heterocyclyl each of which may be substituted as specified above or below), each of $R^{3A}$ and $R^{3B}$ is independently selected from the group consisting of $C_{1-6}$ alkyl, $C_{2-6}$ alkenyl, $C_{2-6}$ alkynyl, $C_{3-7}$ cycloalkyl, $C_{6-10}$ aryl, 3- to 7-membered heterocyclyl, 3- to 7-membered heteroaryl, halogen, —CN, $—NO_2$, —OH, $—O(C_{1-6}$ alkyl), $—CF_3$, $—OCF_3$, $—O(CH_2)_{0-2}(C_{3-7}$ cycloalkyl), $—O(CH_2)_{0-2}(C_{6-10}$ aryl), $—O(CH_2)_{0-2}(3$- to 7-membered heteroaryl), $—O(CH_2)_{0-2}(3$- to 7-membered heterocyclyl), $—NH_2$, $—NH(C_{1-6}$ alkyl), $—N(C_{1-6}$ alkyl)$_2$, $—NHS(O)_2(C_{1-6}$ alkyl), $—S(O)_2NH_{2-z}(C_{1-6}$ alkyl)$_z$, $—C(=O)(C_{1-6}$ alkyl), —C(=O)OH, $—OC(=O)R^{11a}$, $—C(=O)O(C_{1-6}$ alkyl), $—C(=O)NH_{2-z}(C_{1-6}$ alkyl)$_z$, —NHC(=O)H, $—NHC(=O)(C_{1-6}$ alkyl), $—NHC(=NH)NH_{2-z}(C_{1-6}$ alkyl)$_z$, $—N(C_{1-6}$ alkyl)C(=NH)NH$_{2-z}(C_{1-6}$ alkyl)$_z$, and $—(C_{1-6}$ alkylene)OH, wherein z is 0, 1, or 2; and $R^{11a}$ is selected from the group consisting of $C_{1-6}$ alkyl, $C_{3-7}$ cycloalkyl, $C_{6-10}$ aryl, 3- to 7-membered heterocyclyl, and 3- to 7-membered heteroaryl, and is optionally substituted with one or two independently selected $R^{30}$; and/or any two $R^{3A}$ which are bound to the same carbon atom of ring A may join together to form =O and/or any two $R^{3B}$ which are bound to the same carbon atom of ring B may join together to form =O and/or any two $R^{3A}$ on adjacent ring atoms of ring A may join together with the adjacent ring atoms of ring A to form a 5- to 6-membered ring which is optionally substituted with one, two or three moieties independently selected from the group consisting of —OH, methyl, ethyl, —OCH$_3$, —SCH$_3$, and —NH$_{2-z}$(CH$_3$)$_z$ and/or any two $R^{3B}$ on adjacent ring atoms of ring B may join together with the adjacent ring atoms of ring B to form a 5- to 6-membered ring which is optionally substituted with one, two or three moieties independently selected from the group consisting of —OH, methyl, ethyl, —OCH$_3$, —SCH$_3$, and —NH$_{2-z}$(CH$_3$)$_z$. For example, each of $R^{3A}$ and $R^{3B}$ may be independently selected from the group consisting of $C_{1-4}$ alkyl, halogen, —CN, —NO$_2$, —OH, —O($C_{1-3}$ alkyl), —O(CH$_2$)$_{1-2}$($C_{3-7}$ cycloalkyl), —O(CH$_2$)$_{1-2}$($C_{6-10}$ aryl), —O(CH$_2$)$_{1-2}$ (3- to 7-membered heteroaryl), —O(CH$_2$)$_{1-2}$(3- to 7-membered heterocyclyl), —NH$_2$, —NH($C_{1-3}$ alkyl), —N($C_{1-3}$ alkyl)$_2$, —OC(=O)(R$^{11a}$), —C(=O)NH$_{2-z}$($C_{1-6}$ alkyl)$_z$, —NHC(=O)H, —NHC(=O)($C_{1-6}$ alkyl), and —($C_{1-3}$ alkylene) OH, wherein z is 0, 1, or 2; and $R^{11a}$ is selected from the group consisting of $C_{1-3}$ alkyl and phenyl, each of which is optionally substituted with one or two independently selected $R^{30}$; and/or any two $R^{3A}$ which are bound to the same carbon atom of ring A may join together to form =O and/or any two $R^{3B}$ which are bound to the same carbon atom of ring B may join together to form =O and/or any two $R^{3A}$ on adjacent ring atoms of ring A may join together with the adjacent ring atoms of ring A to form a 5- to 6-membered heterocyclyl which is optionally substituted with one, two or three moieties independently selected from the group consisting of —OH, methyl, ethyl, —OCH$_3$, and —NH$_{2-z}$(CH$_3$)$_z$ and/or any two $R^{3B}$ on adjacent ring atoms of ring B may join together with the adjacent ring atoms of ring B to form a 5- to 6-membered heterocyclyl which is optionally substituted with one, two or three moieties independently selected from the group consisting of —OH, methyl, ethyl, —OCH$_3$, and —NH$_{2-z}$(CH$_3$)$_z$.

In one embodiment of the first aspect (irrespective of whether ring Q is a 9-membered bicyclic heterocyclyl or an 8-membered monocyclic heterocyclyl each of which may be substituted as specified above), $R^1$ is selected from the group consisting of H, —P(O)(OH)$_z$(OR$^{15}$)$_{2-z}$, and —C(=O)R$^{85}$, wherein $R^{85}$ is selected from the group consisting of $C_{1-6}$ alkyl, $C_{3-7}$ cycloalkyl, $C_{6-10}$ aryl, $C_{6-10}$ halogenaryl, 3- to 7-membered heterocyclyl, and 3- to 7-membered heteroaryl; and z is 0, 1, or 2. For example, $R^1$ may be selected from the group consisting of H, —C(=O)($C_6$ halogenaryl), and —C(=O)($C_{1-3}$ alkyl).

In a second aspect, the present invention provides a pharmaceutical composition comprising a compound as defined in the first aspect and one or more pharmaceutically acceptable excipients. In one embodiment, the pharmaceutical composition comprises at least one additional therapeutic agent.

In a third aspect, the present invention provides the compound of the first aspect or the pharmaceutical composition of the second aspect for use in a method of treating a disease or condition caused by or associated with a mutation of CALR. In one embodiment, the disease or condition is a myeloid malignancy, such as a myeloproliferative neoplasm or a myelodysplasia syndrome. Preferably, the myeloproliferative neoplasm is selected from the group consisting of prefibrotic myelofibrosis (pre-PMF), primary myelofibrosis (PMF) and essential thrombocythemia (ET). In one embodiment, the myeloproliferative neoplasm is primary myelofibrosis (PMF). The myelodysplastic syndrome may be refractory anemia with ringed sideroblasts and thrombocythemia (RARS-T).

In a fourth aspect, the present invention provides a compound selected from the compounds shown in Table 1b and solvates, salts, complexes, polymorphs, crystalline forms, racemic mixtures, diastereomers, enantiomers, tautomers, isotopically labeled forms, prodrugs, and combinations thereof.

In a fifth aspect, the present invention provides a use of a compound of the first aspect in a method of screening for compounds that selectively inhibit growth of CALR mutant cells and/or exhibit selective cytotoxicity towards CALR mutant cells.

In a sixth aspect, the present invention provides a method of screening for compounds that are suitable for treating a disease or condition caused by or associated with a mutation of CALR, said method comprising the steps:
  (a) providing a compound;
  (b) testing the compound for binding to one or more glycan-, Ca$^{2+}$—and/or ATP-binding sites of calreticulin, and
  (c) testing the compound for selective inhibition of growth of CALR mutant cells and/or selective cytotoxicity towards CALR mutant cells,
wherein a compound that (i) binds to one or more glycan-, Ca$^{2+}$—and/or ATP-binding sites of calreticulin and (ii) selectively inhibits growth of CALR mutant cells and/or exhibits selective cytotoxicity towards CALR mutant cells is identified as a compound that is suitable for treating a disease or condition caused by or associated with a mutation of CALR. In one embodiment, the compound is tested for binding to the N-glycan binding site of calreticulin. In one embodiment of the sixth aspect, step (b) is performed in silico. In one embodiment of the sixth aspect, the disease or condition is as defined in the third aspect.

Further aspects of the invention are disclosed herein.

77), 3O0W (Kozlov G et al., J Biol Chem., 2010, 285(49): 38612-20); calreticulin P-domain: 1HHN (Ellgaard L et al., Proc Natl Acad Sci USA, 2001, 98(6):3133-8). The SEQ ID NOs of the amino acid sequences shown in the figure are as follows (top to bottom): CALR (human wild-type; residues 18-417)-SEQ ID NO: 11; 3POW-SEQ ID NO: 12; 3RG0-SEQ ID NO: 13; 3O0W-SEQ ID NO: 14.

Figure 4:
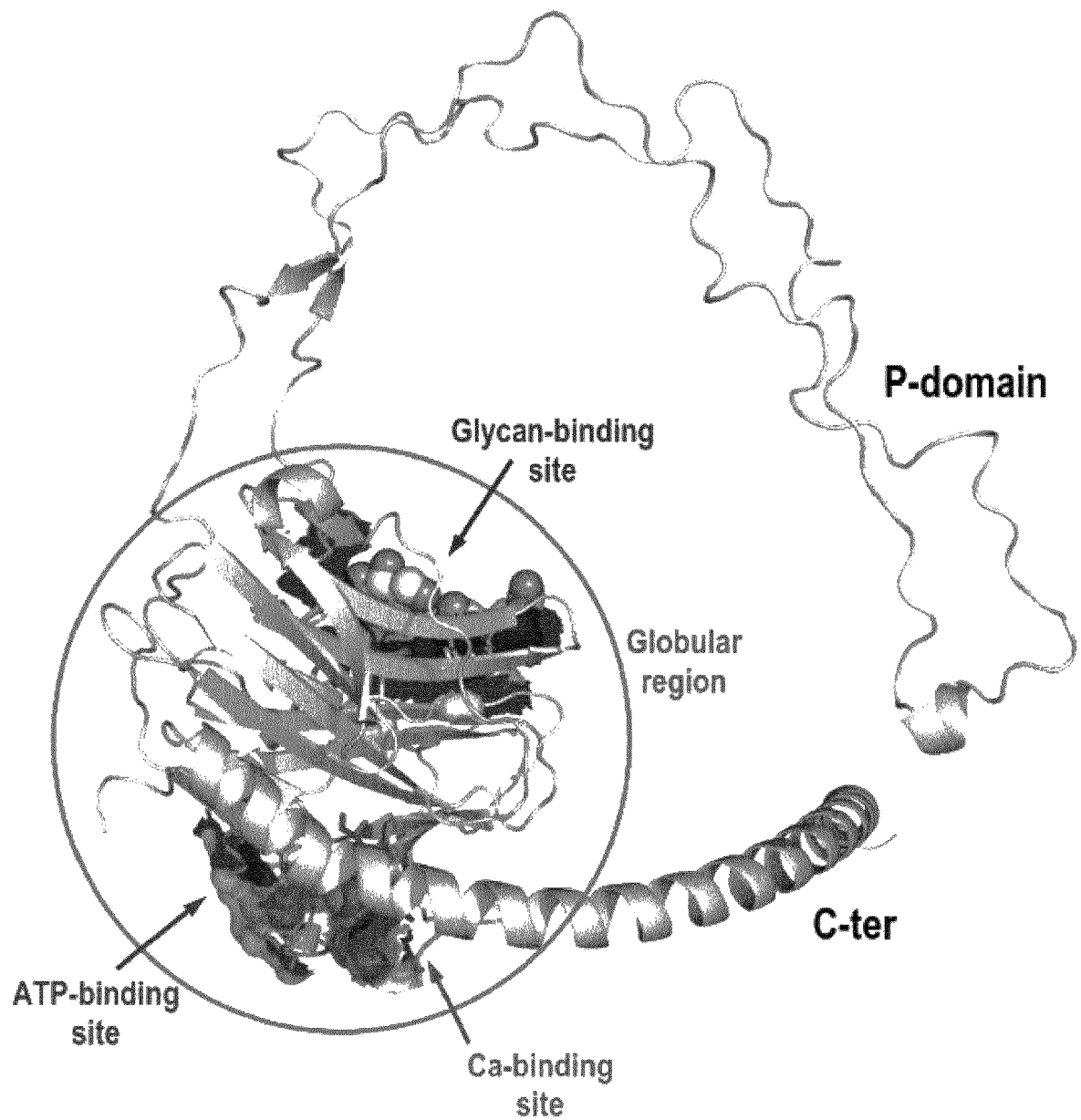

FIG. 4: Structural model of human calreticulin. Arrows indicate the positions of experimentally identified interaction sites: the glycan binding site, the ATP-binding site and the main Ca2+ binding site.

Figure 5:
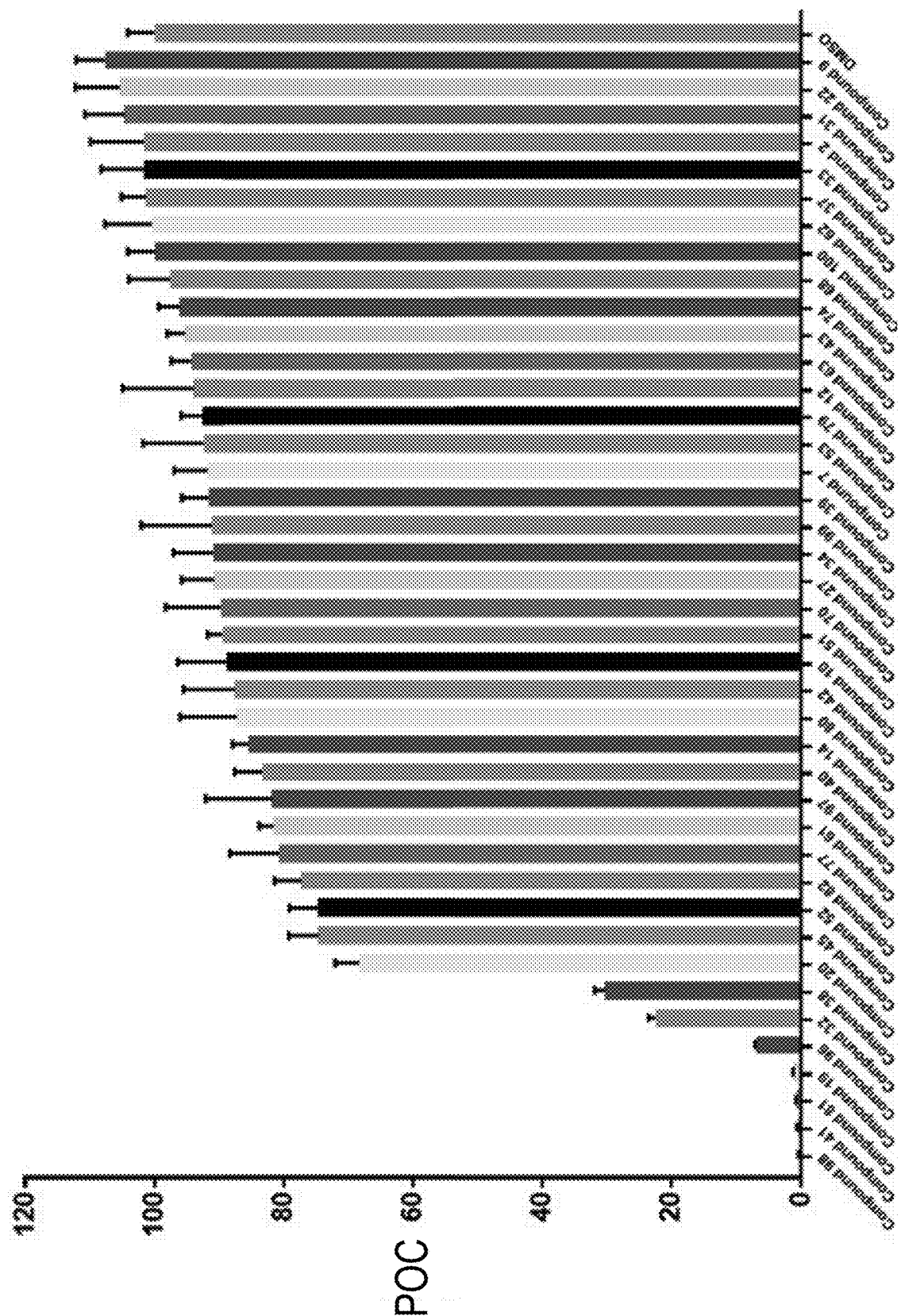

FIG. 5: Single dose cytotoxic screen of docking library compounds. Ba/F3-MPL CALR del79/WT was treated with each compound at a concentration of 10 uM for 72 h. All luminescent signals were normalized to the DMSO control to calculate the percentage of control (POC). Error bars represent the standard deviation calculated from 3 replicates.

Figure 6:
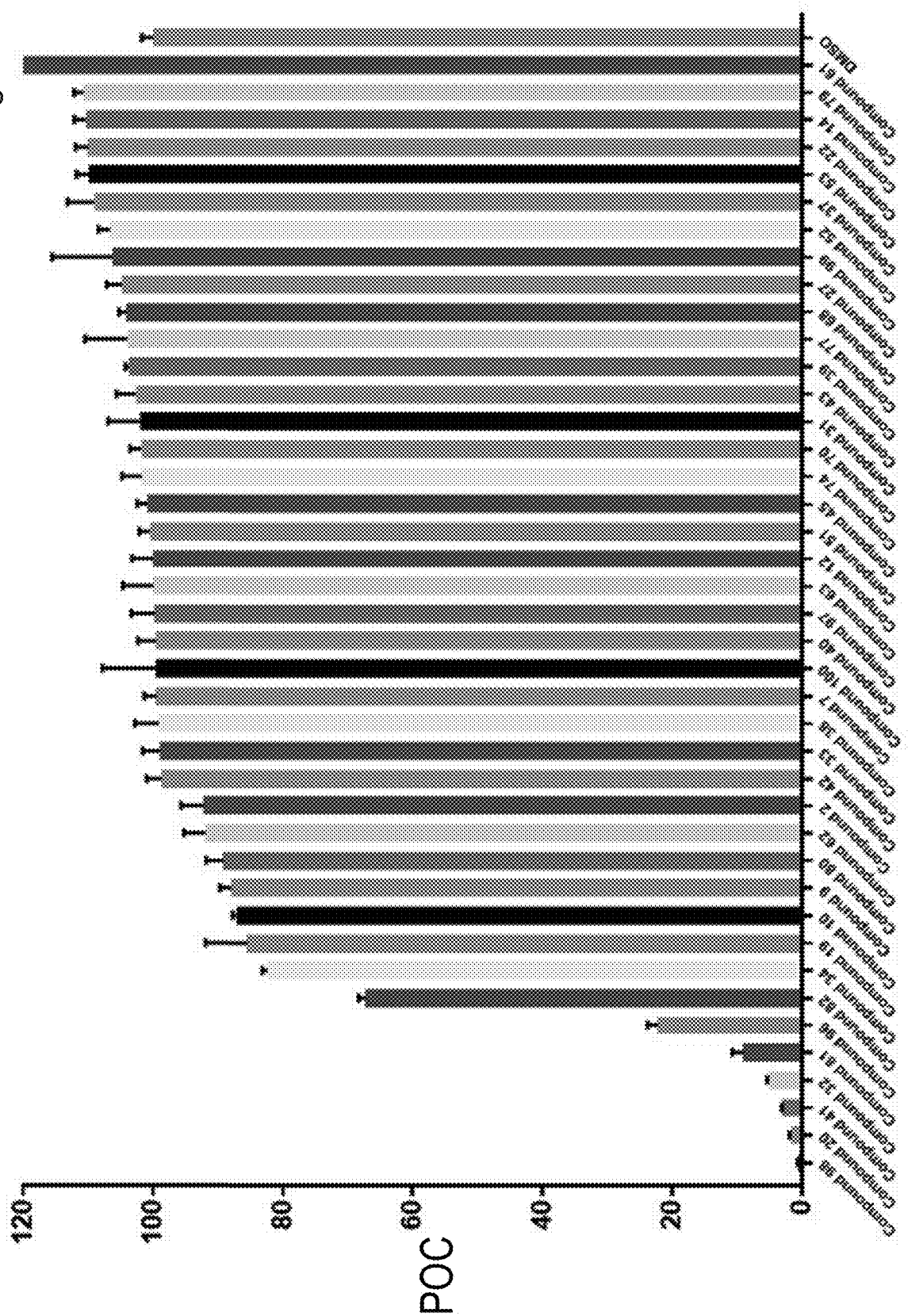

FIG. 6: Single dose cytotoxic screen of docking library compounds. UT-7-TPO CALR del61/WT was treated with each compound at a concentration of 10 uM for 72 h. All luminescent signals were normalized to the DMSO control to calculate the percentage of control (POC). Error bars represent the standard deviation calculated from 3 replicates.

Figure 7:
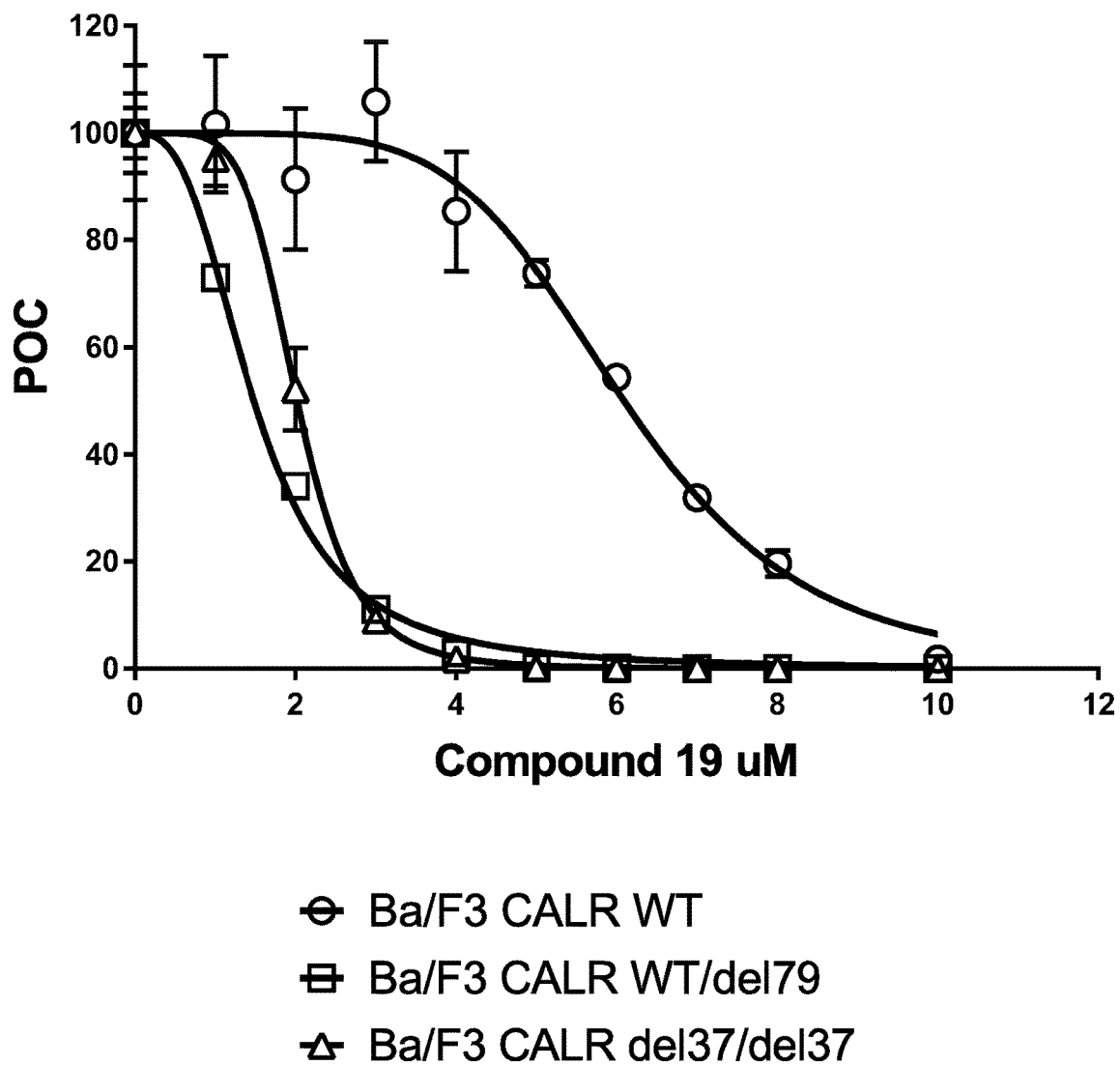

FIG. 7: Dose response test of Compound 19 (hematoxylin; A-1) in Ba/F3-MPL cell lines. One heterozygous CALR mutant cell line and one homozygous CALR mutant cell line were used in comparison to the wild-type control. Wild-type cell lines were grown in 1% TPO conditioned media, and mutant cell lines were grown without the cytokine. All drug treatment groups contained equal amounts of DMSO. Error bars represent the standard deviation.

Figure 8:
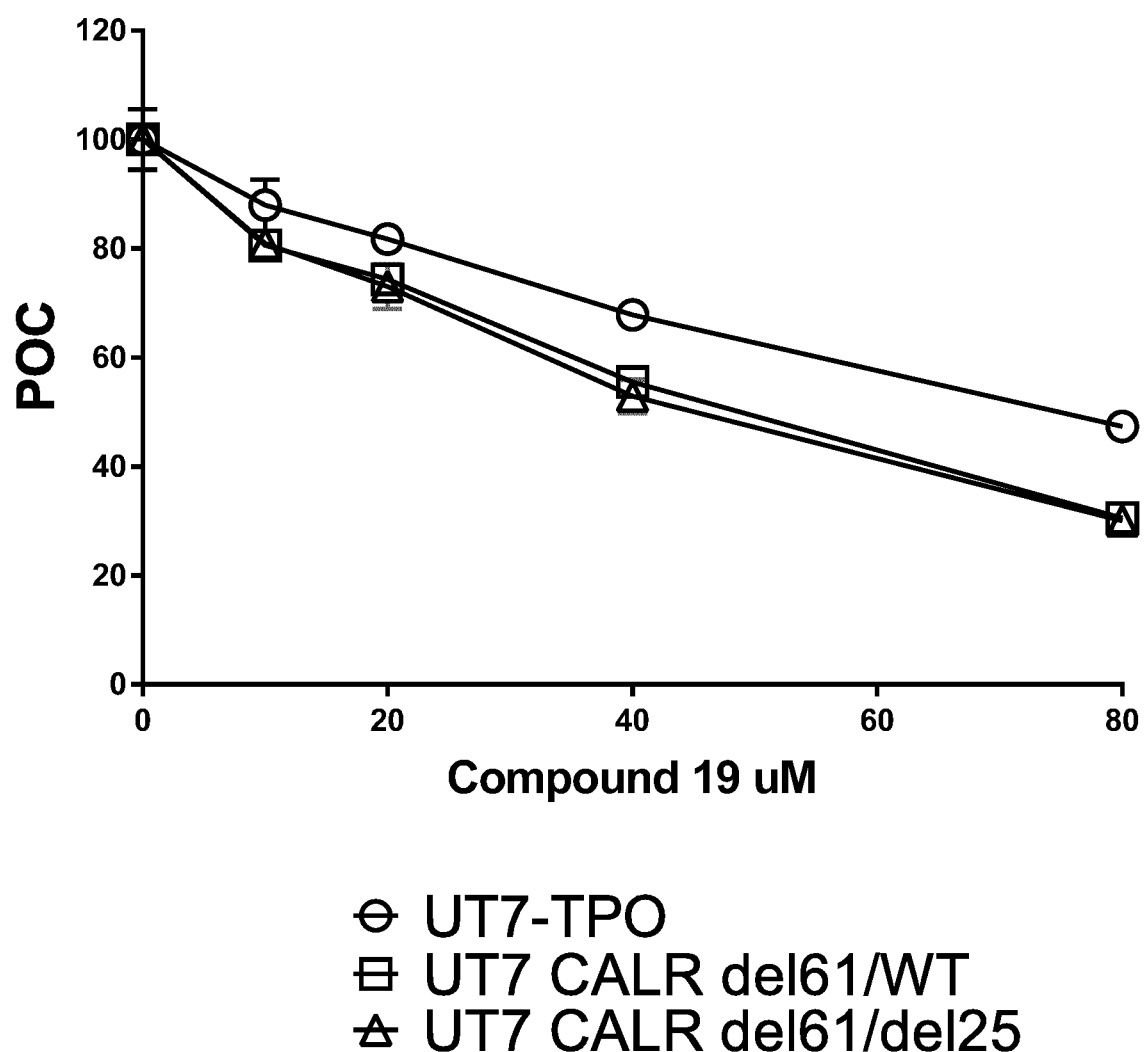

FIG. 8: Dose response test of Compound 19 (hematoxylin; A-1) in UT-7-TPO cell lines. One heterozygous CALR mutant cell line and one homozygous CALR mutant cell line were used in comparison to wild-type control. Wild-type cell lines were grown in 1% TPO conditioned media, and mutant cell lines were grown without the cytokine. All drug treatment groups contained equal amount of DMSO. Error bars represent the standard deviation.

Figure 9:
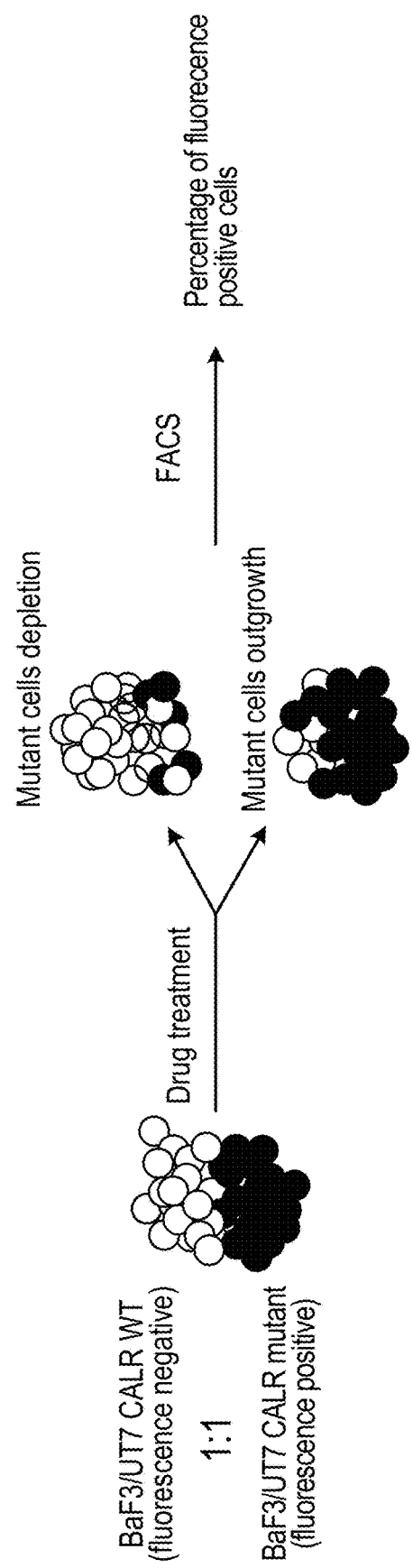

FIG. 9: Schematic diagram of the workflow of a two-color competition assay.

Figure 10:
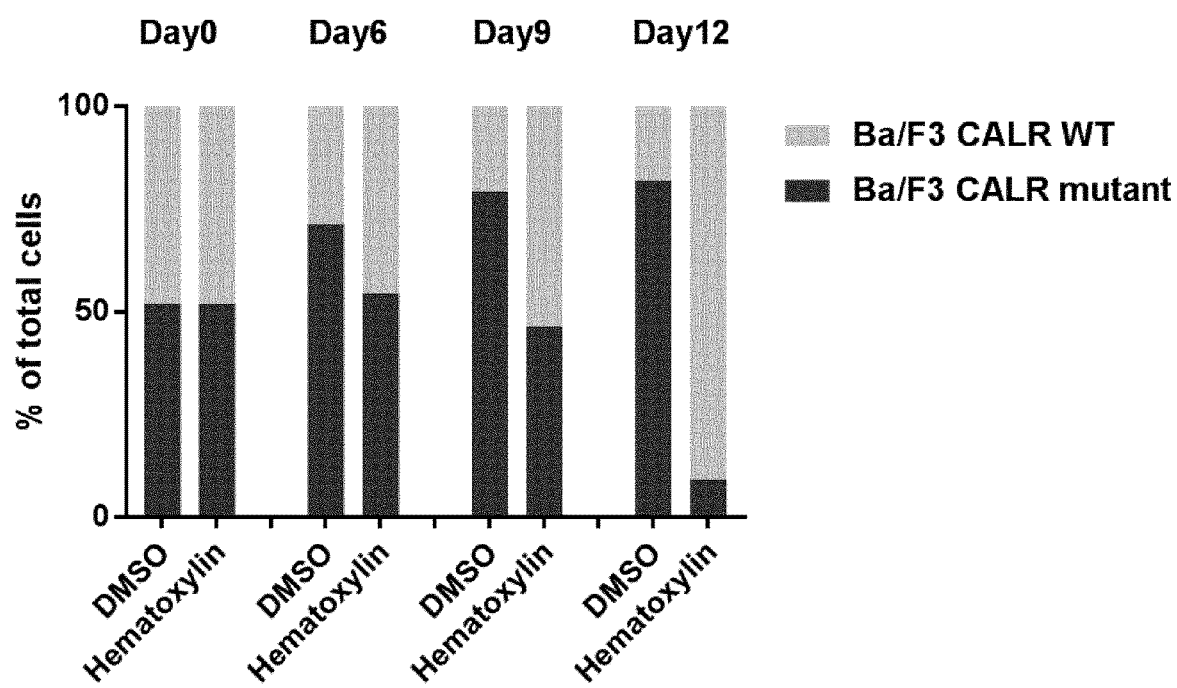

FIG. 10: Competition assay of hematoxylin treatment in Ba/F3-MPL cells. Ba/F3-MPL CALR WT (GFP negative) and Ba/F3-MPL CALR del52/WT (GFP positive) cells were mixed and underwent hematoxylin treatment for 12 days. Drug and cytokine were refreshed every 3 days. Percentage of GFP positive cells were recorded by FACs.

Figure 11:
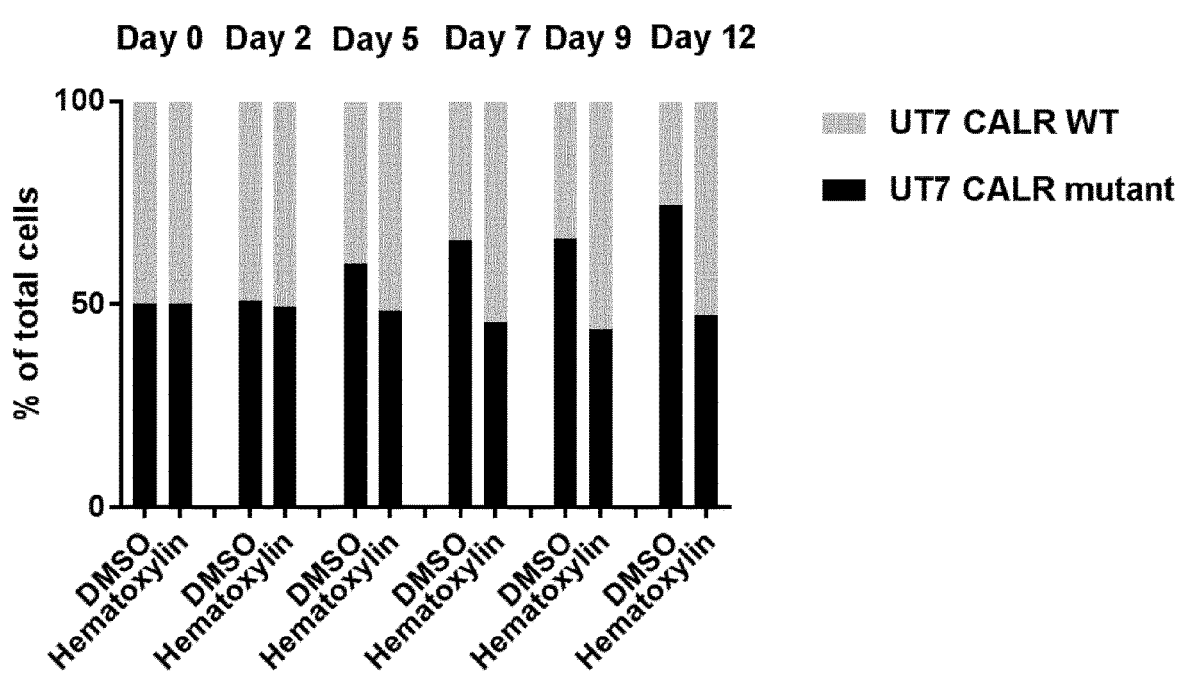

FIG. 11: Competition assay of hematoxylin treatment in UT-7-TPO cells. UT-7-TPO CALR WT (mCherry negative) and UT-7-TPO CALR del58/WT (mCherry positive) cells were mixed and underwent hematoxylin treatment for 12 days. Drug and cytokine were refreshed every 3 days. Percentage of mCherry positive cells were recorded by FACs.

Figure 12:
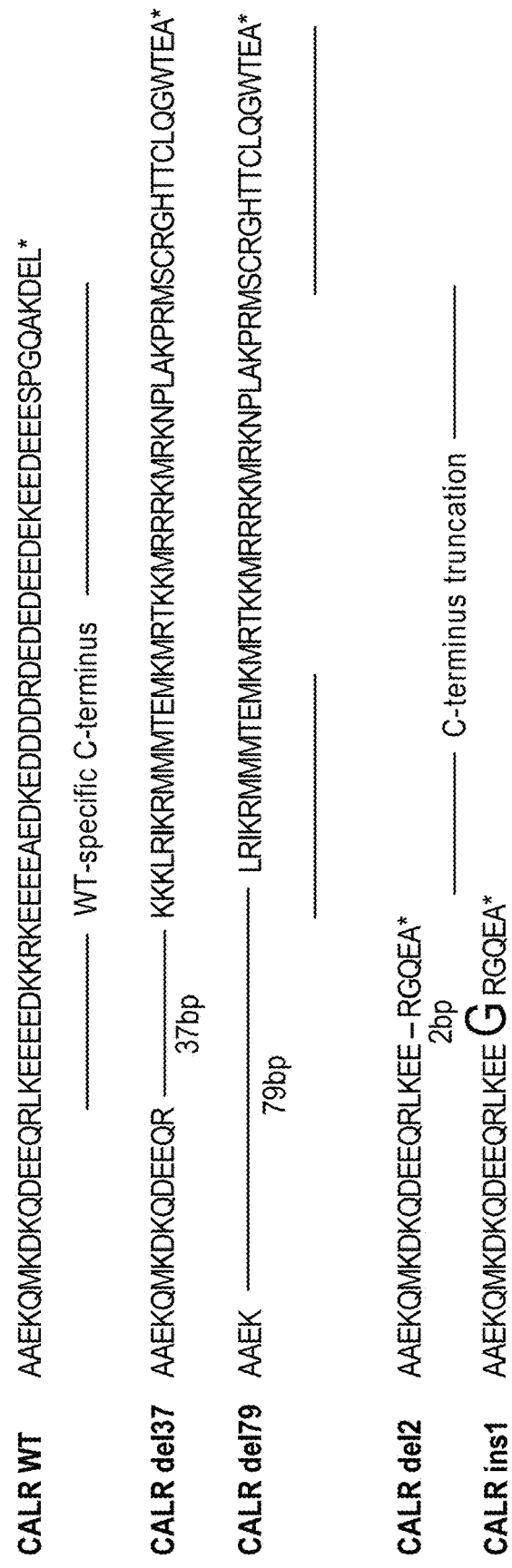

FIG. 12: Sequence alignment of C-terminal sequences of wild-type CALR, disease frameshift mutant CALR (CALR del79 and CALR del37 as two examples), C-terminally truncated CALR (CALR del2 and CALR ins1 as two examples) from Ba/F3 cells. * stands for stop codon. The SEQ ID NOs of the amino acid sequences shown in the figure are as follows (top to bottom): CALR WT (mouse; residues 352-416)-SEQ ID NO: 15; CALR del37-SEQ ID NO: 7; CALR del79-SEQ ID NO: 8; CALR del2-SEQ ID NO: 16; CALR ins1-SEQ ID NO: 17.

Figure 13:
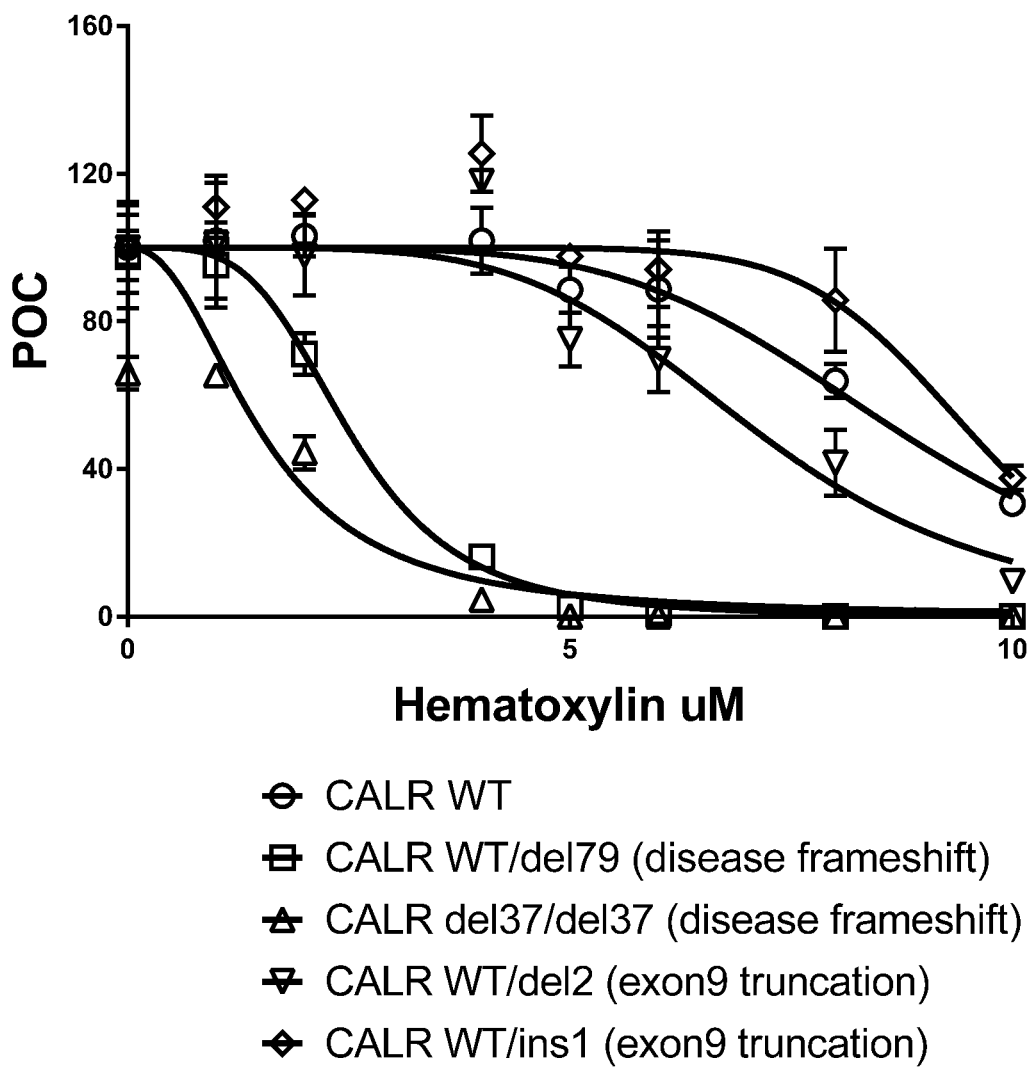

FIG. 13: Dose response of Ba/F3-MPL cell lines carrying wild-type CALR, disease frameshift mutant CALR and C-terminal truncated CALR. Error bar represents the standard deviation.

Figure 14:
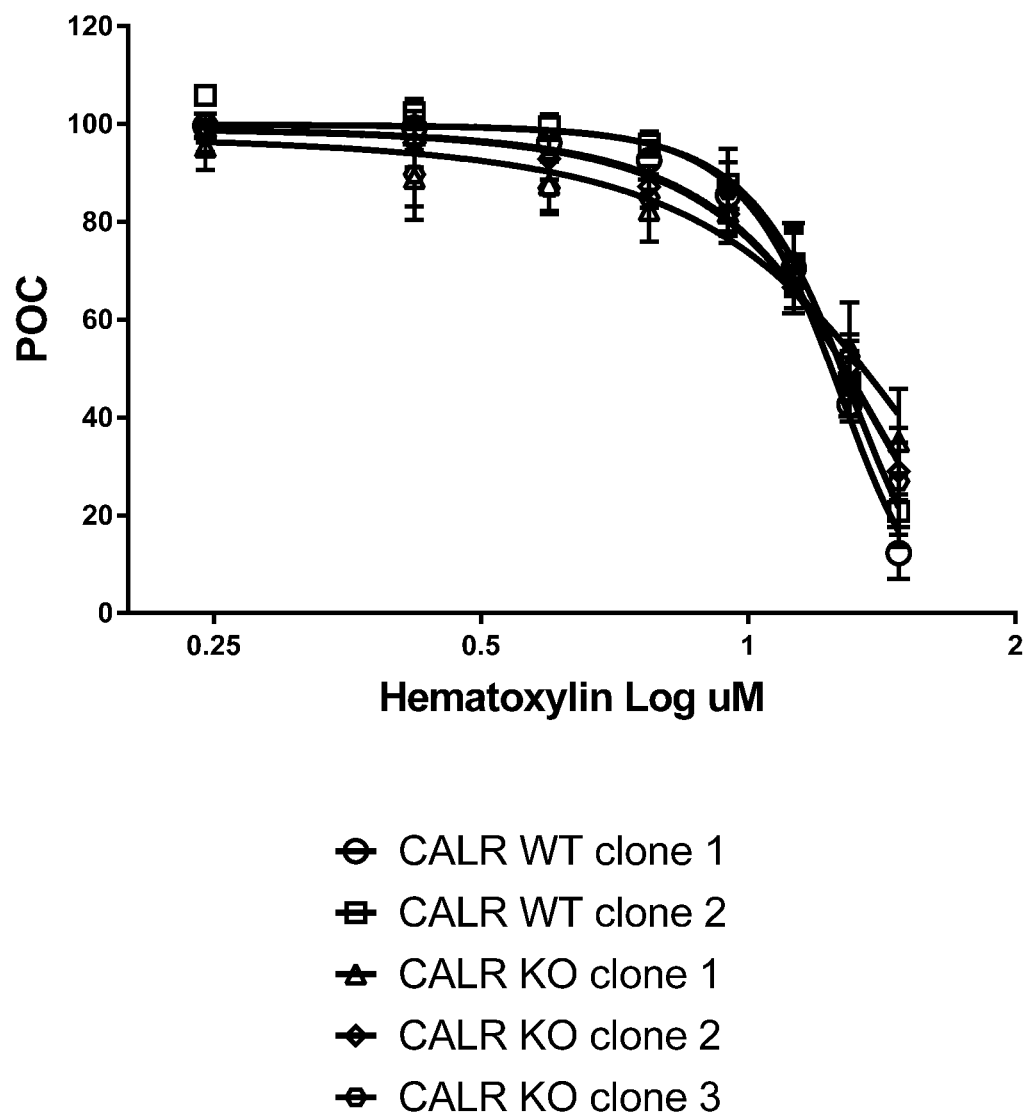

FIG. 14: Dose response of Ba/F3-MPL CALR WT and CALR knockout (CALR KO) cell lines. Three individual KO clones and two WT clones were used in the experiment. Error bar represents the standard deviation.

FIG. 15: Chemical structure and dose response of hematoxylin (A-1) and its analogues Brazilin (A-2), Hematein (A-3) and NSC7241 (A-5). All dose response experiments were performed as 72 h assays.

FIG. 16: Chemical structure and dose response of hematoxylin analogues Protosappanin B (A-4), L-HEM3 (A-5) and L-HEM1 (B-1). All dose response experiments were performed as 72 h assays.

FIG. 17: Chemical structure and dose response of the hematoxylin analogue RJ002 (B-2) and the control compounds hydroxyurea and ruxolitinib. All dose response experiments were performed as 72 h assays.

Figure 18:
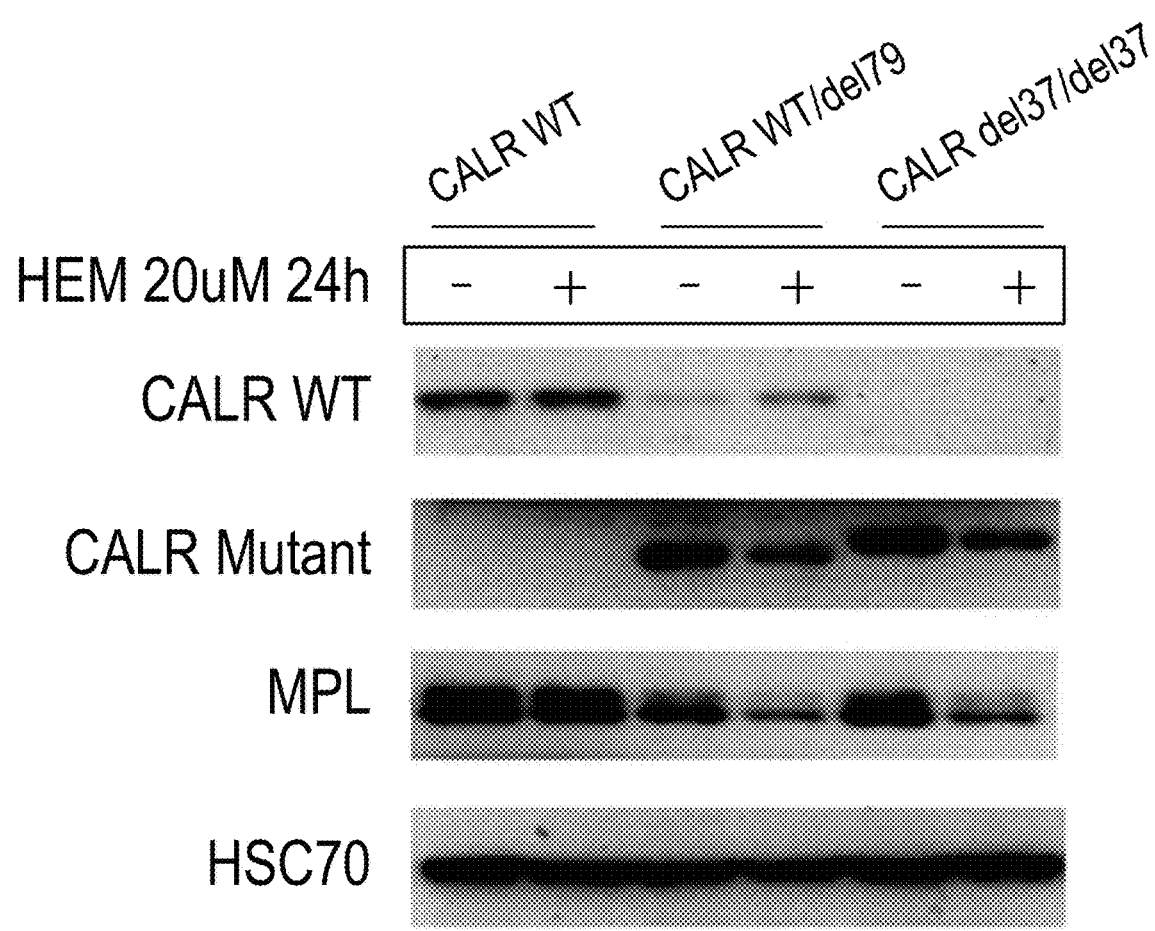

FIG. 18: Western blot analysis of Ba/F3-MPL cell lines after a 24 h treatment with hematoxylin. Ba/F3-MPL CALR WT, CALR WT/del79 and CALR del37/del37 cell lines were treated with 20 uM hematoxylin or an equivalent amount of DMSO as control for 24 h before cell extraction and lysis.

Figure 19:
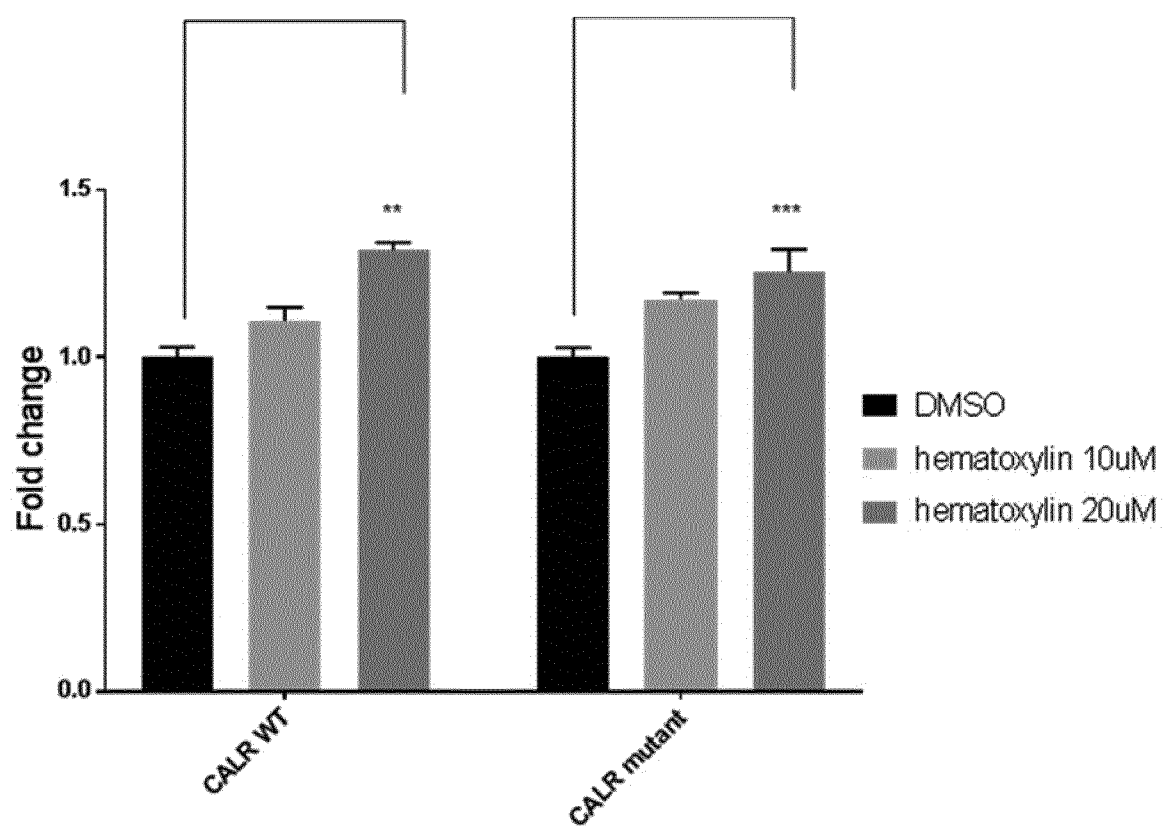

FIG. 19: Real-time PCR analysis of Ba/F3-MPL cell lines after a 24 h treatment with hematoxylin. Ba/F3-MPL CALR WT, CALR homozygous mutant del37/del37 cell line were treated with 20 uM hematoxylin or an equivalent amount of DMSO as control for 24 h before cell collection and RNA extraction. P<0.01; *P<0.001

Figure 20:
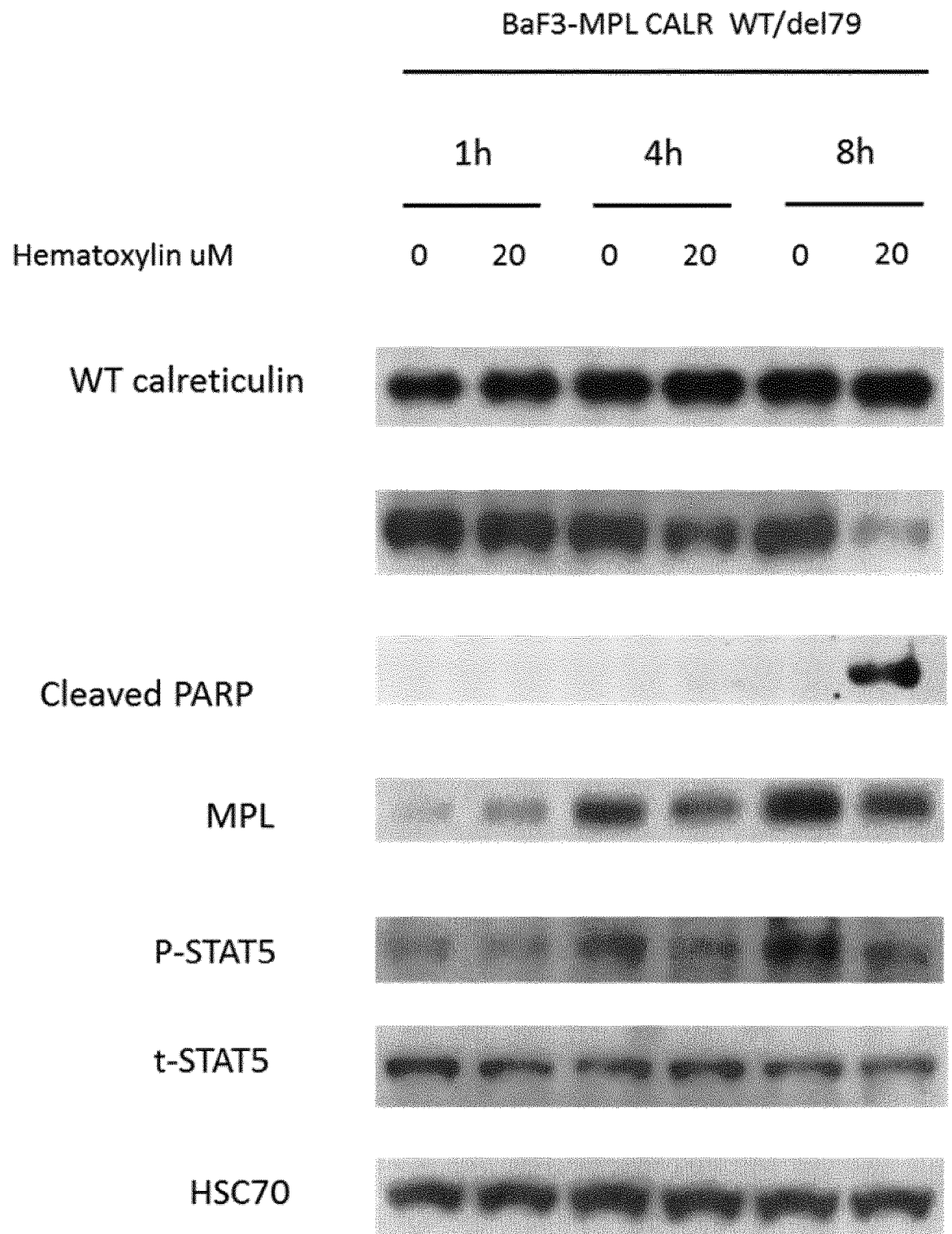

FIG. 20: Western blot analysis of hematoxylin treated Ba/F3-MPL CALR WT/del79 cell lines over time.

Figure 21:
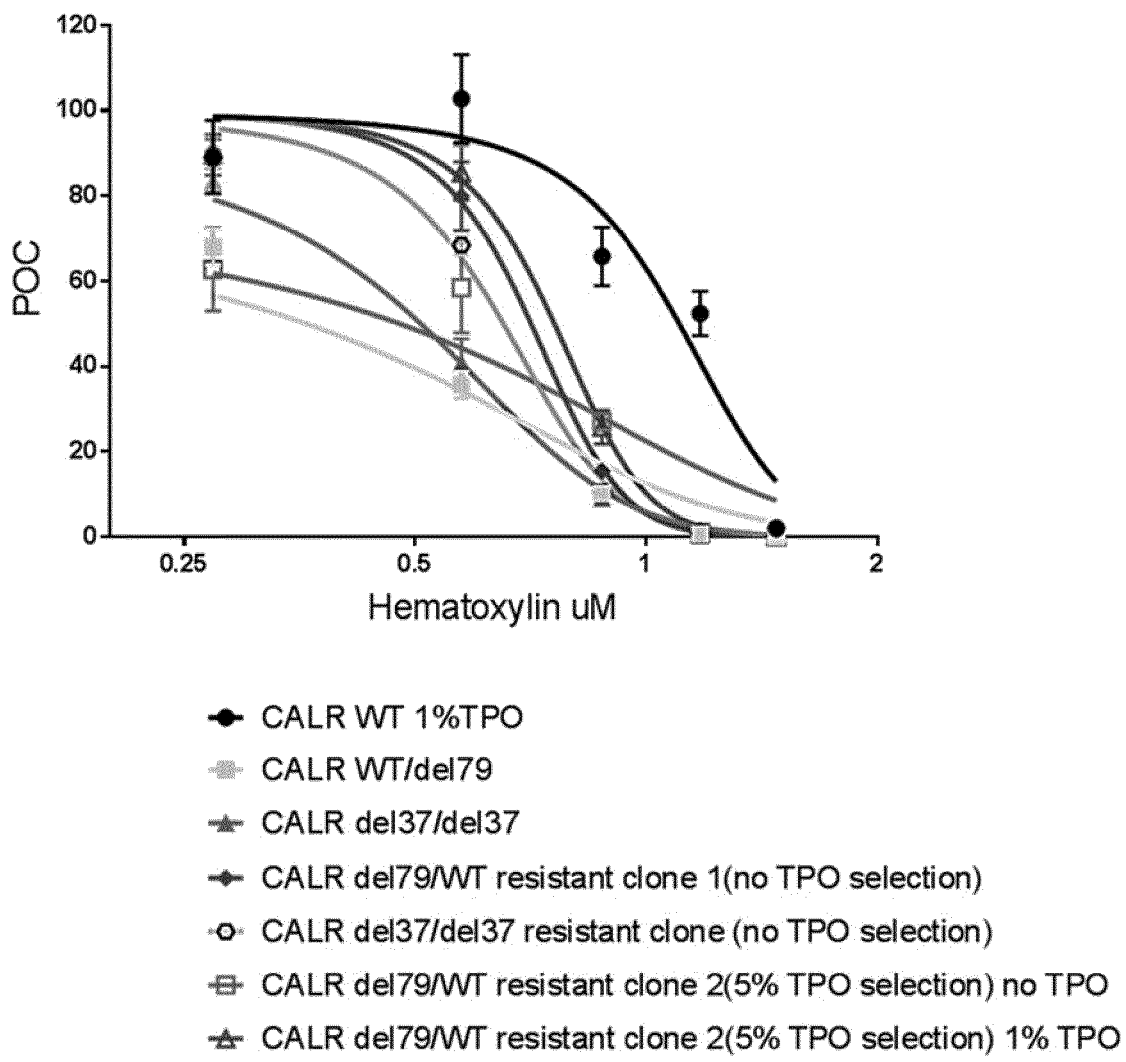

FIG. 21: Dose response of hematoxylin in Ba/F3-MPL resistant cell lines. Ba/F3-MPL CALR del79/WT and Ba/F3-MPL CALR del37/del37 were cultured with hematoxylin at a concentration of 20 uM for 4 weeks. CALR del79/WT resistant clone 1 and CALR del37/del37 resistant clone were cultured without cytokine. CALR del79/WT resistant clone 2 were cultured with 5% TPO.

Figure 22:
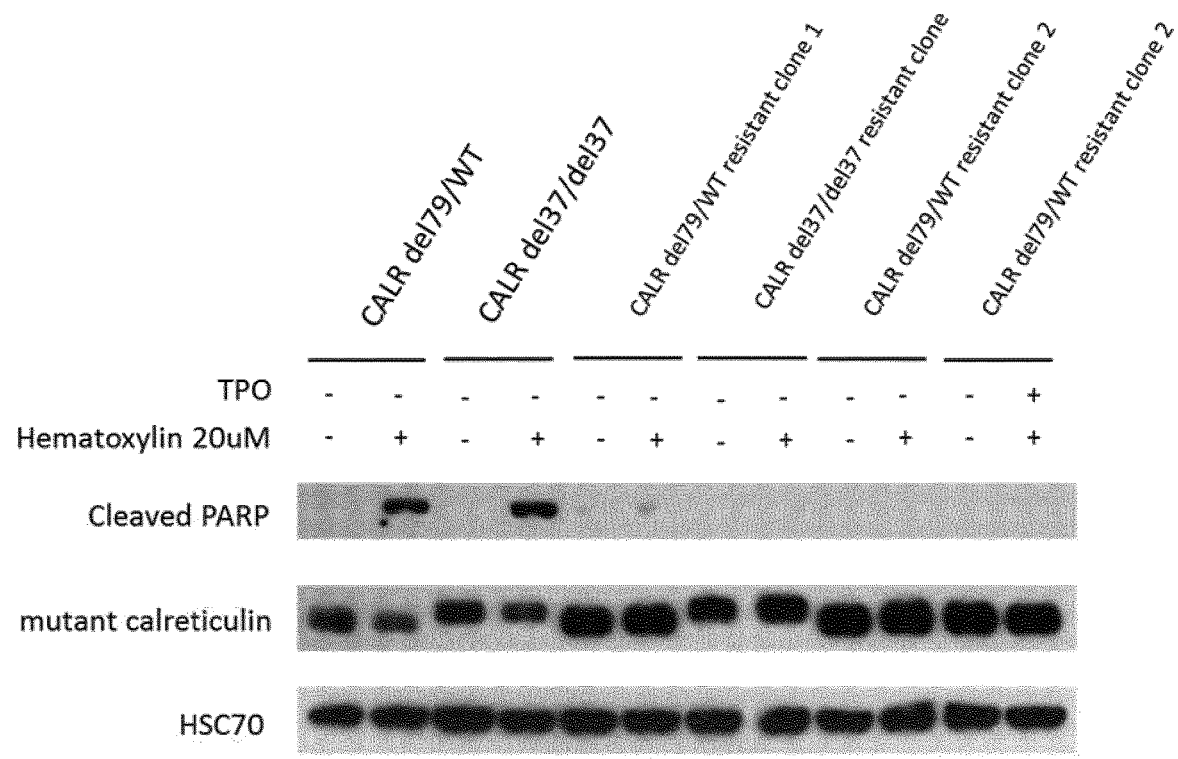

FIG. 22: Western blot analysis of hematoxylin resistant clones. All cells were treated for 24 h with hematoxylin before collection.

Figure 23:
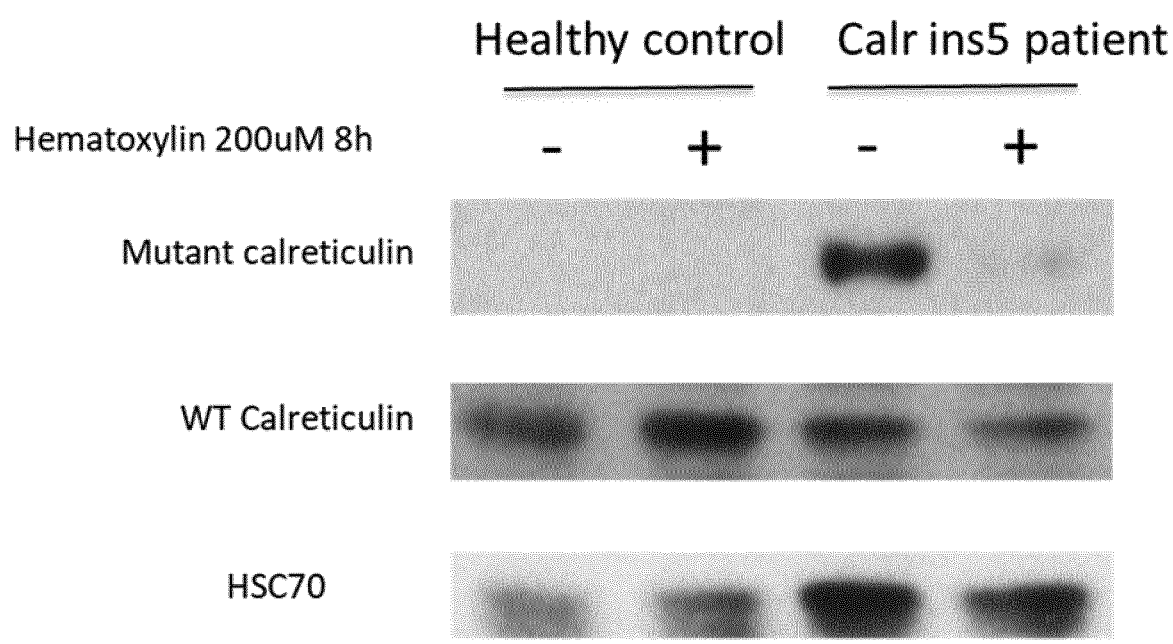

FIG. 23: Western blot analysis of CD34-positive cells isolated from a healthy control and a CALR ins5 mutant patient and treated with 200 μM hematoxylin or DMSO control for 8 h. HSC70 was used as loading control.

Figure 24:
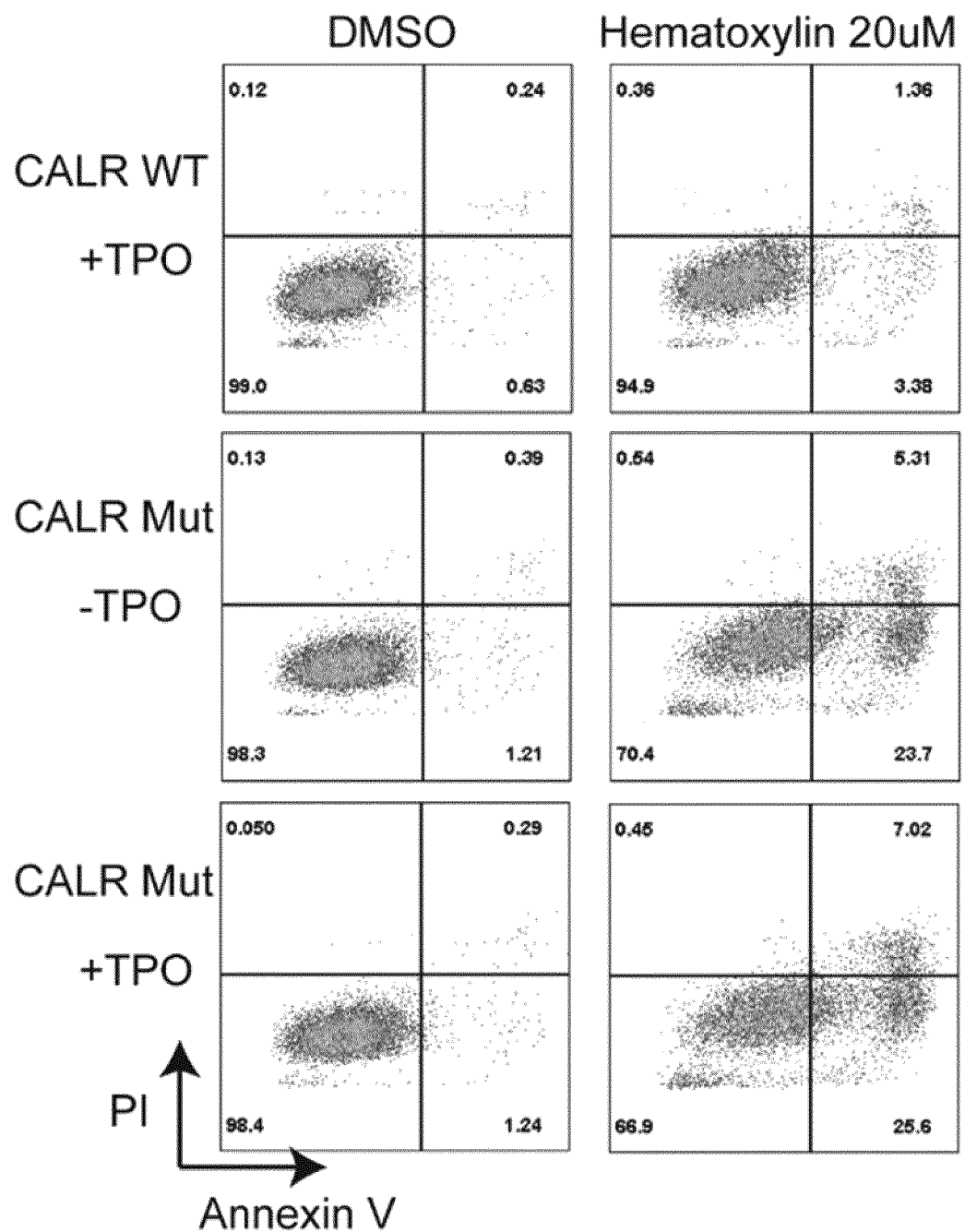

FIG. 24: Annexin V/PI staining of Ba/F3-MPL cells following hematoxylin treatment for 24 h. Representative FACS plots of Annexin V/PI staining in both CALR WT and mutant cell lines. Mutant cell lines were tested in +/−1% TPO condition.

Figure 25:
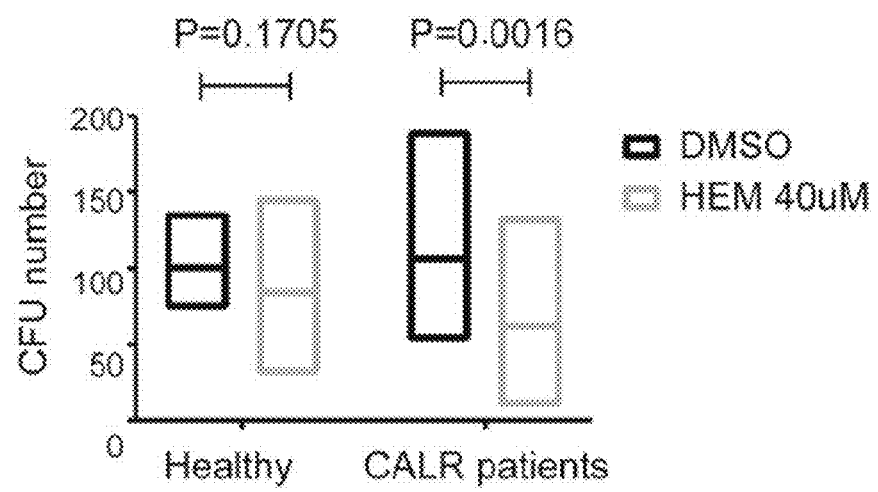

FIG. 25: Colony formation assay of healthy individuals and CALR patients following hematoxylin treatment. CD34-positive cells from 5 healthy control and 5 CALR patients were isolated and plated for 7 days with DMSO or 40 uM of hematoxylin treatment before colony counting. Two-way ANOVA followed by Sidak's multiple comparisons test was used for p value calculation.

DETAILED DESCRIPTION OF THE INVENTION

Although the present invention is further described in more detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described in more detail. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a one embodiment of the compound of the invention ring A is benzo and in another embodiment of the compound of the invention $R^1$ is H, then in a preferred embodiment of the compound of the invention, ring A is benzo and $R^1$ is H.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., Molecular Cloning: A Laboratory Manual, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The term "consisting essentially of" means excluding other members, integers or steps of any essential significance or group of members, integers or steps of any essential significance. For example, a pharmaceutical composition consisting essentially of the members/components as defined herein (such as a compound as defined in any of the aspects of the invention and optionally one additional therapeutic agent) would exclude further therapeutic agents (besides the compound as defined in any of the aspects of the invention and the optional one additional therapeutic agent) but would not exclude contaminants (e.g., those from the isolation and purification method) in trace amounts (e.g., the amount of the contaminant (preferably the amount of all contaminants present in the composition) is less than 5% by weight, such as less than 4% by weight, 3% by weight, 2% by weight, 1% by weight, 0.5% by weight, 0.4% by weight, 0.3% by weight, 0.2% by weight, 0.1% by weight, 0.05% by weight, with respect to the total composition) and/or pharmaceutically acceptable excipients (such as carriers, e.g., phosphate buffered saline, preservatives, and the like). The term "consisting of" means excluding all other members, integers or steps of significance or group of members, integers or steps of significance. For example, a pharmaceutical composition consisting of the members/components as defined herein (such as a compound as defined in any of the aspects of the invention, one excipient, and optionally one additional therapeutic agent) would exclude any other compound (including a second or further excipient) in an amount of more than 2% by weight (such as any other compound in an amount of more 1% by weight, more than 0.5% by weight, more than 0.4% by weight, more than 0.3% by weight, more than 0.2% by weight, more than 0.1% by weight, more than 0.09% by weight, more than 0.08% by weight, more than 0.07% by weight, more than 0.06% by weight, more than 0.05% by weight, more than 0.04% by weight, more than 0.03% by weight, more than 0.02% by weight, more than 0.01% by weight) with respect to the total composition. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

The terms "a", "an" and "the" and similar references used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by the context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "alkyl" refers to a monoradical of a saturated straight or branched hydrocarbon. Preferably, the alkyl group comprises from 1 to 12 (such as 1 to 10) carbon atoms, i.e., 1, 2, 3, 4, 5, 6, 7, 8, 9, 10, 11, or 12 carbon atoms (such as 1, 2, 3, 4, 5, 6, 7, 8, 9, or 10 carbon atoms), more preferably 1 to 8 carbon atoms, such as 1 to 6 or 1 to 4 carbon atoms. Exemplary alkyl groups include methyl, ethyl, propyl, iso-propyl (also called 2-propyl or 1-methylethyl), butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethyl-hexyl, n-nonyl, n-decyl, n-undecyl, n-dodecyl, and the like. A "substituted alkyl" means that one or more (such as 1 to the maximum number of hydrogen atoms bound to an alkyl group, e.g., 1, 2, 3, 4, 5, 6, 7, 8, 9, or up to 10, such as between 1 to 5, 1 to 4, or 1 to 3, or 1 or 2) hydrogen atoms of the alkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. Examples of a substituted alkyl include trifluoromethyl, 2,2,2-trichloroethyl, arylalkyl (also called "aralkyl", e.g., benzyl, chloro(phenyl)methyl, 4-methylphenylmethyl, (2,4-dimethylphenyl)methyl, o-fluorophenylmethyl, 2-phenylpropyl, 2-, 3-, or 4-carboxyphenylalkyl), or heteroarylalkyl (also called "heteroaralkyl").

The term "alkylene" refers to a diradical of a saturated straight or branched hydrocarbon. Preferably, the alkylene comprises from 1 to 12 (such as 1 to 10) carbon atoms, i.e., 1, 2, 3, 4, 5, 6, 7, 8, 9, 10, 11, or 12 carbon atoms (such as 1, 2, 3, 4, 5, 6, 7, 8, 9, or 10 carbon atoms), more preferably 1 to 8 carbon atoms, such as 1 to 6 or 1 to 4 carbon atoms. Exemplary alkylene groups include methylene, ethylene (i.e., 1,1-ethylene, 1,2-ethylene), propylene (i.e., 1,1-propylene, 1,2-propylene (—CH(CH$_3$)CH$_2$—), 2,2-propylene (—C(CH$_3$)$_2$—), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexylene isomers (e.g., 1,1-hexylene, 1,2-hexylene, 1,3-hexylene, 1,4-hexylene, 1,5-hexylene, 1,6-hexylene, and 1,1-isohexylene), the heptylene isomers (e.g., 1,1-heptylene, 1,2-heptylene, 1,3-heptylene, 1,4-heptylene, 1,5-heptylene, 1,6-heptylene, 1,7-heptylene, and 1,1-isoheptylene), the octylene isomers (e.g., 1,1-octylene, 1,2-octylene, 1,3-octylene, 1,4-octylene, 1,5-octylene, 1,6-octylene, 1,7-octylene, 1,8-octylene, and 1,1-isooctylene), and the like. The straight alkylene moieties having at least 3 carbon atoms and a free valence at each end can also be designated as a multiple of methylene (e.g., 1,4-butylene can also be called tetramethylene). Generally, instead of using the ending "ylene" for alkylene moieties as specified above, one can also use the ending "diyl" (e.g., 1,2-butylene can also be called butan-1,2-diyl). A "substituted alkylene" means that one or more (such as 1 to the maximum number of hydrogen atoms bound to an alkylene group, e.g., 1, 2, 3, 4, 5, 6, 7, 8, 9, or up to 10, such as between 1 to 5, 1 to 4, or 1 to 3, or 1 or 2) hydrogen atoms of the alkylene group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. Examples of a substituted alkylene include chloromethylene, dichloromethylene, fluoromethylene, and difluoromethylene.

The term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 6 (such as 1 to 4), i.e., 1, 2, 3, 4, 5, or 6, carbon-carbon double bonds. Preferably, the alkenyl group comprises from 2 to 12 (such as 2 to 10) carbon atoms, i.e., 2, 3, 4, 5, 6, 7, 8, 9, 10, 11, or 12 carbon atoms (such as 2, 3, 4, 5, 6, 7, 8, 9, or 10 carbon atoms), more preferably 2 to 8 carbon atoms, such as 2 to 6 carbon atoms or 2 to 4 carbon atoms. Thus, in a preferred embodiment, the alkenyl group comprises from 2 to 12 (e.g., 2 to 10) carbon atoms and 1, 2, 3, 4, 5, or 6 (e.g., 1, 2, 3, 4, or 5) carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, and the like. If an alkenyl group is attached to a nitrogen atom, the double bond cannot be alpha to the nitrogen atom. A "substituted alkenyl" means that one or more (such as 1 to the maximum number of hydrogen atoms bound to an alkenyl group, e.g., 1, 2, 3, 4, 5, 6, 7, 8, 9, or up to 10, such as between 1 to 5, 1 to 4, or 1 to 3, or 1 or 2) hydrogen atoms of the alkenyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. An example of a substituted alkenyl is styryl (i.e., 2-phenylvinyl).

The term "alkenylene" refers to a diradical of an unsaturated straight or branched hydrocarbon having at least one carbon-carbon double bond. Generally, the maximal number of carbon-carbon double bonds in the alkenylene group can be equal to the integer which is calculated by dividing the number of carbon atoms in the alkenylene group by 2 and, if the number of carbon atoms in the alkenylene group is uneven, rounding the result of the division down to the next integer. For example, for an alkenylene group having 9 carbon atoms, the maximum number of carbon-carbon double bonds is 4. Preferably, the alkenylene group has 1 to 6 (such as 1 to 4), i.e., 1, 2, 3, 4, 5, or 6, carbon-carbon double bonds. Preferably, the alkenylene group comprises from 2 to 12 (such as 2 to 10) carbon atoms, i.e., 2, 3, 4, 5, 6, 7, 8, 9, 10, 11, or 12 carbon atoms (such as 2, 3, 4, 5, 6, 7, 8, 9, or 10 carbon atoms), more preferably 2 to 8 carbon atoms, such as 2 to 6 carbon atoms or 2 to 4 carbon atoms. Thus, in a preferred embodiment, the alkenylene group comprises from 2 to 12 (such as 2 to 10 carbon) atoms and 1, 2, 3, 4, 5, or 6 (such as 1, 2, 3, 4, or 5) carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenylene groups include ethen-1,2-diyl, vinylidene (also called ethenylidene), 1-propen-1,2-diyl, 1-propen-1,3-diyl, 1-propen-2,3-diyl, allylidene, 1-buten-1,2-diyl, 1-buten-1,3-diyl, 1-buten-1,4-diyl, 1-buten-2,3-diyl, 1-buten-2,4-diyl, 1-buten-3,4-diyl, 2-buten-1,2-diyl, 2-buten-1,3-diyl, 2-buten-1,4-diyl, 2-buten-2,3-diyl, 2-buten-2,4-diyl, 2-buten-3,4-diyl, and the like. If an alkenylene group is attached to a nitrogen atom, the double bond cannot be alpha to the nitrogen atom. A "substituted alkenylene" means that one or more (such as 1 to the maximum number of hydrogen atoms bound to an alkenylene group, e.g., 1, 2, 3, 4, 5, 6, 7, 8, 9, or up to 10, such as between 1 to 5, 1 to 4, or 1 to 3, or 1 or 2) hydrogen atoms of the alkenyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. Examples of a substituted alkenylene are 1-phenyl-ethen-1,2-diyl and 2-phenyl-ethen-1,2-diyl.

The term "alkynyl" refers to a monoradical of an unsaturated straight or branched hydrocarbon having at least one carbon-carbon triple bond. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 6 (such as 1 to 4), i.e., 1, 2, 3, 4, 5, or 6, more preferably 1 or 2 carbon-carbon triple bonds. Preferably, the alkynyl group comprises from 2 to 12 (such as 2 to 10) carbon atoms (such as 1, 2, 3, 4, 5, 6, 7, 8, 9, or 10 carbon atoms), i.e., 2, 3, 4, 5, 6, 7, 8, 9, 10, 11, or 12 carbon atoms, more preferably 2 to 8 carbon atoms, such as 2 to 6 carbon atoms or 2 to 4 carbon atoms. Thus, in a preferred embodiment, the alkynyl group comprises from 2 to 12 (such as 2 to 10) carbon atoms and 1, 2, 3, 4, 5, or 6 (such as 1, 2, 3, 4, or 5 (preferably 1, 2, or 3)) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom. A "substituted alkynyl" means that one or more (such as 1 to the maximum number of hydrogen atoms bound to an alkynyl group, e.g., 1, 2, 3, 4, 5, 6, 7, 8, 9, or up to 10, such as between 1 to 5, 1 to 4, or 1 to 3, or 1 or 2) hydrogen atoms of the alkynyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl.

The term "alkynylene" refers to a diradical of an unsaturated straight or branched hydrocarbon having at least one carbon-carbon triple bond. Generally, the maximal number of carbon-carbon triple bonds in the alkynylene group can be equal to the integer which is calculated by dividing the number of carbon atoms in the alkynylene group by 2 and, if the number of carbon atoms in the alkynylene group is uneven, rounding the result of the division down to the next integer. For example, for an alkynylene group having 9 carbon atoms, the maximum number of carbon-carbon triple bonds is 4. Preferably, the alkynylene group has 1 to 6 (such as 1 to 4), i.e., 1, 2, 3, 4, 5, or 6 (such as 1, 2, 3, or 4), more preferably 1 or 2 carbon-carbon triple bonds. Preferably, the alkynylene group comprises from 2 to 12 (such as 2 to 10) carbon atoms, i.e., 2, 3, 4, 5, 6, 7, 8, 9, 10, 11, or 12 carbon atoms (such as 2, 3, 4, 5, 6, 7, 8, 9, or 10 carbon atoms), more preferably 2 to 8 carbon atoms, such as 2 to 6 carbon atoms or 2 to 4 carbon atoms. Thus, in a preferred embodiment, the alkynylene group comprises from 2 to 12 (such as 2 to 10) carbon atoms and 1, 2, 3, 4, 5, or 6 (such as 1, 2, 3, 4, or 5 (preferably 1, 2, or 3)) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynylene groups include ethyn-1,2-diyl, 1-propyn-1,3-diyl, 1-propyn-3,3-diyl, 1-butyn-1,3-diyl, 1-butyn-1,4-diyl, 1-butyn-3,4-diyl, 2-butyn-1,4-diyl and the like. If an alkynylene group is attached to a nitrogen atom, the triple bond cannot be alpha to the nitrogen atom.

The term "aryl" or "aromatic ring" refers to a monoradical of an aromatic cyclic hydrocarbon. Preferably, the aryl group contains 3 to 14 (e.g., 5, 6, 7, 8, 9, or 10, such as 5, 6, or 10) carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl. Aryl does not encompass fullerenes. A "substituted aryl" means that one or more (such as 1 to the maximum number of hydrogen atoms bound to an aryl group, e.g., 1, 2, 3, 4, 5, 6, 7, 8, 9, or up to 10, such as between 1 to 5, 1 to 4, or 1 to 3, or 1 or 2) hydrogen atoms of the aryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., C$_{1-6}$ alkyl), alkenyl (e.g., C$_{2-6}$ alkenyl), and alkynyl (e.g., C$_{2-6}$ alkynyl). Examples of a substituted aryl include biphenyl, 2-fluorophenyl, anilinyl, 3-nitrophenyl, 4-hydroxyphenyl, methoxyphenyl (i.e., 2-, 3-, or 4-methoxyphenyl), and 4-ethoxyphenyl. The term "halogenaryl" as used herein refers to an aryl group as specified above (in particular phenyl) which is substituted with one or more (such as 1 to the maximum number of hydrogen atoms bound to the aryl, e.g., 1, 2, 3, 4, 5, 6, 7, 8, 9, or up to 10, such as between 1 to 5, 1 to 4, or 1 to 3, or 1 or 2) independently selected halogens.

The term "heteroaryl" or "heteroaromatic ring" means an aryl group as defined above in which one or more carbon atoms in the aryl group are replaced by heteroatoms (such as O, S, or N). Preferably, heteroaryl refers to a five or six-membered aromatic monocyclic ring, wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. For example, 3- to 14-membered heteroaryl encompasses monocyclic heteroaryl (e.g., 5- or 6-membered), bicyclic heteroaryl (e.g., 9- or 10-membered), and tricyclic heteroaryl (e.g., 13- or 14-membered). Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolothiazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, and pyrrolopyrrolyl. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl. A "substituted heteroaryl" means that one or more (such as 1 to the maximum number of hydrogen atoms bound to a heteroaryl group, e.g., 1, 2, 3, 4, 5, 6, 7, 8, 9, or up to 10, such as between 1 to 5, 1 to 4, or 1 to 3, or 1 or 2) hydrogen atoms of the heteroaryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl). Examples of a substituted heteroaryl include 3-phenylpyrrolyl, 2,3'-bifuryl, 4-methylpyridyl, 2-, or 3-ethylindolyl.

The term "cycloalkyl" or "cycloaliphatic" represents cyclic non-aromatic versions of "alkyl" and "alkenyl" with preferably 3 to 14 carbon atoms, such as 3 to 12 or 3 to 10 carbon atoms, i.e., 3, 4, 5, 6, 7, 8, 9, 10, 11, 12, 13, or 14 carbon atoms (such as 3, 4, 5, 6, 7, 8, 9, or 10 carbon atoms), more preferably 3 to 7 carbon atoms. Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_{3-8}$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl. Cycloalkyl does not encompass fullerenes. A "substituted cycloalkyl" means that one or more (such as 1 to the maximum number of hydrogen atoms bound to a cycloalkyl group, e.g., 1, 2, 3, 4, 5, 6, 7, 8, 9, or up to 10, such as between 1 to 5, 1 to 4, or 1 to 3, or 1 or 2) hydrogen atoms of the cycloalkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl). Examples of a substituted cycloalkyl include oxocyclohexyl, oxocyclopentyl, fluorocyclohexyl, and oxocyclohexenyl.

The term "heterocyclyl" or "heterocyclic ring" means a cycloalkyl group as defined above in which from 1, 2, 3, or 4 carbon atoms in the cycloalkyl group are replaced by heteroatoms (such as those selected from the group consisting of O, S, N, B, Si, and P, preferably selected from the group consisting of O, S, and N). If a ring of the heterocyclyl group only contains one type of heteroatom, the maximum number of said heteroatom in the ring of said heterocyclyl group may be as follows: 2 O atoms (preferably 1 O atom); 2 S atoms (preferably 1 S atom); 4 N atoms (such as 1, 2, or 3 N atoms); 2 B atoms (preferably 1 B atom); 1 Si atom; and/or 1 P atom. If a ring of the heterocyclyl group contains two or more types of heteroatoms, the maximum number of said heteroatoms in the ring of said heterocyclyl group may be as follows: 1 O atom; 1 S atom; 2 N atoms (preferably 1 N atom); 1 B atom; 1 Si atom; and/or 1 P atom, wherein the maximum total number of heteroatoms in the ring of said heterocyclyl group is 4 and the maximum total number of each heteroatom in the ring of said heterocyclyl group is as follows: 1 O atom; 1 S atom; 1 or 2 N atoms; 1 B atom (preferably 0 B atom); 1 Si atom (preferably 0 Si atom); and/or 1 P atom (preferably 0 P atom). In one embodiment, the heteroatoms of the heterocyclyl group are selected from the group consisting of O, S, and N. In this embodiment, preferably, in each ring of the heterocyclyl group the maximum number of O atoms is 1, the maximum number of S atoms is 1, and the maximum total number of O and S atoms is 2. For example, 3- to 14-membered heterocyclyl encompasses monocyclic heterocyclyl (e.g., 3-, 4-, 5-, 6-, or 7-membered), bicyclic heterocyclyl (e.g., 8-, 9-, or 10-membered), and tricyclic heterocyclyl (e.g., 12-, 13-, or 14-membered). The term "heterocyclyl" is also meant to encompass partially or completely hydrogenated forms (such as dihydro, tetrahydro, hexahydro, octahydro, decahydro, dodecahydro, etc., or perhydro forms) of the above-mentioned heteroaryl groups. Exemplary heterocyclyl groups include morpholino, isochromanyl, chromanyl, pyrrolidinyl, imidazolidinyl, pyrazolidinyl, piperidinyl, piperazinyl, indolinyl, isoindolinyl, triazininanyl (1,2,3-, 1,2,4-, and 1,3, 5-), di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydrothiadiazolyl (1,2,3- and 1,2,5-), di- and tetrahydropyridyl, di-, tetra- and hexahydropyrimidinyl, di- and tetrahydropyrazinyl, di- and tetrahydrotriazinyl (1,2,3-, 1,2,4-, and 1,3,5-), di-, tetra-, hexa- and octahydrobenzofuranyl (1- and 2-), di-, tetra-, hexa- and octahydroindolyl, di-, tetra-, hexa- and octahydroisoindolyl, di-, tetra-, hexa- and octahydrobenzothienyl (1- and 2), di-, tetra-, hexa- and octahydro-1H-indazolyl, di-, tetra-, hexa- and octahydrobenzimidazolyl, di-, tetra-, hexa- and octahydrobenzoxazolyl, di-, tetra-, hexa- and octahydroindoxazinyl, di-, tetra-, hexa- and octahydrobenzisoxazolyl, di-, tetra-, hexa- and octahydrobenzothiazolyl, di-, tetra-, hexa- and octahydrobenzisothiazolyl, di-, tetra-, hexa- and octahydrobenzotriazolyl, di-, tetra-, hexa-, octa- and decahydroquinolinyl, di-, tetra-, hexa-, octa- and decahydroisoquinolinyl, di-, tetra-, hexa-, octa- and decahydrobenzodiazinyl, di-, tetra-, hexa-, octa- and decahydroquinoxalinyl, di-, tetra-, hexa-, octa- and decahydroquinazolinyl, di-, tetra-, hexa-, octa- and decahydrobenzotriazinyl (1,2,3- and 1,2,4-), di-, tetra-, and hexahydropyridazinyl, di-, tetra-, hexa-, octa-, deca- and dodecahydrophenoxazinyl, di-, tetra-, hexa-, and octahydrothiazolopyridinyl (such as 4,5,6-7-tetrahydro[1,3]thiazolo[5,4-c]pyridinyl or 4,5,6-7-tetrahydro[1,3]thiazolo[4,5-c]pyridinyl, e.g., 4,5,6-7-tetrahydro [1,3]thiazolo[5,4-c]pyridin-2-yl or 4,5,6-7-tetrahydro[1,3]thiazolo[4,5-c]pyridin-2-yl), di-, tetra-, and hexahydropyrrolothiazolyl, di-, tetra-, hexa-, octa- and decahydrophenothiazinyl, di-, tetra-, hexa-, and octahydroisobenzofuranyl, di-, tetra-, hexa-, and octahydrochromenyl, di-, tetra-, hexa-, octa-, deca-, and dodecahydroxanthenyl, di-, tetra-, hexa-, octa-, deca-, and dodecahydrophenoxathiinyl, di-, tetra-, and hexahydropyrrolizinyl, di-, tetra-, hexa-, and octahydroindolizinyl, di-, tetra-, hexa-, and octahydroindazolyl, di-, tetra-, hexa-, and octahydropurinyl, di-, tetra-, hexa-, and octahydroquinolizinyl, di-, tetra-, hexa-, octa- and decahydrophthalazinyl, di-, tetra-, hexa-, octa- and decahydronaphthyridinyl (1,5-, 1,6-, 1,7-, 1,8-, and 2,6-), di-, tetra-, hexa-, octa- and decahydrocinnolinyl, di-, tetra-, hexa-, octa-, and decahydropteridinyl, di-, tetra-, hexa-, octa-, deca- and dodecahydrocarbazolyl, di-, tetra-, hexa-, octa-, deca-, dodeca-, and tetradecahydrophenanthridinyl, di-, tetra-, hexa-, octa-, deca-, dodeca-, and tetradecahydroacridinyl, di-, tetra-, hexa-, octa-, deca- and dodecahydroperimidinyl, di-, tetra-, hexa-, octa-, deca-, dodeca-, and tetradecahydrophenanthrolinyl (1,7-, 1,8-, 1,10-, 3,8-, and 4,7-), di-, tetra-, hexa-, octa-, deca-, dodeca-, and tetradecahydrophenazinyl, di-, tetra-, hexa- and octahydrooxazolopyridinyl, di-, tetra-, hexa- and octahydroisoxazolopyridinyl, di-, tetra-, hexa- and octahydrocyclopentapyrrolyl, di-, tetra-, hexa- and octahydrocyclopentpyrazolyl, di-, tetra-, hexa- and octahydrocyclopentaimidazolyl, di-, tetra-, hexa- and octahydrocyclopentathiazolyl, di-, tetra-, hexa- and octahydrocyclopentaoxazolyl, di-, tetra-, hexa- and octahydropyrrolopyrrolyl, di-, tetra-, hexa- and octahydropyrrolopyrazolyl, di-, tetra-, hexa- and octahydropyrroloimidazolyl, di-, tetra-, hexa- and octahydropyrrolothiazolyl (such as 5,6-dihydro-4H-pyrrolo[3,4-d][1,3]thiazolyl), di-, tetra-, hexa- and octahydropyrrolooxazolyl, di-, tetra-, hexa- and octahydropyrazolopyrazolyl, di-, tetra-, hexa- and octahydropyrazoloimidazolyl, di-, tetra-, hexa- and octahydropyrazolothiazolyl, di-, tetra-, hexa- and octahydropyrazolooxazolyl, di-, tetra-, hexa- and octahydroimidazoimidazolyl, di-, tetra-, hexa- and octahydroimidazothiazolyl, di-, tetra-, hexa- and octahydroimidazooxazolyl, di-, tetra-, hexa- and octahydrothiazolothiazolyl, di-, tetra-, hexa- and octahydrothiazolooxazolyl, and di-, tetra-, hexa- and octahydrooxazolooxazolyl. Exemplary 5- or 6-membered heterocyclyl groups include morpholino, pyrrolidinyl, imidazolidinyl, pyrazolidinyl, piperidinyl, piperazinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrotriazolyl (1,2,3- and 1,2,4-), di- and tetrahydrothiazolyl, di- and tetrahydroisothiazolyl, di- and tetrahydrothiadiazolyl (1,2,3- and 1,2,5-), di- and tetrahydropyridyl, di-, tetra-, and hexahydropyrimidinyl, di- and tetrahydropyrazinyl, di- and tetrahydrotriazinyl (1,2,3-, 1,2,4-, and 1,3,5-), and triazinanyl (1,2,3-, 1,2,4-, and 1,3,5-). A "substituted heterocyclyl" means that one or more (such as 1 to the maximum number of hydrogen atoms bound to a heterocyclyl group, e.g., 1, 2, 3, 4, 5, 6, 7, 8, 9, or up to 10, such as between 1 to 5, 1 to 4, or 1 to 3, or 1 or 2) hydrogen atoms of the heterocyclyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR$^{11}$ (e.g., —OH), —SR$^{11}$ (e.g., —SH), —N(R$^{12}$)(R$^{13}$) (e.g., —NH$_2$), =X (e.g., =O, =S, or =NH), alkyl (e.g., C$_{1-6}$ alkyl), alkenyl (e.g., C$_{2-6}$ alkenyl), and alkynyl (e.g., C$_{2-6}$ alkynyl).

The term "heterocyclylidene" refers to a diradical version of a heterocyclyl as specified above, wherein both free valences of the heterocyclylidene are located at the same ring carbon atom of the heterocyclylidene. In other words, a heterocyclylidene can be obtained from a parent heterocyclyl having a free valence on a ring carbon atom, wherein the ring carbon atom having a free valence (i.e., the "yl" position) bears a hydrogen atom, by removing the hydrogen atom from said ring carbon atom of the parent heterocyclyl. An example for a heterocyclylidene is 1,3-thiazolidin-5-ylidene having the structure

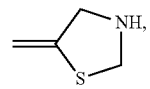

which can be obtained by the parent heterocyclyl 1,3-thiazolidin-5-yl having the structure

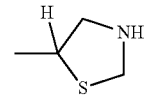

by removing 1H atom from the ring carbon atom at position 5.

The term "aromatic" as used in the context of hydrocarbons means that the whole molecule has to be aromatic. For example, if a monocyclic aryl is hydrogenated (either partially or completely) the resulting hydrogenated cyclic structure is classified as cycloalkyl for the purposes of the present invention. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present invention (even if one ring, such as in 1,2-dihydronaphthyl, is still aromatic). A similar distinction is made within the present application between heteroaryl and heterocyclyl. For example, indolinyl, i.e., a dihydro variant of indolyl, is classified as heterocyclyl for the purposes of the present invention, since only one ring of the bicyclic structure is aromatic and one of the ring atoms is a heteroatom.

The expression "heterocyclyl containing a quaternary carbon atom to which the moiety —OR$^1$ is bound" as used herein means that the heterocyclyl group comprises a ring carbon atom to which four other atoms selected from C, O, and N are bound, wherein at least two of these four other atoms are ring atoms of the heterocyclyl group and one of these four other atoms is the oxygen atom of —OR$^1$. In the embodiment, where ring Q is a 9-membered bicyclic heterocyclyl, it is preferred that the quaternary carbon atom to which the moiety —OR$^1$ is bound is a ring carbon atom of the heterocyclyl group to which four other atoms selected from C, O, and N are bound, wherein three of these four other atoms are ring atoms of the heterocyclyl group (i.e., the quaternary carbon atom is one of the bridgeheads of the heterocyclyl group). In the embodiment, where ring Q is a 8-membered monocyclic heterocyclyl, it is preferred that the quaternary carbon atom to which the moiety —OR$^1$ is bound is a ring carbon atom of the heterocyclyl group to which three carbon atoms and the oxygen atom of the —OR$^1$ group is bound, wherein two of these three carbon atoms are ring atoms of the heterocyclyl group.

The expressions "ring 1 fused to a ring 2" and "ring 1 condensed with ring 2" and similar expressions as used herein mean that rings 1 and 2 are connected to each other in such a way that both rings share two adjacent ring atoms (these two adjacent ring atoms shared by both rings can also be designated as bridgeheads). For example, a naphthyl moiety can be considered as a benzo moiety fused to a phenyl ring. Likewise, the expression "each of rings A and B is fused to ring Q" means that rings A and Q are connected to each other in such a way that both rings share two adjacent ring atoms and rings B and Q are connected to each other in such a way that both rings share two adjacent ring atoms. For example, if each of rings A and B is benzo and ring Q is

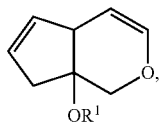

then the compound of formula (I) has the following structure:

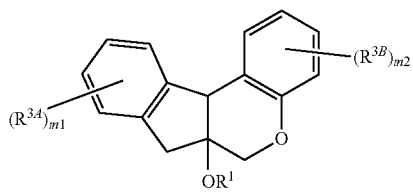

Furthermore, if ring A is a hydrated form of benzo (e.g., cyclohexeno), ring B is benzo, and ring Q is

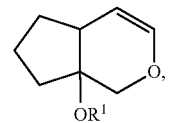

then the compound of formula (I) encompasses the following structures:

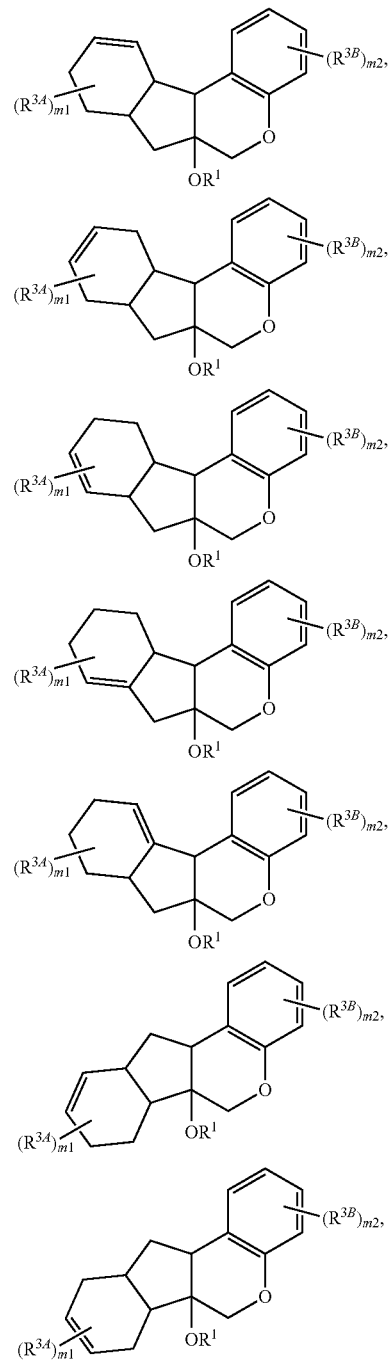

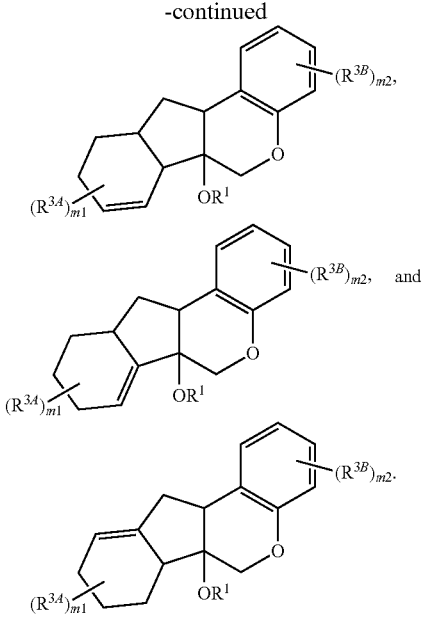

Likewise, if ring A is a hydrated form of pyrimidine (e.g., 1,6-dihydropyrimidino), ring B is benzo, and ring Q is

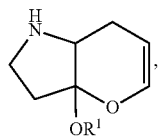

then the compound of formula (I) encompasses the following structures:

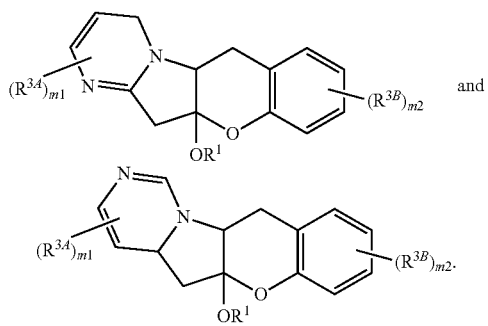

The term "polycyclic" as used herein means that the structure has two or more (such as 2, 3, 4, 5, 6, 7, 8, 9, or 10), preferably, 2, 3, 4, or 5, more preferably, 2, 3, or 4, rings. Therefore, according to the invention, the term "polycyclic" does not encompass monocyclic structures, wherein the structures only contain one ring. Examples of polycyclic groups are fused structures (such as naphthyl or anthryl), spiro compounds, rings that are linked via single or double bonds (such as biphenyl), and bridged structures (such as bornyl). Exemplary polycyclic structures are those aryl, heteroaryl, cycloalkyl, and heterocyclyl groups specified above which have at least two rings.

The term "halogen" or "halo" means fluoro, chloro, bromo, or iodo.

The term "azido" means —$N_3$.

The term "any two $R^2$ which are bound to the same carbon atom of ring Q may join together to form =$X^Q$" as used herein means that two monoradicals (i.e., $R^2$) when substituting in total 2 hydrogen atoms bound to only one ring carbon atom of ring Q can form the diradical =$X^Q$. For example, according to the invention, ring Q being

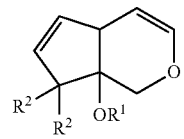

encompasses not only (1) the possibility that both $R^2$ groups are monoradicals independently selected from the particular moieties specified herein (e.g., methyl, —Cl, —$CH_3$, or —CN) but also (2) the possibility that the two $R^2$ groups join together to form the diradical =$X^Q$ resulting in a ring Q having the formula

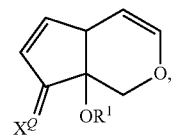

wherein $X^Q$ is O, S, or NH. Similar terms such as "any two $R^{3A}$ which are bound to the same carbon atom of ring A may join together to form =$X^A$" or "any two $R^{3B}$ which are bound to the same carbon atom of ring B may join together to form =$X^B$" as used herein are to be interpreted in an analogous manner. In this respect, it is to be understood that in those embodiments, where any two $R^{3A}$ which are bound to the same carbon atom of ring A join together to form =$X^A$, ring A initially (i.e., without the modification =$X^A$) has to be a cycloaliphatic or heterocyclic ring (because in an aromatic or heteroaromatic ring there is no carbon ring atom having two free valences). Likewise, it is to be understood that in those embodiments, where any two $R^{3B}$ which are bound to the same carbon atom of ring B join together to form =$X^B$, ring B initially (i.e., without the modification =$X^B$) has to be a cycloaliphatic or heterocyclic ring (because in an aromatic or heteroaromatic ring there is no carbon ring atom having two free valences).

The term "any two $R^{3A}$ on adjacent ring atoms of ring A may join together with the adjacent ring atoms of ring A to form a ring" as used herein means that two monoradicals (i.e., $R^{3A}$) when substituting in total 2 hydrogen atoms bound to two adjacent ring atoms of ring A can form a ring. For example, according to the invention, ring A being

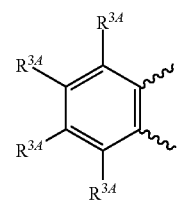

(wherein ⁓ represents the attachment of ring A to ring Q) encompasses not only (1) the possibility that the $R^{3A}$ groups are monoradicals independently selected from the particular moieties specified herein (e.g., —OH, —OCH₃, or —C(O)CH₃) but also (2) the possibility that two adjacent R³·⁴ groups on adjacent carbon atoms of rings A join together to form a ring resulting, e.g., in the following structures:

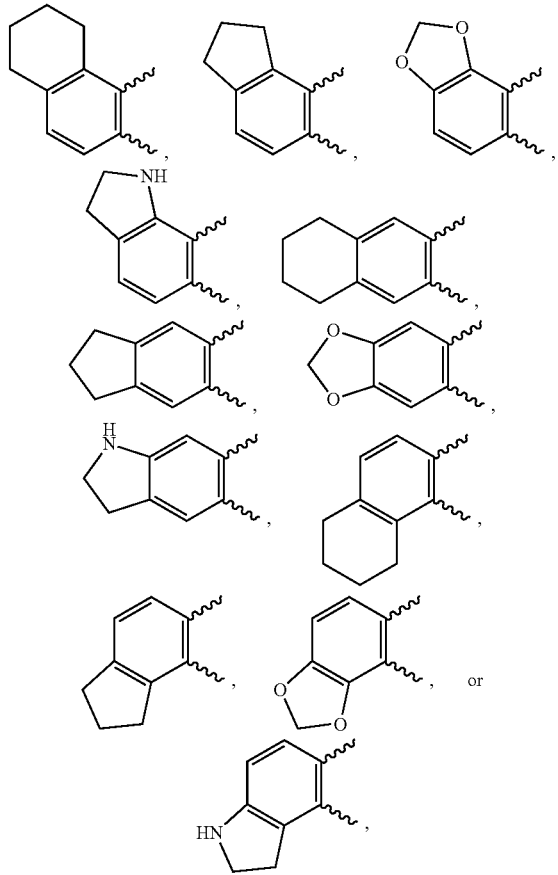

wherein in each case the ring formed on ring A can be substituted with one or more (such as 1 to the maximum number of hydrogen atoms bound to the ring formed on ring A, e.g., 1, 2, 3, 4, 5, 6, 7, 8, 9, or up to 10, such as between 1 to 5, 1 to 4, or 1 to 3, or 1 or 2) independently selected R³⁰.

The term "—C(R⁷¹)=(heterocyclylidene)" as used herein refers to a monoradical, wherein a ring carbon atom of the heterocyclylidene moiety is bound to —C(R⁷¹) moiety via a double bond. An example of —C(R⁷¹)=(heterocyclylidene) has the structure

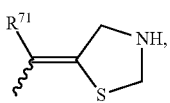

wherein ⸺ represents the attachment of the —C(R⁷¹)=(heterocyclylidene) group to the remainder of the compound of formula (I). The heterocyclylidene moiety may be optionally substituted by one or more (such as 1 to the maximum number of hydrogen atoms bound to the heterocyclylidene moiety, e.g., 1, 2, 3, 4, 5, 6, 7, 8, 9, or up to 10, such as between 1 to 5, 1 to 4, or 1 to 3, or 1 or 2) independently selected 2ⁿᵈ level substituents as specified herein. Thus, the term "—C(R⁷¹)=(heterocyclylidene)" also encompasses the structure

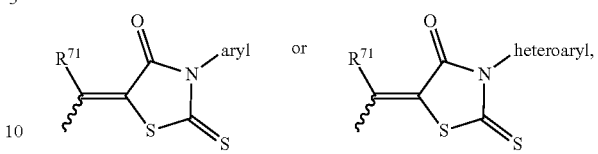

wherein the aryl moiety is preferably a 6- to 10-membered aryl (such as phenyl) and the heteroaryl moiety is preferably a 3- to 14-membered heteroaryl (such as 5- to 7-membered heteroaryl), wherein each of the aryl and heteroaryl moieties may be optionally substituted with one or more (such as 1 to the maximum number of hydrogen atoms bound to the aryl or heteroaryl moiety, e.g., 1, 2, 3, 4, 5, 6, 7, 8, 9, or up to 10, such as between 1 to 5, 1 to 4, or 1 to 3, or 1 or 2) 3ʳᵈ level substituents (such as with one, two or three 3ʳᵈ level substituents independently selected from halogen and —CF₃).

The term "=C(R⁸¹)(6- to 14-membered aryl)" as used herein refers to the diradical methylene, wherein the carbon atom of the methylene moiety bears two substituents, i.e., R⁸¹ and a 6- to 14-membered aryl (such as 6- to 10-membered aryl, e.g., phenyl) group. Likewise, the term "=C(R⁸¹)(3- to 14-membered heteroaryl)" as used herein is to be interpreted in an analogous manner and refers to the diradical methylene, wherein the carbon atom of the methylene moiety bears two substituents, i.e., R⁸¹ and a 3- to 14-membered heteroaryl (such as 5- to 7-membered heteroaryl) group.

The term "optionally substituted" indicates that one or more (such as 1 to the maximum number of hydrogen atoms bound to a group, e.g., 1, 2, 3, 4, 5, 6, 7, 8, 9, or up to 10, such as between 1 to 5, 1 to 4, or 1 to 3, or 1 or 2) hydrogen atom(s) may be replaced with a group (i.e., a 1ˢᵗ level substituent) different from hydrogen such as alkyl (preferably, C₁₋₆ alkyl), alkenyl (preferably, C₂₋₆ alkenyl), alkynyl (preferably, C₂₋₆ alkynyl), aryl (preferably, 6- to 14-membered aryl), heteroaryl (preferably, 3- to 14-membered heteroaryl), cycloalkyl (preferably, 3- to 14-membered cycloalkyl), heterocyclyl (preferably, 3- to 14-membered heterocyclyl), —C(R⁷¹)=(heterocyclylidene), halogen, —CN, azido, —NO₂, —OR⁷¹, —N(R⁷²)(R⁷³), —S(O)₀₋₂R⁷¹, —S(O)₁₋₂OR⁷¹, —OS(O)₁₋₂R⁷¹, —OS(O)₁₋₂OR⁷¹, —S(O)₁₋₂N(R⁷²)(R⁷³), —OS(O)₁₋₂N(R⁷²)(R⁷³), —N(R⁷¹)S(O)₁₋₂R⁷¹, —NR⁷¹S(O)₁₋₂OR⁷¹, —NR⁷¹S(O)₁₋₂N(R⁷²)(R⁷³), —OP(O)(OR⁷¹)₂, —C(=X¹)R⁷¹, —C(=X¹)X¹R⁷¹, —X¹C(=X¹)R⁷¹, and —X¹C(=X¹)X¹R⁷¹, and/or any two 1ˢᵗ level substituents which are bound to the same carbon atom of a cycloalkyl or heterocyclyl group may join together to form =X¹, wherein each of the alkyl, alkenyl, alkynyl, aryl, heteroaryl, cycloalkyl, heterocyclyl, and heterocyclylidene groups of the 1ˢᵗ level substituent may themselves be substituted by one or more (e.g., one, two or three) substituents (i.e., a 2ⁿᵈ level substituent) selected from the group consisting of C₁₋₆ alkyl, C₂₋₆ alkenyl, C₂₋₆ alkynyl, 6- to 14-membered aryl, 3- to 14-membered heteroaryl, 3- to 14-membered cycloalkyl, 3- to 14-membered heterocyclyl, halogen, —CF₃, —CN, azido, —NO₂, —OR⁸¹, —N(R⁸²)(R⁸³), —S(O)₀₋₂R⁸¹, —S(O)₁₋₂OR⁸¹, —OS(O)₁₋₂R⁸¹, —OS(O)₁₋₂OR⁸¹, —S(O)₁₋₂N(R⁸²)(R⁸³), —OS(O)₁₋₂N(R⁸²)(R⁸³), —N(R⁸¹)S(O)₁₋₂R⁸¹, —NR⁸¹S(O)₁₋₂OR⁸¹, —NR⁸¹S(O)₁₋₂N(R⁸²)(R⁸³), —OP(O)(OR⁸¹)₂, —C(=X²)R⁸¹, —C(=X²)X²R⁸¹, —X²C(=X²)R⁸¹, and —X²C(=X²)

$X^2R^{81}$, and/or any two $2^{nd}$ level substituents which are bound to the same carbon atom of a cycloalkyl or heterocyclyl group being a $1^{st}$ level substituent may join together to form $=X^2$ and/or any two $2^{nd}$ level substituents which are bound to the same carbon atom of a cycloalkyl or heterocyclyl group being a $1^{st}$ level substituent may join together to form $=C(R^{81})$(6- to 14-membered aryl) or $=C(R^{81})$(3- to 14-membered heteroaryl), wherein each of the $C_{1-6}$ alkyl, $C_{2-6}$ alkenyl, $C_{2-6}$ alkynyl, 6- to 14-membered aryl (including 6- to 14-membered aryl of the $=C(R^{81})$(6- to 14-membered aryl) group), 3- to 14-membered heteroaryl (including 3- to 14-membered heteroaryl of the $=C(R^{81})$(3- to 14-membered heteroaryl) group), 3- to 14-membered cycloalkyl, 3- to 14-membered heterocyclyl groups of the $2^{nd}$ level substituent is optionally substituted with one or more (e.g., one, two or three) substituents (i.e., a $3^{rd}$ level substituent) independently selected from the group consisting of $C_{1-3}$ alkyl, halogen, —$CF_3$, —CN, azido, —$NO_2$, —OH, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O) ($C_{1-3}$ alkyl), —NHC(=NH)NH$_{z-2}$ ($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a 3- to 14-membered cycloalkyl or heterocyclyl group being a $2^{nd}$ level substituent may join together to form =O, =S, =NH, or =N($C_{1-3}$ alkyl);

wherein $R^{71}$, $R^{72}$, and $R^{73}$ are independently selected from the group consisting of H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —$CF_3$, —CN, azido, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O) ($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{z-z}$($C_{1-3}$ alkyl)$_z$, wherein z is 0, 1, or 2 and $C_{1-3}$ alkyl is methyl, ethyl, propyl or isopropyl;

$R^{81}$, $R^{82}$, and $R^{83}$ are independently selected from the group consisting of H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —$CF_3$, —CN, azido, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS (O)$_2$($C_{1-3}$ alkyl), —S(O)$_2$NH$_{2-z}$($C_{1-3}$ alkyl)$_z$, —C(=O) ($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl) C(=NH)NH$_{2-z}$($C_{1-3}$ alkyl)$_z$, wherein z is 0, 1, or 2 and $C_{1-3}$ alkyl is methyl, ethyl, propyl or isopropyl; and $X^1$ and $X^2$ are independently selected from O, S, and N($R^{84}$), wherein $R^{84}$ is —H or $C_{1-3}$ alkyl.

Typical $1^{st}$ level substituents are preferably selected from the group consisting of $C_{1-6}$ alkyl, $C_{2-6}$ alkenyl, $C_{2-6}$ alkynyl, 6- to 14-membered (such as 6- to 10-membered) aryl, 3- to 14-membered (such as 5- or 6-membered) heteroaryl, 3- to 14-membered (such as 3- to 7-membered) cycloalkyl, 3- to 14-membered (such as 3- to 7-membered) heterocyclyl, —C($R^{71}$)=(3- to 14-membered (such as 3- to 7-membered) heterocyclylidene), halogen, —CN, azido, —$NO_2$, —$OR^{71}$, —N($R^{72}$)($R^{73}$), —S(O)$_{0-2}R^{71}$, —S(O)$_{1-2}OR^{71}$, —OS(O)$_{1-2}R^{71}$, —OS(O)$_{1-2}OR^{71}$, —S(O)$_{1-2}$N($R^{72}$)($R^{73}$), —OS(O)$_{1-2}$N($R^{72}$)($R^{73}$), —N($R^{71}$)S(O)$_{1-2}R^{71}$, —$NR^{71}$S(O)$_{1-2}OR^{71}$, —C(=$X^1$)$R^{71}$, —C(=$X^1$)$X^1R^{71}$, —$X^1$C(=$X^1$)$R^{71}$, and —$X^1$C(=$X^1$)$X^1R^{71}$, such as $C_{1-4}$ alkyl, $C_{2-4}$ alkenyl, $C_{2-4}$ alkynyl, 6-membered aryl, 5- or 6-membered heteroaryl, 3- to 7-membered cycloalkyl, 3- to 7-membered (such as 5- or 6-membered) heterocyclyl, —C($R^{71}$)=(5- to 7-membered heterocyclylidene) (such as —C(H)=(5- or 6-membered heterocyclylidene)), halogen, —$CF_3$, —CN, azido, —$NO_2$, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$ NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C (=NH)NH$_{z-z}$($C_{1-3}$ alkyl)$_z$, wherein z is 0, 1, or 2 and $C_{1-3}$ alkyl is methyl, ethyl, propyl or isopropyl; wherein $X^1$ is independently selected from O, S, NH and N(CH$_3$); and $R^{71}$, $R^{72}$, and $R^{73}$ are as defined above or, preferably, are independently selected from the group consisting of —H, $C_{1-4}$ alkyl, $C_{2-4}$ alkenyl, $C_{2-4}$ alkynyl, 5- or 6-membered cycloalkyl, 5- or 6-membered aryl, 5- or 6-membered heteroaryl, and 5- or 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of $C_{1-3}$ alkyl, halogen, —$CF_3$, —CN, azido, —$NO_2$, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$ ($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C (=NH)NH$_{2-z}$($C_{1-3}$ alkyl)$_z$, wherein z is 0, 1, or 2 and $C_{1-3}$ alkyl is methyl, ethyl, propyl or isopropyl. Particular examples of $1^{st}$ level substituents are selected from the group consisting of $C_{1-3}$ alkyl, phenyl, imidazolyl, thiazolyl, cyclopentyl, cyclohexyl, dihydrothiazolyl, thiazolidinyl, —C(H)= (thiazolidinylidene) (such as —C(H)=(1,3-thiazolidin-5-ylidene)), halogen, —$CF_3$, —CN, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —C(=O)OH, —C(=O)O ($C_{1-3}$ alkyl), —C(=O)NH$_{2-z}$($C_{1-3}$ alkyl)$_z$, —NHC(=O) ($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl. Particularly preferred $1^{st}$ level substituents are selected from the group consisting of $C_{1-3}$ alkyl, phenyl, thiazolidinyl, —C(H)=(thiazolidinylidene) (such as —C(H)=(1,3-thiazolidin-5-ylidene)), halogen (such as F or Cl), —$NH_2$, —NHS (O)$_2$($C_{1-3}$ alkyl), —NHC(=O)($C_{1-3}$ alkyl), and —NHC (=NH)NH$_{z-2}$($C_{1-3}$ alkyl)$_z$, wherein z is 0, 1, or 2 and $C_{1-3}$ alkyl is methyl, ethyl, propyl or isopropyl.

Typical $2^{nd}$ level substituents are preferably selected from the group consisting of $C_{1-4}$ alkyl, $C_{2-4}$ alkenyl, $C_{2-4}$ alkynyl, 6- or 10-membered aryl, 5- or 6-membered heteroaryl, 5- or 6-membered cycloalkyl, 5- or 6-membered heterocyclyl, halogen, =O, =S, =C($R^{81}$)(6- or 10-membered aryl), =C($R^{81}$)(3- to 14-membered heteroaryl), —$CF_3$, —CN, azido, —$NO_2$, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$ ($C_{1-3}$ alkyl), —S(O)$_2$$NH_{2-z}$($C_{1-3}$ alkyl)$_z$, —C(=O)OH, —C(=O)O($C_{1-3}$ alkyl), —C(=O)$NH_{2-z}$($C_{1-3}$ alkyl)$_z$, —NHC(=O)($C_{1-3}$ alkyl), —NHC(=NH)$NH_{z-2}$($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl. Particular examples of $2^{nd}$ level substituents are selected from the group consisting of $C_{1-3}$ alkyl, phenyl, 5- or 6-membered heteroaryl, 5- or 6-membered cycloalkyl, 5- or 6-membered heterocyclyl, halogen, =O, =S, =C($R^{81}$)(6- or 10-membered aryl) (such as =C(H)(6-membered aryl)), =C($R^{81}$)(3- to 14-membered heteroaryl) (such as =C(H)(5- to 7-membered heteroaryl)), —$CF_3$, —CN, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —C(=O)OH, —C(=O)O($C_{1-3}$ alkyl), —C(=O)$NH_{2-z}$($C_{1-3}$ alkyl)$_z$, —NHC(=O)($C_{1-3}$ alkyl), —NHC(=NH)$NH_{z-2}$($C_{1-3}$ alkyl)$_z$, and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl. Particularly preferred $2^{nd}$ level substituents are selected from the group consisting of methyl, ethyl, propyl, isopropyl, phenyl, =O, =S, and =C($R^{81}$)(6- or 10-membered aryl) (such as =C(H)(phenyl)).

Typical $3^{rd}$ level substituents are preferably selected from the group consisting of $C_{1-3}$ alkyl, phenyl, halogen, —$CF_3$, —OH, —$OCH_3$, —$SCH_3$, —$NH_{2-z}$($CH_3$)$_z$, —C(=O)OH, and —C(=O)$OCH_3$, wherein z is 0, 1, or 2 and $C_{1-3}$ alkyl is methyl, ethyl, propyl or isopropyl. Particularly preferred $3^{rd}$ level substituents are selected from the group consisting of methyl, ethyl, propyl, isopropyl, halogen (such as F or Cl), and —$CF_3$, such as halogen (such as F or Cl), and —$CF_3$.

The phrase "partially hydrogenated form" of an unsaturated compound or group as used herein means that part of the unsaturation has been removed by formally adding hydrogen to the initially unsaturated compound or group without removing all unsaturated moieties. The phrase "completely hydrogenated form" of an unsaturated compound or group is used herein interchangeably with the term "perhydro" and means that all unsaturation has been removed by formally adding hydrogen to the initially unsaturated compound or group. For example, partially hydrogenated forms of a 5-membered heteroaryl group (containing 2 double bonds in the ring, such as furan) include dihydro forms of said 5-membered heteroaryl group (such as 2,3-dihydrofuran or 2,5-dihydrofuran), whereas the tetrahydro form of said 5-membered heteroaryl group (e.g., tetrahydrofuran, i.e., THF) is a completely hydrogenated (or perhydro) form of said 5-membered heteroaryl group. Likewise, for a 6-membered heteroaryl group having 3 double bonds in the ring (such as pyridyl), partially hydrogenated forms include di- and tetrahydro forms (such as di- and tetrahydropyridyl), whereas the hexahydro form (such as piperidinyl in case of the heteroaryl pyridyl) is the completely hydrogenated (or perhydro) derivative of said 6-membered heteroaryl group. Consequently, a hexahydro form of an aryl or heteroaryl can only be considered a partially hydrogenated form according to the present invention if the aryl or heteroaryl contains at least 4 unsaturated moieties consisting of double and triple bonds between ring atoms.

The term "optional" or "optionally" as used herein means that the subsequently described event, circumstance or condition may or may not occur, and that the description includes instances where said event, circumstance, or condition occurs and instances in which it does not occur.

"Isomers" are compounds having the same molecular formula but differ in structure ("structural isomers") or in the geometrical (spatial) positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (±). "Diastereomers" are stereoisomers which are non-superimposable and which are not mirror-images of each other. "Tautomers" are structural isomers of the same chemical substance that spontaneously and reversibly interconvert into each other, even when pure, due to the migration of individual atoms or groups of atoms; i.e., the tautomers are in a dynamic chemical equilibrium with each other.

In case a structural formula shown in the present application can be interpreted to encompass more than one isomer, said structural formula, unless explicitly stated otherwise, encompasses all possible isomers and, hence, each individual isomer. For example, a compound of formula (I) having the formula

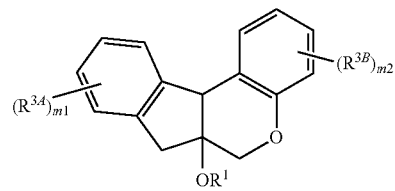

encompasses four isomers, i.e., the isomers having the following formulas (B1) to (B4):

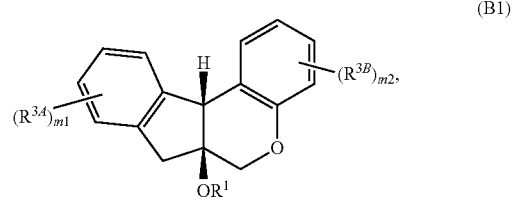
(B1)

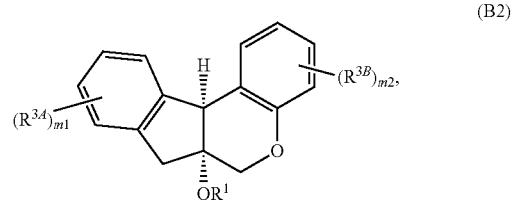
(B2)

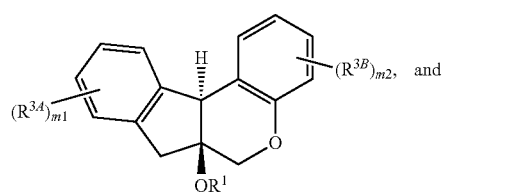
(B3)

and

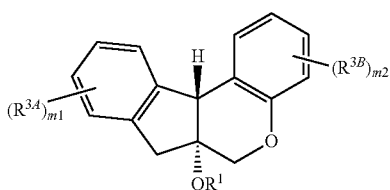

(B4)

The skilled person will appreciate that such groups of isomers occur if ring Q of formula (I) is a 9-membered bicyclic heterocyclyl, wherein each of the bridgehead atoms (i.e., the two ring atoms of the 9-membered bicyclic heterocyclyl which are shared by both partial rings (i.e., the 5-membered ring and the 6-membered ring) of the 9-membered bicyclic heterocyclyl) is saturated. In this respect, the term "saturated" means that the bridgehead only forms single (σ) bonds (but no double (π) bond) with its directly adjacent atoms.

Thus, in one embodiment, a compound of formula (I), wherein Q is a 9-membered bicyclic heterocyclyl (such as a compound of any one of formulas (I), (IIa), (III), (IV), (V), (VIa), (VIb), (VIc), (VId), (VIe), (VIf), (VIIa), (VIIb), (VIIc), (VIId), (VIIe), and (VIIf), in particular a compound of formula (IIa) (VIa), (VIb), (VIc), (VId), (VIe), (VIf), (VIIa), (VIIb), (VIIc), (VIId), (VIIe), or (VIIf)) is an isomer represented by a formula identical or similar to one of the above formulas (B1) to (B4), i.e., wherein (1) the moieties (e.g., lone electron pairs, atoms, or groups) of the two bridgeheads of ring Q project towards the viewer (cf. the depicted H atom and the OR$^1$ moiety in Formula (B1); (2) the moieties (e.g., lone electron pairs, atoms, or groups) of the two bridgeheads of ring Q project away from the viewer (cf. the depicted H atom and the OR$^1$ moiety in Formula (B2); (3) the moiety (e.g., lone electron pair, atom, or group) on the upper bridgehead (cf. the depicted H atom in Formula (B3)) projects away from the viewer, whereas the OR$^1$ moiety on the lower bridgehead projects towards the viewer; or (4) the moiety (e.g., lone electron pair, atom, or group) on the upper bridgehead (cf. the depicted H atom in Formula (B4)) projects towards the viewer, whereas the OR$^1$ moiety on the lower bridgehead projects away from the viewer.

"Polymorphism" as referred to herein means that a solid material (such as a compound) is able to exist in more than one form or crystalline structure, i.e., "polymorphic modifications" or "polymorphic forms". The terms "polymorphic modifications", "polymorphic forms", and "polymorphs" are used interchangeable in the present invention. According to the present invention, these "polymorphic modifications" include crystalline forms, amorphous forms, solvates, and hydrates. Mainly, the reason for the existence of different polymorphic forms lies in the use of different conditions during the crystallization process, such as the following:
  solvent effects (the packing of crystal may be different in polar and nonpolar solvents);
  certain impurities inhibiting growth pattern and favor the growth of a metastable polymorphs;
  the level of supersaturation from which material is crystallized (in which generally the higher the concentration above the solubility, the more likelihood of metastable formation);
  temperature at which crystallization is carried out;
  geometry of covalent bonds (differences leading to conformational polymorphism);
  change in stirring conditions.

Polymorphic forms may have different chemical, physical, and/or pharmacological properties, including but not limited to, melting point, X-ray crystal and diffraction pattern, chemical reactivity, solubility, dissolution rate, vapor pressure, density, hygroscopicity, flowability, stability, compactability, and bioavailability. Polymorphic forms may spontaneously convert from a metastable form (unstable form) to the stable form at a particular temperature. According to Ostwald's rule, in general it is not the most stable but the least stable polymorph that crystallizes first. Thus, quality, efficacy, safety, processability and/or manufacture of a chemical compound, such as a compound of the present invention, can be affected by polymorphism. Often, the most stable polymorph of a compound (such as a compound of the present invention) is chosen due to the minimal potential for conversion to another polymorph. However, a polymorphic form which is not the most stable polymorphic form may be chosen due to reasons other than stability, e.g. solubility, dissolution rate, and/or bioavailability.

The term "crystalline form" of a material as used herein means that the smallest components (i.e., atoms, molecule or ions) of said material form crystal structures. A "crystal structure" as referred to herein means a unique three-dimensional arrangement of atoms or molecules in a crystalline liquid or solid and is characterized by a pattern, a set of atoms arranged in a particular manner, and a lattice exhibiting long-range order and symmetry. A lattice is an array of points repeating periodically in three dimensions and patterns are located upon the points of a lattice. The subunit of the lattice is the unit cell. The lattice parameters are the lengths of the edges of a unit cell and the angles between them. The symmetry properties of the crystal are embodied in its space group. In order to describe a crystal structure the following parameters are required: chemical formula, lattice parameters, space group, the coordinates of the atoms and occupation number of the point positions.

The term "amorphous form" of a material as used herein means that the smallest components (i.e., atoms, molecule or ions) of said material are not arranged in a lattice but are arranged randomly. Thus, unlike crystals in which a short-range order (constant distances to the next neighbor atoms) and a long-range order (periodical repetition of a basic lattice) exist, only a short-range order exists in an amorphous form. The term "complex of a compound" as used herein refers to a compound of higher order which is generated by association of the compound with other one or more other molecules. Exemplary complexes of a compound include, but are not limited to, solvates, clusters, and chelates of said compound.

The term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

In isotopically labeled compounds one or more atoms are replaced by a corresponding atom having the same number of protons but differing in the number of neutrons. For example, a hydrogen atom may be replaced by a deuterium atom. Exemplary isotopes which can be used in the compounds of the present invention include deuterium, $^{11}C$, $^{13}C$, $^{14}C$, $^{15}N$, $^{18}F$, $^{32}P$, $^{32}S$, $^{35}S$, $^{36}Cl$, and $^{125}I$.

The term "half-life" relates to the period of time which is needed to eliminate half of the activity, amount, or number of molecules. In the context of the present invention, the half-life of a compound of formula (I) is indicative for the stability of said compound.

The terms "patient", "individual", "animal" or "subject" relate to multicellular animals, such as vertebrates. For example, vertebrates in the context of the present invention are mammals, birds (e.g., poultry), reptiles, amphibians, bony fishes, and cartilaginous fishes, in particular domesticated animals of any of the foregoing as well as animals (in particular vertebrates) in captivity such as animals (in particular vertebrates) of zoos. Mammals in the context of the present invention include, but are not limited to, humans, non-human primates, domesticated mammals, such as dogs, cats, sheep, cattle, goats, pigs, horses etc., laboratory mammals such as mice, rats, rabbits, guinea pigs, etc. as well as mammals in captivity such as mammals of zoos. The term "animal" as used herein also includes humans. Particular non-limiting examples of birds include domesticated poultry, and include birds such as chickens, turkeys, ducks, geese, guinea fowl, pigeons, pheasants etc.; while particular non-limiting examples of bony or cartilaginous fish include those suitable for cultivation by aquiculture, and include bony fish such as salmon, trout, perch, carp, cat-fish, etc. Preferably, the "patient", "individual", "animal" or "subject" is a mammal, and most preferably the "patient", "individual", "animal" or "subject" is a human.

Compounds

The present invention provides a compound selected from the group consisting of a polyheterocyclic derivative having the general formula (I):

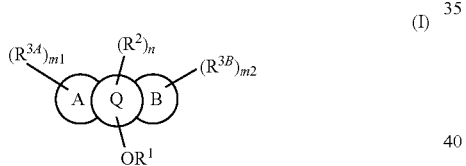

and solvates, salts, complexes, polymorphs, crystalline forms, racemic mixtures, diastereomers, enantiomers, tautomers, isotopically labeled forms, prodrugs, and combinations thereof, particularly for use in therapy, wherein ring Q is a 9- or 8-membered bi- or monocyclic heterocyclyl which contains (i) one or two heteroatoms selected from N and O and (ii) a quaternary C atom to which the moiety —$OR^1$ is bound;

each of rings A and B is fused to ring Q and is independently selected from benzo, pyridino, pyrimidino, pyridazino, pyrazino, and hydrated forms thereof;

$R^1$ is selected from the group consisting of H, alkyl, alkenyl, alkynyl, cycloalkyl, aryl, heterocyclyl, heteroaryl, —$S(O)_{1-2}OR^{11}$, —$S(O)_{1-2}N(R^{12})(R^{13})$, —$P(O)(OR^{11})_2$, —$C(=X)R^{11}$, and —$C(=X)XR^{11}$, wherein each of the alkyl, alkenyl, alkynyl, cycloalkyl, aryl, heterocyclyl, and heteroaryl groups is optionally substituted with one or more (such as 1 to the maximum number of hydrogen atoms bound to $R^1$, e.g., 1, 2, 3, 4, 5, 6, 7, 8, 9, or up to 10, such as between 1 to 5, 1 to 4, or 1 to 3, or 1 or 2) independently selected $R^{30}$;

each $R^2$ is independently selected from the group consisting of alkyl, alkenyl, alkynyl, cycloalkyl, aryl, heterocyclyl, heteroaryl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$P(O)(OR^{11})_2$, —$OP(O)(OR^{11})_2$, —$C(=X)R^{11}$, —$C(=X)XR^{11}$, —$XC(=X)R^{11}$, and —$XC(=X)XR^{11}$, and/or any two $R^2$ which are bound to the same carbon atom of ring Q may join together to form =$X^Q$, wherein each of the alkyl, alkenyl, alkynyl, cycloalkyl, aryl, heterocyclyl, and heteroaryl groups is optionally substituted with one or more (such as 1 to the maximum number of hydrogen atoms bound to $R^2$, e.g., 1, 2, 3, 4, 5, 6, 7, 8, 9, or up to 10, such as between 1 to 5, 1 to 4, or 1 to 3, or 1 or 2) independently selected $R^{30}$;

each of $R^{3A}$ and $R^{3B}$ is independently selected from the group consisting of alkyl, alkenyl, alkynyl, cycloalkyl, aryl, heterocyclyl, heteroaryl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$P(O)(OR^{11})_2$, —$OP(O)(OR^{11})_2$, —$C(=X)R^{11}$, —$C(=X)XR^{11}$, —$XC(=X)R^{11}$, and —$XC(=X)XR^{11}$, and/or any two $R^{3A}$ which are bound to the same carbon atom of ring A may join together to form =$X^A$ and/or any two $R^{3B}$ which are bound to the same carbon atom of ring B may join together to form =$X^B$ and/or any two $R^{3A}$ on adjacent ring atoms of ring A may join together with the adjacent ring atoms of ring A to form a ring (such as a monocyclic ring preferably 6-membered aryl, 5- to 7-membered heteroaryl, 5- to 7-membered heterocyclyl, or 5- to 7-membered cycloalkyl) which is optionally substituted with one or more (such as 1 to the maximum number of hydrogen atoms bound to the ring formed at ring A, e.g., 1, 2, 3, 4, 5, 6, 7, 8, 9, or up to 10, such as between 1 to 5, 1 to 4, or 1 to 3, or 1 or 2) independently selected $R^{30}$ and/or any two $R^{3B}$ on adjacent ring atoms of ring B may join together with the adjacent ring atoms of ring B to form a ring (such as a monocyclic ring preferably 6-membered aryl, 5- to 7-membered heteroaryl, 5- to 7-membered heterocyclyl, or 5- to 7-membered cycloalkyl) which is optionally substituted with one or more (such as 1 to the maximum number of hydrogen atoms bound to the ring formed at ring B, e.g., 1, 2, 3, 4, 5, 6, 7, 8, 9, or up to 10, such as between 1 to 5, 1 to 4, or 1 to 3, or 1 or 2) independently selected $R^{30}$, wherein each of the alkyl, alkenyl, alkynyl, cycloalkyl, aryl, heterocyclyl, and heteroaryl groups is optionally substituted with one or more (such as 1 to the maximum number of hydrogen atoms bound to the alkyl, alkenyl, alkynyl, cycloalkyl, aryl, heterocyclyl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$;

n is 0, 1, 2, 3, or 4;

each of m1 and m2 is independently 0, 1, 2, 3, or 4;

X is independently selected from O, S, and $N(R^{14})$;

each of $X^Q$, $X^A$ and $X^B$ is independently selected from O, S, and NH;

$R^{11}$ is independently selected from the group consisting of H, alkyl, alkenyl, alkynyl, cycloalkyl, aryl, heteroaryl, and heterocyclyl, wherein each of the alkyl, alkenyl, alkynyl, cycloalkyl, aryl, heterocyclyl, and heteroaryl groups is optionally substituted with one or more (such as 1 to the maximum number of hydrogen atoms bound to $R^{11}$, e.g., 1, 2, 3, 4, 5, 6, 7, 8, 9, or up to 10, such as between 1 to 5, 1 to 4, or 1 to 3, or 1 or 2) independently selected $R^{30}$;

each of $R^{12}$ and $R^{13}$ is independently selected from the group consisting of H, alkyl, alkenyl, alkynyl, cycloalkyl, aryl, heteroaryl, and heterocyclyl, or $R^{12}$ and $R^{13}$ may join together with the nitrogen atom to which they are attached to form the group —N=$CR^{15}R^{16}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{14}$ is independently selected from the group consisting of H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

each of $R^{15}$ and $R^{16}$ is independently selected from the group consisting of H, alkyl, alkenyl, alkynyl, cycloalkyl, aryl, heteroaryl, heterocyclyl, and —$NH_yR^{20}_{2-y}$, or $R^{15}$ and $R^{16}$ may join together with the atom to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

y is an integer from 0 to 2;

$R^{20}$ is independently selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, —$C(R^{71})$=(heterocyclylidene), halogen, —CN, azido, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-2}OR^{71}$, —$NR^{71}S(O)_{1-2}N(R^{72})(R^{73})$, —$OP(O)(OR^{71})_2$, —$C(=X^1)R^{71}$, —$C(=X^1)X^1R^{71}$, —$X^1C(=X^1)R^{71}$, and —$X^1C(=X^1)X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, heterocyclyl, and heterocyclylidene groups being a $1^{st}$ level substituent is optionally substituted by one or more (such as 1 to the maximum number of hydrogen atoms bound to the alkyl, alkenyl, alkynyl, aryl, heteroaryl, cycloalkyl, heterocyclyl, or heterocyclylidene group being a $1^{st}$ level substituent, e.g., 1, 2, 3, 4, 5, 6, 7, 8, 9, or up to 10, such as between 1 to 5, 1 to 4, or 1 to 3, or 1 or 2) $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 6- to 14-membered aryl, 3- to 14-membered heteroaryl, 3- to 14-membered cycloalkyl, 3- to 14-membered heterocyclyl, halogen, —$CF_3$, —CN, azido, —$NO_2$, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}S(O)_{1-2}N(R^{82})(R^{83})$, —$OP(O)(OR^{81})_2$, —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents which are bound to the same carbon atom of a cycloalkyl or heterocyclyl group being a $1^{st}$ level substituent may join together to form =$X^2$ and/or any two $2^{nd}$ level substituents which are bound to the same carbon atom of a cycloalkyl or heterocyclyl group being a $1^{st}$ level substituent may join together to form =$C(R^{81})$(6- to 14-membered aryl) or =$C(R^{81})$(3- to 14-membered heteroaryl), wherein each of the $C_{1-6}$ alkyl, $C_{2-6}$ alkenyl, $C_{2-6}$ alkynyl, 6- to 14-membered aryl, 3- to 14-membered heteroaryl, 3- to 14-membered cycloalkyl, and 3- to 14-membered heterocyclyl groups being a $2^{nd}$ level substituent is optionally substituted with one or more (such as 1 to the maximum number of hydrogen atoms bound to the $C_{1-6}$ alkyl, $C_{2-6}$ alkenyl, $C_{2-6}$ alkynyl, 6- to 14-membered aryl, 3- to 14-membered heteroaryl, 3- to 14-membered cycloalkyl, or 3- to 14-membered heterocyclyl group being a $2^{nd}$ level substituent, e.g., 1, 2, 3, 4, 5, 6, 7, 8, 9, or up to 10, such as between 1 to 5, 1 to 4, or 1 to 3, or 1 or 2) $3^{rd}$ level substituents, wherein said $3^{rd}$ level substituent is, in each case, independently selected from the group consisting of $C_{1-3}$ alkyl, halogen, —$CF_3$, —CN, azido, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)OH$, —$C(=O)O(C_{1-3}$ alkyl), —$C(=O)NH_{2-z}(C_{1-3}$ alkyl)$_z$, —$NHC(=O)(C_{1-3}$ alkyl), —$NHC(=NH)NH_{z-2}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a 3- to 14-membered cycloalkyl or heterocyclyl group being a $2^{nd}$ level substituent may join together to form =O, =S, =NH, or =$N(C_{1-3}$ alkyl);

wherein $R^{71}$, $R^{72}$, and $R^{73}$ are independently selected from the group consisting of H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —CF₃, —CN, azido, —NO₂, —OH, —O(C₁₋₃ alkyl), —OCF₃, =O, —S(C₁₋₃ alkyl), —NH₂, —NH(C₁₋₃ alkyl), —N(C₁₋₃ alkyl)₂, —NHS(O)₂(C₁₋₃ alkyl), —S(O)₂NH$_{2-z}$(C₁₋₃ alkyl)$_z$, —C(=O)(C₁₋₃ alkyl), —C(=O)OH, —C(=O)O(C₁₋₃ alkyl), —C(=O)NH$_{2-z}$(C₁₋₃ alkyl)$_z$, —NHC(=O)(C₁₋₃ alkyl), —NHC(=NH)NH$_{2-z}$(C₁₋₃ alkyl)$_z$, and —N(C₁₋₃ alkyl)C(=NH)NH$_{2-z}$(C₁₋₃ alkyl)$_z$, wherein z is 0, 1, or 2 and C₁₋₃ alkyl is methyl, ethyl, propyl or isopropyl;

$R^{81}$, $R^{82}$, and $R^{83}$ are independently selected from the group consisting of H, C₁₋₄ alkyl, C₂₋₄ alkenyl, C₂₋₄ alkynyl, 3- to 6-membered cycloalkyl, 5- or 6-membered aryl, 5- or 6-membered heteroaryl, and 3- to 6-membered heterocyclyl, wherein each of the C₁₋₄ alkyl, C₂₋₄ alkenyl, C₂₋₄ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of C₁₋₃ alkyl, halogen, —CF₃, —CN, azido, —NO₂, —OH, —O(C₁₋₃ alkyl), —OCF₃, =O, —S(C₁₋₃ alkyl), —NH₂, —NH(C₁₋₃ alkyl), —N(C₁₋₃ alkyl)₂, —NHS(O)₂(C₁₋₃ alkyl), —S(O)₂NH$_{2-z}$(C₁₋₃ alkyl)$_z$, —C(=O)(C₁₋₃ alkyl), —C(=O)OH, —C(=O)O(C₁₋₃ alkyl), —C(=O)NH$_{2-z}$(C₁₋₃ alkyl)$_z$, —NHC(=O)(C₁₋₃ alkyl), —NHC(=NH)NH$_{2-z}$(C₁₋₃ alkyl)$_z$, and —N(C₁₋₃ alkyl)C(=NH)NH$_{2-z}$(C₁₋₃ alkyl)$_z$, wherein z is 0, 1, or 2 and C₁₋₃ alkyl is methyl, ethyl, propyl or isopropyl; and $X^1$ and $X^2$ are independently selected from O, S, and N($R^{84}$), wherein $R^{84}$ is —H or C₁₋₃ alkyl.

In one embodiment, the polyheterocyclic derivative has the formula (IIa):

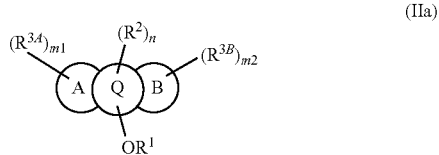

(IIa)

wherein A, B, $R^1$, $R^2$, $R^{3A}$, $R^{3B}$, n, m1, and m2 are as defined above or below and Q is a 9-membered bicyclic heterocyclyl which is optionally substituted with one, two, three or four independently selected $R^2$. In certain embodiments of the polyheterocyclic derivative of formula (IIa), Q is selected from the group consisting of:

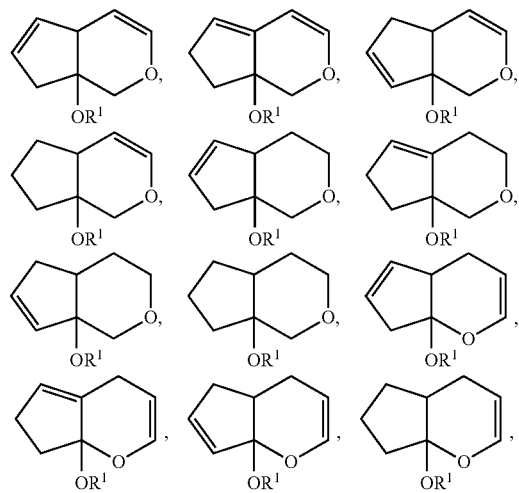

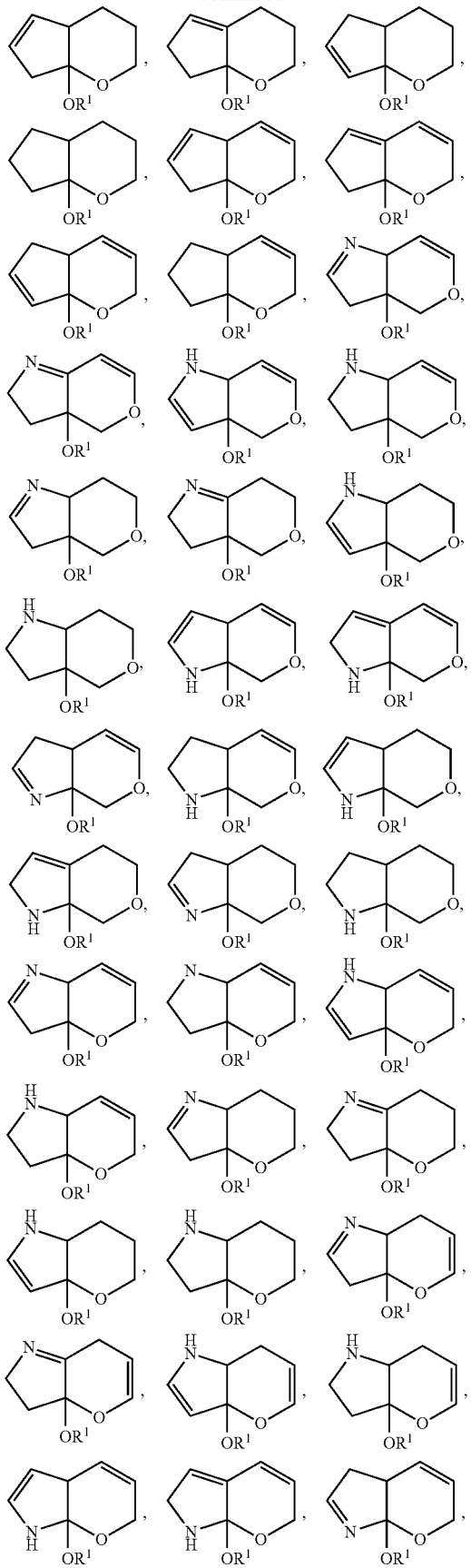

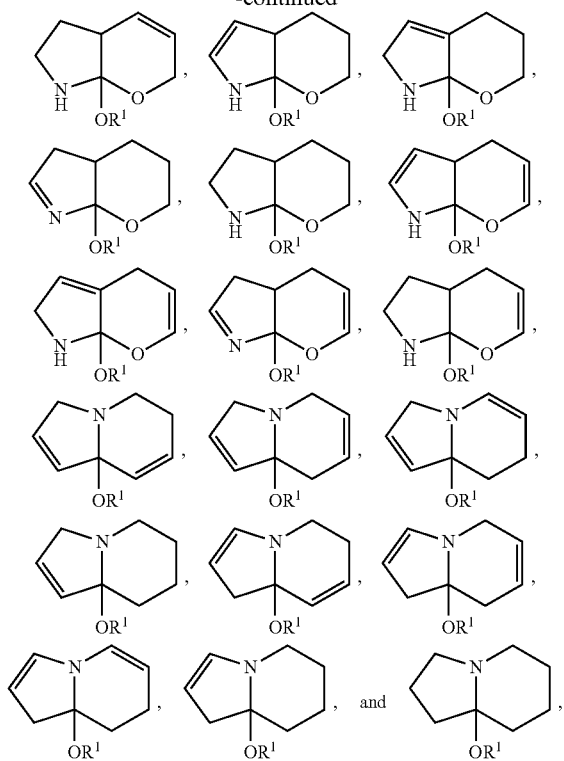

each of which is optionally substituted with one, two, three, or four independently selected $R^2$, wherein $R^2$ is as defined above or below (e.g., each $R^2$ may be independently selected from the group consisting of $C_{1-3}$ alkyl, halogen, —CN, —OH, —O($C_{1-3}$ alkyl), —NH$_2$, —NH($C_{1-3}$ alkyl), and —N($C_{1-3}$ alkyl)$_2$, or any two $R^2$ which are bound to the same carbon atom of ring Q may join together to form =O. Preferably, the total number of =O formed by any two $R^2$ which are bound to the same carbon atom of ring Q is 0 or 1).

In certain embodiments of the polyheterocyclic derivative of formula (IIa), Q has a formula selected from the group consisting of:

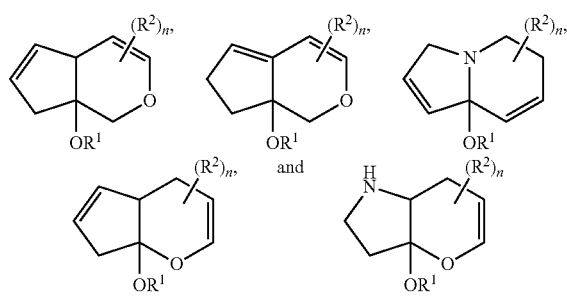

wherein n is 0, 1, 2, 3, or 4 (preferably, 0, 1, or 2); and each $R^2$ is independently selected from the group consisting of $C_{1-3}$ alkyl, halogen, —CN, —OH, —O($C_{1-3}$ alkyl), —NH$_2$, —NH($C_{1-3}$ alkyl), and —N($C_{1-3}$ alkyl)$_2$, or any two $R^2$ which are bound to the same carbon atom of ring Q may join together to form =O. For example, ring Q may have a formula selected from the group consisting of:

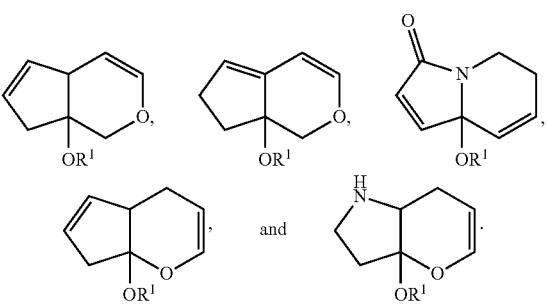

In certain embodiments of the polyheterocyclic derivative of formula (IIa), Q has a formula selected from the group consisting of:

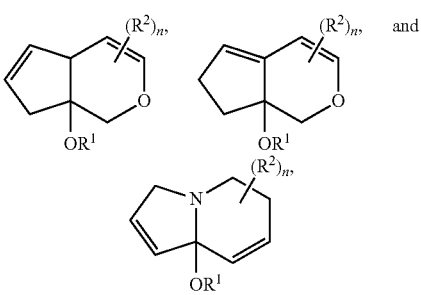

wherein n is 0, 1, 2, 3, or 4 (preferably, 0, 1, or 2); and each $R^2$ is independently selected from the group consisting of $C_{1-3}$ alkyl, halogen, —CN, —OH, —O($C_{1-3}$ alkyl), —NH$_2$, —NH($C_{1-3}$ alkyl), and —N($C_{1-3}$ alkyl)$_2$, or any two $R^2$ which are bound to the same carbon atom of ring Q may join together to form =O. For example, ring Q may have a formula selected from the group consisting of:

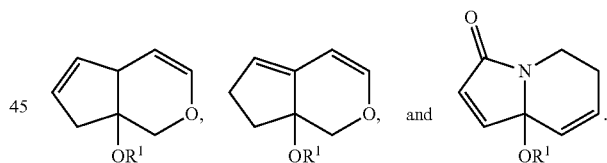

In certain embodiments of the polyheterocyclic derivative of formula (IIa), Q has the formula

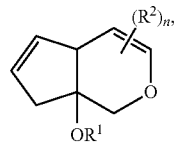

wherein n is 0, 1, 2, 3, or 4 (preferably, 0, 1, or 2); and each $R^2$ is independently selected from the group consisting of $C_{1-3}$ alkyl, halogen, —CN, —OH, —O($C_{1-3}$ alkyl), —NH$_2$, —NH($C_{1-3}$ alkyl), and —N($C_{1-3}$ alkyl)$_2$, or any two $R^2$ which are bound to the same carbon atom of ring Q may join together to form =O. For example, ring Q may have the formula

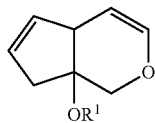

(i.e., n is 0).

In one embodiment, the heterocyclic polyheterocyclic has the formula (IIb):

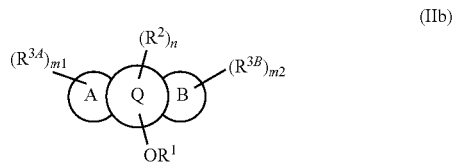

wherein A, B, $R^1$, $R^2$, $R^{3A}$, $R^{3B}$, n, m1, and m2 are as defined above or below and Q is a 8-membered monocyclic heterocyclyl which is optionally substituted with one, two, three or four independently selected $R^2$. In certain embodiments of the polyheterocyclic derivative of formula (IIb), Q is selected from the group consisting of:

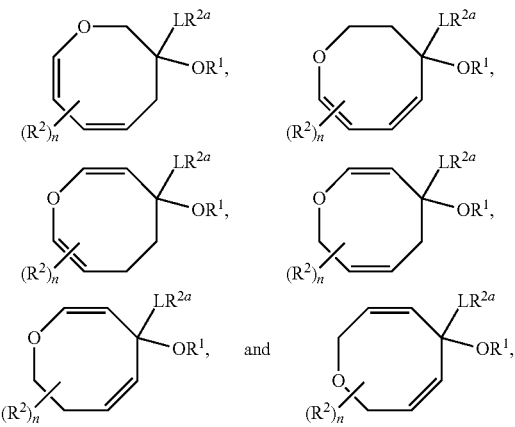

wherein
L is selected from the group consisting of $C_{1-6}$ alkylene, $C_{2-6}$ alkenylene, $C_{2-6}$ alkynylene, and —$(CH_2)_m$—$[Y-(CH_2)_n]_o$—, wherein m is an integer between 1 and 6, n is an integer between 0 and 3, o is an integer between 1 and 3, wherein if n is 0 then o is 1; Y is independently selected from O, S, and —$N(R^{13})$—; and each of the $C_{1-6}$ alkylene, $C_{2-6}$ alkenylene, $C_{2-6}$ alkynylene, —$(CH_2)_m$—, and —$(CH_2)_n$— groups is optionally substituted with one or two independently selected $R^{30}$;

$R^2$, is selected from the group consisting of alkenyl, alkynyl, cycloalkyl, aryl, heterocyclyl, heteroaryl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$P(O)(OR^{11})_2$, —$OP(O)(OR^{11})_2$, —$C(=X)R^{11}$, —$C(=X)XR^{11}$, —$XC(=X)R^{11}$, and —$XC(=X)XR^1$, wherein each of the alkyl, alkenyl, alkynyl, cycloalkyl, aryl, heterocyclyl, and heteroaryl groups is optionally substituted with one or more (such as 1 to the maximum number of hydrogen atoms bound to an alkyl, alkenyl, alkynyl, cycloalkyl, aryl, heterocyclyl, or heteroaryl group, e.g., 1, 2, 3, 4, 5, 6, 7, 8, 9, or up to 10, such as between 1 to 5, 1 to 4, or 1 to 3, or 1 or 2) independently selected $R^{30}$; and n is 0, 1, 2, or 3.

In certain embodiments of the polyheterocyclic derivative of formula (IIb), L, $R^{2a}$, $R^2$, and n are as defined above or below, and Q has the following formula:

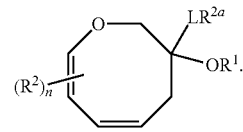

In certain embodiments of the polyheterocyclic derivative of formula (IIb), Q, $R^{2a}$, $R^2$, and n are as defined above or below, and L is $C_{1-6}$ alkylene or —$(CH_2)_m$—$[Y-(CH_2)_n]_o$—, wherein m is an integer between 1 and 6, n is an integer between 0 and 3, o is an integer between 1 and 3, wherein if n is 0 then o is 1; Y is independently selected from O, S, and —$N(R^{13a})$—, wherein $R^{13a}$ is selected from the group consisting of H and $C_{1-3}$ alkyl. In certain embodiments of the polyheterocyclic derivative of formula (IIb), L is $C_{1-6}$ alkylene, such as $C_{1-3}$ alkylene, e.g., methylene.

In certain embodiments of the polyheterocyclic derivative of formula (IIb), Q, L, $R^2$, and n are as defined above or below, and $R^{2a}$ is selected from the group consisting of halogen, —CN, azido, —$NO_2$, —OH, —O($C_{1-3}$ alkyl), —$NH_2$, —$NH(C_{1-3}$ alkyl), —$N(C_{1-3}$ alkyl)$_2$, —OP(O)$(OR^{11})_2$, and —OC(=O)$R^{11}$. For example, $R^{2a}$ is selected from the group consisting of halogen, —CN, azido, —$NO_2$, —OH, —O($C_{1-3}$ alkyl), —$NH_2$, —$NH(C_{1-3}$ alkyl), —$N(C_{1-3}$ alkyl)$_2$, —OP(O)($C_{1-3}$ alkoxy)$_2$, and —OC(=O)($C_{1-3}$ alkyl), such as from the group consisting of —OH, —O($C_{1-3}$ alkyl), —OP(O)($C_{1-3}$ alkoxy)$_2$, and —OC(=O)($C_{1-3}$ alkyl), preferably from the group consisting of —OH, —O($C_{1-3}$ alkyl), and —OC(=O)($C_{1-3}$ alkyl).

In certain embodiments of the polyheterocyclic derivative of formula (IIb), Q, L, and $R^{2a}$ are as defined above or below, n is 0, 1, 2, or 3 (such as 0 or 2) and $R^2$ is selected from the group consisting of $C_{1-3}$ alkyl, halogen, —CN, —OH, —O($C_{1-3}$ alkyl), —$NH_2$, —$NH(C_{1-3}$ alkyl), and —$N(C_{1-3}$ alkyl)$_2$, or any two $R^2$ which are bound to the same carbon atom of ring Q may join together to form =O. In one embodiment of the heterocyclic polyheterocyclic of formula (IIb), L and $R^{2a}$ are as defined above or below, and n is 0.

For example, in certain embodiments of the polyheterocyclic derivative of formula (IIb), Q has the following formula:

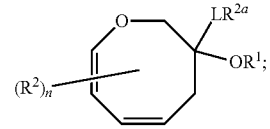

L is $C_{1-6}$ alkylene, such as $C_{1-3}$ alkylene, e.g., methylene; $R^{2a}$ is selected from the group consisting of halogen, —CN, azido, —$NO_2$, —OH, —O($C_{1-3}$ alkyl), —$NH_2$, —$NH(C_{1-3}$ alkyl), —$N(C_{1-3}$ alkyl)$_2$, —OP(O)($C_{1-3}$ alkoxy)$_2$, and —OC(=O)($C_{1-3}$ alkyl), such as from the group consisting of —OH, —O($C_{1-3}$ alkyl), —OP(O)($C_{1-3}$ alkoxy)$_2$, and —OC(=O)($C_{1-3}$ alkyl), preferably from the group consisting of —OH, —O($C_{1-3}$ alkyl), and —OC(=O)($C_{1-3}$ alkyl); n is 0, 1, 2, or 3 (such as 0 or 2, preferably 0); and $R^2$ is selected from the group consisting of $C_{1-3}$ alkyl, halogen, —CN, —OH, —O($C_{1-3}$ alkyl), —NH$_2$, —NH($C_{1-3}$ alkyl), and —N($C_{1-3}$ alkyl)$_2$, or any two $R^2$ which are bound to the same carbon atom of ring Q may join together to form =O.

In one embodiment, the polyheterocyclic derivative has the formula (III):

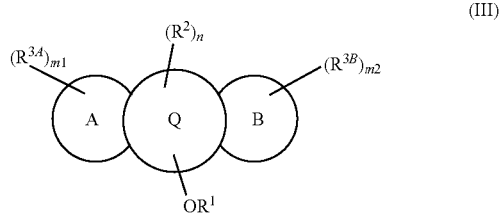

(III)

wherein Q, A, B, $R^2$, $R^{3A}$, $R^{3B}$, n, m1, and m2 are as defined above (in particular with respect to formula (I), (IIa), and/or (IIb)) or below, and $R^1$ is selected from the group consisting of H, —P(O)(OH)$_z$(OR$^{85}$)$_{2-z}$, and —C(=O)R$^{85}$, wherein $R^{85}$ is selected from the group consisting of $C_{1-6}$ alkyl, $C_{3-7}$ cycloalkyl, $C_{6-10}$ aryl, $C_{6-10}$ halogenaryl, 3- to 7-membered heterocyclyl, and 3- to 7-membered heteroaryl; and z is 0, 1, or 2. In one embodiment of the polyheterocyclic derivative of formula (III), $R^1$ is selected from the group consisting of H, —C(=O)($C_6$ halogenaryl), and —C(=O)($C_{1-3}$ alkyl), such as from the group consisting of H, —C(=O)(halogenphenyl), and —C(=O)($C_{1-3}$ alkyl), wherein halogenphenyl is a moiety selected from the group consisting of monohalogenphenyl, dihalogenphenyl, and trihalogenphenyl; and $C_{1-3}$ alkyl is methyl, ethyl, n-propyl, or isopropyl. In one embodiment of the polyheterocyclic derivative of formula (III), $R^1$ is selected from the group consisting of H, —C(=O)(monohalogenphenyl), —C(=O)CH$_3$, and —C(=O)(isopropyl).

In one embodiment, the polyheterocyclic derivative has the formula (IV):

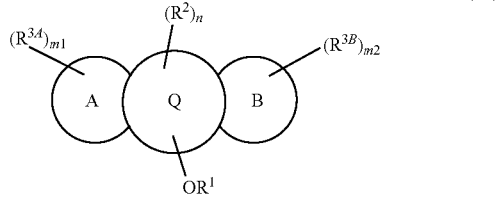

(IV)

wherein Q, $R^1$, $R^2$, $R^{3A}$, $R^{3B}$, n, m1, and m2 are as defined above (in particular with respect to formula (I), (IIa), (IIb), and/or (III)) or below, and each of rings A and B is independently selected from benzo, pyridino, pyrimidino, and hydrated forms thereof, wherein the hydrated forms of the benzo, pyridino, and pyrimidino groups are preferably selected from the group consisting of cyclohexadieno (such as cyclohexa-1,4-dieno and cyclohexa-1,3-dieno), cyclohexeno, dihydropyridino (such as 1,4-dihydropyridino, 2,5-dihydropyridino, 1,2-dihydropyridino, 2,3-dihydropyridino, and 3,4-dihydropyridino), tetrahydropyridino (such as 1,2,3,4-tetrahydropyridino, 1,2,3,6-tetrahydropyridino, and 2,3,4,5-tetrahydropyridino), dihydropyrimidino (such as 4,5-dihydropyrimidino, 2,5-dihydropyrimidino, 1,6-dihydropyrimidino, and 1,4-dihydropyrimidino), and tetrahydropyrimidino (such as 1,4,5,6-tetrahydropyrimidino, 1,2,5,6-tetrahydropyrimidino, and 1,2,3,4-tetrahydropyrimidino). In one embodiment of the polyheterocyclic derivative of formula (IV), Q, $R^1$, $R^2$, $R^{3A}$, $R^{3B}$, n, m1, and m2 are as defined above (in particular with respect to formula (I), (IIa), (IIb), and/or (III)) or below, and each of rings A and B is independently selected from benzo, pyridino, pyrimidino, and cyclohexadieno (such as cyclohexa-1,4-dieno). In one embodiment of the polyheterocyclic derivative of formula (IV), Q, $R^1$, $R^2$, $R^{3A}$, $R^{3B}$, n, m1, and m2 are as defined above (in particular with respect to formula (I), (IIa), (IIb), and/or (III)) or below, and one of rings A and B is benzo and the other is selected from the group consisting of benzo, pyridino, pyrimidino, and cyclohexadieno (such as cyclohexa-1,4-dieno).

In one embodiment, the polyheterocyclic derivative has the formula (V):

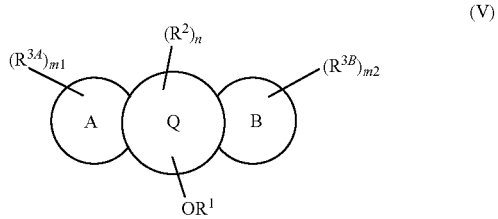

(V)

wherein Q, A, B, $R^1$, $R^2$, and n are as defined above (in particular with respect to formula (I), (IIa), (IIb), (III), and/or (IV)) or below, the sum of m1 and m2 is 1 to 7 (such as 1, 2, 3, 4, 5, or 6, or 1 to 4), and each of $R^{3A}$ and $R^{3B}$ is independently selected from the group consisting of $C_{1-6}$ alkyl, $C_{2-6}$ alkenyl, $C_{2-6}$ alkynyl, $C_{3-7}$ cycloalkyl, $C_{6-10}$ aryl, 3- to 7-membered heterocyclyl, 3- to 7-membered heteroaryl, halogen, —CN, —NO$_2$, —OR$^{11a}$, —CF$_3$, —N(R$^{11a}$)$_2$, —NHS(O)$_2$(R$^{11a}$), —S(O)$_2$N(R$^{11a}$)$_2$, —C(=O)(R$^{11a}$), —C(=O)O$^{11a}$, —OC(=O)R$^{11a}$, —C(=O)OR$^{11a}$, —C(=O)N(R$^{11a}$)$_2$, —NHC(=O)R$^{11a}$, —NHC(=NH)N(R$^{11a}$)$_2$, —N($C_{1-6}$ alkyl)C(=NH)N(R$^{11a}$)$_2$, and —($C_{1-6}$ alkylene)OH, wherein $R^{11a}$ is selected from the group consisting of $C_{1-6}$ alkyl, $C_{3-7}$ cycloalkyl, $C_{6-10}$ aryl, 3- to 7-membered heterocyclyl, and 3- to 7-membered heteroaryl, and is optionally substituted with one or two independently selected $R^{30}$; and/or any two $R^{3A}$ which are bound to the same carbon atom of ring A may join together to form =$X^A$ (preferably =O) and/or any two $R^{3B}$ which are bound to the same carbon atom of ring B may join together to form =$X^B$ (preferably =O) and/or any two $R^{3A}$ on adjacent ring atoms of ring A may join together with the adjacent ring atoms of ring A to form a 5- to 6-membered ring which is optionally substituted with one, two or three moieties independently selected from the group consisting of —OH, methyl, ethyl, —OCH$_3$, —SCH$_3$, and —NH$_{2-z}$(CH$_3$)$_z$, wherein z is 0, 1, or 2, and/or any two $R^{3B}$ on adjacent ring atoms of ring B may join together with the adjacent ring atoms of ring B to form a 5- to 6-membered ring which is optionally substituted with one, two or three moieties independently selected from the group consisting of —OH, methyl, ethyl, —OCH$_3$, —SCH$_3$, and —NH$_{2-z}$(CH$_3$)$_z$, wherein z is 0, 1, or 2. In one embodiment of the polyheterocyclic derivative of formula (V), Q, A, B, $R^1$, $R^2$, and n are as defined above (in particular with respect to formula (I), (IIa), (IIb), (III), and/or (IV)) or below, the sum of m1 and m2 is 1 to 7 (such as 1, 2, 3, 4, 5, or 6, or 1 to 4), and each of $R^{3A}$ and $R^{3B}$ is independently selected from the group consisting of $C_{1-6}$ alkyl, $C_{2-6}$ alkenyl, $C_{2-6}$ alkynyl, $C_{3-7}$ cycloalkyl, $C_{6-10}$ aryl, 3- to 7-membered heterocyclyl, 3- to 7-membered heteroaryl, halogen, —CN, —NO$_2$, —OH, —O($C_{1-6}$ alkyl), —CF$_3$, —OCF$_3$, —O(CH$_2$)$_{0-2}$($C_{3-7}$ cycloalkyl), —O(CH$_2$)$_{0-2}$($C_{6-10}$ aryl), —O(CH$_2$)$_{0-2}$(3- to 7-membered heteroaryl), —O(CH$_2$)$_{0-2}$(3- to 7-membered heterocyclyl), —NH$_2$, —NH($C_{1-6}$ alkyl), —N($C_{1-6}$ alkyl)$_2$, —NHS(O)$_2$($C_{1-6}$ alkyl), —S(O)$_2$NH$_{2-z}$($C_{1-6}$ alkyl)$_z$, —C(=O)($C_{1-6}$ alkyl), —C(=O)OH, —OC(=O)$R^{11a}$, —C(=O)O($C_{1-6}$ alkyl), —C(=O)NH$_{2-z}$($C_{1-6}$ alkyl)$_z$, —NHC(=O)H, —NHC(=O)($C_{1-6}$ alkyl), —NHC(=NH)NH$_{2-2}$($C_{1-6}$ alkyl)$_z$, —N($C_{1-6}$ alkyl)C(=NH)NH$_{2-z}$($C_{1-6}$ alkyl)$_z$, and —($C_{1-6}$ alkylene)OH, wherein z is 0, 1, or 2; and $R^{11a}$ is selected from the group consisting of $C_{1-6}$ alkyl, $C_{3-7}$ cycloalkyl, $C_{6-10}$ aryl, 3- to 7-membered heterocyclyl, and 3- to 7-membered heteroaryl, and is optionally substituted with one or two independently selected $R^{30}$; and/or any two $R^{3A}$ which are bound to the same carbon atom of ring A may join together to form =O and/or any two $R^{3B}$ which are bound to the same carbon atom of ring B may join together to form =O and/or any two $R^{3A}$ on adjacent ring atoms of ring A may join together with the adjacent ring atoms of ring A to form a 5- to 6-membered ring which is optionally substituted with one, two or three moieties independently selected from the group consisting of —OH, methyl, ethyl, —OCH$_3$, —SCH$_3$, and —NH$_{2-z}$(CH$_3$)$_z$ and/or any two $R^{3B}$ on adjacent ring atoms of ring B may join together with the adjacent ring atoms of ring B to form a 5- to 6-membered ring which is optionally substituted with one, two or three moieties independently selected from the group consisting of —OH, methyl, ethyl, —OCH$_3$, —SCH$_3$, and —NH$_{2-z}$(CH$_3$)$_z$. In one embodiment of the polyheterocyclic derivative of formula (V), Q, A, B, $R^1$, $R^2$, and n are as defined above (in particular with respect to formula (I), (IIa), (IIb), (III), and/or (IV)) or below, the sum of m1 and m2 is 1 to 7 (such as 1, 2, 3, 4, 5, or 6, or 1 to 4), and each of $R^{3A}$ and $R^{3B}$ is independently selected from the group consisting of $C_{1-6}$ alkyl, $C_{2-6}$ alkenyl, $C_{2-6}$ alkynyl, $C_{3-7}$ cycloalkyl, $C_{6-10}$ aryl, 3- to 7-membered heterocyclyl, 3- to 7-membered heteroaryl, halogen, —CN, —NO$_2$, —OH, —O($C_{1-6}$ alkyl), —CF$_3$, —OCF$_3$, —O(CH$_2$)$_{0-2}$($C_{3-7}$ cycloalkyl), —O(CH$_2$)$_{0-2}$($C_{6-10}$ aryl), —O(CH$_2$)$_{0-2}$(3- to 7-membered heteroaryl), —O(CH$_2$)$_{0-2}$(3- to 7-membered heterocyclyl), —NH$_2$, —NH($C_{1-6}$ alkyl), —N($C_{1-6}$ alkyl)$_2$, —NHS(O)$_2$($C_{1-6}$ alkyl), —S(O)$_2$NH$_{2-z}$($C_{1-6}$ alkyl)$_z$, —C(=O)($C_{1-6}$ alkyl), —C(=O)OH, —OC(=O)$R^{11a}$, —C(=O)O($C_{1-6}$ alkyl), —C(=O)NH$_{2-z}$($C_{1-6}$ alkyl)$_z$, —NHC(=O)H, —NHC(=O)($C_{1-6}$ alkyl), —NHC(=NH)NH$_{2-2}$($C_{1-6}$ alkyl)$_z$, —N($C_{1-6}$ alkyl)C(=NH)NH$_{2-z}$($C_{1-6}$ alkyl)$_z$, and —($C_{1-6}$ alkylene)OH, wherein z is 0, 1, or 2; and $R^{11a}$ is selected from the group consisting of $C_{1-6}$ alkyl, $C_{3-7}$ cycloalkyl, $C_{6-10}$ aryl, 3- to 7-membered heterocyclyl, and 3- to 7-membered heteroaryl, and is optionally substituted with one or two independently selected $R^{30}$; and/or any two $R^{3A}$ which are bound to the same carbon atom of ring A may join together to form =O and/or any two $R^{3B}$ which are bound to the same carbon atom of ring B may join together to form =O and/or any two $R^{3A}$ on adjacent ring atoms of ring A may join together with the adjacent ring atoms of ring A to form a 5- to 6-membered ring which is optionally substituted with one, two or three moieties independently selected from the group consisting of —OH, methyl, ethyl, —OCH$_3$, —SCH$_3$, and —NH$_{2-z}$(CH$_3$)$_z$ and/or any two $R^{3B}$ on adjacent ring atoms of ring B may join together with the adjacent ring atoms of ring B to form a 5- to 6-membered ring which is optionally substituted with one, two or three moieties independently selected from the group consisting of —OH, methyl, ethyl, —OCH$_3$, —SCH$_3$, and —NH$_{2-z}$(CH$_3$)$_z$. In one embodiment of the polyheterocyclic derivative of formula (V), Q, A, B, $R^1$, $R^2$, and n are as defined above (in particular with respect to formula (I), (IIa), (IIb), (III), and/or (IV)) or below, the sum of m1 and m2 is 1 to 7 (such as 1, 2, 3, 4, 5, or 6, or 1 to 4), and each of $R^{3A}$ and $R^{3B}$ is independently selected from the group consisting of $C_{1-4}$ alkyl, halogen, —CN, —NO$_2$, —OH, —O($C_{1-3}$ alkyl), —O(CH$_2$)$_{1-2}$($C_{3-7}$ cycloalkyl), —O(CH$_2$)$_{1-2}$($C_{6-10}$ aryl), —O(CH$_2$)$_{1-2}$(3- to 7-membered heteroaryl), —O(CH$_2$)$_{1-2}$(3- to 7-membered heterocyclyl), —NH$_2$, —NH($C_{1-3}$ alkyl), —N($C_{1-3}$ alkyl)$_2$, —OC(=O)($R^{11a}$), —C(=O)NH$_{2-z}$($C_{1-6}$ alkyl)$_z$, —NHC(=O)H, —NHC(=O)($C_{1-6}$ alkyl), and —($C_{1-3}$ alkylene)OH, wherein z is 0, 1, or 2; and $R^{11a}$ is selected from the group consisting of $C_{1-3}$ alkyl and phenyl, each of which is optionally substituted with one or two independently selected $R^{30}$; and/or any two $R^{3A}$ which are bound to the same carbon atom of ring A may join together to form =O and/or any two $R^{3B}$ which are bound to the same carbon atom of ring B may join together to form =O and/or any two $R^{3A}$ on adjacent ring atoms of ring A may join together with the adjacent ring atoms of ring A to form a 5- to 6-membered heterocyclyl which is optionally substituted with one, two or three moieties independently selected from the group consisting of —OH, methyl, ethyl, —OCH$_3$, and —NH$_{2-z}$(CH$_3$)$_z$ and/or any two $R^{3B}$ on adjacent ring atoms of ring B may join together with the adjacent ring atoms of ring B to form a 5- to 6-membered heterocyclyl which is optionally substituted with one, two or three moieties independently selected from the group consisting of —OH, methyl, ethyl, —OCH$_3$, and —NH$_{2-z}$(CH$_3$)$_z$. In one embodiment of the polyheterocyclic derivative of formula (V), Q, A, B, $R^1$, $R^2$, and n are as defined above (in particular with respect to formula (I), (IIa), (IIb), (III), and/or (IV)) or below, the sum of m1 and m2 is 1 to 7 (such as 1, 2, 3, 4, 5, or 6, or 1 to 4), and each of $R^{3A}$ and $R^{3B}$ is independently selected from the group consisting of $C_{1-4}$ alkyl, halogen, —CN, —NO$_2$, —OH, —O($C_{1-3}$ alkyl), —O(CH$_2$)$_{1-2}$(phenyl), —NH$_2$, —OC(=O)($R^{11a}$), —NHC(=O)H, and —($C_{1-3}$ alkylene)OH, wherein z is 0, 1, or 2; and $R^{11a}$ is selected from the group consisting of $C_{1-3}$ alkyl and phenyl, each of which is optionally substituted with one or two independently selected $R^{30}$; and/or any two $R^{3A}$ which are bound to the same carbon atom of ring A may join together to form =O and/or any two $R^{3B}$ which are bound to the same carbon atom of ring B may join together to form =O and/or any two $R^{3A}$ on adjacent ring atoms of ring A may join together with the adjacent ring atoms of ring A to form a 5- to 6-membered heterocyclyl which is optionally substituted with one, two or three moieties independently selected from the group consisting of —OH, methyl, ethyl, —OCH$_3$, and —NH$_{2-z}$(CH$_3$)$_z$ and/or any two $R^{3B}$ on adjacent ring atoms of ring B may join together with the adjacent ring atoms of ring B to form a 5- to 6-membered heterocyclyl which is optionally substituted with one, two or three moieties independently selected from the group consisting of —OH, methyl, ethyl, —OCH$_3$, and —NH$_{2-z}$(CH$_3$)$_z$, wherein z is 0, 1, or 2.

In any of the above embodiments of the polyheterocyclic derivative of formula (V), wherein a ring is formed by any two $R^{3A}$ on adjacent ring atoms of ring A, said ring preferably is a 3- to 7-membered ring (e.g., a ring having 5 or 6 members) which is optionally substituted with one, two or three moieties independently selected from the group consisting of —OH, methyl, ethyl, —OCH$_3$, —SCH$_3$, and —NH$_{2-z}$(CH$_3$)$_z$, wherein z is 0, 1, or 2. The ring formed by any two R$^{3A}$ on adjacent ring atoms of ring A is preferably monocyclic and may be an aromatic, cycloaliphatic, heteroaromatic, or heterocyclic ring, wherein the heteroaromatic/heterocyclic ring contains 1 or 2 heteroatoms selected from the group consisting of O, S, and N. In one embodiment, the ring formed by any two R$^{3A}$ on adjacent ring atoms of ring A is a monocyclic ring selected from the group consisting of a 5- or 6-membered aromatic, 5- or 6-membered cycloaliphatic, 5- or 6-membered heteroaromatic, and 5- or 6-membered heterocyclic ring (in particular those 5- or 6-membered rings specified above in the definitions of "aromatic ring", "heteroaromatic ring", "cycloaliphatic ring" or "heterocyclic ring"), each of which is optionally substituted with one, two or three moieties independently selected from the group consisting of —OH, methyl, ethyl, —OCH$_3$, and —NH$_{2-z}$(CH$_3$)$_z$, wherein z is 0, 1, or 2. In one embodiment, the ring formed by any two R$^{3A}$ on adjacent ring atoms of ring A is selected from the group consisting of cyclopentadieno, benzo, pyrrolo, imidazo (from imidazole), pyrazolo, furo (from furan), dioxolo, thieno (from thiophene), oxazolo, isoxazolo, thiazolo, isothiazolo, pyrano, pyridino, pyrimidino, pyridazino, and their hydrated (e.g., di- or tetrahydro) forms thereof (such as dihydropyrrolo, pyrrolidino, dioxolano (e.g., 1,3-dioxolano), dihydropyrazolo, and morpholino), wherein each of these rings is optionally substituted with one, two or three moieties independently selected from the group consisting of —OH, methyl, ethyl, —OCH$_3$, and —NH$_{2-z}$(CH$_3$)$_z$, wherein z is 0, 1, or 2. In one embodiment, the ring formed by any two R$^{3A}$ on adjacent ring atoms of ring A is selected from the group consisting of benzo, pyrrolidino, dioxolano (e.g., 1,3-dioxolano), dihydropyrazolo, and morpholino, each of which is optionally substituted with one, two or three moieties independently selected from the group consisting of —OH, methyl, ethyl, —OCH$_3$, and —NH$_{2-z}$(CH$_3$)$_z$, wherein z is 0, 1, or 2. In one embodiment, the total number of rings formed by any two R$^{3A}$ on adjacent ring atoms of ring A is 0 or 1. Thus, in the embodiment, wherein the total number of rings formed by any two R$^{3A}$ on adjacent ring atoms of ring A is 1, only two R$^{3A}$ groups on adjacent ring atoms of ring A join together with the atoms to which they are attached to form a ring, wherein the remaining R$^{3A}$ groups are selected from the particular groups specified above for the situation that R$^{3A}$ groups do not join together to form a ring. For example, if m1 is 3, ring A is substituted with three independently selected R$^{3A}$, wherein either these three R$^{3A}$ groups can represent three individual groups (such as methyl, —OH, and —C(O)CH$_3$) or two of these three R$^{3A}$ groups on adjacent ring atoms of ring A join together with the atoms to which they are attached to form a ring as specified above and the last of these three R$^{3A}$ groups is, e.g., —OH.

In any of the above embodiments of the polyheterocyclic derivative of formula (V), wherein a ring is formed by any two R$^{3B}$ on adjacent ring atoms of ring B, said ring preferably is a 3- to 7-membered ring (e.g., a ring having 5 or 6 members) which is optionally substituted with one, two or three moieties independently selected from the group consisting of —OH, methyl, ethyl, —OCH$_3$, —SCH$_3$, and —NH$_{2-z}$(CH$_3$)$_z$, wherein z is 0, 1, or 2. The ring formed by any two R$^{3B}$ on adjacent ring atoms of ring B is preferably monocyclic and may be an aromatic, cycloaliphatic, heteroaromatic, or heterocyclic ring, wherein the heteroaromatic/heterocyclic ring contains 1 or 2 heteroatoms selected from the group consisting of O, S, and N. In one embodiment, the ring formed by any two R$^{3B}$ on adjacent ring atoms of ring B is a monocyclic ring selected from the group consisting of a 5- or 6-membered aromatic, 5- or 6-membered cycloaliphatic, 5- or 6-membered heteroaromatic, and 5- or 6-membered heterocyclic ring (in particular those 5- or 6-membered rings specified above in the definitions of "aromatic ring", "heteroaromatic ring", "cycloaliphatic ring" or "heterocyclic ring"), each of which is optionally substituted with one, two or three moieties independently selected from the group consisting of —OH, methyl, ethyl, —OCH$_3$, and —NH$_{2-z}$(CH$_3$)$_z$, wherein z is 0, 1, or 2. In one embodiment, the ring formed by any two R$^{3B}$ on adjacent ring atoms of ring B is selected from the group consisting of cyclopentadieno, benzo, pyrrolo, imidazo (from imidazole), pyrazolo, furo (from furan), dioxolo, thieno (from thiophene), oxazolo, isoxazolo, thiazolo, isothiazolo, pyrano, pyridino, pyrimidino, pyridazino, and their hydrated (e.g., di- or tetrahydro) forms thereof (such as dihydropyrrolo, pyrrolidino, dioxolano (e.g., 1,3-dioxolano), dihydropyrazolo, and morpholino), wherein each of these rings is optionally substituted with one, two or three moieties independently selected from the group consisting of —OH, methyl, ethyl, —OCH$_3$, and —NH$_{2-z}$(CH$_3$)$_z$, wherein z is 0, 1, or 2. In one embodiment, the ring formed by any two R$^{3B}$ on adjacent ring atoms of ring B is selected from the group consisting of benzo, pyrrolidino, dioxolano (e.g., 1,3-dioxolano), dihydropyrazolo, and morpholino, each of which is optionally substituted with one, two or three moieties independently selected from the group consisting of —OH, methyl, ethyl, —OCH$_3$, and —NH$_{2-z}$(CH$_3$)$_z$, wherein z is 0, 1, or 2. In one embodiment, the total number of rings formed by any two R$^{3B}$ on adjacent ring atoms of ring B is 0 or 1. Thus, in the embodiment, wherein the total number of rings formed by any two R$^{3B}$ on adjacent ring atoms of ring B is 1, only two R$^{3B}$ groups on adjacent ring atoms of ring B join together with the atoms to which they are attached to form a ring, wherein the remaining R$^{3B}$ groups are selected from the particular groups specified above for the situation that R$^{3B}$ groups do not join together to form a ring. For example, if m2 is 3, ring B is substituted with three independently selected R$^{3B}$, wherein either these three R$^{3B}$ groups can represent three individual groups (such as methyl, —OH, and —C(O)CH$_3$) or two of these three R$^{3B}$ groups on adjacent ring atoms of ring B join together with the atoms to which they are attached to form a ring as specified above and the last of these three R$^{3B}$ groups is, e.g., —OH.

In any of the above embodiments (in particular with respect to formula (I), (IIa), (IIb), (III), (IV), and/or (V)), the sum of (i) the total number of rings formed by any two R$^{3A}$ on adjacent ring atoms of ring A and (ii) the total number of rings formed by any two R$^{3B}$ on adjacent ring atoms of ring B preferably is 0 or 1.

In any of the above embodiments (in particular with respect to formula (I), (IIa), (IIb), (III), (IV), and/or (V)), the total number of =X$^A$ (such as =O) formed by any two R$^{3A}$ which are bound to the same carbon atom of ring A preferably is 0 or 1. In any of the above embodiments (in particular with respect to formulas (I), (IIa), (IIb), (III), (IV), and (V)), the total number of =X$^B$ (such as =O) formed by any two R$^{3B}$ which are bound to the same carbon atom of ring B preferably is 0 or 1. In any of the above embodiments (in particular with respect to formulas (I), (IIa), (IIb), (III), (IV), and (V)), the sum of (i) the total number of =X$^A$ (such as =O) formed by any two R$^{3A}$ which are bound to the same carbon atom of ring A and (ii) the total number of =X$^B$ (such as =O) formed by any two R$^{3B}$ which are bound to the same carbon atom of ring B may be 0, 1, or 2, preferably 0 or 1, more preferably 0.

In any of the above embodiments (in particular with respect to formula (I), (IIa), (IIb), (III), (IV), and/or (V)), the sum of (i) the total number of rings formed by any two $R^{3A}$ on adjacent ring atoms of ring A and (ii) the total number of rings formed by any two $R^{3B}$ on adjacent ring atoms of ring B preferably is 0 or 1 and the sum of (1) the total number of $=X^A$ (such as $=O$) formed by any two $R^{3A}$ which are bound to the same carbon atom of ring A and (2) the total number of $=X^B$ (such as $=O$) formed by any two $R^{3B}$ which are bound to the same carbon atom of ring B may be 0, 1, or 2, preferably 0 or 1, more preferably 0. For example, in one embodiment, the sum of (i) and (ii) is 0 and the sum of (1) and (2) is 1. In an alternative embodiment, the sum of (i) and (ii) is 1 and the sum of (1) and (2) is 0. In a further alternative embodiment, the sum of (i) and (ii) is 1 and the sum of (1) and (2) is 1 (in this embodiment, it is preferred that the modification under (i) or (ii) is on one of the rings A and B and the modification under (1) or (2) is on the other of the rings A and B). In a further alternative embodiment, the sum of (i) and (ii) is 0 and the sum of (1) and (2) is 0.

In any of the above embodiments (in particular with respect to formula (I), (IIa), (IIb), (III), (IV), and/or (V)), where $R^{11}$ is substituted with one or more independently selected $R^{30}$ (e.g., where $R^{11a}$ is substituted with one or two independently selected $R^{30}$), it is preferred that $R^{11}$ (e.g., $R^{11a}$) is selected from the group consisting of $C_{1-6}$ alkyl, $C_{3-7}$ cycloalkyl, $C_{6-10}$ aryl, 3- to 7-membered heterocyclyl, and 3- to 7-membered heteroaryl, more preferred from the group consisting of $C_{1-6}$ alkyl (such as $C_{1-4}$ alkyl), $C_{5-6}$ cycloalkyl, 6-membered aryl, 5- or 6-membered heterocyclyl, and 5- or 6-membered heteroaryl, more preferred from the group consisting of $C_{1-6}$ alkyl (such as $C_{1-4}$ or $C_{1-2}$ alkyl) and phenyl; and each $R^{30}$ is as specified above, more preferably $R^{30}$ is a $1^{st}$ level substituent selected from the group consisting of 6- to 10-membered aryl, 3- to 7-membered heteroaryl, 3- to 7-membered cycloalkyl, 3- to 7-membered heterocyclyl, $-C(R^{71})=$(3- to 7-membered heterocyclylidene), halogen, $-CN$, azido, $-NO_2$, $-OR^{71}$, $-N(R^{72})(R^{73})$, $-S(O)_{0-2}R^{71}$, $-S(O)_{1-2}OR^{71}$, $-OS(O)_{1-2}R^{71}$, $-OS(O)_{1-2}OR^{71}$, $-S(O)_{1-2}N(R^{72})(R^{73})$, $-OS(O)_{1-2}N(R^{72})(R^{73})$, $-N(R^{71})S(O)_{1-2}R^{71}$, $-NR^{71}S(O)_{1-2}OR^{71}$, $-NR^{71}S(O)_{1-2}N(R^{72})(R^{73})$, $-OP(O)(OR^{71})_2$, $-C(=X^1)R^{71}$, $-C(=X^1)X^1R^{71}$, $-X^1C(=X^1)R^{71}$, and $-X^1C(=X^1)X^1R^{71}$, and/or any two $R^{30}$ which are bound to the same carbon atom of a cycloalkyl or heterocyclyl group may join together to form $=X^1$, wherein each of the of 6- to 10-membered aryl, 3- to 7-membered heteroaryl, 3- to 7-membered cycloalkyl, 3- to 7-membered heterocyclyl and 3- to 7-membered heterocyclylidene groups being a $1^{st}$ level substituent is optionally substituted by one or more (e.g., 1, 2, 3, 4, 5, or 6) $2^{nd}$ level substituents, wherein said $2^{nd}$ level substituent is, in each case, independently selected from the group consisting of $C_{1-6}$ alkyl, 6-membered aryl, 5- to 7-membered heteroaryl, 5- to 7-membered cycloalkyl, 5- to 7-membered heterocyclyl, halogen, $-CF_3$, $-CN$, azido, $-NO_2$, $-OH$, and $-NH_2$, and/or any two $2^{nd}$ level substituents which are bound to the same carbon atom of a cycloalkyl or heterocyclyl group being a $1^{st}$ level substituent may join together to form $=O$ or $=S$ and/or any two $2^{nd}$ level substituents which are bound to the same carbon atom of a cycloalkyl or heterocyclyl group being a $1^{st}$ level substituent may join together to form $=C(R^{81})$(6- to 14-membered aryl) or $=C(R^{81})$(3- to 14-membered heteroaryl), wherein each of the $C_{1-6}$ alkyl, 6-membered aryl, 6- to 14-membered aryl (from the $=C(R^{81})$(6- to 14-membered aryl) group), 5- to 7-membered heteroaryl, 3- to 14-membered heteroaryl (from the $=C(R^{81})$(3- to 14-membered heteroaryl) group), 5- to 7-membered cycloalkyl, 5- to 7-membered heterocyclyl groups being a $2^{nd}$ level substituent is optionally substituted with one or more (e.g., 1, 2, or 3, such as 1 or 2) $3^{rd}$ level substituents, wherein said $3^{rd}$ level substituent is, in each case, independently selected from the group consisting of $C_{1-3}$ alkyl, halogen, $-CF_3$, $-CN$, azido, $-NO_2$, $-OH$, $-O(C_{1-3}$ alkyl), $-OCF_3$, $-S(C_{1-3}$ alkyl), $-NH_2$, $-NH(C_{1-3}$ alkyl), $-N(C_{1-3}$ alkyl$)_2$, $-NHS(O)_2(C_{1-3}$ alkyl), $-S(O)_2NH_{2-z}(C_{1-3}$ alkyl$)_z$, $-C(=O)OH$, $-C(=O)O(C_{1-3}$ alkyl), $-C(=O)NH_{2-z}(C_{1-3}$ alkyl$)_z$, $-NHC(=O)(C_{1-3}$ alkyl), $-NHC(=NH)NH_{z-2}(C_{1-3}$ alkyl$)_z$, and $-N(C_{1-3}$ alkyl)$C(=NH)NH_{2-z}(C_{1-3}$ alkyl$)_z$, wherein z is 0, 1, or 2 and $C_{1-3}$ alkyl is methyl, ethyl, propyl or isopropyl, and/or any two $3^{rd}$ level substituents which are bound to the same carbon atom of a 5- to 7-membered cycloalkyl or heterocyclyl group being a $2^{nd}$ level substituent may join together to form $=O$, $=S$, or $=NH$.

In any of the above embodiments (in particular with respect to formula (I), (IIa), (IIb), (III), (IV), and/or (V)), where $R^{11}$ is substituted with one or more independently selected $R^{30}$ (e.g., where $R^{11a}$ is substituted with one or two independently selected $R^{30}$), it is preferred that $R^{11}$ (e.g., $R^{11a}$) is selected from the group consisting of $C_{1-6}$ alkyl, 3- to 7-membered cycloalkyl, 6- to 10-membered aryl, 3- to 7-membered heterocyclyl, and 3- to 7-membered heteroaryl, more preferred from the group consisting of $C_{1-6}$ alkyl (such as $C_{1-4}$ alkyl), 5- to 6-membered cycloalkyl, 6-membered aryl, 5- or 6-membered heterocyclyl, and 5- or 6-membered heteroaryl, more preferred from the group consisting of $C_{1-6}$ alkyl (such as $C_{1-4}$ or $C_{1-2}$ alkyl) and phenyl; and each $R^{30}$ is a $1^{st}$ level substituent selected from the group consisting of 5- or 6-membered heterocyclyl, $-C(R^{71})=$(5- to 6-membered heterocyclylidene), halogen, $-CN$, and azido, wherein each of the 5- to 6-membered heterocyclyl and 5- to 6-membered heterocyclylidene groups being a $1^{st}$ level substituent is optionally substituted by one or more (e.g., 1, 2, 3, 4, 5, or 6) $2^{nd}$ level substituents, wherein said $2^{nd}$ level substituent is, in each case, independently selected from the group consisting of $C_{1-4}$ alkyl and phenyl, and/or any two $2^{nd}$ level substituents which are bound to the same carbon atom of a heterocyclyl group being a $1^{st}$ level substituent may join together to form $=O$ or $=S$ and/or any two $2^{nd}$ level substituents which are bound to the same carbon atom of a heterocyclyl group being a $1^{st}$ level substituent may join together to form $=C(R^{81})$(phenyl), wherein each of the $C_{1-4}$ alkyl and phenyl (including phenyl of the $=C(R^{81})$(phenyl) group) groups being a $2^{nd}$ level substituent is optionally substituted with one or more (e.g., 1, 2, or 3, such as 1 or 2) $3^{rd}$ level substituents, wherein said $3^{rd}$ level substituent is, in each case, independently selected from the group consisting of $C_{1-3}$ alkyl, halogen, $-CF_3$, $-CN$, azido, $-NO_2$, $-OH$, $-O(C_{1-3}$ alkyl), $-OCF_3$, $-NH_2$, $-NH(C_{1-3}$ alkyl), $-N(C_{1-3}$ alkyl$)_2$, $-C(=O)OH$, and $-C(=O)O(C_{1-3}$ alkyl), wherein $C_{1-3}$ alkyl is methyl, ethyl, propyl or isopropyl.

In any of the above embodiments (in particular with respect to formula (I), (IIa), (IIb), (III), (IV), and/or (V)), where $R^{11}$ is substituted with one or more independently selected $R^{30}$ (e.g., where $R^{11a}$ is substituted with one or two independently selected $R^{30}$), it is preferred that $R^{11}$ (e.g., $R^{11a}$) is selected from the group consisting of $C_{1-6}$ alkyl, 3- to 7-membered cycloalkyl, 6- to 10-membered aryl, 3- to 7-membered heterocyclyl, and 3- to 7-membered heteroaryl, more preferred from the group consisting of $C_{1-6}$ alkyl (such as $C_{1-4}$ alkyl), 5- to 6-membered cycloalkyl, 6-membered aryl, 5- or 6-membered heterocyclyl, and 5- or 6-membered heteroaryl, more preferred from the group consisting of $C_{1-6}$ alkyl (such as $C_{1-4}$ or $C_{1-2}$ alkyl) and phenyl; and each $R^{30}$ is a 1$^{st}$ level substituent selected from the group consisting of 5- or 6-membered heterocyclyl, —C(H)=(5- to 6-membered heterocyclylidene), and halogen, wherein each of the 5- to 6-membered heterocyclyl and 5- to 6-membered heterocyclylidene groups being a 1$^{st}$ level substituent is optionally substituted by one or more (e.g., 1, 2, 3, 4, 5, or 6) 2$^{nd}$ level substituents, wherein said 2$^{nd}$ level substituent is, in each case, independently selected from the group consisting of $C_{1-4}$ alkyl and phenyl, and/or any two 2$^{nd}$ level substituents which are bound to the same carbon atom of a heterocyclyl group being a 1$^{st}$ level substituent may join together to form =O or =S and/or any two 2$^{nd}$ level substituents which are bound to the same carbon atom of a heterocyclyl group being a 1$^{st}$ level substituent may join together to form =C(H)(phenyl), wherein each of the $C_{1-4}$ alkyl and phenyl (including phenyl of the =C(H)(phenyl) group) groups being a 2$^{nd}$ level substituent is optionally substituted with one or more (e.g., 1, 2, or 3, such as 1 or 2) 3$^{rd}$ level substituents, wherein said 3$^{rd}$ level substituent is, in each case, independently selected from the group consisting of methyl, halogen, and —CF$_3$.

In one embodiment, the polyheterocyclic derivative has one of the following formulas (VIa) to (VIf):

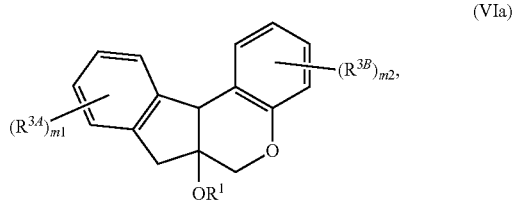

(VIa)

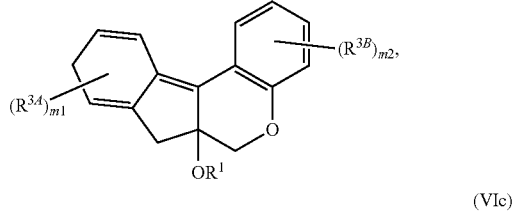

(VIb)

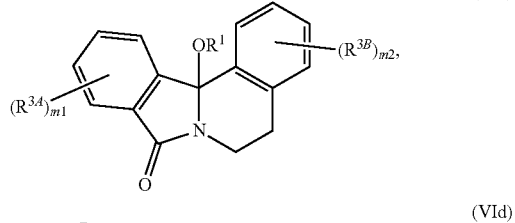

(VIc)

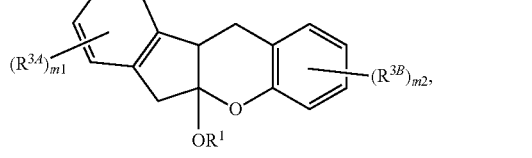

(VId)

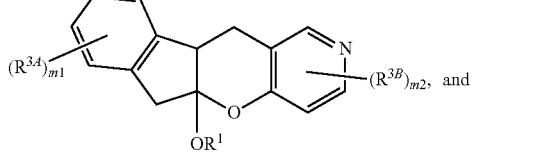

(VIe)

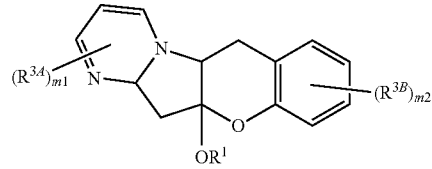

(VIf)

wherein $R^1$, $R^{3A}$, $R^{3b}$, m1, and m2 are as defined above (in particular with respect to formula (I), (III), and/or (V)) or below. Thus, in one preferred embodiment of the polyheterocyclic derivative of any one of formulas (VIa), (VIb), (VIc), (VId), (VIe), and (VIf), $R^{3A}$, $R^{3B}$, m1, and m2 are as defined above (in particular with respect to formula (I) and/or (V)) or below, and $R^1$ is selected from the group consisting of H, —P(O)(OH)$_z$(OR$^{15}$)$_{2-z}$, and —C(=O)R$^{85}$, wherein $R^{85}$ is selected from the group consisting of $C_{1-6}$ alkyl, $C_{3-7}$ cycloalkyl, $C_{6-10}$ aryl, $C_{6-10}$ halogenaryl, 3- to 7-membered heterocyclyl, and 3- to 7-membered heteroaryl; and z is 0, 1, or 2. In one embodiment of the polyheterocyclic derivative of any one of formulas (VIa), (VIb), (VIc), (VId), (VIe), and (VIf), $R^1$ is selected from the group consisting of H, —C(=O)(C$_6$ halogenaryl), and —C(=O)(C$_{1-3}$ alkyl), such as from the group consisting of H, —C(=O)(halogenphenyl), and —C(=O)(C$_{1-3}$ alkyl), wherein halogenphenyl is a moiety selected from the group consisting of monohalogenphenyl, dihalogenphenyl, and trihalogenphenyl; and $C_{1-3}$ alkyl is methyl, ethyl, n-propyl, or isopropyl. In one embodiment of the polyheterocyclic derivative of any one of formulas (VIa), (VIb), (VIc), (VId), (VIe), and (VIf), $R^1$ is selected from the group consisting of H, —C(=O)(monohalogenphenyl), —C(=O)CH$_3$, and —C(=O)(isopropyl).

In one embodiment, the polyheterocyclic derivative has the following formula (VIg):

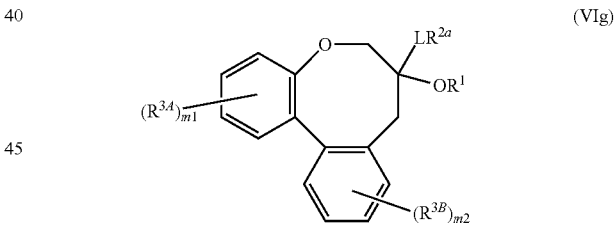

(VIg)

wherein $R^1$, $R^{3A}$, $R^{3B}$, m1, m2, L, and $R^{2a}$ are as defined above (in particular with respect to formula (I), (IIb), (III), and/or (V)) or below. Thus, in one preferred embodiment of the polyheterocyclic derivative of formula (VIg), $R^{3A}$, $R^{3B}$, m1, and m2 are as defined above (in particular with respect to formula (I) and/or (V)) or below, $R^1$ is selected from the group consisting of H, —P(O)(OH)$_z$(OR$^{15}$)$_{2-z}$, and —C(=O)R$^{85}$, wherein $R^{85}$ is selected from the group consisting of $C_{1-6}$ alkyl, $C_{3-7}$ cycloalkyl, $C_{6-10}$ aryl, $C_{6-10}$ halogenaryl, 3- to 7-membered heterocyclyl, and 3- to 7-membered heteroaryl; z is 0, 1, or 2; L is $C_{1-6}$ alkylene, such as $C_{1-3}$ alkylene, preferably methylene; and $R^{2a}$ is selected from the group consisting of halogen, —CN, azido, —NO$_2$, —OH, —O(C$_{1-3}$ alkyl), —NH$_2$, —NH(C$_{1-3}$ alkyl), —N(C$_{1-3}$ alkyl)$_2$, —OP(O)(C$_{1-3}$ alkoxy)$_2$, and —OC(=O)(C$_{1-3}$ alkyl), such as from the group consisting of —OH, —O(C$_{1-3}$ alkyl), —OP(O)(C$_{1-3}$ alkoxy)$_2$, and —OC(=O)(C$_{1-3}$ alkyl), preferably from the group consisting of —OH, —O($C_{1-3}$ alkyl), and —OC(=O)($C_{1-3}$ alkyl). In one embodiment of the polyheterocyclic derivative of formula (VIg), $R^1$ is selected from the group consisting of H, —C(=O)($C_6$ halogenaryl), and —C(=O)($C_{1-3}$ alkyl), such as from the group consisting of H, —C(=O)(halogenphenyl), and —C(=O)($C_{1-3}$ alkyl), wherein halogenphenyl is a moiety selected from the group consisting of monohalogenphenyl, dihalogenphenyl, and trihalogenphenyl; and $C_{1-3}$ alkyl is methyl, ethyl, n-propyl, or isopropyl; L is $C_{1-3}$ alkylene, preferably methylene; and $R^{2a}$ is selected from the group consisting of halogen, —CN, azido, —$NO_2$, —OH, —O($C_{1-3}$ alkyl), —$NH_2$, —NH($C_{1-3}$ alkyl), —N($C_{1-3}$ alkyl)$_2$, —OP(O)($C_{1-3}$ alkoxy)$_2$, and —OC(=O)($C_{1-3}$ alkyl), such as from the group consisting of —OH, —O($C_{1-3}$ alkyl), —OP(O)($C_{1-3}$ alkoxy)$_2$, and —OC(=O)($C_{1-3}$ alkyl), preferably from the group consisting of —OH, —O($C_{1-3}$ alkyl), and —OC(=O)($C_{1-3}$ alkyl). In one embodiment of the polyheterocyclic derivative of formula (VIg), $R^1$ is selected from the group consisting of H, —C(=O)(monohalogenphenyl), —C(=O)$CH_3$, and —C(=O)(isopropyl); L is $C_{1-3}$ alkylene, preferably methylene; and $R^{2a}$ is selected from the group consisting of halogen, —CN, azido, —$NO_2$, —OH, —O($C_{1-3}$ alkyl), —$NH_2$, —NH($C_{1-3}$ alkyl), —N($C_{1-3}$ alkyl)$_2$, —OP(O)($C_{1-3}$ alkoxy)$_2$, and —OC(=O)($C_{1-3}$ alkyl), such as from the group consisting of —OH, —O($C_{1-3}$ alkyl), —OP(O)($C_{1-3}$ alkoxy)$_2$, and —OC(=O)($C_{1-3}$ alkyl), preferably from the group consisting of —OH, —O($C_{1-3}$ alkyl), and —OC(=O)($C_{1-3}$ alkyl).

In one embodiment, the polyheterocyclic derivative has one of the following formulas (VIIa) to (VIIf):

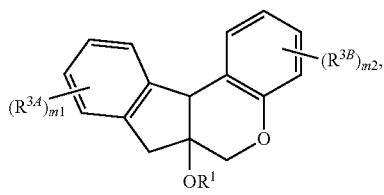
(VIIa)

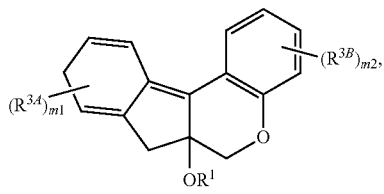
(VIIb)

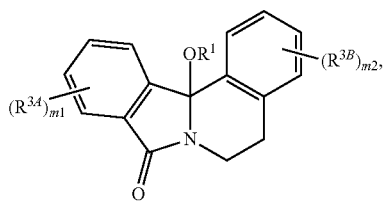
(VIIc)

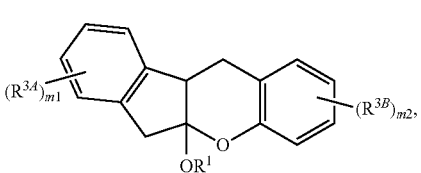
(VIId)

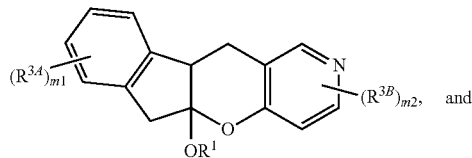
(VIIe)

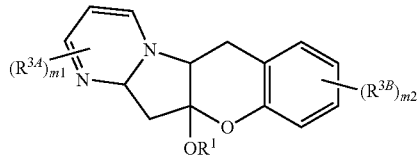
(VIIf)

wherein $R^1$, $R^{3A}$, $R^{3B}$, m1, and m2 are as defined above (in particular with respect to formula (I), (III), (V), and/or (VIa) to (VIf)) or below. Thus, in one preferred embodiment of the polyheterocyclic derivative of any one of formula (VIIa), (VIIb), (VIIc), (VIId), (VIIe), and/or (VIIf), $R^1$ is as defined above (in particular with respect to formulas (I) and (III)), the sum of m1 and m2 is 1 to 7 (such as 1, 2, 3, 4, 5, or 6, or 1 to 4), and each of $R^{3A}$ and $R^{3B}$ is independently selected from the group consisting of $C_{1-4}$ alkyl, halogen, —CN, —$NO_2$, —OH, —O($C_{1-3}$ alkyl), —O($CH_2$)$_{1-2}$(phenyl), —$NH_2$, —OC(=O)($R^{11a}$), —NHC(=O)H, and —($C_{1-3}$ alkylene)OH, wherein z is 0, 1, or 2; wherein $R^{11a}$ is selected from the group consisting of $C_{1-3}$ alkyl and phenyl, each of which is optionally substituted with one or two independently selected $R^{30}$; and/or two $R^{3A}$ which are bound to the same carbon atom of ring A may join together to form =O (only for formula (VIIb)) and/or any two $R^{3A}$ on adjacent ring atoms of ring A may join together with the adjacent ring atoms of ring A to form a 5- to 6-membered heterocyclic ring selected from the group consisting of benzo, pyrrolidino, dioxolano (e.g., 1,3-dioxolano), dihydropyrazolo, and morpholino, each of which is optionally substituted with one, two or three moieties independently selected from the group consisting of —OH, methyl, ethyl, —$OCH_3$, and —$NH_{2-z}$($CH_3$)$_z$, or any two $R^{3B}$ on adjacent ring atoms of ring B may join together with the adjacent ring atoms of ring B to form a 5- to 6-membered heterocyclic ring selected from the group consisting of benzo, pyrrolidino, dioxolano (e.g., 1,3-dioxolano), dihydropyrazolo, and morpholino, each of which is optionally substituted with one, two or three moieties independently selected from the group consisting of —OH, methyl, ethyl, —$OCH_3$, and —$NH_{2-z}$($CH_3$)$_z$, wherein z is 0, 1, or 2, wherein the sum of (i) the total number of rings formed by any two $R^{3A}$ on adjacent ring atoms of ring A and (ii) the total number of rings formed by any two $R^{3B}$ on adjacent ring atoms of ring B preferably is 0 or 1; and $R^{30}$ is as specified above with respect to the substitution pattern of $R^{11a}$ specified for formula (V), preferably $R^{30}$ is a $1^{st}$ level substituent selected from the group consisting of 5- or 6-membered heterocyclyl, —C($R^{71}$)=(5- to 6-membered heterocyclylidene), halogen, —CN, and azido, wherein each of the 5- to 6-membered heterocyclyl and 5- to 6-membered heterocyclylidene groups being a $1^{st}$ level substituent is optionally substituted by one or more (e.g., 1, 2, 3, 4, 5, or 6) $2^{nd}$ level substituents, wherein said $2^{nd}$ level substituent is, in each case, independently selected from the group consisting of $C_{1-4}$ alkyl and phenyl, and/or any two $2^{nd}$ level substituents which are bound to the same carbon atom of a heterocyclyl group being a $1^{st}$ level substituent may join together to form =O or =S and/or any two $2^{nd}$ level substituents which are bound to the same carbon atom of a heterocyclyl group being a 1st level substituent may join together to form =C(R81)(phenyl), wherein each of the C1-4 alkyl and phenyl (including phenyl of the =C(R81)(phenyl) group) groups being a 2nd level substituent is optionally substituted with one or more (e.g., 1, 2, or 3, such as 1 or 2) 3rd level substituents, wherein said 3rd level substituent is, in each case, independently selected from the group consisting of C1-3 alkyl, halogen, —CF3, —CN, azido, —NO2, —OH, —O(C1-3 alkyl), —OCF3, —NH2, —NH(C1-3 alkyl), —N(C1-3 alkyl)2, —C(=O)OH, and —C(=O)O(C1-3 alkyl), wherein C1-3 alkyl is methyl, ethyl, propyl or isopropyl; more preferably R30 is a 1st level substituent selected from the group consisting of 5- or 6-membered heterocyclyl, —C(H)=(5- to 6-membered heterocyclylidene), and halogen, wherein each of the 5- to 6-membered heterocyclyl and 5- to 6-membered heterocyclylidene groups being a 1st level substituent is optionally substituted by one or more (e.g., 1, 2, 3, 4, 5, or 6) 2nd level substituents, wherein said 2nd level substituent is, in each case, independently selected from the group consisting of C1-4 alkyl and phenyl, and/or any two 2nd level substituents which are bound to the same carbon atom of a heterocyclyl group being a 1st level substituent may join together to form =O or =S and/or any two 2nd level substituents which are bound to the same carbon atom of a heterocyclyl group being a 1st level substituent may join together to form =C(H)(phenyl), wherein each of the C1-4 alkyl and phenyl (including phenyl of the =C(H)(phenyl) group) groups being a 2nd level substituent is optionally substituted with one or more (e.g., 1, 2, or 3, such as 1 or 2) 3rd level substituents, wherein said 3rd level substituent is, in each case, independently selected from the group consisting of methyl, halogen, and —CF3.

Particular preferred is a polyheterocyclic derivative having the formula (VIIa), wherein R1, R3A, R3b, m1, and m2 are as defined above for formulas (VIIa) to (VIIf).

In one embodiment, the polyheterocyclic derivative of formula (I) is selected from the compounds shown in Table 1a and/or Table 1b.

It is intended that the compounds disclosed in the present invention (in particular, the compounds of any one of formulas (I), (IIa), (IIb), (III), (IV), (V), (VIa), (VIb), (VIc), (VId), (VIe), (VIf), (VIg), (VIIa), (VIIb), (VIIc), (VIId), (VIIe), and (VIIf) such as those depicted in Table 1a and/or Table 1b) encompass not only the compounds as depicted but also their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically labeled forms, prodrugs, and any combinations thereof.

A selection of compounds, including those which have been synthesized and tested, within the scope of, or for use within the methods of, the present invention—and/or that represent examples of various exemplary or preferred ring Q, ring A, ring B, R1, R2, R3A, R3B substituents and/or n, m1, m2 indices, each individually or in any combination are useful for synthesising further compounds according to formula (I)—is listed in the following Table 1a and/or Table 1b.

TABLE 1a

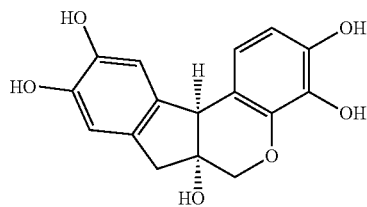 [SMILES: Oc1cc2c(cc1O)[C@H]1c3ccc(O)c(O)c3OC[C@@]1(O)C2]

A-1

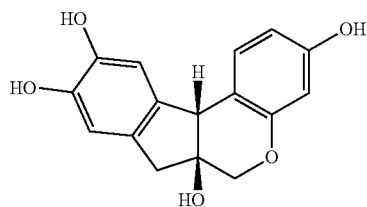 [SMILES: Oc1ccc2c(c1)OC[C@]1(O)Cc3cc(O)c(O)cc3[C@H]21]

A-2

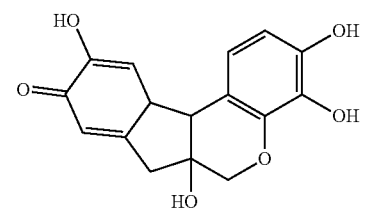 [SMILES: O=C1C=C2CC3(O)COc4c(ccc(O)c4O)C3C2C=C1O]

A-3

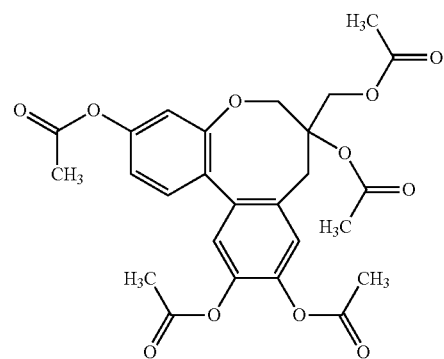 [SMILES: CC(=O)OCC1(OC(C)=O)COc2cc(OC(C)=O)ccc2-c2cc(OC(C)=O)c(OC(C)=O)cc2C1]

A-4

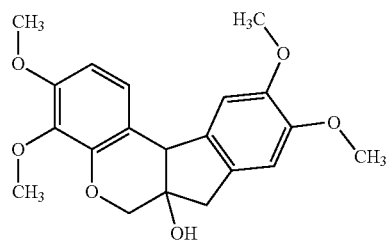 [SMILES: COc1cc2c(cc1OC)C1c3ccc(OC)c(OC)c3OCC1(O)C2]

A-5

TABLE 1b
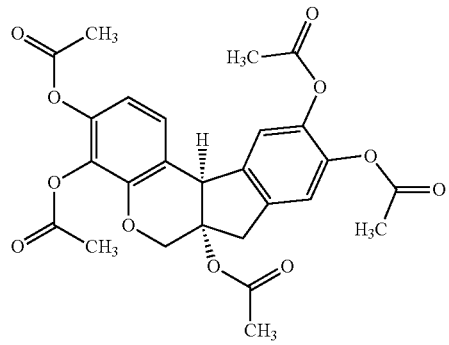 [SMILES: CC(=O)Oc1cc2c(cc1OC(C)=O)[C@@H]1c3ccc(OC(C)=O)c(OC(C)=O)c3OC[C@]1(OC(C)=O)C2]
B-1
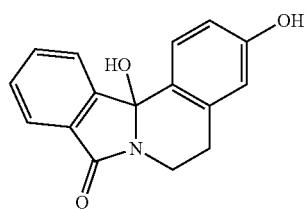 [SMILES: O=C1c2ccccc2C2(O)c3ccc(O)cc3CCN12]
B-2
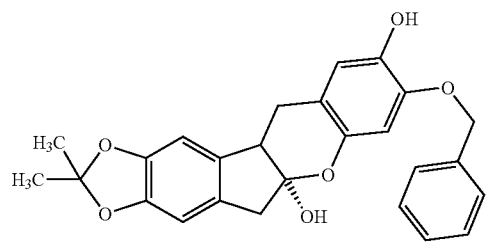
B-3
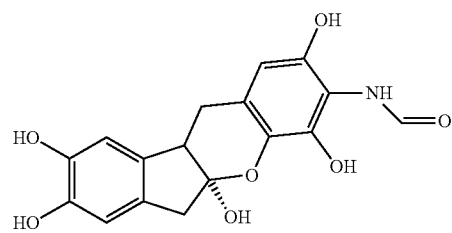
B-4
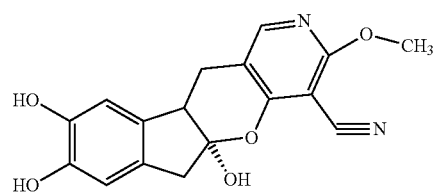
B-5
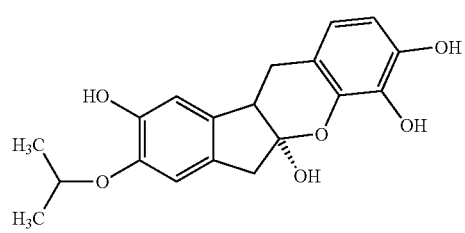
B-6

TABLE 1b-continued
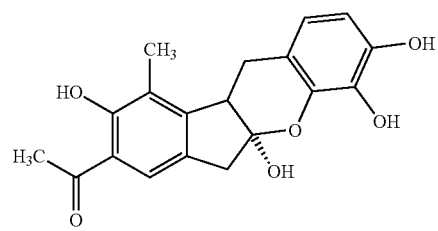
B-7
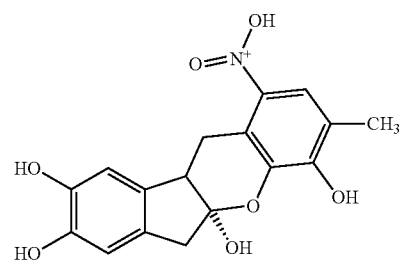
B-8
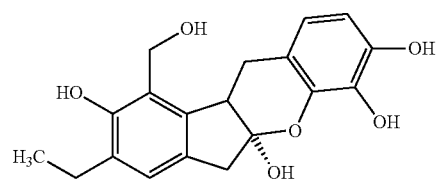
B-9
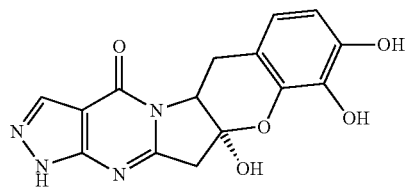
B-10
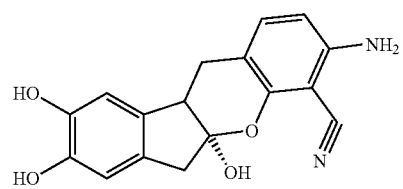
B-11
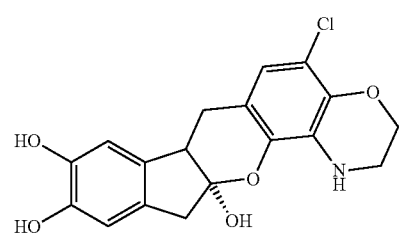
B-12
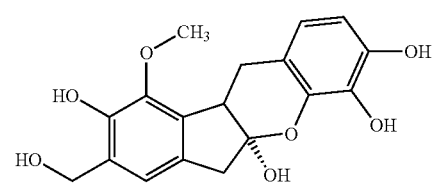
B-13

TABLE 1b-continued
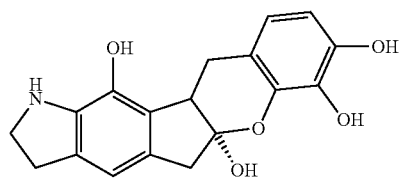
B-14
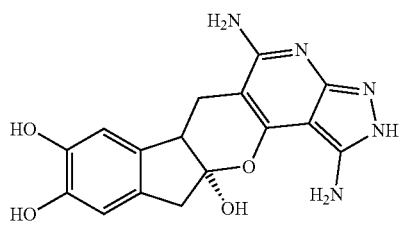
B-15
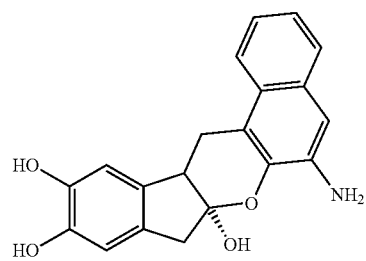
B-16
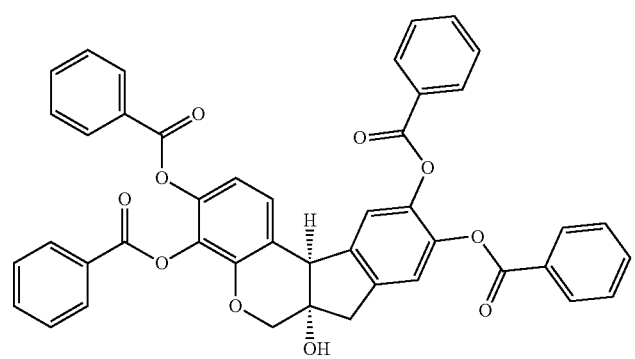 [SMILES: O=C(Oc1cc2c(cc1OC(=O)c1ccccc1)[C@@H]1c3ccc(OC(=O)c4ccccc4)c(OC(=O)c4ccccc4)c3OC[C@]1(O)C2)c1ccccc1]
B-17

TABLE 1b-continued
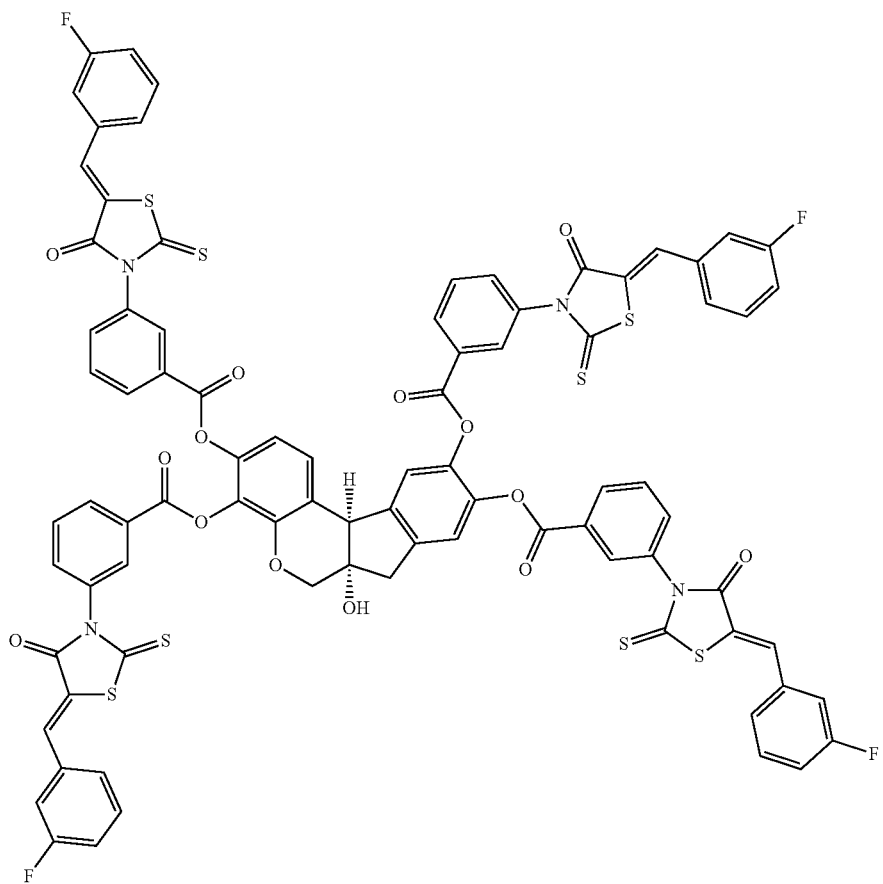 [SMILES: O=C(Oc1cc2c(cc1OC(=O)c1cccc(N3C(=O)/C(=C/c4cccc(F)c4)SC3=S)c1)[C@@H]1c3ccc(OC(=O)c4cccc(N5C(=O)/C(=C/c6cccc(F)c6)SC5=S)c4)c(OC(=O)c4cccc(N5C(=O)/C(=C/c6cccc(F)c6)SC5=S)c4)c3OC[C@]1(O)C2)c1cccc(N2C(=O)/C(=C/c3cccc(F)c3)SC2=S)c1]
B-18
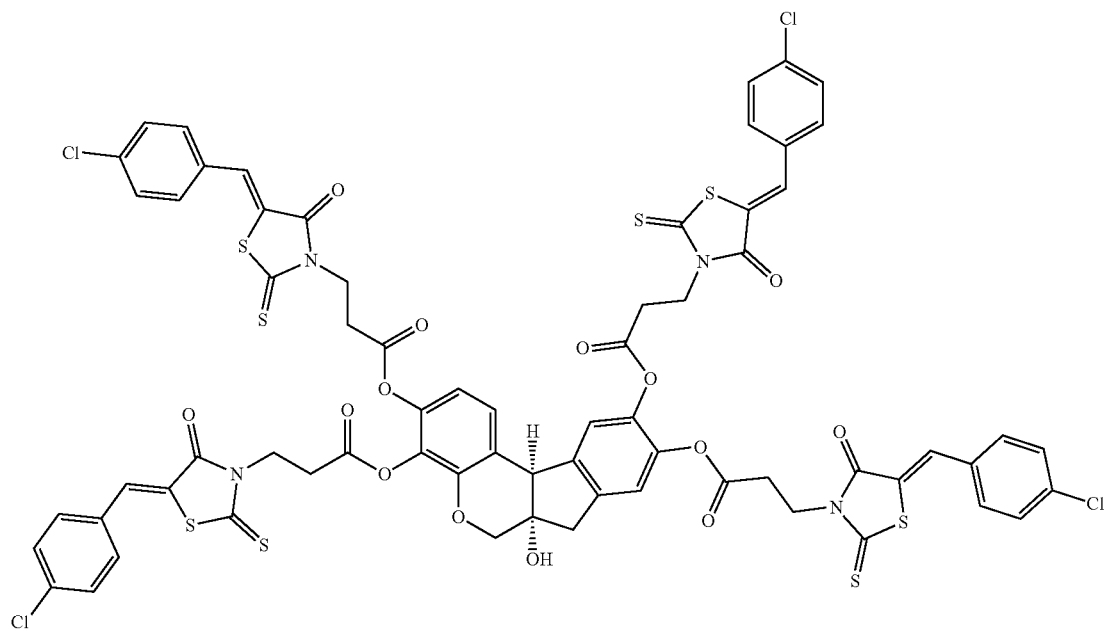 [SMILES: O=C(CCN1C(=O)/C(=C/c2ccc(Cl)cc2)SC1=S)Oc1cc2c(cc1OC(=O)CCN1C(=O)/C(=C/c3ccc(Cl)cc3)SC1=S)[C@@H]1c3ccc(OC(=O)CCN4C(=O)/C(=C/c5ccc(Cl)cc5)SC4=S)c(OC(=O)CCN4C(=O)/C(=C/c5ccc(Cl)cc5)SC4=S)c3OC[C@]1(O)C2]
B-19

TABLE 1b-continued
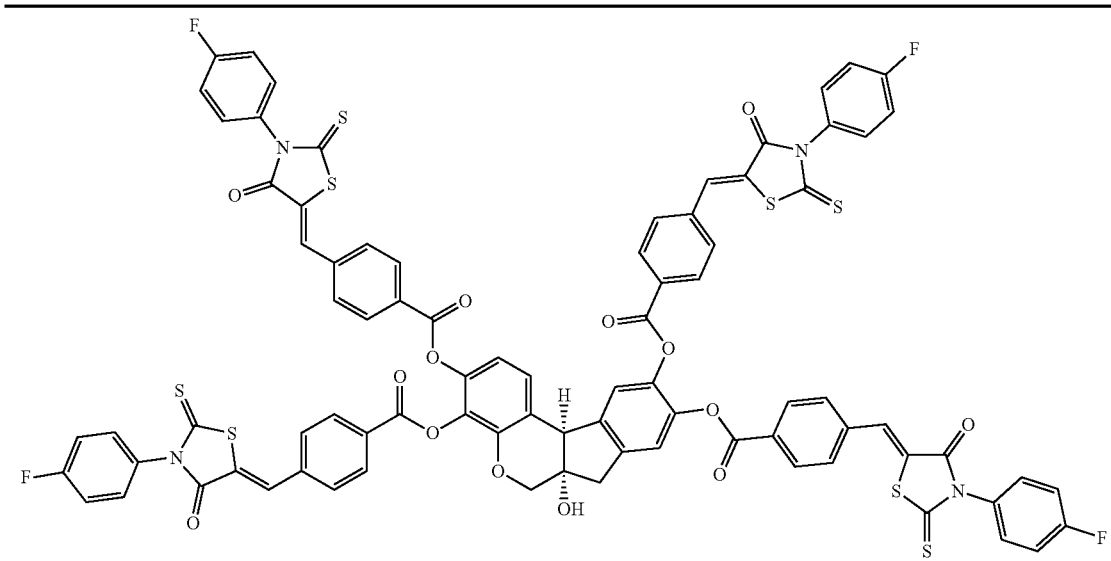
B-20
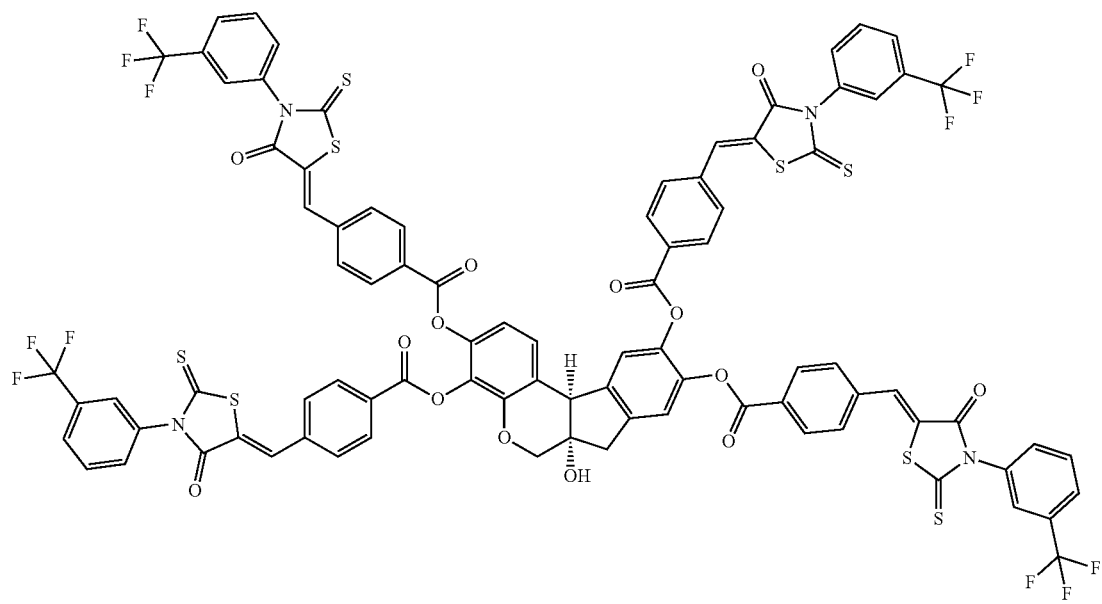 [SMILES: O=C(Oc1cc2c(cc1OC(=O)c1ccc(/C=C3\SC(=S)N(c4cccc(C(F)(F)F)c4)C3=O)cc1)[C@@H]1c3ccc(OC(=O)c4ccc(/C=C5\SC(=S)N(c6cccc(C(F)(F)F)c6)C5=O)cc4)c(OC(=O)c4ccc(/C=C5\SC(=S)N(c6cccc(C(F)(F)F)c6)C5=O)cc4)c3OC[C@]1(O)C2)c1ccc(/C=C2\SC(=S)N(c3cccc(C(F)(F)F)c3)C2=O)cc1]
B-21
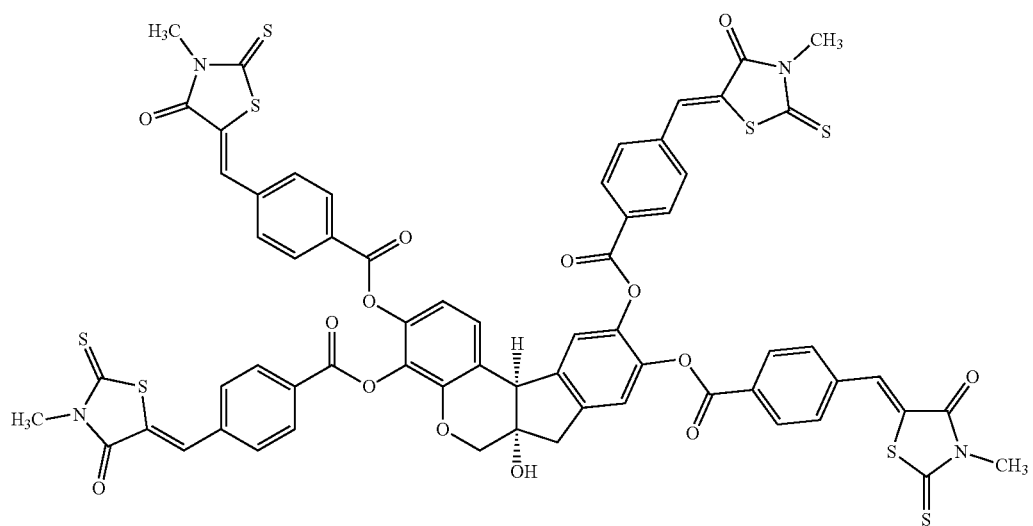
B-22

TABLE 1b-continued
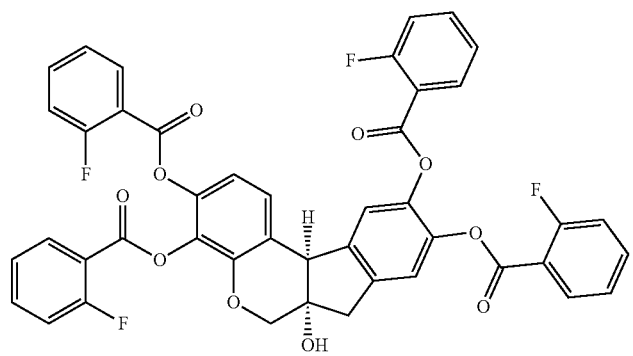 [SMILES: O=C(Oc1cc2c(cc1OC(=O)c1ccccc1F)[C@@H]1c3ccc(OC(=O)c4ccccc4F)c(OC(=O)c4ccccc4F)c3OC[C@]1(O)C2)c1ccccc1F]
B-23
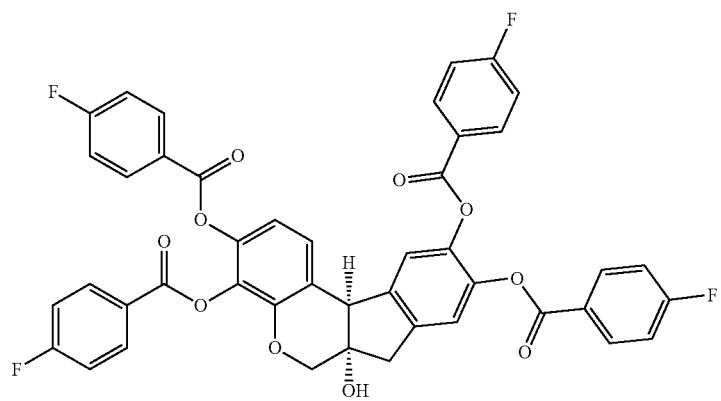 [SMILES: O=C(Oc1cc2c(cc1OC(=O)c1ccc(F)cc1)[C@@H]1c3ccc(OC(=O)c4ccc(F)cc4)c(OC(=O)c4ccc(F)cc4)c3OC[C@]1(O)C2)c1ccc(F)cc1]
B-24
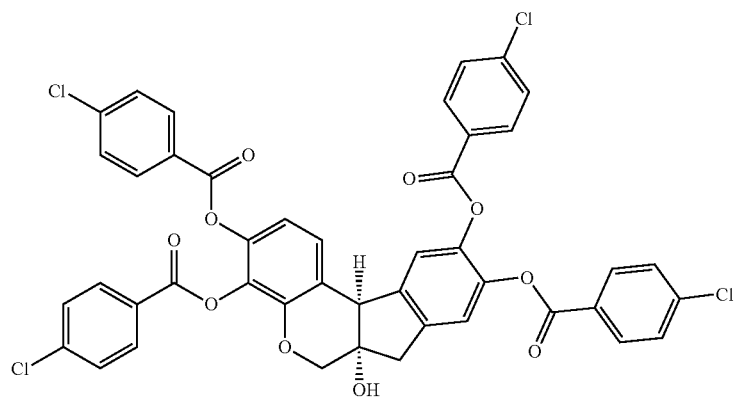 [SMILES: O=C(Oc1cc2c(cc1OC(=O)c1ccc(Cl)cc1)[C@@H]1c3ccc(OC(=O)c4ccc(Cl)cc4)c(OC(=O)c4ccc(Cl)cc4)c3OC[C@]1(O)C2)c1ccc(Cl)cc1]
B-25

TABLE 1b-continued
B-26
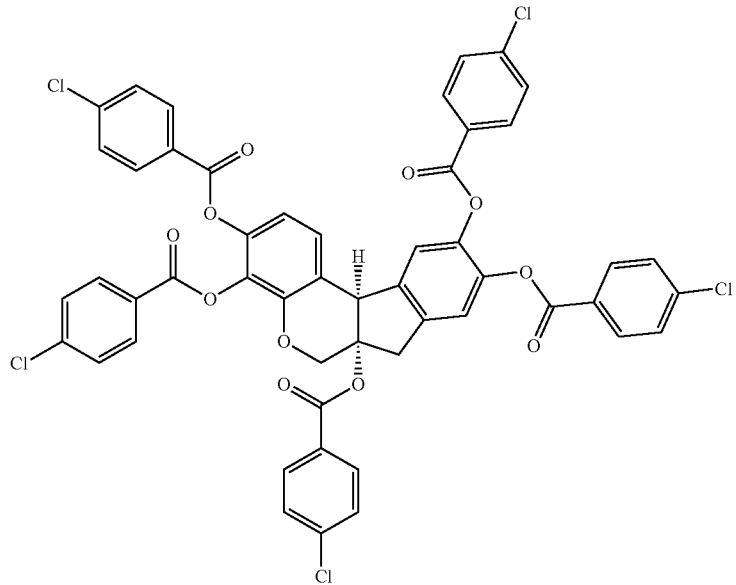 [SMILES: O=C(Oc1cc2c(cc1OC(=O)c1ccc(Cl)cc1)[C@@H]1c3ccc(OC(=O)c4ccc(Cl)cc4)c(OC(=O)c4ccc(Cl)cc4)c3OC[C@]1(OC(=O)c1ccc(Cl)cc1)C2)c1ccc(Cl)cc1]
B-27
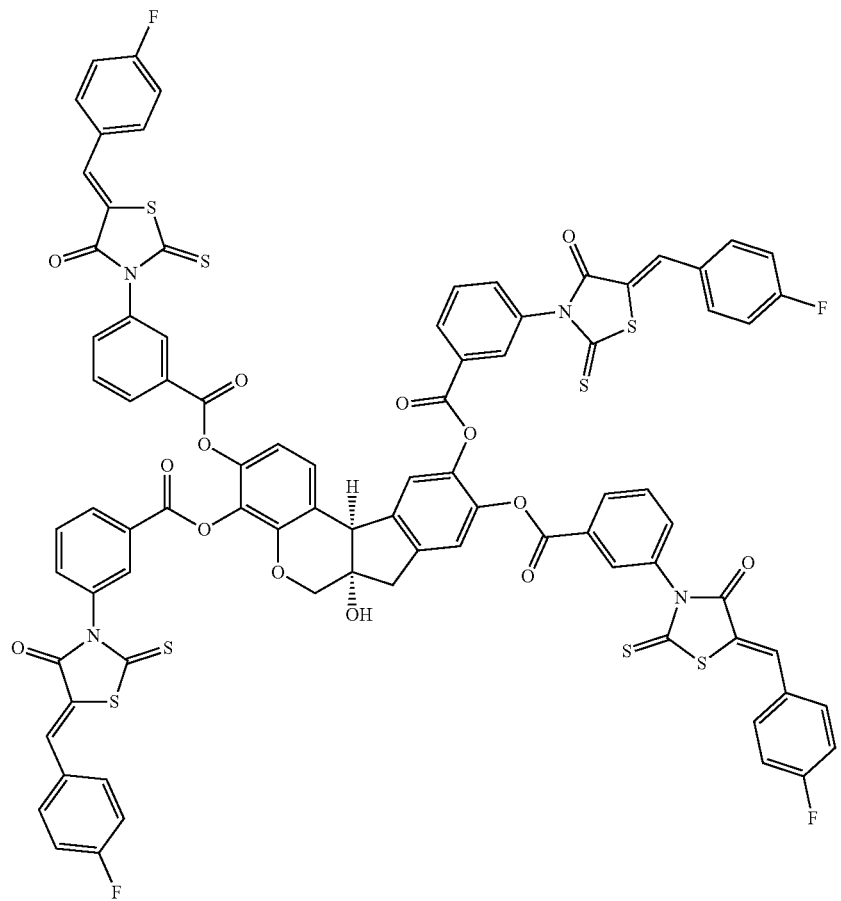 [SMILES: O=C(Oc1cc2c(cc1OC(=O)c1cccc(N3C(=O)/C(=C/c4ccc(F)cc4)SC3=S)c1)[C@@H]1c3ccc(OC(=O)c4cccc(N5C(=O)/C(=C/c6ccc(F)cc6)SC5=S)c4)c(OC(=O)c4cccc(N5C(=O)/C(=C/c6ccc(F)cc6)SC5=S)c4)c3OC[C@]1(O)C2)c1cccc(N2C(=O)/C(=C/c3ccc(F)cc3)SC2=S)c1]

TABLE 1b-continued
B-28
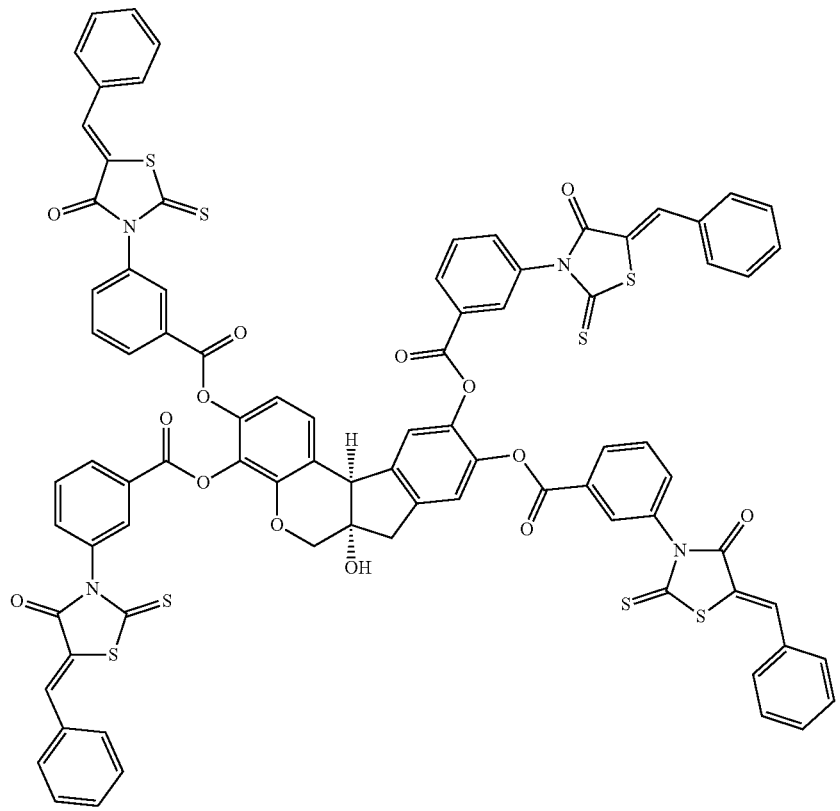 [SMILES: O=C(Oc1cc2c(cc1OC(=O)c1cccc(N3C(=O)/C(=C/c4ccccc4)SC3=S)c1)[C@@H]1c3ccc(OC(=O)c4cccc(N5C(=O)/C(=C/c6ccccc6)SC5=S)c4)c(OC(=O)c4cccc(N5C(=O)/C(=C/c6ccccc6)SC5=S)c4)c3OC[C@]1(O)C2)c1cccc(N2C(=O)/C(=C/c3ccccc3)SC2=S)c1]
B-29
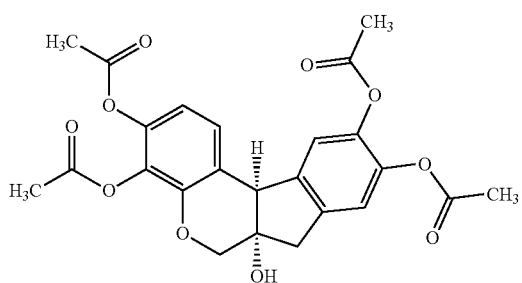 [SMILES: CC(=O)Oc1cc2c(cc1OC(C)=O)[C@@H]1c3ccc(OC(C)=O)c(OC(C)=O)c3OC[C@]1(O)C2]
B-30
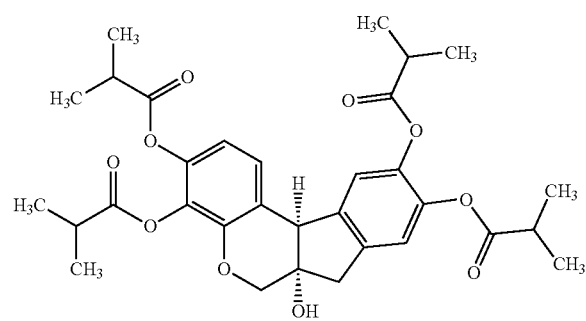 [SMILES: CC(C)C(=O)Oc1cc2c(cc1OC(=O)C(C)C)[C@@H]1c3ccc(OC(=O)C(C)C)c(OC(=O)C(C)C)c3OC[C@]1(O)C2]

TABLE 1b-continued
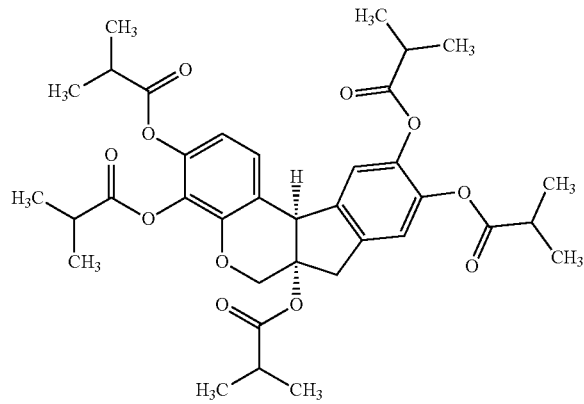 [SMILES: CC(C)C(=O)Oc1cc2c(cc1OC(=O)C(C)C)[C@@H]1c3ccc(OC(=O)C(C)C)c(OC(=O)C(C)C)c3OC[C@]1(OC(=O)C(C)C)C2]
B-31
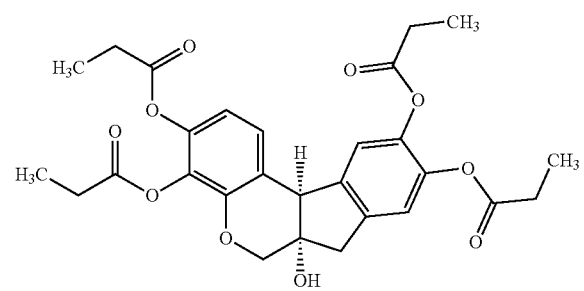 [SMILES: CCC(=O)Oc1cc2c(cc1OC(=O)CC)[C@@H]1c3ccc(OC(=O)CC)c(OC(=O)CC)c3OC[C@]1(O)C2]
B-32
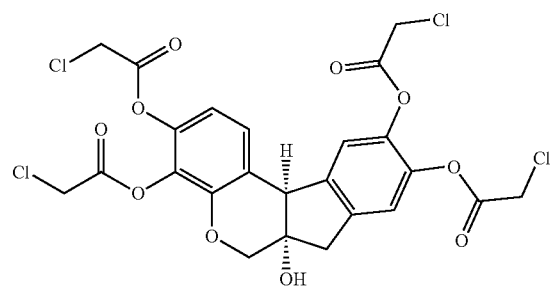 [SMILES: O=C(CCl)Oc1cc2c(cc1OC(=O)CCl)[C@@H]1c3ccc(OC(=O)CCl)c(OC(=O)CCl)c3OC[C@]1(O)C2]
B-33
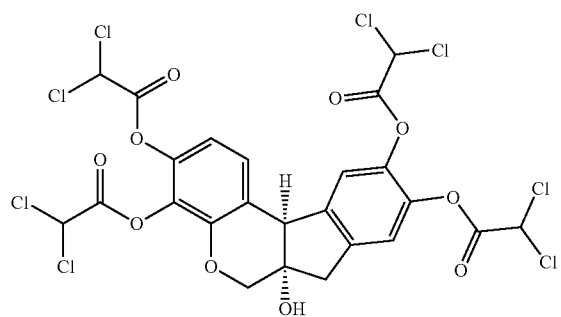 [SMILES: O=C(Oc1cc2c(cc1OC(=O)C(Cl)Cl)[C@@H]1c3ccc(OC(=O)C(Cl)Cl)c(OC(=O)C(Cl)Cl)c3OC[C@]1(O)C2)C(Cl)Cl]
B-34

TABLE 1b-continued
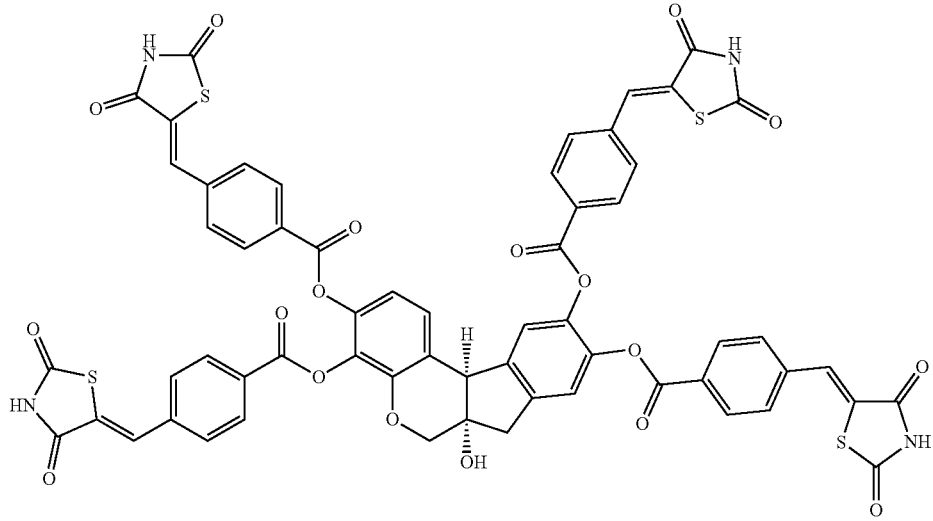 [SMILES: O=C1NC(=O)/C(=C/c2ccc(C(=O)Oc3cc4c(cc3OC(=O)c3ccc(/C=C5\SC(=O)NC5=O)cc3)[C@@H]3c5ccc(OC(=O)c6ccc(/C=C7\SC(=O)NC7=O)cc6)c(OC(=O)c6ccc(/C=C7\SC(=O)NC7=O)cc6)c5OC[C@]3(O)C4)cc2)S1]
B-35
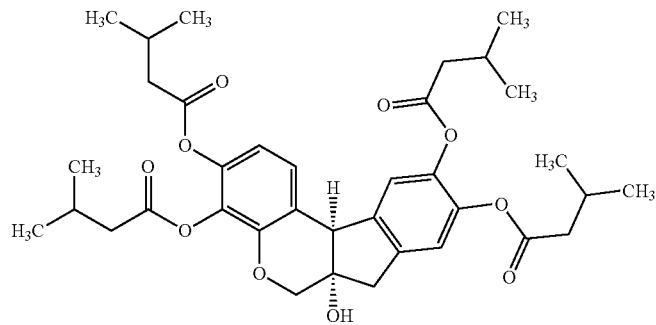 [SMILES: CC(C)CC(=O)Oc1cc2c(cc1OC(=O)CC(C)C)[C@@H]1c3ccc(OC(=O)CC(C)C)c(OC(=O)CC(C)C)c3OC[C@]1(O)C2]
B-36
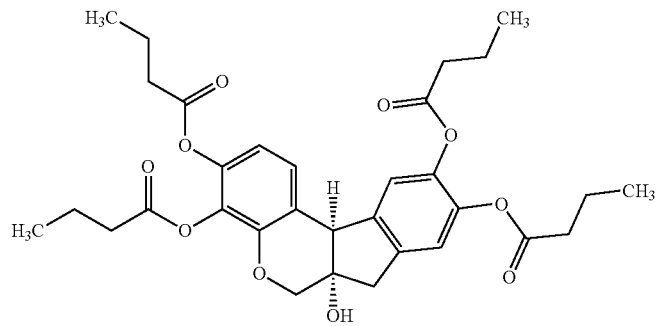 [SMILES: CCCC(=O)Oc1cc2c(cc1OC(=O)CCC)[C@@H]1c3ccc(OC(=O)CCC)c(OC(=O)CCC)c3OC[C@]1(O)C2]
B-37
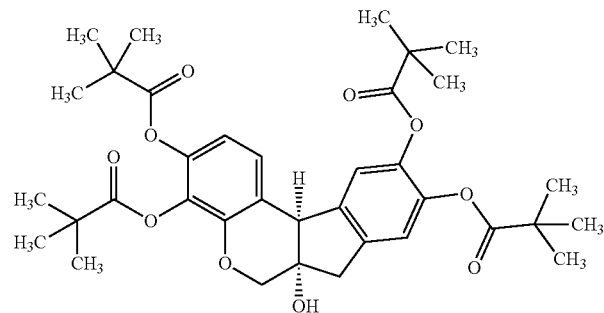 [SMILES: CC(C)(C)C(=O)Oc1cc2c(cc1OC(=O)C(C)(C)C)[C@@H]1c3ccc(OC(=O)C(C)(C)C)c(OC(=O)C(C)(C)C)c3OC[C@]1(O)C2]
B-38

Unless specified herein by the contrary, compounds of the invention are in particular those specified above such as those of formula (I), (IIa), (IIb), (III), (IV), (V), (VIa), (VIb), (VIc), (VId), (VIe), (VIf), (VIg), (VIIa), (VIIb), (VIIc), (VIId), (VIIe), or (VIIf), including the compounds listed in Table 1a and/or Table 1b.

The compounds of the invention which contain a basic functionality may form salts with a variety of inorganic or organic acids. The compounds of the invention which contain an acidic functionality may form salts with a variety of inorganic or organic bases. Exemplary inorganic and organic acids/bases as well as exemplary acid/base addition salts of the compounds of the present invention are given in the definition of "pharmaceutically acceptable salt" in the section "Pharmaceutical composition", below. The compounds of the invention which contain both basic and acidic functionalities may be converted into either base or acid addition salt. The neutral forms of the compounds of the invention may be regenerated by contacting the salt with a base or acid and isolating the parent compound in the conventional manner.

The compounds of the invention may be in a prodrug form. Prodrugs of the compounds of the invention are those compounds that upon administration to an individual undergo chemical conversion under physiological conditions to provide the compounds of the invention. Additionally, prodrugs can be converted to the compounds of the invention by chemical or biochemical methods in an ex vivo environment. For example, prodrugs can be slowly converted to the compounds of the invention when, for example, placed in a transdermal patch reservoir with a suitable enzyme or chemical reagent. Exemplary prodrugs are esters (using an alcohol or a carboxy group contained in the polyheterocyclic derivative disclosed herein) or amides (using an amino or a carboxy group contained in the polyheterocyclic derivative disclosed herein) which are hydrolyzable in vivo. Specifically, any amino group which is contained in the polyheterocyclic derivative disclosed herein and which bears at least one hydrogen atom can be converted into a prodrug form. Typical N-prodrug forms include carbamates (1), Mannich bases (2), enamines (3), and enaminones (4).

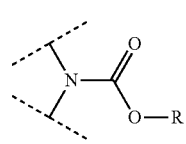

(1)

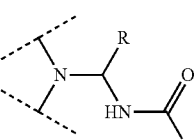

(2)

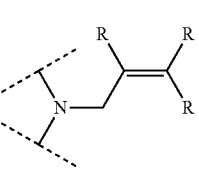

(3)

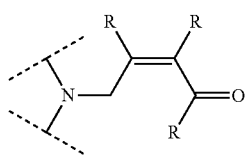

(4)

The prodrug properties (such as solubility, permeability, stability, how fast cleaved, where in the body cleaved under what conditions, target specificity, etc.) can be fine-tuned via modification of R.

In one embodiment of the aspect of the invention which is directed to compounds as such, the compounds of the invention do not encompass compounds of Table 1a.

The compounds used in the present invention can be prepared as described below or prepared by methods analogous thereto, which are readily known and available to one of ordinary skill in the art of organic synthesis.

In one aspect, the present invention provides a compound of the invention (in particular those specified above such as those of formula (I), (IIa), (IIb), (III), (IV), (V), (VIa), (VIb), (VIc), (VId), (VIe), (VIf), (VIg), (VIIa), (VIIb), (VIIc), (VIId), (VIIe), or (VIIf), particularly those given in Table 1a and Table 1b), as well as solvates, salts, complexes, polymorphs, crystalline forms, racemic mixtures, diastereomers, enantiomers, tautomers, isotopically labeled forms, prodrugs, and combinations thereof, for use in therapy (i.e., as medicament).

In one embodiment, the compounds of the present invention bind, preferably specifically bind, to wild-type calreticulin and/or mutant calreticulin. In one embodiment, the compounds of the present invention bind, preferably specifically bind, to wild-type calreticulin and/or mutant calreticulin with an equilibrium dissociation constant $K_D$ of $10^{-3}$ M or lower, $10^{-4}$ M or lower, $10^{-5}$ M or lower, $10^{-6}$ M or lower, $10^{-7}$ M or lower, $10^{-8}$ M or lower, $10^{-9}$ M or lower, or $10^{-10}$ M or lower. Methods for determining the $K_D$ of the interaction between two molecules (e.g., a small molecule and a protein, such as wild-type calreticulin and/or mutant calreticulin) are known to a person skilled in the art and are described, e.g., in Pollard T D, Mol Biol Cell, 2010, 21(23): 4061-7. In one embodiment, the compounds of the present invention bind, preferably specifically bind, to wild-type calreticulin and mutant calreticulin. In one embodiment, the compounds of the present invention bind, preferably specifically bind, to glycan-, $Ca^{2+}$—and/or ATP-binding sites of calreticulin. In one embodiment, the compounds of the present invention bind, preferably specifically bind, to the N-glycan binding site of calreticulin.

In one embodiment, the compounds of the present invention selectively inhibit growth of CALR mutant cells and/or show a selective cytotoxicity towards CALR mutant cells. The expressions "selective inhibition of growth of CALR mutant cells" and "selectively inhibit growth of CALR mutant cells" as used herein refer to a scenario where the inhibition of growth of CALR mutant cells is higher than the inhibition of growth of CALR wild-type cells. In one embodiment, the inhibition of growth of CALR mutant cells is at least 5%, at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450% or at least 500% higher than the inhibition of growth of CALR wild-type cells. The expression "selective cytotoxicity towards CALR mutant cells" as used herein refers to a cytotoxicity towards CALR mutant cells which is higher than the cytotoxicity towards CALR wild-type cells. In one embodiment, the cytotoxicity towards CALR mutant cells is at least 5%, at least 10%, at least 20%, at least 30%, at least 40%, at least 50%, at least 60%, at least 70%, at least 80%, at least 90%, at least 100%, at least 150%, at least 200%, at least 250%, at least 300%, at least 350%, at least 400%, at least 450% or at least 500% higher than the cytotoxicity towards CALR wild-type cells. Preferably, the mutant cells and wild-type cells are derived from the same cell line, e.g., Ba/F3 cells, UT-7 cells, UT-7-TPO cells, 32D cells or HEK293T cells. In one embodiment, Ba/F3 cells or UT-7-TPO cells are used. In one embodiment, the above properties of a compound of the present invention are tested essentially as described in the Examples, e.g., by using a luminescent or fluorescent cell viability assay or a two-color competition assay (see also FIG. 9).

In one embodiment, the compounds of the present invention reduce the protein level of mutant calreticulin in CALR mutant cells, as determined, e.g., by Western blotting. In one embodiment, the compounds of the present invention additionally reduce the protein level of thrombopoietin receptor (also known as the myeloproliferative leukemia protein or CD110), which is encoded by the MPL oncogene, as determined, e.g., by Western blotting.

In one embodiment, the compounds of the present invention induce apoptosis of CALR mutant cells. In one embodiment, the compounds of the present invention inhibit formation and/or function of a complex between mutant calreticulin and the thrombopoietin receptor and/or inhibit the JAK-STAT pathway.

The term "wild-type calreticulin (CALR)" or "CALR wild-type" preferably refers to human wild-type (WT) calreticulin (NCBI accession numbers NG_029662.1 (gene) and NP_004334.1 (protein); UniProt ID: P27797). An exemplary amino acid sequence of human wild-type calreticulin is shown in SEQ ID NO: 1.

The term "mutation" or "mutant" as used herein in connection with calreticulin refers to mutations or mutants which are based on a frameshift caused by insertions and/or deletions in exon 9 of the coding sequence of wild-type calreticulin. This frameshift results in the replacement of the C-terminal negatively charged amino acids (aspartic and glutamic acid rich) of wild-type calreticulin by a predominantly positively charged polypeptide rich in arginine and methionine ("disease frameshift"). The common minimum amino acid sequence of the mutant proteins is shown in SEQ ID NO: 2. Thus, in one embodiment, the term "mutant calreticulin (CALR)" or "CALR mutant" as used herein refers to a calreticulin protein comprising the amino acid sequence:

```
                                          (SEQ ID NO: 2)
  Arg Met Met Arg Thr Lys Met Arg Met Arg Arg
  1               5                   10

Met Arg Arg Thr Arg Arg Lys Met Arg Lys
                15                  20

Met Ser Pro Ala Arg Pro Arg Thr Ser Cys Arg
                25                  30

Glu Ala Cys Leu Gln Gly Trp Thr Glu Ala.
                35                  40
```

For example, $(1+(3 \times n_0))$ nucleotides can be deleted from exon 9 of the coding sequence of wild-type calreticulin, whereby no can be any natural number including zero.

Non-limiting examples of the number of nucleotides that can be deleted from exon 9 of the coding sequence of wild-type calreticulin to generate a nucleic acid encoding a mutant calreticulin are 1, 4, 19, 22, 31, 34, 37, 46, 52, 58, 61 and 79 nucleotides (referred to as del1, del4, del19, del22, del31, del34, del37, del46, del52, del58, del61 and del79 mutations).

Additionally or alternatively, $(2+(3 \times n_0))$ nucleotides can be inserted into exon 9, whereby no can be any natural number including zero. For example, 5 nucleotides can be inserted into exon 9 to generate a nucleic acid encoding a mutant calreticulin (ins5 mutation).

The frameshift mutation can also be caused by a combination of insertion and deletion of one or more nucleotides into/from the coding sequence of wild-type calreticulin, provided that the resulting mutant protein comprises the characteristic C-terminus (as shown in SEQ ID NO: 2).

Numerous mutant calreticulins have been described in the prior art, e.g., in WO 2015/036599 A1 and WO 2016/098514 A1, which are incorporated herein by reference.

In one embodiment, the mutant calreticulin is a CALR del52 mutant ("Type 1") comprising the amino acid sequence:

```
                                          (SEQ ID NO: 3)
  Thr Arg Arg Met Met Arg Thr Lys Met Arg Met
  1               5                   10

Arg Arg Met Arg Arg Thr Arg Arg Lys Met Arg
                15                  20

Arg Lys Met Ser Pro Ala Arg Pro Arg Thr Ser
                25                  30

Cys Arg Glu Ala Cys Leu Gln Gly Trp Thr Glu Ala.
        35              40                  45
```

In one embodiment, the mutant calreticulin comprises or consists of the amino acid sequence of SEQ ID NO: 4.

In one embodiment, the mutant calreticulin is a CALR ins5 mutant ("Type 2") comprising the amino acid sequence:

```
                                          (SEQ ID NO: 5)
  Asn Cys Arg Arg Met Met Arg Thr Lys Met Arg
  1               5                   10

Met Arg Arg Met Arg Arg Thr Arg Arg Lys Met
                15                  20

Arg Arg Lys Met Ser Pro Ala Arg Pro Arg Thr
                25                  30

Ser Cys Arg Glu Ala Cys Leu Gln Gly Trp Thr Glu
        35              40                  45
  Ala.
```

In one embodiment, the mutant calreticulin comprises or consists of the amino acid sequence of SEQ ID NO: 6.

In one embodiment, the mutant calreticulin is a CALR del37 mutant comprising the amino acid sequence of SEQ ID NO: 7.

In one embodiment, the mutant calreticulin is a CALR del79 mutant comprising the amino acid sequence of SEQ ID NO: 8.

The term "CALR mutant cell" as used herein refers to cells (transiently or stably) expressing a mutant calreticulin. In contrast, the term "CALR wild-type cell" as used herein refers to cells (transiently or stably) expressing wild-type calreticulin.

Pharmaceutical Compositions

The compounds described in present invention (in particular those specified above such as those of formula (I), (IIa), (IIb), (III), (IV), (V), (VIa), (VIb), (VIc), (VId), (VIe), (VIf), (VIg), (VIIa), (VIIb), (VIIc), (VIId), (VIIe), or (VIIf), particularly those given in Table 1a and Table 1b) are preferably administered to a patient in need thereof via a pharmaceutical composition. Thus, in a further aspect, the present invention provides a pharmaceutical composition comprising a polyheterocyclic derivative as specified above under the heading "Compounds" (e.g., a polyheterocyclic derivative having the general formula (I), (IIa), (IIb), (III), (IV), (V), (VIa), (VIb), (VIc), (VId), (VIe), (VIf), (VIg), (VIIa), (VIIb), (VIIc), (VIId), (VIIe), or (VIIf), or a solvate, salt (in particular pharmaceutically acceptable salt), complex, polymorph, crystalline form, racemic mixture, diastereomer, enantiomer, tautomer, isotopically labeled form, prodrug, or combination thereof) and one or more pharmaceutically acceptable excipients, and optionally one or more additional therapeutic agents.

The term "pharmaceutically acceptable" refers to the non-toxicity of a material which does not interact with the action of the active component (i.e., polyheterocyclic derivative as specified above, either alone or in combination with one or more additional therapeutic agents) of the pharmaceutical composition.

The pharmaceutical composition may be administered to an individual by any route, such as enterally or parenterally.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, inhalational, or through mucous membranes (such as buccal, sublingual or vaginal)).

The compounds of the present invention are generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, Berge et al., "Pharmaceutical Salts", J. Pharm. Sci., 66, pp. 1-19 (1977)).

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, emulsifiers, buffers, flavoring agents, colorants, or antioxidants.

The compositions described in the present invention may comprise a pharmaceutically acceptable carrier. As used herein, "pharmaceutically acceptable carrier" includes any and all solvents, dispersion media, coatings, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, i.e., the compound of the present invention, either alone or in combination with one or more additional therapeutic agents, may be coated in a material to protect the active compound(s) from the action of acids and other natural conditions that may inactivate the active compound.

Examples of suitable aqueous and non-aqueous carriers which may be employed in the pharmaceutical compositions according to the present invention include water (e.g., water for injection), ethanol, polyols (such as glycerol, propylene glycol, polyethylene glycol, and the like), aqueous solutions of a salt, carbohydrate, sugar alcohol, or an amino acid (such as saline or an aqueous amino acid solution), and suitable mixtures and/or buffered forms thereof, vegetable oils (such as olive oil), and injectable organic esters (such as ethyl oleate). Proper fluidity can be maintained, for example, by the use of coating materials, such as lecithin, by the maintenance of the required particle size in the case of dispersions, and by the use of surfactants.

Pharmaceutically acceptable carriers include sterile aqueous solutions or dispersions and sterile powders for the extemporaneous preparation of sterile injectable solutions or dispersions. The use of such media and agents for pharmaceutically active compounds is known in the art. Except insofar as any conventional media or agent is incompatible with the active compound, use thereof in the pharmaceutical compositions according to the present invention is contemplated.

Additional therapeutic agents can be administered together with, before or after the compound of the present invention (in particular that specified above such as those of formula (I), (IIa), (IIb), (III), (IV), (V), (VIa), (VIb), (VIc), (VId), (VIe), (VIf), (VIg), (VIIa), (VIIb), (VIIc), (VIId), (VIIe), or (VIIf)) or incorporated into the compositions). In one embodiment, the pharmaceutical composition described herein comprises a polyheterocyclic derivative as described above (e.g. having the general formula (I), (IIa), (IIb), (III), (IV), (V), (VIa), (VIb), (VIc), (VId), (VIe), (VIf), (VIg), (VIIa), (VIIb), (VIIc), (VIId), (VIIe), or (VIIf) or a solvate, salt (in particular pharmaceutically acceptable salt), complex, polymorph, crystalline form, racemic mixture, diastereomer, enantiomer, tautomer, isotopically labeled form, prodrug, or combination of any of the foregoing), at least one additional therapeutic agent, and one or more pharmaceutically acceptable excipients.

The "additional therapeutic agent" (which is not a polyheterocyclic derivative having formula (I) as specified herein) may be selected from any compound which can be used in the treatment of a disease or condition caused by or associated with a mutation of CALR, such as hydroxyurea or interferon alpha. The additional therapeutic agent may induce an additive or synergistic therapeutic effect. Examples of additional therapeutic agents include, but are not limited to, JAK inhibitors (e.g., ruxolitinib, fedratinib, momelitinib, pacritinib), imetelstat, interferons (e.g., interferon alpha), hydroxyurea, radioactive phosphorus, anagrelide, busulfan, melphalan, melphalan plus prednisone, doxorubicin, dexamethasone, bortezomib, Bcr-Abl, Flt-3, RAF and FAK kinase inhibitors, BET inhibitors, immunotherapeutic agents targeting mutant CALR (e.g., vaccines, CAR T cells, monoclonal antibodies or fragments thereof, antibody-drug conjugates, bispecific antibodies), allogeneic hematopoietic stem cells, activin receptor antagonists, acetylsalicylic acid, agents targeting TP53 inactivation by MDM4 and MDM2 (e.g., idasanutlin (RG7388)), inhibitors of the TGFβ pathway (e.g., AVID200), PD-1/PD-L1 targeting agents (e.g., nivolumab, pembrolizumab), thalidomide, lenalidomide and pomalidomide.

The pharmaceutical composition described herein may comprise, in addition to the polyheterocyclic derivative as described above, at least one, e.g., 1, 2, 3, 4, 5, 6, 7 or 8, additional therapeutic agents. According to the present teaching, the at least one additional therapeutic agent may be formulated together with the polyheterocyclic derivative as described above in a single pharmaceutical composition.

Alternatively, the pharmaceutical composition may be structured as kit of parts, wherein the polyheterocyclic derivative is provided in a first formulation and the at least one additional therapeutic agent is provided in a second formulation, i.e., a second pharmaceutical composition. The first and the second pharmaceutical compositions may be combined prior to use. In other words, before administering the pharmaceutical composition, a formulation comprising the additional therapeutic agent may be added to the first pharmaceutical composition comprising the polyheterocyclic derivative. Alternatively, the present teaching envisages administering the polyheterocyclic derivative formulated in a first pharmaceutical composition and administering the at least one additional therapeutic agent formulated in a second pharmaceutical composition. The pharmaceutical compositions may be administered concomitantly or in succession. For example, the first pharmaceutical composition may be administered at a first point in time and the second pharmaceutical composition may be administered at a second point in time, wherein the points in time may be separated by, for example, 0, or up to 1, 2, 3, 4, 5 or 10 min, up to 1, 2, 3, 4, 5 or 10 hours, up to 1, 2, 3, 4, 5 or 10 days, up to 1, 2, 3, 4, 5 or 10 weeks, up to 1, 2, 3, 4, 5 or 10 months or up to 1, 2, 3, 4, 5 or 10 years.

The compositions may also contain adjuvants such as preservatives, wetting agents, emulsifying agents, pH buffering agents, and dispersing agents. Prevention of the presence of microorganisms may be ensured by sterilization procedures and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the active compounds, which may be used in a suitable hydrated form, and/or the pharmaceutical compositions according to the present invention, are formulated into pharmaceutically acceptable dosage forms by conventional methods known to those of skill in the art (cf., e.g., Remington, "The Science and Practice of Pharmacy" edited by Allen, Loyd V., Jr., $22^{nd}$ edition, Pharmaceutical Sciences, September 2012; Ansel et al., "Pharmaceutical Dosage Forms and Drug Delivery Systems", $7^{th}$ edition, Lippincott Williams & Wilkins Publishers, 1999).

A pharmaceutical composition can be administered by a variety of methods known in the art. As will be appreciated by the skilled artisan, the route and/or mode of administration will vary depending upon the desired results. The pharmaceutical compositions containing one or more active compounds can be prepared with carriers that will protect the one or more active compounds against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such compositions are generally known to those skilled in the art. See, e.g., Sustained and Controlled Release Drug Delivery Systems, J. R. Robinson, ed., Marcel Dekker, Inc., New York, 1978.

To administer a compound of the present invention by certain routes of administration, it may be necessary to coat the compound with, or co-administer the compound with, a material to prevent its inactivation. For example, the compound may be administered to an individual in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol., 1984, 7:27).

Pharmaceutical compositions typically are sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

An injectable composition should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms used according to the present invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic/pharmaceutical formulations, compositions according to the present invention include those suitable for enteral administration (such as oral or rectal) or parenteral administration (such as nasal, topical (including vaginal, buccal and sublingual)). The compositions may conveniently be presented in unit dosage form and may be prepared by any methods known in the art of pharmacy. The amount of active ingredient (in particular, the amount of a compound according to the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of active ingredient (in particular, the amount of the compound according to the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active ingredient, e.g., a compound according to the present invention, in a unit dosage form and/or when administered to an individual or used in therapy, may range from about 0.1 mg to about 1000 mg (for example, from about 1 mg to about 500 mg, such as from about 10 mg to about 200 mg) per unit, administration or therapy. In certain embodiments, a suitable amount of such active ingredient may be calculated using the mass or body surface area of the individual, including amounts of between about 1 mg/kg and 10 mg/kg (such as between about 2 mg/kg and 5 mg/kg), or between about 1 mg/m$^2$ and about 400 mg/m$^2$ (such as between about 3 mg/m$^2$ and about 350 mg/m$^2$ or between about 10 mg/m$^2$ and about 200 mg/m$^2$).

Actual dosage levels of the active ingredients in the pharmaceutical compositions according to the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the compounds according to the present invention at levels lower than that required in order to achieve the desired therapeutic effect and gradually increase the dosage until the desired effect is achieved. In general, a suitable daily dose of a composition according to the present invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound according to the present invention to be administered alone, it is preferable to administer the compound as a pharmaceutical formulation/composition.

For oral administration, the pharmaceutical composition according to the present invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-p-hydroxycarbonates, sorbic acids). The preparations can also contain buffer salts, flavouring, coloring and sweetening agents as deemed appropriate. Preparations for oral administration can be suitably formulated to give controlled release of the pharmaceutical composition of the invention.

In one embodiment, the compound is orally administered in a concentration of at most 100 mg/kg body weight (such as at most 50 mg/kg body weight, at most 40 mg/kg body weight, at most 30 mg/kg body weight, at most 20 mg/kg body weight, at most 10 mg/kg body weight, at most 5 mg/kg body weight, at most 4 mg/kg body weight, at most 3 mg/kg body weight, at most 2 mg/kg body weight, at most 1 mg/kg body weight).

In one embodiment, the compound is parenterally administered (e.g., intravenously, intramuscularly, or subcutaneously), in a concentration of at most 10 mg/kg body weight (such as at most 5 mg/kg body weight, at most 4 mg/kg body weight, at most 3 mg/kg body weight, at most 2 mg/kg body weight, at most 1 mg/kg body weight, at most 0.5 mg/kg body weight, at most 0.4 mg/kg body weight, at most 0.3 mg/kg body weight, at most 0.2 mg/kg body weight, at most 0.1 mg/kg body weight).

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

For administration by inhalation, the pharmaceutical composition according to the present invention is conveniently delivered in the form of an aerosol spray presentation from a pressurized pack or a nebulizer, with the use of a suitable propellant (e.g., dichlorodifluoromethane, trichlorofluoromethane, dichlorotetrafluoroethane, carbon dioxide, nitrogen, or other suitable gas). In the case of a pressurized aerosol, the dosage unit can be determined by providing a valve to deliver a metered amount. Capsules and cartridges of, for example, gelatine, for use in an inhaler or insufflator can be formulated containing a powder mix of the pharmaceutical composition according to the present invention and a suitable powder base such as lactose or starch.

The pharmaceutical composition according to the present invention can be formulated for parenteral administration by injection, for example, by bolus injection or continuous infusion. In one embodiment, the compounds or compositions according to the present invention may be administered by slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions according to the present invention are administered by maintenance therapy, such as, e.g., once a week for a period of 6 months or more.

Formulations for injection can be presented in units dosage form (e.g., in phial, in multi-dose container), and with an added preservative. The pharmaceutical composition according to the present invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Compositions according to the present invention which are suitable for vaginal administration also include pessaries, tampons, creams, gels, pastes, foams or spray formulations containing such carriers as are known in the art to be appropriate. Dosage forms for the topical or transdermal administration of compositions according to the present invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

Therapeutic/pharmaceutical compositions can be administered with medical devices known in the art. For example, in a preferred embodiment, a therapeutic/pharmaceutical composition according to the present invention can be administered with a needleless hypodermic injection device, such as the devices disclosed in U.S. Pat. Nos. 5,399,163; 5,383,851; 5,312,335; 5,064,413; 4,941,880; 4,790,824; or U.S. Pat. No. 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,916, which discloses an osmotic drug delivery system.

Many other such implants, delivery systems, and modules are known to those skilled in the art. In certain embodiments, the compounds according to the present invention can be formulated to ensure proper distribution in vivo. For example, the blood-brain barrier (BBB) excludes many highly hydrophilic compounds. To ensure that the compounds according to the present invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, and thus enhance targeted drug delivery (see, e.g., Ranade V V, J. Clin. Pharmacol., 1989, 29:685). Exemplary targeting moieties include folate or biotin (see, e.g., U.S. Pat. No. 5,416,016); mannosides (Umezawa et al., Biochem. Biophys. Res. Commun., 1988, 153:1038); antibodies (Bloeman P G et al., FEBS Lett., 1995, 357:140; Owais M et al., Antimicrob. Agents Chemother., 1995, 39:180); and surfactant protein A receptor (Briscoe et al., Am. J. Physiol., 1995, 1233:134).

In one embodiment, the compounds according to the present invention are formulated in liposomes. In a more preferred embodiment, the liposomes include a targeting moiety. In a most preferred embodiment, the compounds in the liposomes are delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective dosage" for therapy/treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective tumor response.

A "therapeutically effective dosage" for therapy/treatment can also be measured by its ability to stabilize the progression of a condition, disorder or disease. A therapeutically effective amount of a compound according to the present invention can cure, heal, alleviate, relieve, alter, remedy, ameliorate, improve or affect the condition, disorder or disease or the symptoms of the condition, disorder or disease or the predisposition toward the condition, disorder or disease in an individual. One of ordinary skill in the art would be able to determine such amounts based on such factors as the individual's size, the severity of the individual's symptoms, and the particular composition or route of administration selected.

The pharmaceutical composition according to the invention can also, if desired, be presented in a pack, or dispenser device which can contain one or more unit dosage forms containing the active compound. The pack can for example comprise metal or plastic foil, such as blister pack. The pack or dispenser device can be accompanied with instruction for administration.

Therapeutic Applications

In a further aspect, the present invention provides a compound or a pharmaceutical composition of the present invention for use in a method of treating a disease or condition caused by or associated with a mutation of CALR.

A "disease or condition caused by or associated with a mutation of CALR" may also be referred to as a CALR mutant-positive disease or condition.

In a further aspect, the present invention provides a method of treatment of a disease or condition caused by or associated with a mutation of CALR, wherein the method comprises administering a therapeutically effective dosage of a compound or a pharmaceutical composition of the present invention to a patient in need thereof.

In a further aspect, the present invention provides the use of a compound or a pharmaceutical composition of the present invention in the manufacture of a medicament for treating a disease or condition caused by or associated with a mutation of CALR.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing a disease related in a subject which may be predisposed to the disease; (b) inhibiting the disease, i.e. arresting its development; or (c) relieving the disease, i.e. causing regression of the disease.

In one embodiment of these aspects, the disease or condition is a myeloid malignancy. The term "myeloid malignancy" as used herein refers to clonal haematological diseases affecting the myeloid blood lineages including those with chronic and those with acute clinical course. Myeloid malignancies include myeloproliferative neoplasms, myelodysplastic syndromes and acute myeloid leukemias. Preferably, the myeloproliferative neoplasm is selected from the group consisting of prefibrotic myelofibrosis (pre-PMF), primary myelofibrosis (PMF) and essential thrombocythemia (ET). In one embodiment, the myeloproliferative neoplasm is primary myelofibrosis (PMF). The myelodysplastic syndrome may be refractory anemia with ringed sideroblasts and thrombocythemia (RARS-T).

In a further aspect, the present invention provides a combination comprising a compound of the present invention and at least one additional therapeutic agent, e.g., for use in a method as described above or for the use as described above.

The term "combination", as used herein, is meant to include means that allow to apply the combination either by separate administration of the compound of the present invention and the at least one additional therapeutic agent to the patient or in the form of combination products in which the compound of the present invention and the at least one additional therapeutic agent are present, e.g., in one pharmaceutical composition. When administered separately, administration may occur simultaneously or sequentially, in any order. The amount of the compound of the present invention and the at least one additional therapeutic agent as well as the relative timings of administration will be selected in order to achieve the desired combined therapeutic effect. The administration of the combination may be concomitantly in: (1) a unitary pharmaceutical composition including all active pharmaceutical ingredients; or (2) separate pharmaceutical compositions each including at least one of the active pharmaceutical ingredients. Alternatively, the combination may be administered separately in a sequential manner wherein one treatment agent is administered first and the other second or vice versa. Such sequential administration may be close in time or remote in time. In one embodiment, the combination is provided in the form of a kit. Examples of additional therapeutic agents include, but are not limited to, JAK inhibitors (e.g., ruxolitinib, fedratinib, momelitinib, pacritinib), imetelstat, interferons (e.g., interferon alpha), hydroxyurea, radioactive phosphorus, anagrelide, busulfan, melphalan, melphalan plus prednisone, doxorubicin, dexamethasone, bortezomib, Bcr-Abl, Flt-3, RAF and FAK kinase inhibitors, BET inhibitors, immunotherapeutic agents targeting mutant CALR (e.g., vaccines, CAR T cells, monoclonal antibodies or fragments thereof, antibody-drug conjugates, bispecific antibodies), allogeneic hematopoietic stem cells, activin receptor antagonists, acetylsalicylic acid, agents targeting TP53 inactivation by MDM4 and MDM2 (e.g., idasanutlin (RG7388)), inhibitors of the TGFβ pathway (e.g., AVID200), PD-1/PD-L1 targeting agents (e.g., nivolumab, pembrolizumab), thalidomide, lenalidomide and pomalidomide.

Screening Assays

In a further aspect, the present invention provides the use of a compound of the present invention in a method of screening for compounds that selectively inhibit growth of CALR mutant cells and/or exhibit selective cytotoxicity towards CALR mutant cells.

In one embodiment, the compound of the present invention is used as a reference compound/molecule (e.g., as a positive control).

In a further aspect, the present invention provides a method of screening for compounds that are suitable for treating a disease or condition caused by or associated with a mutation of CALR, said method comprising the steps:

(a) providing a compound;
(b) testing the compound for binding to one or more glycan-, Ca2+—and/or ATP-binding sites of calreticulin, and
(c) testing the compound for selective inhibition of growth of CALR mutant cells and/or selective cytotoxicity towards CALR mutant cells, wherein a compound that (i) binds to one or more glycan-, Ca2+—and/or ATP-binding sites of calreticulin and (ii) selectively inhibits growth of CALR mutant cells and/or exhibits selective cytotoxicity towards CALR mutant cells is identified as a compound that is suitable for treating a disease or condition caused by or associated with a mutation of CALR.

In one embodiment of the method, the compound is tested for binding to the N-glycan binding site of calreticulin. In one embodiment, step (b) is performed in silico, for example, by performing a 3-D molecular docking study based on a 3-D structural model of human calreticulin, e.g., essentially as described in Example 1. Respective tools are well known to a person skilled in the art and are described, e.g., in Pagadala et al. "Software for molecular docking: a review" Biophys Rev., 2017, 9(2):91-102. In one embodiment, the disease or condition is as defined herein above. In one embodiment, a compound of the present invention is used as a reference compound/molecule (e.g., as a positive control).

Synthesis

The compounds disclosed herein can be prepared as described below or prepared by methods analogous thereto, which are readily known and available to one of ordinary skill in the art of organic synthesis.

Compounds disclosed herein which bear the hematoxylin core structure and which are substituted at the corresponding hydroxyl groups of hematoxylin can generally be prepared by the general synthetic sequence shown in Scheme 1, below.

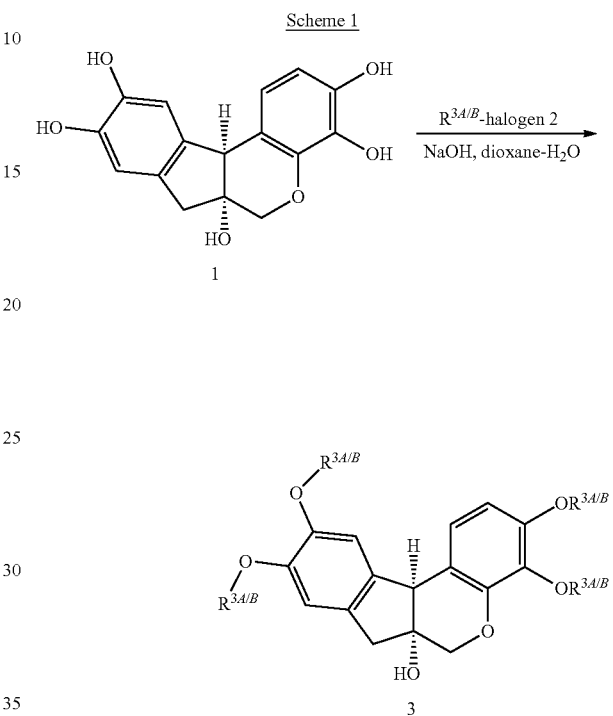

For example, compound 3 may be synthesized from hematoxylin 1 and an applicable derivative of $R^{3A/3B}$ 2 (e.g., a corresponding halogenide). To a solution of 0.33 mmol of hematoxylin 1 and 1.7 mmol NaOH in 2 ml of water is added a solution of 1.7 mmol $R^{3A/3B}$—Cl 2 in 8 ml of dioxane. The obtained mixture is stirred at 50-70° C. for 1-2 h. The progress of the reaction can be monitored by TLC. After 12 h, the mixture is diluted with 100 ml of water. The precipitate is separated by filtration and recrystallized with ethanol. Yield: typically >50%.

Suitable derivatives of $R^{3A/3B}$ are obtained from commercial sources, or are synthesised by standard procedures; cf., e.g., Kaminskyy et al., Biopolymers and Cell, 2010, 26(2): 136-145; Kaminskyy et al., Eur. J. Med. Chem., 2009, 44(9):3627-3636; Kaminskyy et al., Medicinal Chemistry Research, 2012, 21(11):3568-3580; Kaminskyy et al., Expert Opinion on Drug Discovery, 2017, 12(12):1233-1252; and Kaminskyy et al., European Journal of Medicinal Chemistry, 2017, 140:542-594. In particular, 5-arylidene-2-thioxo-4-thiazolidinone-3-R'-carboxylic acids 4 and 5-(4-carboxyphenyl)methylidene-2-thioxo-4-thiazolidinones 5 can be synthesized as shown in the following schemes 2a and 2b, respectively:

Scheme 2a

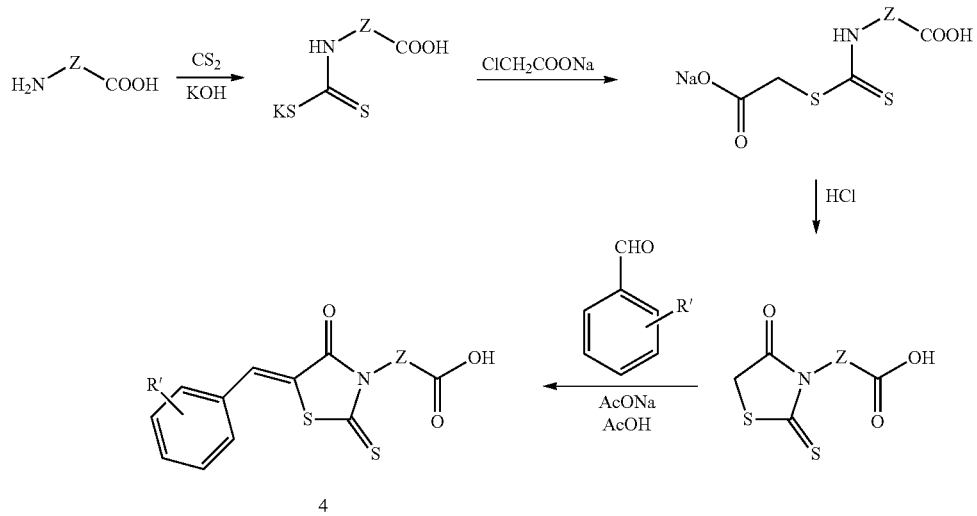

Scheme 2b

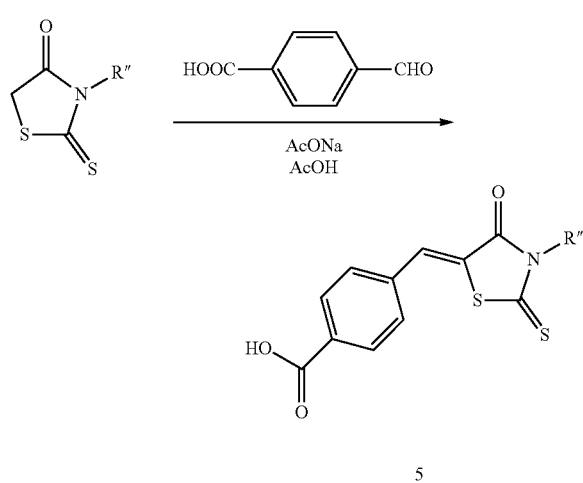

Other features and advantages of the present invention will be apparent from the following examples which are included to demonstrate preferred embodiments of the present invention but which do not limit the present invention. Rather, in light of the present disclosure, the skilled person will appreciate that many changes can be made in the specific embodiments which are disclosed and still obtain a like or similar result without departing from the scope of the invention.

EXAMPLES

Materials and Methods

Cell Culture

Ba/F3, UT-7-TPO and HEK293T cells were cultured in RPMI, IMDM and DMEM media (Sigma) respectively, supplemented with 10% fetal bovine serum (Sigma) and 1% Penicillin Streptomycin (Sigma). Ba/F3 cells were maintained with 2% WEHI-3B conditioned media as murine IL-3 supplement. UT-7-TPO cells were maintained with 2% TPO conditioned media as human thrombopoietin supplement. Ba/F3-MPL cell lines were generated as previously described (Nivarthi H et al., Leukemia, 2016, 30(8):1759-63).

Transduction

Human CALR wild-type (WT) and CALR del52 sequences were cloned into the pMSCV-IRES-puromycin retroviral vector. The plasmids were then used to transfect the Platinum-E (Plat-E) Retroviral Packaging Cell Line (CELL BIOLABS, INC) using the Calcium Phosphate Transfection Kit (Thermo Fisher Scientific) for retroviral production. Viral supernatant was then collected, and spin-infection of Ba/F3-MPL cells at 12.000 g, 37° C., for 45 min, was performed for viral transduction. The transduced cell lines were selected with 1 ug/ml puromycin until they were stably proliferating.

Compounds

All tested compounds were dissolved in DMSO.

Hematoxylin (CAS 517-28-2; A-1), Hematein (CAS 475-25-2; A-3) and Hydroxyurea (CAS 127-07-1) were purchased from Sigma. Brazilin (CAS 474-07-7; A-2), NSC7241 (A-5) was provided by the NCI Developmental Therapeutic Program's Open Compound Repository. Protosappanin B (CAS 102036-29-3; A-4) was purchased from Cambridge Chemicals. Ruxolitinib (CAS 1092939-17-7) was purchased from Selleckchem. L-HEM1 (B-1) and L-HEM3 (A-5) were synthesized by Lesyk group from Danylo Halytsky Lviv National Medical University (Ukraine). RJ002 (B-2) was synthesized by Enamine (Ukraine).

The synthesis of further compounds is described further above and in Example 4 below.

Generation of a Hematoxylin-Resistant Cell Line

Ba/F3-MPL CALR del79/WT and CALR del37/del37 cell lines were cultured with 20 uM of hematoxylin with or without 5% TPO continuously for 4 weeks. The cells were passaged every 3 days and seeded at 0.5 million per well in 6-well plates with addition of fresh hematoxylin and cytokine.

Site-Directed Mutagenesis

Mutagenesis of pMSCV-CALR del52 constructs was performed using the Q5@ Site-Directed Mutagenesis Kit (New England Biolabs) according to manufacturer's instructions. The successful clones were selected according to Sanger sequencing results.

Cell Viability Assay

Ba/F3 and UT-7-TPO were plated 5.000 cells/well and 16.000 cells/well into 96-well plates with the desirable concentrations of compounds or cytokines added to a total volume of 100 ul. 72 hours later, the CellTiter-Glo luminescent Cell Viability Assay (Promega) was used to determine the cell viability. The luminescent signal was detected by a VICTOR Multilabel Plate Reader (PerkinElmer). Dose response data was analyzed by Graphpad Prism 7.0.

To determine long-term viability, a two-color competition assay was used. Cell lines were transduced with pMSCV-IRES-GFP/mCherry construct, and the fluorescence-positive cells were sorted by a SH800Z Cell Sorter (Sony). GFP/mCherry-positive cell lines were mixed with their non-fluorescent control cells in a 1:1 ratio and underwent compound treatment for 3-12 days. Compounds and cytokines were refreshed every 3 days. Cell samples were analyzed at each time point by a BD LSRFortessa™ cell analyzer (BD Biosciences).

Alternatively, the QIAamp DNA Mini Kit (Qiagen) was used to extract DNA samples from the mixed population, and a polymerase chain reaction was performed with the following primer pairs to amplify the human CALR mutant sequence:

5'-[FAM]GGCAAGGCCCTGAGGTGT-3' SEQ ID NO: 9

3'-GGCCTCAGTCCAGCCCTG-5' SEQ ID NO: 10

The PCR products were diluted 1:50 and analyzed by Fragment Length Analysis (Microsynth), and the mutant CALR allelic burden was calculated as follows:

Mutant CALR allelic burden=Mutant peak height/
(Mutant peak height+WT peak height).

Western Blotting 2 million Ba/F3-MPL CALR WT or mutant cells were treated with hematoxylin or the equivalent volume of DMSO in a total volume of 15 ml of RPMI media in T75 flasks (Thermal Fisher Scientific). Cells were collected and washed with PBS before being lysed in whole cell lysis buffer containing 20 mM HEPES, 20% glycerol, 50 mM KCl, 400 mM NaCl, 1 mM EDTA, 1 mM DTT, 5 mM Na orthovanadate, 0.5% NP40, 0.1% Tween 20, supplemented with cOmplete™, Mini, EDTA-free Protease Inhibitor Cocktail (Sigma) and PhosSTOP™ (Sigma). Samples were rotated at 4° C. for 20 min prior to centrifugation at 140.000 rpm for 20 min. The soluble fraction of the sample was collected. Protein concentration was quantified by the Bio-Rad Protein Assay (Bio-Rad) according to the manufacturer's instructions and measured by a SpectraMax Microplate Reader (Molecular Devices). Equal amounts of protein were loaded for 8% or 10% SDS-polyacrylamide gel electrophoresis prior to transfer to Amersham™ Protran® nitrocellulose membranes at 35V, 4° C. overnight. Membranes were then blocked by 5% bovine serum albumin fraction V (Sigma) or milk. Mutant calreticulin was detected by a polyclonal rabbit antibody against the mutant specific C-terminal peptide (Myelopro). The other primary antibodies used were as follows: Calregulin Antibody (F-4)(sc-373863 Santa Cruz), Anti-HSC70(B-6) (J2212, Santa Cruz), Anti-Stat5 (N20)(L1112, Santa Cruz), anti-pYSTAT5 (Tyr694) (71-6900, Life Technologies), anti-TPOR/cMpl (#6944, Millipore), Cleaved PARP (Asp214) (#9548, Cell Signaling). HRP-linked anti-mouse and anti-rabbit antibodies (NA931/4, GE Healthcare Life Sciences) were used as secondary antibodies. Clarity™ Western ECL Blotting Substrates (Biorad) were used for the chemiluminescence detection method.

Real-Time PCR 1 million cells from each sample were collected and washed with PBS twice. RNA samples were extracted by using the RNeasy Mini Kit (Qiagen). Taqman® Gene Expression Assays (Mm01545399_m1) was used to quantify the expression of CALR, and the real-time PCR reaction was performed using a 7500 Fast Real-Time PCR machine (Applied Biosystems™). Statistical test was calculated by Graphpad Prism 7.0 using the two-tailed Student's t test.

Analytical Methods and Devices

Melting points were measured in open capillary tubes on a BÜCHI B-545 melting point apparatus and are uncorrected.

The elemental analyses (C, H, N) were performed using the Perkin-Elmer 2400 CHN analyzer and were within ±0.4% of the theoretical values.

The $^1$H-NMR spectra were recorded on Varian Gemini 300 MHz in DMSO-$d_6$ or DMSO-$d_6$+CCl$_4$ mixture using tetramethylsilane (TMS) as an internal standard. Chemical shifts are reported in ppm units with use of δ scale.

LC-MS and EI-MS were obtained on Agilent 1100 and Varian 1200L instruments correspondingly.

Apoptosis Assay by Annexin V/PI Staining

Ba/F3-MPL CALR wild-type and mutant cell lines were treated with hematoxylin at 20 uM or the equivalent volume of DMSO for 24 h before collection. Annexin V Apoptosis Detection Kit (eBioscience, #88-8007-74) was used based on the manufacturer's instructions. 5 ul of Propidium Iodide Staining Solution (Invitrogen, #00-6990-50) was added to each sample for 10 min before being analyzed with the BD LSRFortessa™ cell analyzer without washing.

CD34-Positive Cell Isolation and Expansion

Whole blood or buffy coat was collected in EDTA tubes. Peripheral blood mononuclear cells (PBMCs) were isolated by SepMate™-50 (STEMCELL Technologies, #15460) according to manufacturer's instructions.

CD34-positive cells from healthy controls and CALR mutant patients were isolated by EasySep™ Human CD34 Positive Selection Kit (#18056; STEMCELL Technologies) according to the manufacturer's instructions. StemSpan™ SFEM II (#09655 or #17856; STEMCELL Technologies) supplemented with 1x StemSpan™ CD34+ Expansion Supplement (#02691; STEMCELL Technologies) was used to culture and expand the isolated CD34-positive cells, preferably for no more than 8 days before experiments or storage.

Colony Formation Assay 1000 human CD34-positive cells were plated in 1 ml of Methocult classic medium (STEMCELL Technologies, #H4434) with 40 uM hematoxylin or DMSO control. Cells were incubated for 14 days before colony counting. Statistical test was calculated using two-way ANOVA with Sidak's multiple comparisons test.

Example 1: Molecular Docking Studies

Figure 1:
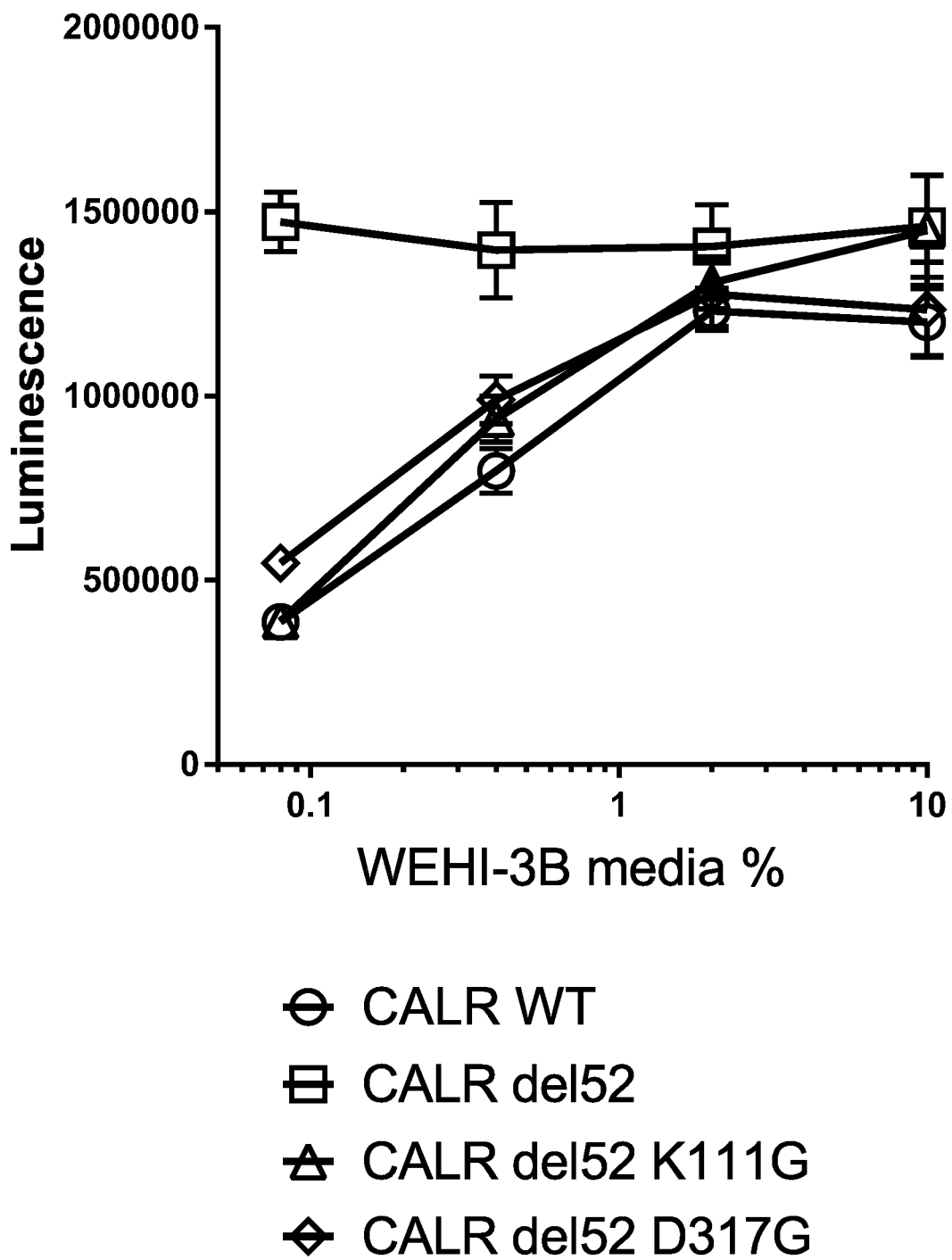
FIG. 1: IL-3 dose response of glycan domain mutated Ba/F3-MPL cells. Ba/F3-MPL cells were transduced with retroviral constructs carrying CALR WT, del52 as well as Lys-111 and Asp-317 mutated CALR del52. WEHI-3B conditioned media was used as murine IL-3 supplement. CellTiter-Glo luminescent Cell Viability Assay was used to detect cell viability after 72 h of cytokine treatment.
Figure 2:
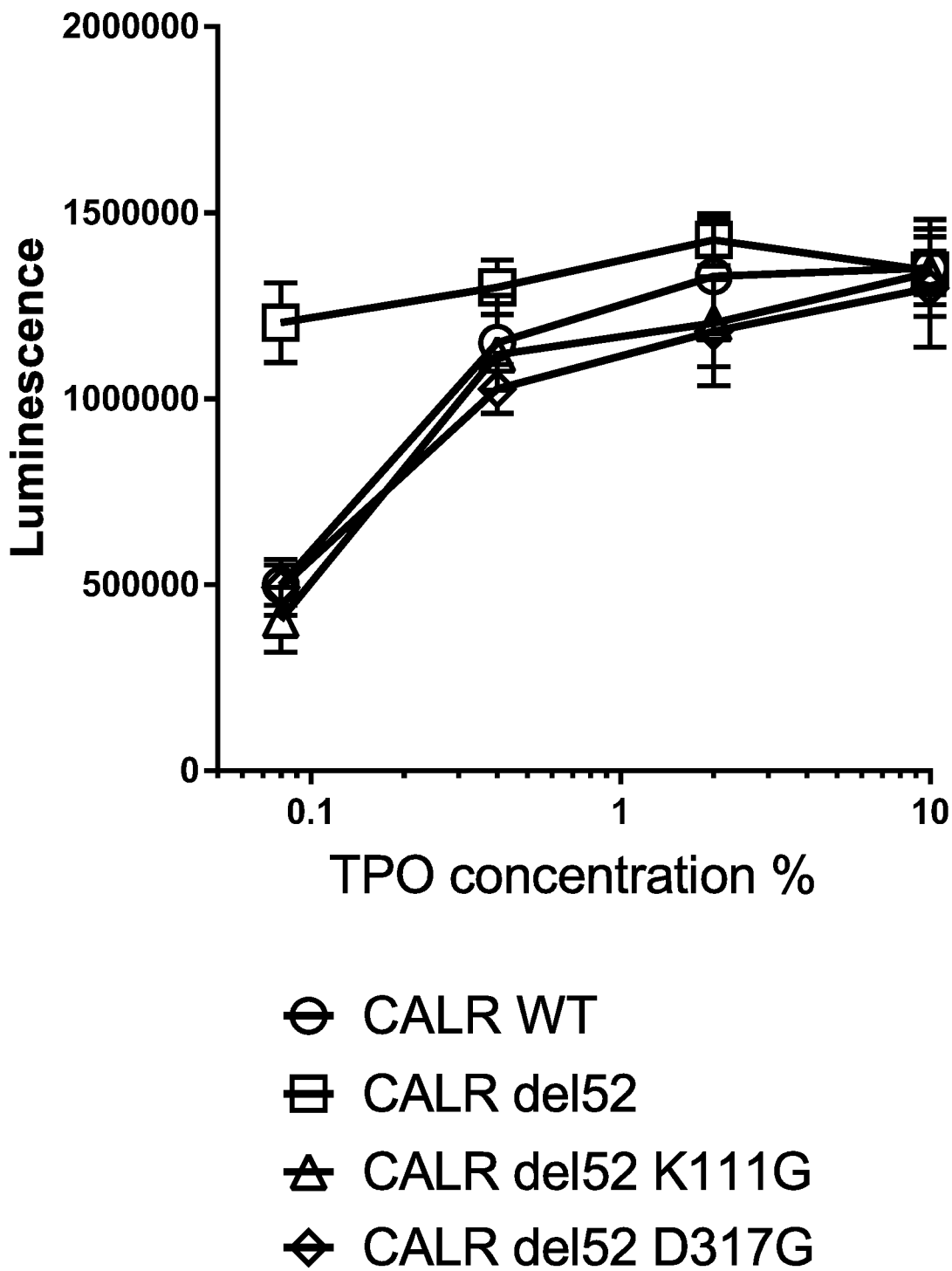
FIG. 2: TPO dose response of glycan domain mutated Ba/F3-MPL cells. Ba/F3-MPL cells were transduced with retroviral constructs carrying CALR WT, del52 as well as Lys-111 and Asp-317 mutated CALR del52. TPO conditioned media produced by murine 3T3 fibroblasts overexpressing human TPO was used as human TPO supplement. CellTiter-Glo luminescent Cell Viability Assay was used to detect cell viability after 72 h of cytokine treatment.

To validate the therapeutic potential of targeting the N-glycan binding domain of calreticulin, the human CALR del52 sequence was mutated at residue Lysine-111 and Aspartate acid-317, respectively. These are two amino acid residues which have been shown to be essential for the N-glycan binding capacity of calreticulin (Kapoor M et al., Biochemistry, 2004, 43(1):97-106; Kozlov G et al., J Biol Chem., 2010, 285(49):38612-20; Thomson S P et al., Cell Stress Chaperones, 2005 Autumn, 10(3):242-51; Gopalakrishnapai J et al., Biochem Biophys Res Commun., 2006, 351(1):14-20). Ba/F3-MPL cells were transduced with retroviral vectors containing CALR WT and CALR del52 as well as the glycan domain mutant CALR del52 sequences, respectively. Both the K111G and the D317G mutation abrogated the capacity of CALR del52 to transform Ba/F3-MPL cells in response to cytokines, including IL-3 and TPO, which confirmed the importance of the N-glycan binding domain of mutant calreticulin for its oncogenic function, consistent with what has been published (Chachoua I et al., Blood, 2016, 127(10):1325-35) (see FIGS. 1 and 2).

Figure 3:
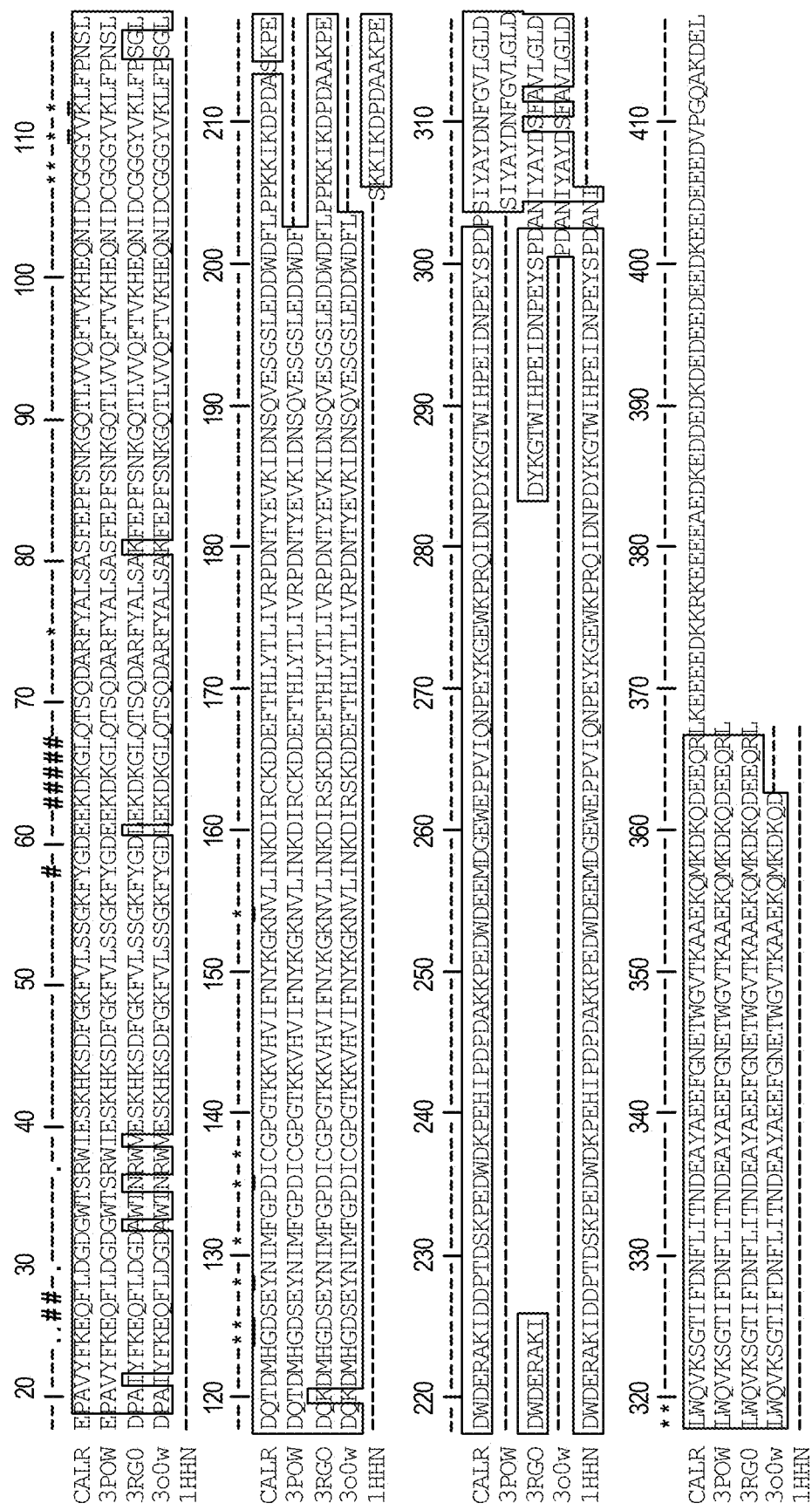
FIG. 3: Structure-guided sequence alignment between the human calreticulin sequence and templates used for homology modeling. ".”=nucleotide binding site; "#”=CA2+ binding site; "*”=GLYC binding site; underlined residues have been experimentally demonstrated to affect glycan binding. PDB IDs of human calreticulin: 3POW (Chouquet A et al., PLoS One, 2011, 6(3):e17886); Mouse calreticulin: 3RG0 (Pocanschi C L et al., J Biol Chem., 2011, 286(31):27266-

Based on the crystal structure of the globular domain of wild-type calreticulin, which has been published (Chouquet A et al., PLoS One, 2011, 6(3):e17886; Kozlov G et al., J Biol Chem., 2010, 285(49):38612-20; Ellgaard L et al., Proc Natl Acad Sci USA, 2001, 98(6):3133-8; Pocanschi C L et al., J Biol Chem., 2011, 286(31):27266-77; Wijeyesakere S J et al., Proc Natl Acad Sci USA, 2015, 112(41):E5608-17; see, in particular, the 3-D structures of PDB IDs 3POW, 3RG0 and 3O0W), a 3-D structural model of human calreticulin was generated, and 3-D molecular docking study was performed to identify potential chemical candidates targeting glycan, $Ca^{2+}$ and ATP binding sites of the protein (FIGS. 3 and 4). Since the pathological mutations of calreticulin in MPN only change the sequence at the C-terminus of the protein, it can be expected that the globular domain of the mutant protein is conserved and that structural information based on the wild-type protein can be used in the study. To get an insight on the specificity and selectivity of each ligand interacting with calreticulin, two other proteins were selected as negative controls, including calnexin, which is structurally and functionally similar to calreticulin (Schrag J D et al., Mol Cell, 2001, 8(3):633-44), and ER Mannosidase I, an enzyme involved in ER-associated degradation of glycoproteins in mammalian cells, but which is structurally different from calreticulin (Vallee F et al., J Biol Chem., 2000, 275(52):41287-98).

Among 140.000 structures, a list of compounds with the highest binding energy and specificity towards calreticulin was generated. Relying on compounds that were either commercially available or available from the DTP Databases of the National Cancer Institute (NCI), a docking compound library including 41 compounds was assembled, and the compounds were used in a cytotoxicity screen at 10 uM concentration in Ba/F3 and UT-7-TPO mutant CALR cell lines (FIGS. 5 and 6). The goal was to exclude compounds that showed no cytotoxic activity at a relatively high concentration in the cell line models. The compounds which showed a cytotoxic effect in both cell lines (inhibitory effect>10%) and had more than 50% inhibitory effect in at least one of the cell lines were taken as hits for a multiple-dose response test in CALR wild-type and mutant cell lines. Two hits were identified as preferentially inhibiting mutant CALR cell line growth. Strikingly, the IC50 of compound 19, known as hematoxylin (A-1), showed a 3-5-fold reduction in mutant CALR Ba/F3 cell lines compared with the wild-type cell line in the 72 h dose response test (FIG. 7). In UT-7-TPO cell lines, the hypersensitivity of mutant cell lines to the compound could be reproduced (FIG. 8). Therefore, hematoxylin and derivatives thereof were used for further testing.

Example 2: Testing Hematoxylin and its Derivatives for Selective Reduction of the Viability of CALR Mutant Cells Vs. Wild-Type Cells In order to further confirm the selective cytotoxicity of hematoxylin in CALR mutant cells, two-color competition assays were performed in both Ba/F3 and UT-7-TPO cells to assess the long-term efficacy of the compound (FIG. 9). In Ba/F3 cells, the CALR mutant cells were almost completely depleted after 12 days of co-cultivation with CALR WT cells compared to the DMSO control group in which mutant cells outgrew the wild-type cells and dominated the cell population at the end time point (FIG. 10). The differential killing effect of hematoxylin could also be reproduced in the UT-7-TPO cell line. While the depletion effect was not achieved, hematoxylin inhibited the outgrowth of the mutant cells from the cell population (FIG. 11). This result is consistent with what was shown in the short-term dose response assay (Example 1). As the CALR mutant cells in this assay were cultured in the presence of TPO, this also suggests that their compound hypersensitivity cannot be rescued by cytokines. To clarify if the efficacy was specifically caused by the mutant calreticulin, Ba/F3-MPL cell lines that carry alternative frameshift mutations in exon 9 of the CALR gene differing from the disease frameshift were generated, as described, e.g., in Nivarthi H et al., Leukemia, 2016, 30:1759-1763. This reading frame encounters a stop codon shortly after the mutation and causes a truncation at the CALR C-terminus (FIG. 12). In the cytotoxicity assay, the cell lines carrying the truncated mutations did not show hypersensitivity towards compound treatment, suggesting that the efficacy of hematoxylin is specific to the mutant protein (FIG. 13). Moreover, CALR KO Ba/F3-MPL cell lines were tested for hematoxylin sensitivity. The result indicates that the selectivity of the compound is not caused by the loss of wild-type calreticulin but the existence of mutant calreticulin, as the CALR KO cell lines did not show hypersensitivity towards the treatment (FIG. 14).

To further explore the chemical space of the compound, a few hematoxylin analogues were also tested (FIGS. 15 to 17). Brazilin (A-2), another wood extract used as dye like hematoxylin and which structurally differs from hematoxylin in only one hydroxyl group, showed comparable cytotoxic selectivity with a slightly reduced IC50 (1.9 uM) in mutant cell lines compared with 2.6 uM of hematoxylin. However, the cytotoxic effect on the wild-type cell line was also stronger than that of hematoxylin (IC506.2 uM vs 11.1 uM). Hematein (A-3), the oxidized hematoxylin, showed a reduced potency (IC50 in mutant cell line 7.5 uM) but retained the cytotoxic selectivity (FIG. 15). The addition of methyl groups at the hydroxyl groups of hematoxylin seemed to compromise both potency and selectivity, as the effects of NSC7251 (A-5), L-HEM1 (B-1) and L-HEM3 (A-5) showed (FIGS. 15 and 16). The compounds Protosappanin B (A-4) and RJ002 (B-2) were also tested. For all of these compounds, however, the effects on mutant and wild-type cells, respectively, were still distinguishable. As a comparison, the clinically used chemotherapeutic drugs hydroxyurea and ruxolitinib were also tested in the cell models. Hydroxyurea did not show any selective killing effect. JAK1/2 inhibitor ruxolitinib showed a mild selective effect with an about 2-fold IC50 reduction in the mutant cell lines compared to wild-type cells (195 nM vs 400 nM) (FIG. 17).

Example 3: Analyzing the Selective Cytotoxicity of Hematoxylin Towards CALR Mutant Cells To confirm that the cytotoxic selectivity of hematoxylin in CALR mutant cell lines is due to a specific effect on mutant calreticulin, Ba/F3-MPL CALR WT and mutant cell lines were treated with the compound for 24 hours. Because of a shorter length of treatment and higher cell density required in this experiment, a higher concentration of the compound (20 uM) was used. Western blot analysis showed a striking down-regulation of both mutant calreticulin and MPL in both heterozygous and homozygous mutant cell lines, whereas the wild-type calreticulin was not affected in the CALR WT cell line. There was an up-regulation of wild-type calreticulin in the CALR heterozygous mutant cell line, which was likely due to an apoptotic effect caused by the compound (FIG. 18). The down-regulation of mutant calreticulin happens at the protein level but not at the mRNA level, as the real-time PCR result suggests a slight up-regulation of both wild-type and mutant CALR expression caused by the compound (FIG. 19). Although the effect on mRNA is statistically significant, the magnitude of change is only around 1.3-fold. It was further investigated how long it took for mutant calreticulin to be reduced by hematoxylin. A time-course experiment showed a start of decrease of mutant calreticulin and MPL after 4 hours of treatment and a more drastic reduction at the 8-hour time point, which was accompanied by a decrease of STAT5 phosphorylation and upregulation of PARP cleavage which was used as an apoptotic marker (FIG. 20). Furthermore, an apoptosis assay using Annexin V/propidium iodide (PI) staining was performed, which revealed significant elevation of apoptotic cell numbers induced by hematoxylin in the CALR mutated cell line, but not in the wild-type control. The addition of TPO did not have a significant impact on apoptosis (FIG. 24). The results suggest that hematoxylin induces cell death of mutant CALR cell lines by inhibiting a mutant calreticulin-MPL complex at the protein level as well as its downstream JAK-STAT pathway. A binding assay showed that hematoxylin bound both to mutant and wild-type CALR proteins (data not shown), which was not surprising, since the target region is a common domain. Moreover, hematoxylin-resistant cell lines were generated from CALR heterozygous and homozygous Ba/F3-MPL cells, and dose response tests and western blot analysis were performed. Increased viability was observed in response to the treatment for all resistant cell lines after they were selected under 20 uM of hematoxylin for 4 weeks without cytokine, except for CALR del79/WT resistant clone 2 which was selected in the presence of TPO. As expected, this clone showed a cytokine rescue effect in the dose response test (FIG. 21). Western blot analysis of the resistant cell lines showed an up-upregulation of mutant calreticulin and resistance towards the compound-induced down-regulation of the protein, which further confirmed mutant calreticulin as the drug target (FIG. 22).

Example 4: Synthesis of Further Hematoxylin Derivatives

Example 4.1: Synthesis of Compound B-17

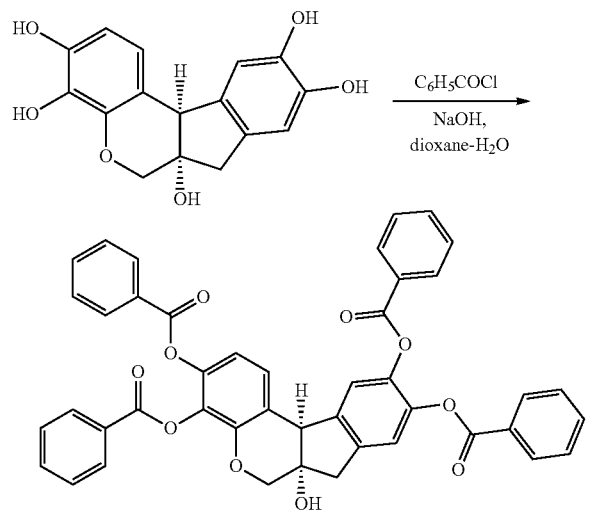

B-17

To a solution of 0.33 mmol of hematoxylin and 1.7 mmol of NaOH in 2 ml of water was added the solution of 1.7 mmol of benzoyl chloride in 8 ml of dioxane. The obtained mixture was stirred at 50-70° C. for 1-2 h. The progress of the reaction was monitored by TLC. After 12 h, the mixture was diluted with 100 ml of water. The precipitate was separated by filtration and recrystallized with ethanol. Yield: 78%; mp: 110-112° C.

Example 4.2: Synthesis of Compound B-18

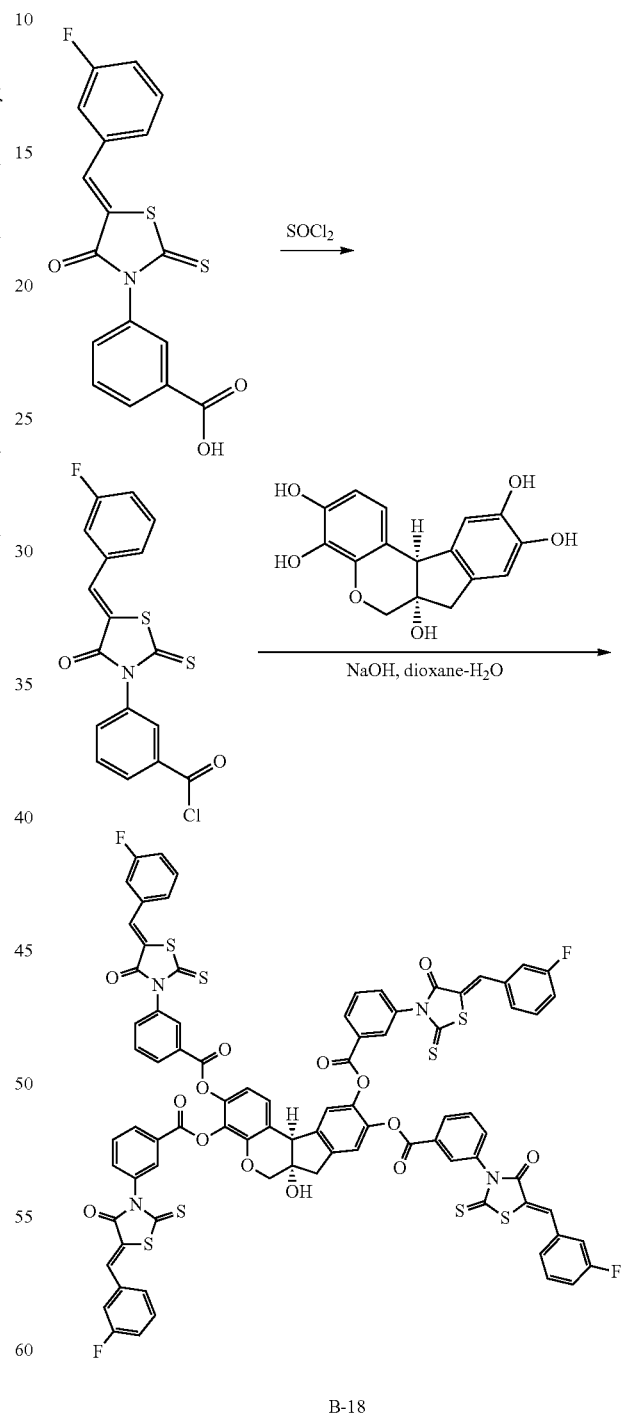

B-18

A mixture of 5 mmol of 5-(3-fluorophenyl)methylidene-3-(3-carboxyphenyl)-2-thioxo-4-thiazolidinone and 1.2 g of thionyl chloride in 3 ml of dioxane was heated under reflux for 0.5 h, cooled, and treated with 10 ml of hexane. The precipitate was separated by filtration and used without further purification.

To a solution of 0.33 mmol of hematoxylin and 1.7 mmol of NaOH in 2 ml of water was added the solution of 1.7 mmol of obtained acid chloride in 8 ml of dioxane. The obtained mixture was stirred at 50-70° C. for 1-2 h. The progress of the reaction was monitored by TLC. After 12 h, the mixture was diluted with 100 ml of water. The precipitate was separated by filtration and recrystallized with ethanol. Yield: 77%; mp: 220° C.

Example 4.3: Synthesis of Compound B-20

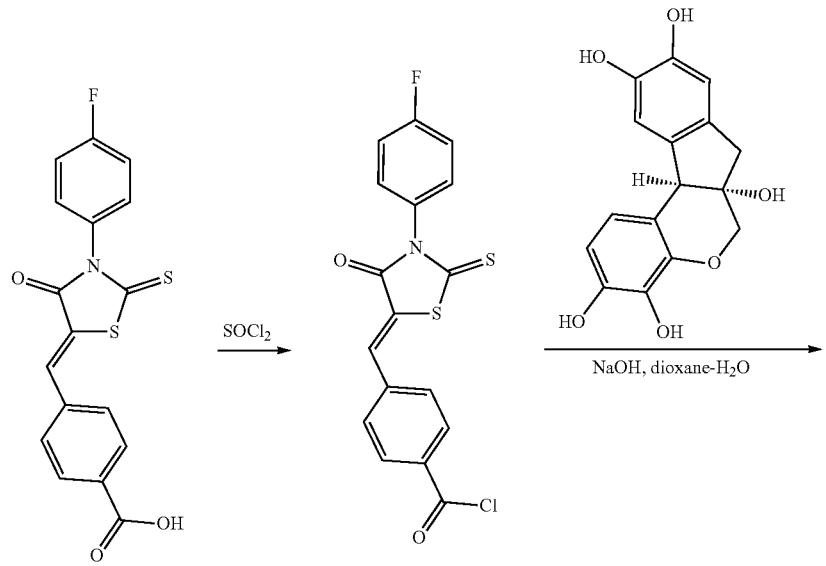

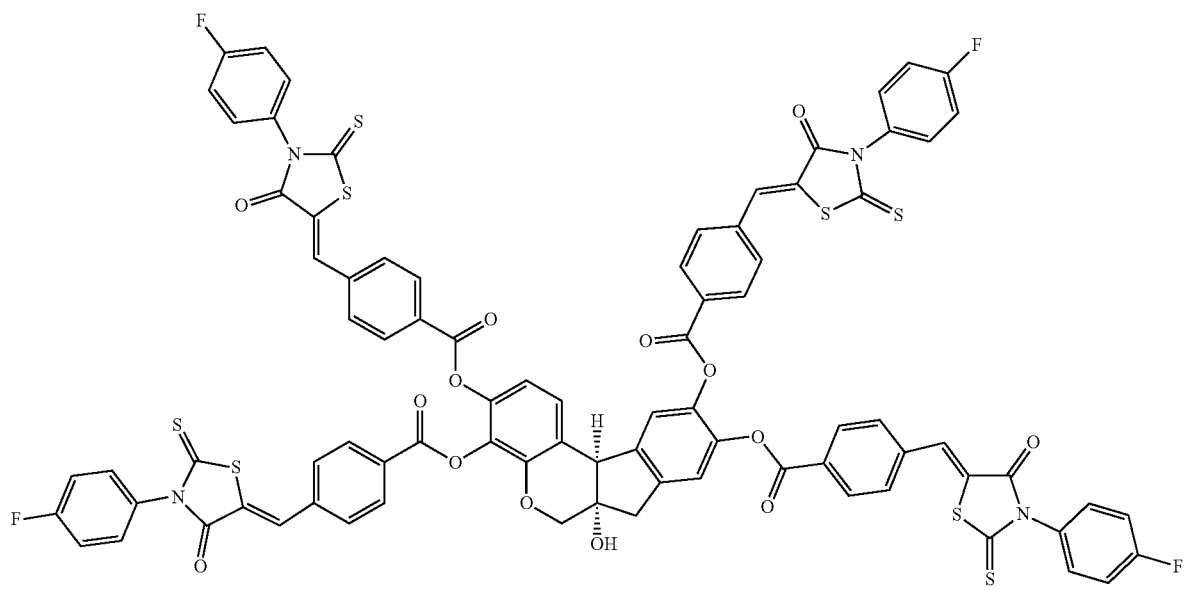

B-20

Compound B-20 was synthesized according to the method used for the synthesis of compound B-18. 5-(4-Carboxyphenyl)methylidene-3-(4-fluorophenyl)-2-thioxo-4-thiazolidinone was used as starting material instead of 5-(3-fluorophenyl)methylidene-3-(3-carboxyphenyl)-2-thioxo-4-thiazolidinone. Yield: 69%; mp: 240° C.
Example 4.4: Synthesis of Compound B-21
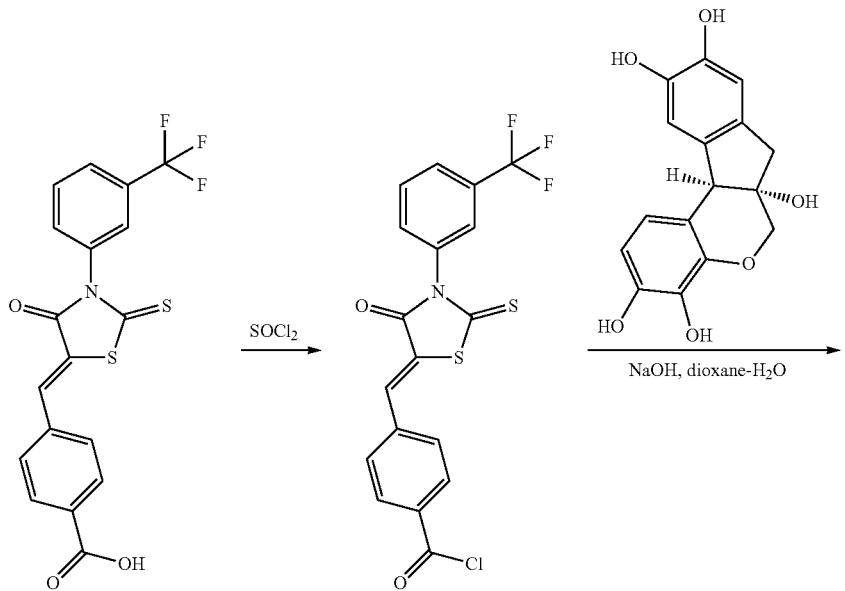
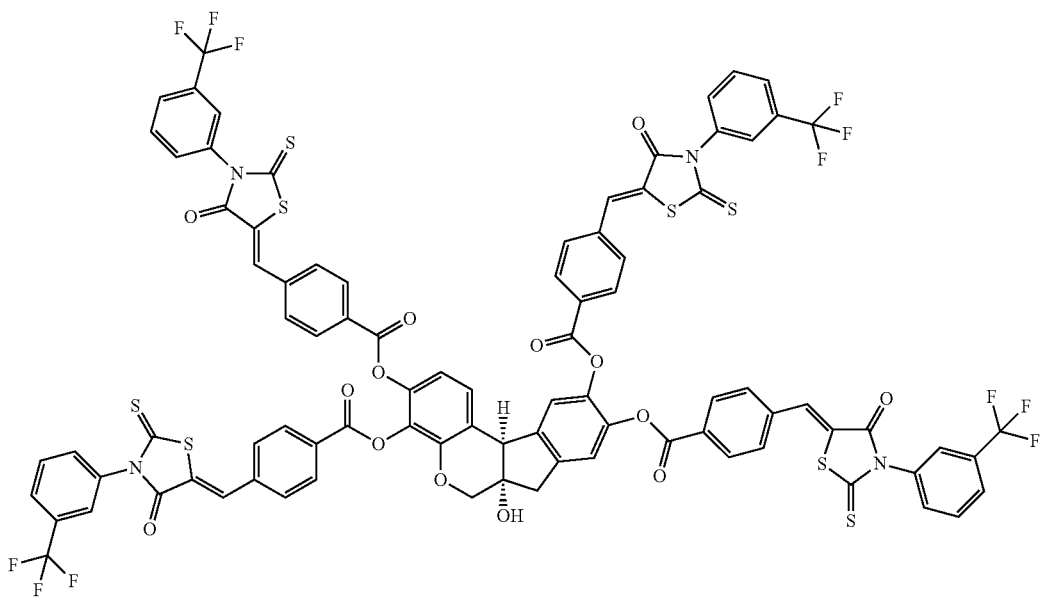
B-21

Compound B-21 was synthesized according to the method used for the synthesis of compound B-18. 5-(4-Carboxyphenyl)methylidene-3-(3-trifluoromethylphenyl)-2-thioxo-4-thiazolidinone was used as starting material instead of 5-(3-fluorophenyl)methylidene-3-(3-carboxyphenyl)-2-thioxo-4-thiazolidinone. Yield: 69%; mp: 245° C.
Example 4.5: Synthesis of Compound B-22
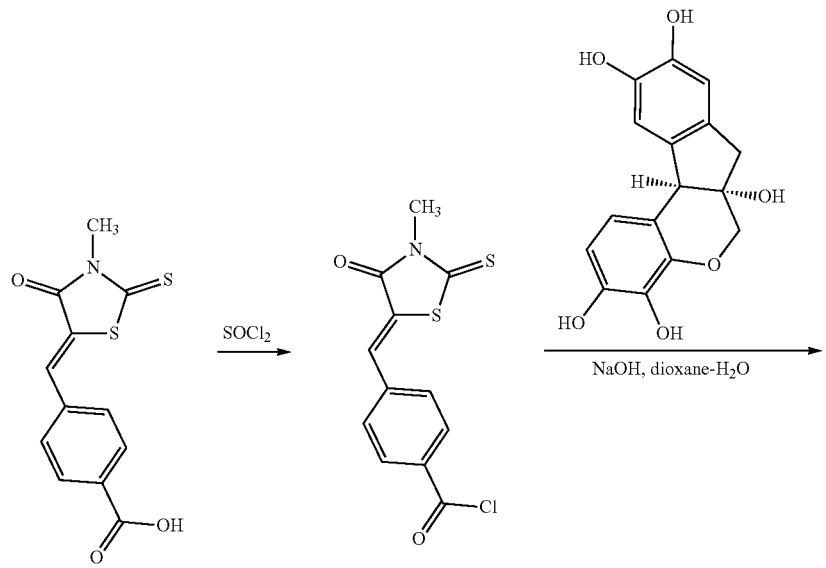
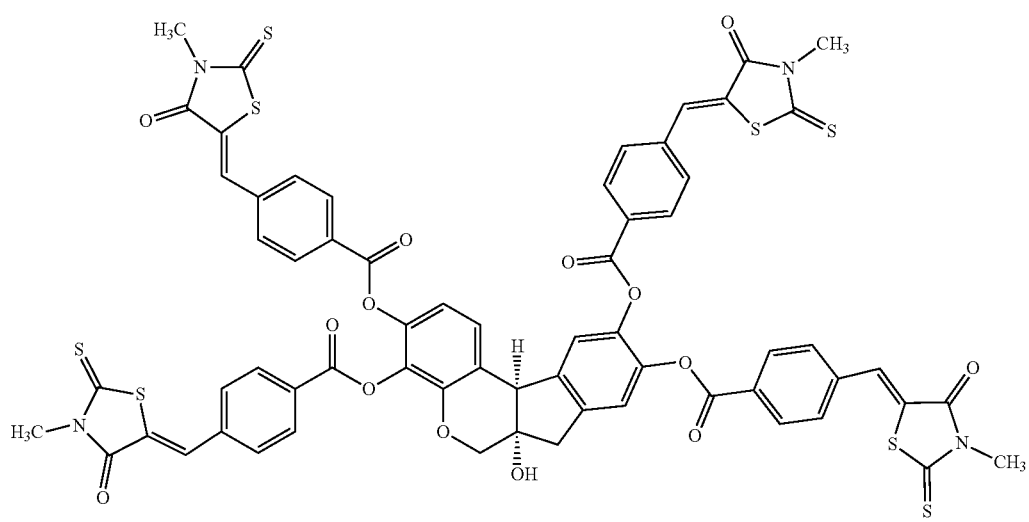
B-22

Compound B-22 was synthesized according to the method used for the synthesis of compound B-18. 5-(4-Carboxyphenyl)methylidene-3-methyl-2-thioxo-4-thiazolidinone was used as starting material instead of 5-(3-fluorophenyl)methylidene-3-(3-carboxyphenyl)-2-thioxo-4-thiazolidinone. Yield: 45%; mp: >260° C.

Example 4.6: Synthesis of Compound B-23

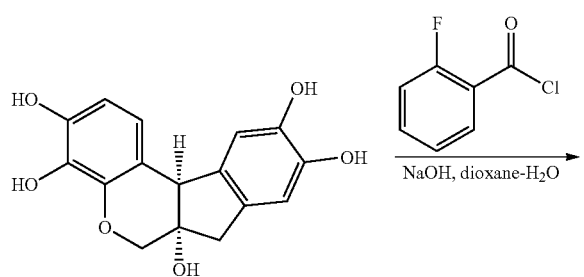

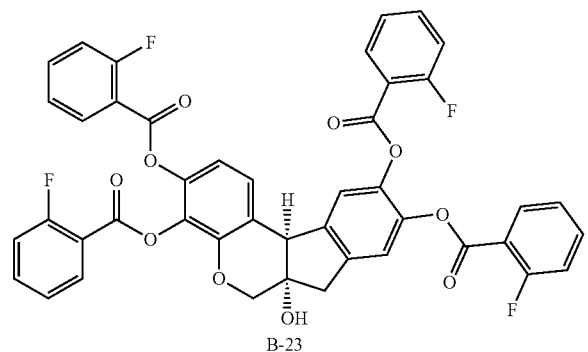

Compound B-23 was synthesized according to the method used for the synthesis of compound B-17. 2-Fluorobenzoyl chloride was used as starting material instead of benzoyl chloride. Yield: 32%; mp: 120-122° C.

Example 4.7: Synthesis of Compound B-24

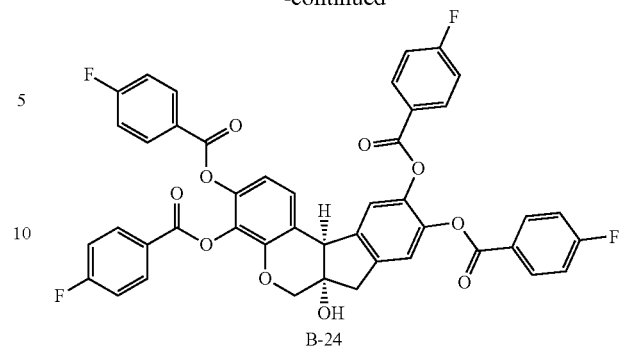

Compound B-24 was synthesized according to the method used for the synthesis of compound B-17. 4-Fluorobenzoyl chloride was used as starting material instead of benzoyl chloride. Yield: 96%, mp: 113-115° C.

Example 4.8: Synthesis of Compound B-25

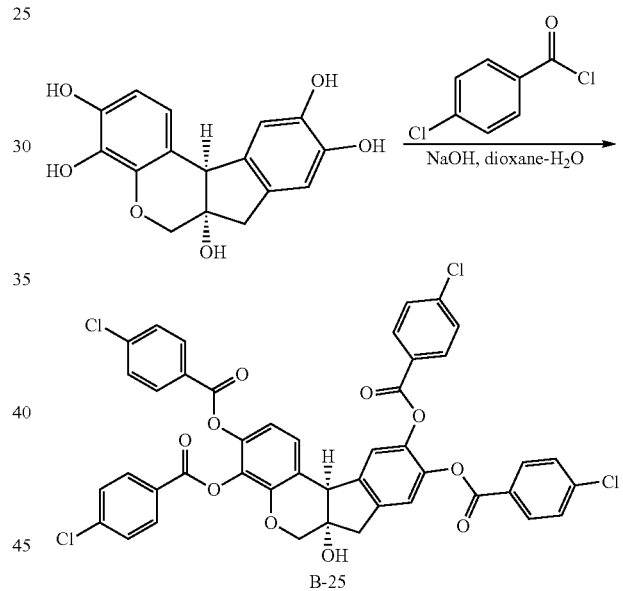

Compound B-25 was synthesized according to the method used for the synthesis of compound B-17. 4-Chlorobenzoyl chloride was used as starting material instead of benzoyl chloride. Yield: 70%; mp: 130-132° C.

Example 4.9: Synthesis of Compound B-26

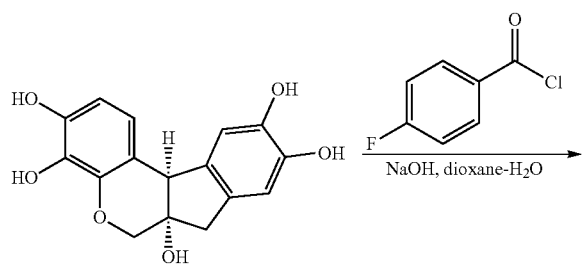

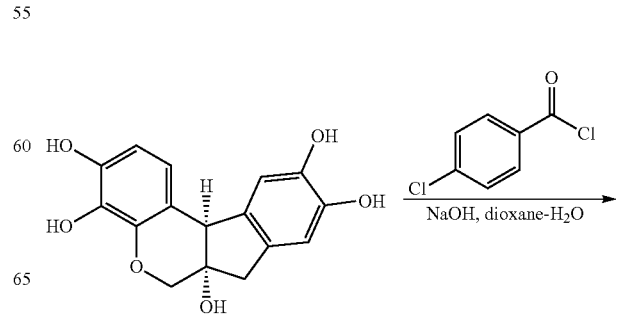

-continued

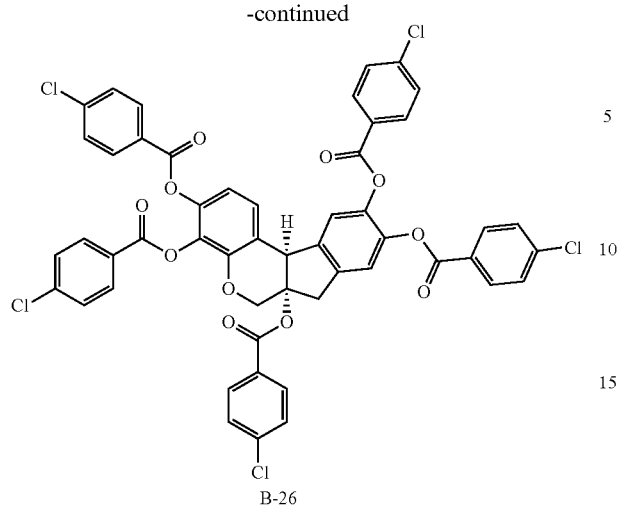

B-26

To a solution of 0.33 mmol of hematoxylin and 1.7 mmol of NaOH in 2 ml of water was added the solution of 1.7 mmol of 4-chlorobenzoyl chloride in 8 ml of dioxane. The obtained mixture was stirred at 50-70° C. for 1-2 h. The progress of the reaction was monitored by TLC. After 12 h the precipitate was separated by filtration and recrystallized with ethanol. Yield: 18%, mp: 187-189° C.

Example 4.10: Synthesis of Compound B-27

-continued

B-27

Compound B-27 was synthesized according to the method used for the synthesis of compound B-18. 5-(4-Fluorophenyl)methylidene-3-(3-carboxyphenyl)-2-thioxo-4-thiazolidinone was used as starting material instead of 5-(3-fluorophenyl)methylidene-3-(3-carboxyphenyl)-2-thioxo-4-thiazolidinone. Yield: 72%, mp: 220-222° C.

Example 4.11: Synthesis of Compound B-28

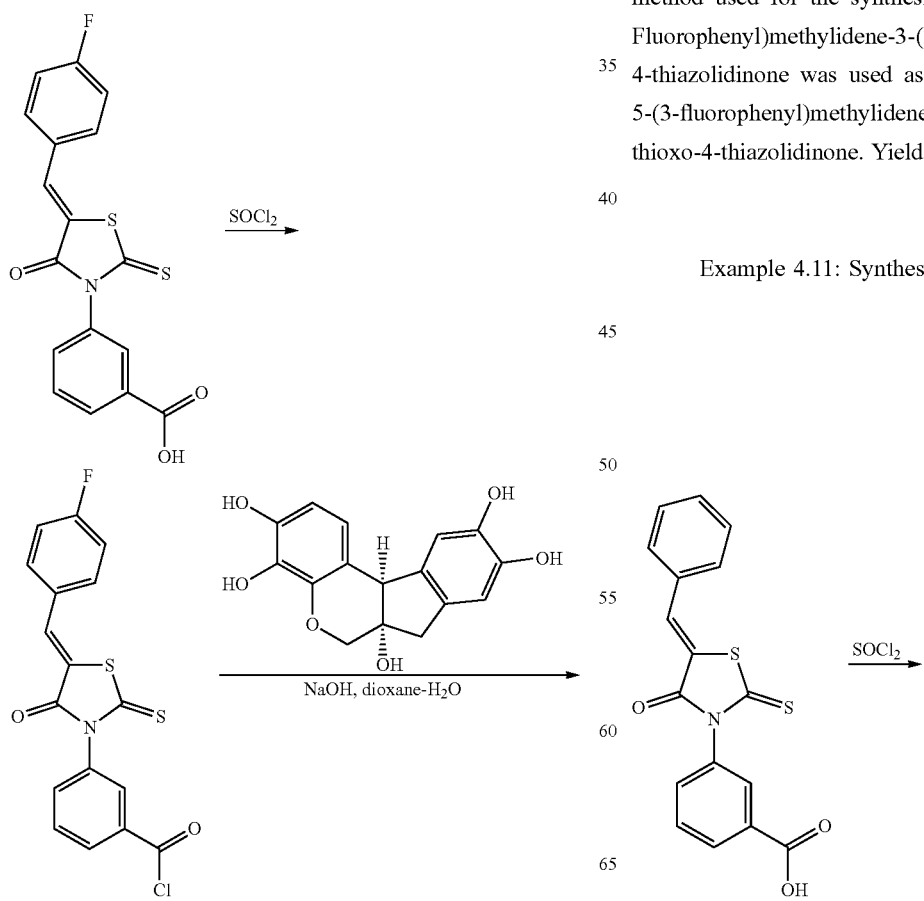

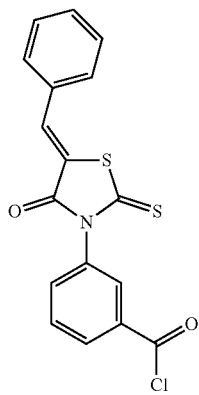
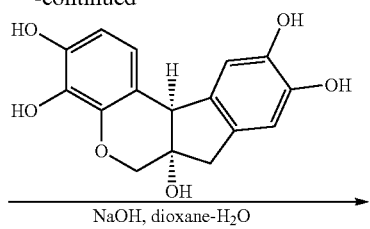
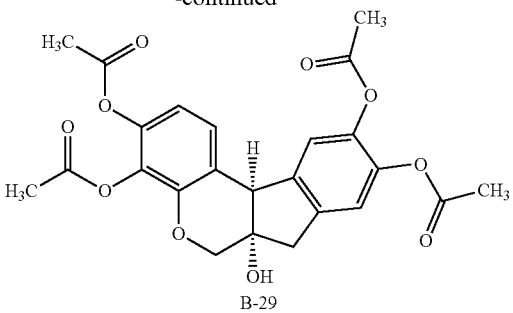

A solution of 0.33 mmol of hematoxylin, 3-4 ml of acetylchloride in 4 ml of toluene was heated under reflux was stirred at 50-70° C. for 30 min. The progress of the reaction was monitored by TLC. After evaporating of solvent the precipitate was recrystallized with a mixture of benzene and hexane or with hexane. Yield: 46%, mp: 101-106° C.

Example 4.13: Synthesis of Compound B-30

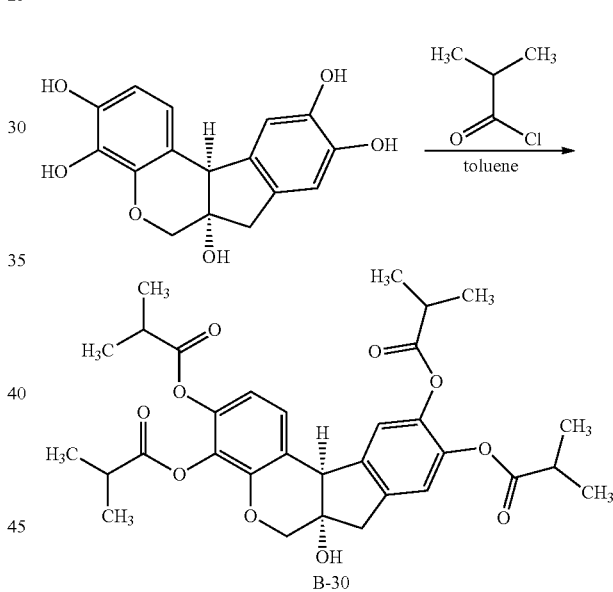

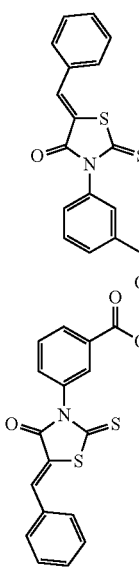

B-28

Compound B-28 was synthesized according to the method used for the synthesis of compound B-18. 5-Phenylmethylidene-3-(3-carboxyphenyl)-2-thioxo-4-thiazolidinone was used as starting material instead of 5-(3-fluorophenyl)methylidene-3-(3-carboxyphenyl)-2-thioxo-4-thiazolidinone. Yield: 79%, mp: 190-192° C.

Example 4.12: Synthesis of Compound B-29

Compound B-30 was synthesized according to the method used for the synthesis of compound B-29. 2-Methylpropionylchloride was used as starting material instead of acetylchloride. Yield: 45%. Yield: 32%, mp: 96-100° C.

Example 4.14: Synthesis of Compound B-31

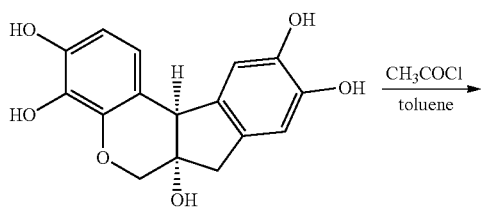

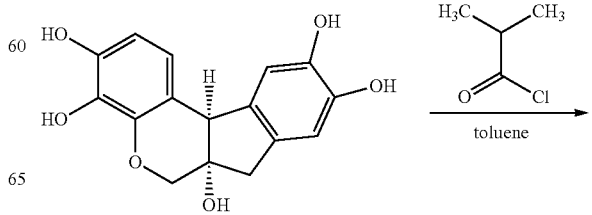

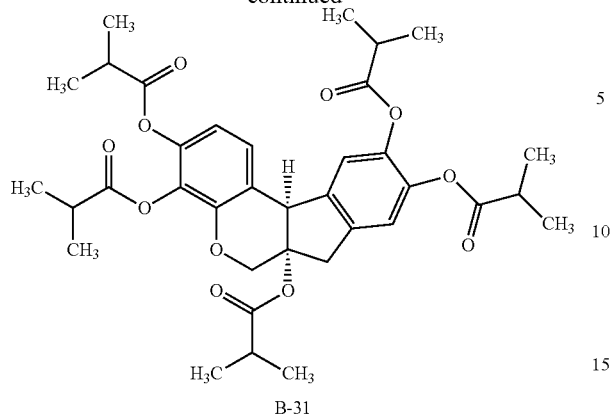

B-31

Compound B-31 was synthesized according to the method used for the synthesis of compound B-26. 2-Methylpropionylchloride was used as starting material instead of 4-chlorobenzoyl chloride. Yield: 10%, mp: 166-168° C.

Example 4.15: Synthesis of Compound B-32

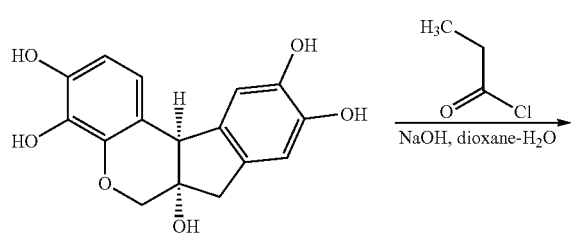

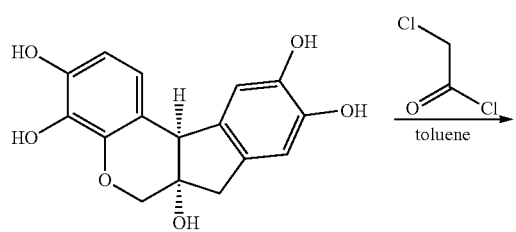

B-32

Compound B-32 was synthesized according to the method used for the synthesis of compound B-29. Propionylchloride was used as starting material instead of acetylchloride. Yield: 52%, mp: 88-93° C.

Example 4.16: Synthesis of Compound B-33

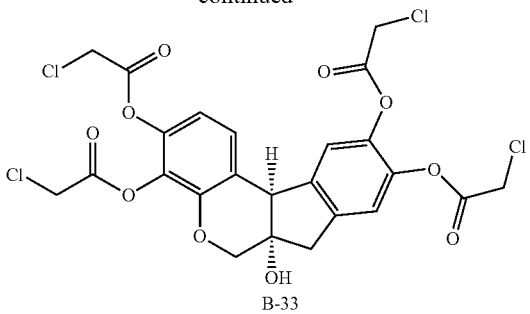

B-33

Compound B-33 was synthesized according to the method used for the synthesis of compound B-29. 2-chloroacetylchloride was used as starting material instead of acetylchloride. Yield: 28%, mp: 104-110° C.

Example 4.17: Synthesis of Compound B-34

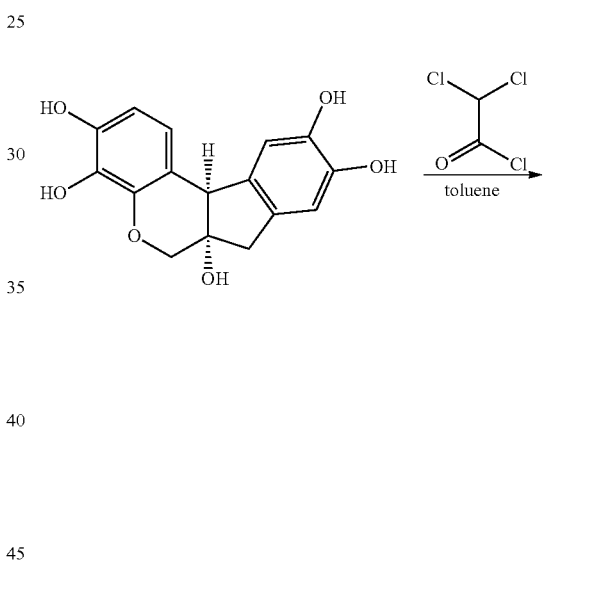

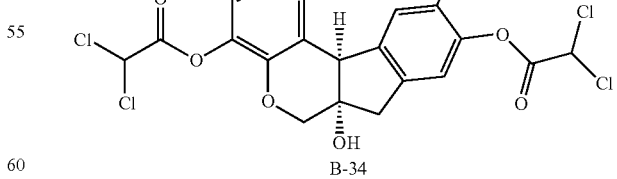

B-34

Compound B-34 was synthesized according to the method used for the synthesis of compound B-29. 2,2-Dichloroacetylchloride was used as starting material instead of acetylchloride. Yield: 45%, mp: 80° C.

Example 4.18: Synthesis of Compound B-35

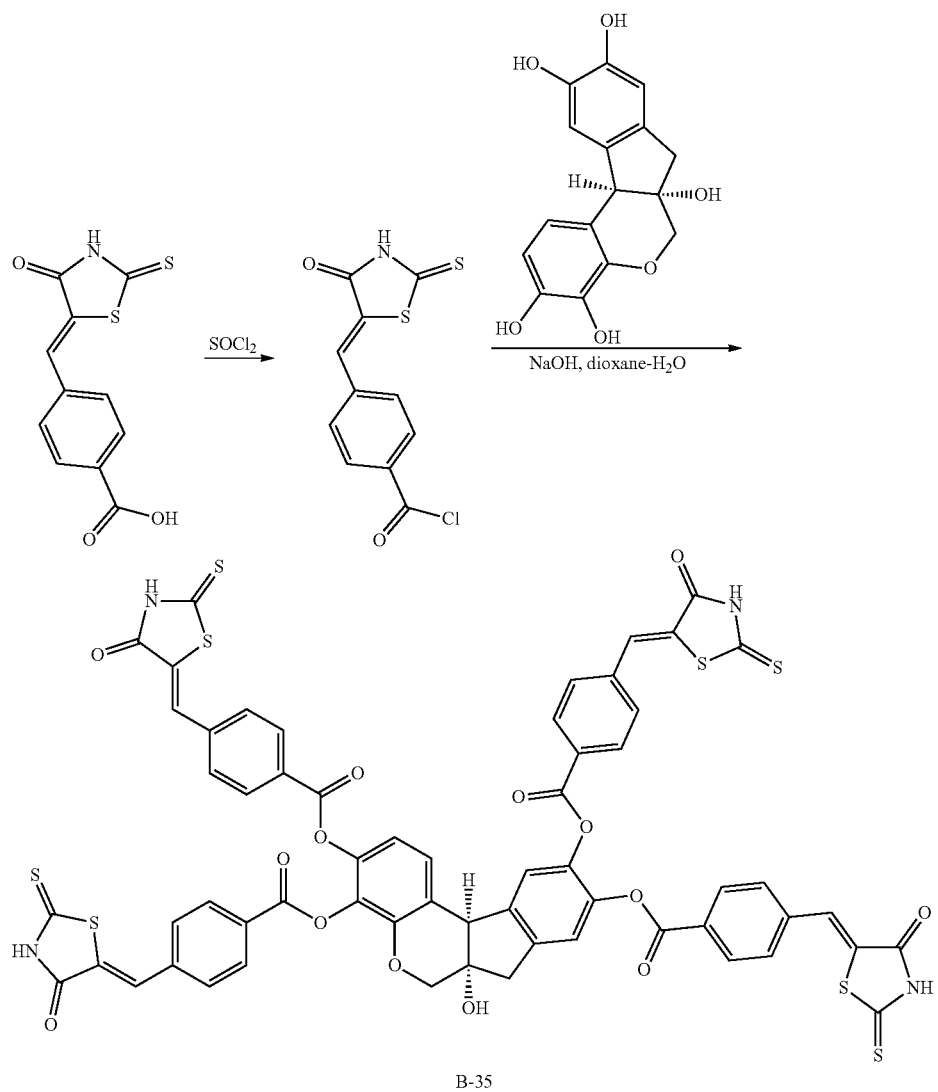

B-35

Compound B-35 was synthesized according to the method used for the synthesis of compound B-18. 5-(4-Carboxyphenyl)methylidene-2-thioxo-4-thiazolidinone was used as starting material instead of 5-(3-fluorophenyl)methylidene-3-(3-carboxyphenyl)-2-thioxo-4-thiazolidinone. Yield: 83%, mp: >250° C.

Example 4.19: Synthesis of Compound B-36

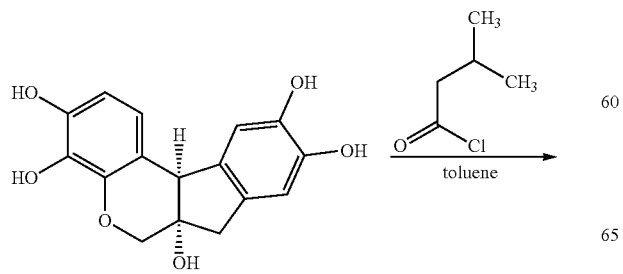

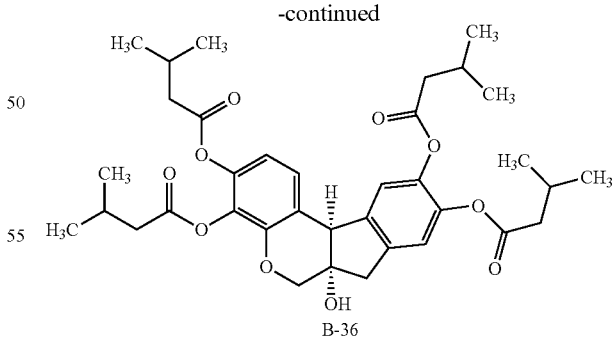

B-36

Compound B-36 was synthesized according to the method used for the synthesis of compound B-29. 3-Methylbutanoylchloride was used as starting material instead of acetylchloride. Yield: 99%, mp: 130-134° C.

Example 4.20: Synthesis of Compound B-37

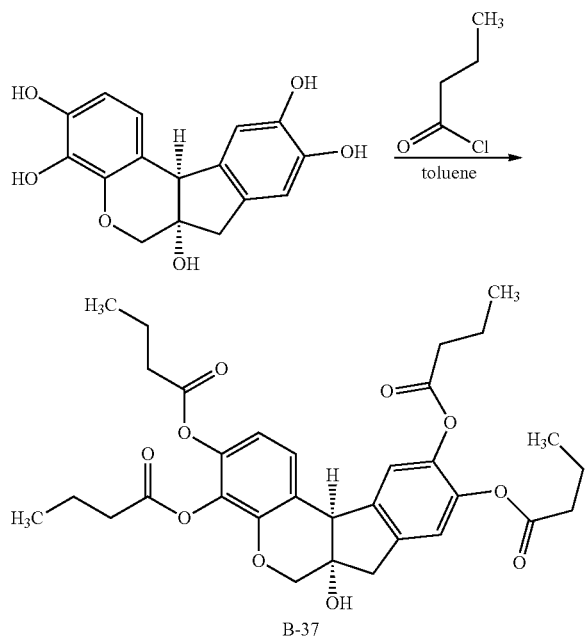

B-37

Compound B-37 was synthesized according to the method used for the synthesis of compound B-29. Butanoylchloride was used as starting material instead of acetylchloride. Yield: 91%, mp: 80° C.

Example 4.21: Synthesis of Compound B-38

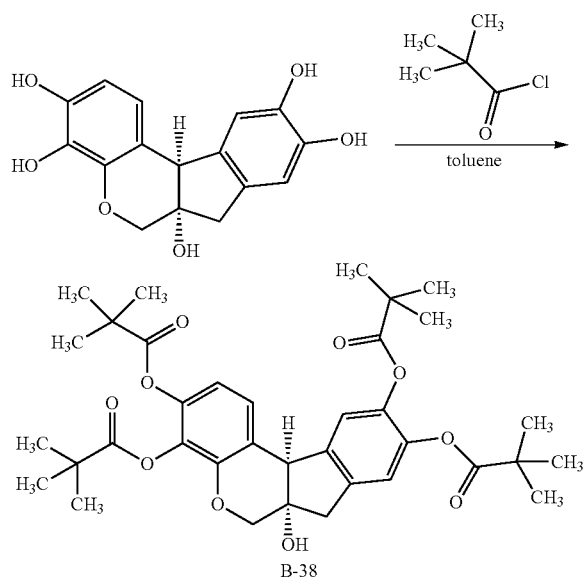

B-38

Compound B-38 was synthesized according to the method used for the synthesis of compound B-17. 2,2,-Dimetylpropanoylchloride was used as starting material instead of benzoyl chloride. Yield: 82%, mp: 80° C.

Example 5: Cytotoxicity Testing of Further Hematoxylin Derivatives

Cytotoxicity screens were performed essentially as described in Example 1.

A concentration of 10 uM was used in Ba/F3 cells, and a concentration of 30 uM was used in UT-7 cells, except for the compounds that were insoluble in a 10 mM stock solution. These included HEM8 (B-18), HEM11 (B-19), HEM30 (B-20), HEM36 (B-26), HEM44 (B-34) and HEM46 (B-36) which were used at $1/10$ of the concentration (1 uM for Ba/F3 and 3 uM for UT-7).

Best results in terms of selectivity and potency were obtained with compounds HEM30 (B-20) and HEM48 (B-38) in Ba/F3 cells as well as compounds HEM32 (B-22), HEM40 (B-30), HEM42 (B-32) and HEM47 (B-37) in UT-7 cells (see also Table 3).

TABLE 3

| Compound | IC50 WT cell line uM | IC50 mutant cell line uM |
|---|---|---|
| HEM32 (B-22) | 18.76 | 16.06 |
| HEM40 (B-30) | 14.45 | 12.04 |
| HEM42 (B-32) | 26.2 | 20.81 |
| HEM47 (B-37) | 14.71 | 12.4 |

Example 6: Analyzing the Mutant-Specific Effect of Hematoxylin in Cells Isolated from Human CALR Mutant Patients CD34-positive cells isolated from a healthy control and a CALR ins5 mutant patient were treated with hematoxylin at 200 M or DMSO control for 8 hours before cell lysis and protein collection. HSC70 was used as loading control.

As shown in FIG. 23, the reduction of mutant calreticulin by hematoxylin could also be detected in hematopoietic stem cells from the mutant CALR patient. Consistent to what was observed in the cell line models, the protein abundance of mutant calreticulin was drastically reduced following hematoxylin treatment for 8 hours.

Furthermore, CD34+ cells from healthy individuals and CALR patients were isolated, and a colony formation assay was performed. As shown in FIG. 25, treatment with hematoxylin significantly reduced the number of colony forming units derived from CALR mutated patients but not in the healthy controls. This confirmed that the preferential cytotoxicity of hematoxylin is also present in human primary CALR mutated hematopoietic progenitor cells.

The invention claimed is:
1. A pharmaceutical composition comprising a compound and one or more pharmaceutically acceptable excipients, wherein the compound is selected from the group consisting of:

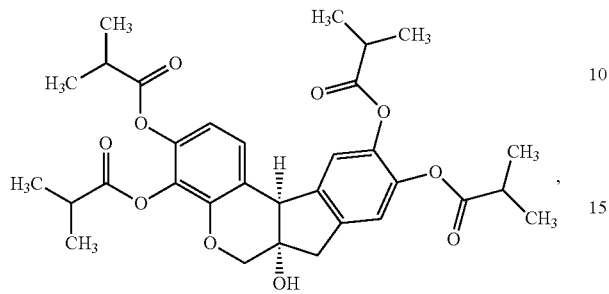

and solvates, salts, complexes, polymorphs, crystalline forms, racemic mixtures, diastereomers, enantiomers, tautomers, isotopically labeled forms, and prodrugs thereof.

* * * * *